United States Patent [19]

Grammenos et al.

[11] Patent Number: 5,416,068
[45] Date of Patent: May 16, 1995

[54] ALPHA-PHENYLACRYLIC ACID DERIVATIVES, THEIR PREPARATION AND THEIR USE FOR CONTROLLING PESTS AND HARMFUL FUNGI

[75] Inventors: Wassilios Grammenos, Ludwigshafen; Reinharad Kirstgen, Neustadt; Klaus Oberdorf, Heidelberg; Hubert Sauter, Mannheim; Franz Roehl, Ludwigshafen; Rainer Otter, Laudenbach; Eberhard Ammermann, Heppenheim; Gisela Lorenz, Neustadt; Uwe Kardorff, Mannheim; Christoph Kuenast, Otterstadt, all of Germany

[73] Assignee: BASF Aktiengesellschaft, Ludwigshafen, Germany

[21] Appl. No.: 176,649

[22] Filed: Jan. 3, 1994

Related U.S. Application Data

[60] Division of Ser. No. 103,154, Aug. 9, 1993, Pat. No. 5,298,527, which is a continuation of Ser. No. 878,295, May 6, 1992, abandoned.

Foreign Application Priority Data

[30] May 17, 1991 [DE] Germany .................. 41 16 090.8

[51] Int. Cl.⁶ ..................... A01N 31/14; C07C 43/215
[52] U.S. Cl. ..................... 504/378; 504/314; 514/532; 514/533; 514/539; 560/17; 560/43; 560/55; 560/60; 560/81; 560/104
[58] Field of Search ............. 560/17, 43, 60, 81, 560/104, 55; 514/532, 533, 539; 504/317, 314

[56] References Cited

U.S. PATENT DOCUMENTS

| | | | |
|---|---|---|---|
| 4,937,372 | 6/1990 | Wenderoth et al. | 560/55 |
| 4,997,973 | 3/1991 | Wenderoth et al. | 560/55 |
| 5,003,101 | 3/1991 | Brand et al. | 560/104 |
| 5,008,438 | 4/1991 | Schuetz et al. | 560/55 |

Primary Examiner—Howard T. Mars
Assistant Examiner—Michael B. Hydorn
Attorney, Agent, or Firm—Keil & Weinkauf

[57] ABSTRACT

α-Phenylacrylic acid derivatives I

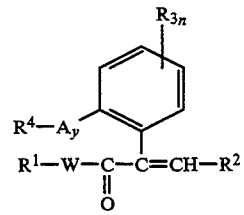

n=1;
y=1;
$R^1$=methyl
$R^2$=methyl, ethyl or methoxymethyl
$R^3$=H;
$R^4$ is 2,5-dimethylphenyl, 2,5-dichlorophenyl, 2-methyl-5-chlorophenyl, 2,4-dimethylphenyl, 2-chloro-5-methylphenyl, 2,3,5-trimethylphenyl or 2-methyl-5-isopropylphenyl.
W=oxygen;
A is —O—, —S—, —OCH$_2$—, —SCH$_2$—, —CH=CH—, —CO—OCH$_2$— or —N(CH$_3$)—CH$_2$—; methods for their preparation, agents containing them for combating injurious fungi and pests, and their use.

3 Claims, No Drawings

ALPHA-PHENYLACRYLIC ACID DERIVATIVES, THEIR PREPARATION AND THEIR USE FOR CONTROLLING PESTS AND HARMFUL FUNGI

This is a division of application Ser. No. 08/103,154, filed Aug. 9, 1993, now U.S. Pat. No. 5,298,527, which is a FWC of Ser. No. 07/878,295, filed May 6, 1992 now abandoned.

The present invention relates to α-phenylacrylic acid derivatives of the general formula I

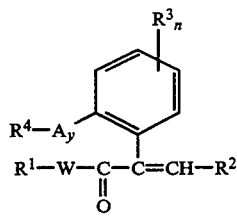

where n is 0, 1, 2, 3 or 4 and the radicals $R^3$ may be different when n is 2, 3 or 4;

y is 0 or 1;

$R^1$ is hydrogen;

$C_1$–$C_{15}$-alkyl, $C_3$–$C_{15}$-alkenyl, $C_3$–$C_8$-alkynyl or $C_3$–$C_8$-cycloalkyl, where these groups may carry from one to five halogen atoms;

vinyl or ethynyl when W is a direct bond;

$R^2$ is cyano, $C_2$–$C_4$-alkenyl, $C_2$–$C_4$-alkynyl;

$C_3$–$C_6$-cycloalkyl where, in addition to carbon atoms, the ring may contain one or two hetero atoms selected from the group consisting of nitrogen, oxygen and sulfur, which in the case of oxygen and/or sulfur must not be adjacent to one another, and where the cyclic structure may additionally carry from one to three of the following radicals: halogen or $C_1$–$C_4$-alkyl;

$C_1$–$C_4$-alkyl which may be unsubstituted or partially or completely halogenated;

$C_1$- or $C_2$-alkyl which carries $C_1$–$C_4$-alkoxy, $C_1$–$C_4$-alkylthio or a 3-membered to 6-membered cyclic radical which, in addition to carbon atoms, may contain one or two hetero atoms selected from the group consisting of nitrogen, oxygen and sulfur, which in the case of oxygen and/or sulfur must not be adjacent to one another, and where the cyclic structure may additionally carry from one to three of the following radicals: halogen or $C_1$–$C_4$-alkyl;

$R^3$ is hydrogen, nitro, cyano, halogen;

$C_1$–$C_4$-alkyl, $C_1$–$C_4$-alkoxy, partially or completely halogenated $C_1$–$C_4$-alkyl, partially or completely halogenated $C_1$–$C_4$-alkoxy or $C_1$–$C_4$-alkylthio, or, where n is 2, 3 or 4, two adjacent substituents $R^3$ together form a 1,3-butadiene-1,4-diyl group which may carry from one to four halogen atoms and/or one or two of the following groups: nitro, cyano, $C_1$–$C_4$-alkyl, $C_1$–$C_4$-alkoxy, partially or completely halogenated $C_1$–$C_4$-alkyl, partially or completely halogenated $C_1$–$C_4$-alkoxy or $C_1$–$C_4$-alkylthio;

$R^4$ is hydrogen; alkyl, alkenyl or alkynyl, each of which is unsubstituted or substituted;

an unsubstituted or substituted saturated or mono- or diunsaturated cyclic structure which, in addition to carbon atoms, may contain from one to three hetero atoms selected from the group consisting of oxygen, sulfur and nitrogen as ring members;

$R'_3P$—, $R'_2P(=O)$— or $R''_2P(=O)$—, where R' is phenyl and R'' is $C_1$–$C_4$-alkoxy;

or an unsubstituted or substituted mononuclear to trinuclear aromatic system which, in addition to carbon atoms, may contain from one to four nitrogen atoms or from one to three hetero atoms selected from a group consisting of two nitrogen atoms and one oxygen or sulfur atom;

W is a direct bond, oxygen, sulfur or nitrogen, where the nitrogen may carry hydrogen, $C_1$–$C_4$-alkyl or $C_1$–$C_4$-alkoxy;

A is —O—; —C(=O)—; —O—C(=O)—; —C(=O)—O—; —S—; —S(=O)—; —O—S—(=O)—; —S(=O)—O; —S(=O)$_2$—; —O—S(=O)$_2$—; —S—(=O)$_2$—O—;
—NR$^5$—; —O—NR$^5$—; —NR$^5$—; —NR$^5$—C(=O)—NR$^6$; —S—(=O)—NR$^5$—; —NR$^5$—S(=O)$_2$—; —S(=O)$_2$—NR$^5$—; —N=N—; —NR$^5$—NR$^6$—; —NR$^5$NR$^6$—C(=O)—; —C(=O)—NR$^5$—NR$^6$; —NR$^5$—NR$^6$—S(=O)$_2$—; —S—(=O)$_2$—NR$^5$—NR$^6$; —O—($C_2$–$C_4$-alkylene)—O—; —C(=O)—($C_2$–$C_4$-alkylene)—O—; —O—C(=O)—($C_2$–$C_4$-alkylene)—O—; —C(=O)—O—($C_2$–$C_4$-alkylene)—O—; —S—($C_2$–$C_4$-alkylene)—O—; —S(=O)$_2$—($C_2$–$C_4$-alkylene)—O—; —O—S(=O)$_2$—($C_2$–$C_4$-alkylene)—O—; —S—(=O)$_2$—O—($C_2$–$C_4$-alkylene)—O—; —NR$^5$—($C_2$–$C_4$-alkylene)—O—; —O—NR$^5$—($C_2$–$C_4$-alkylene)—O—; —NR$^5$—C(=O)—($C_2$–$C_4$-alkylene)—O—; —C(=O)—NR$^5$—($C_2$–$C_4$-alkylene)—O—; —NR$^4$—C(=O)—NR$^6$—($C_2$–$C_4$-alkylene)—O—; —NR$^5$—NR$^6$—($C_2$–$C_4$-alkylene)—O—; —NR$^5$—NR$^6$—C(=O)—($C_2$–$C_4$-alkylene)—O—; —C(=O)—NR$^5$—NR$^6$—($C_2$–$C_4$-alkylene)—O—; $C_1$–$C_6$-alkylene, $C_2$–$C_6$-alkenylene or $C_2$–$C_6$-alkynylene, where these carbon chains may carry from one to four radicals selected from the group consisting of $C_1$–$C_4$-alkyl and halogen, and may be interrupted by one of the following groups or bonded to $R^4$ or to the phenyl ring by one of the following groups: —O—, —S—, —NR$^5$—, —C(=O)—, —C(=O)—O—, —O—C(=O)—, —S(=O)—, —S(=O)—, —S(=O)$_2$—, —S(=O)$_2$—O—, —O—S(=O)$_2$—, —NR$^5$—C(=O)—, —C(=O)—NR$^5$—, —NR$^5$—C(=O)—NR$^6$—, —N=N—, —NR$^5$—NR$^6$—, —NR$^5$NR$^6$—C(=O)— or —C(=O)—NR$^5$—NR$^6$—; $R^5$ and $R^6$ independently of one another are each hydrogen, $C_1$–$C_4$-alkyl or $C_1$–$C_4$-alkoxy; or $R^1$ is not $C_1$–$C_5$-alkyl and n is not 0 or W is not oxygen when $R^4$ is unsubstituted or substituted phenyl and —A$_y$— is one of the following chains: —O—, —CH$_2$O—, —OCH$_2$—, —CH$_2$CH$_2$—, —CH=CH—, —=CH—, —C=C—, oxy-$C_2$–$C_{13}$-alkyleneoxy-, -thio-$C_2$–$C_{12}$-alkyleneoxy or methyleneoxy-$C_2$–$C_{12}$-alkyleneoxy, or where n is not 0 or $R^1$ is not $C_1$–$C_5$-alkyl or W is not oxygen when —A$_y$— is one of the following chains: —C(=O)—O—CH$_2$—, —O—C(=O)—O—CH$_2$—, —C$_1$–$C_{12}$-alkylene-C(=O)—O—CH$_2$—, oxy-($C_1$–$C_{12}$)-alkylene-C(=O)—O—CH$_2$—, $C_1$–$C_{12}$-alkenylene-C(=O)—O—CH$_2$— or oxy-($C_1$–$C_{12}$)-alkenylene-C(=O)—O—CH$_2$—, where the alkylene and the alkenylene groups may carry halogen atoms or hydroxyl groups.

The literature discloses that phenylcrotonic acid derivatives are effective against harmful fungi (EP-A 280 185; EP-A 336 211; EP-A 337 211; EP-A 342 459; EP-A 348 766; German Patent Application P 40 20 384.0; German Patent Application P 40 20 388.3 ).

It is an object of the present invention to provide novel compounds suitable for controlling harmful fungi and pests, and processes for their preparation and their use.

We have found that this object is achieved by the compounds I defined at the outset. We have also found processes for their preparation, fungicides containing them and methods for their use.

We have furthermore found that compounds of the general formula I'

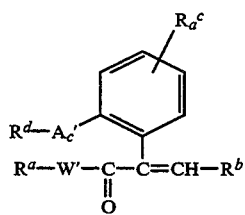

where
a is 0, 1, 2, 3 or 4 where the radicals $R^c$ may be different when a is 2, 3 or 4;
c is 0 or 1;
$R^a$ is hydrogen;
$C_1$–$C_{15}$-alkyl, $C_2$–$C_{15}$-alkenyl, $C_2$–$C_8$-alkynyl or $C_3$–$C_8$-cycloalkyl, where these groups may carry from one to five halogen atoms;
$R^b$ is cyano, $C_2$–$C_4$-alkenyl, $C_2$–$C_4$-alkynyl;
$C_3$–$C_6$-cycloalkyl, where, in addition to carbon atoms, the ring may contain one or two hetero atoms selected from the group consisting of nitrogen, oxygen and sulfur, which in the case of oxygen and/or sulfur must not be adjacent to one another, and where the cyclic structure may additionally carry from one to three of the following radicals: halogen or $C_1$–$C_4$-alkyl;
$C_1$–$C_4$-alkyl which may be unsubstituted or partially halogenated;
$C_1$- or $C_2$-alkyl which carries $C_1$–$C_4$-alkoxy, $C_1$–$C_4$-alkylthio or a 3-membered to 6-membered cyclic radical, which, in addition to carbon atoms, may contain one or two hetero atoms selected from the group consisting of nitrogen, oxygen and sulfur, which in the case of oxygen and/or sulfur must not be adjacent to one another, and where the cyclic structure may additionally carry from one to three of the following radicals: halogen or $C_1$–$C_4$-alkyl;
$R^c$ is hydrogen, nitro, cyano, halogen;
$C_1$–$C_4$-alkyl, $C_1$–$C_4$-alkoxy, partially or completely halogenated $C_1$–$C_4$-alkyl, partially or completely halogenated $C_1$–$C_4$-alkoxy or $C_1$–$C_4$-alkylthio, or, where n is 2, 3 or 4, two adjacent substituents $R^3$ together form a 1,3-butadiene-1,4-diyl group which may carry from one to four halogen atoms and/or one or two of the following groups: nitro, cyano, $C_1$–$C_4$-alkyl, $C_1$–$C_4$-alkoxy, partially or completely halogenated $C_1$–$C_4$-alkyl, partially or completely halogenated $C_1$–$C_4$-alkoxy or $C_1$–$C_4$-alkylthio;
$R^d$ is hydrogen;
alkyl, alkenyl or alkynyl, each of which is unsubstituted or substituted;

an unsubstituted or substituted saturated or mono- or di-unsaturated cyclic structure which, in addition to carbon atoms, may contain from one to three hetero atoms selected from the group consisting of oxygen, sulfur and nitrogen as ring members;
$R'_3P$—, $R'_3P(=O)$— or $R''_2P(=O)$—, where $R''$ is $C_1$–$C_4$-alkoxy and $R'$ is phenyl,
or an unsubstituted or substituted mononuclear to trinuclear aromatic system which, in addition to carbon atoms, may contain from one to four nitrogen atoms or from one to three hetero atoms from the group consisting of two nitrogen atoms and one oxygen or sulfur atom; $W'$ is a direct bond, oxygen, sulfur or nitrogen, which may carry hydrogen, $C_1$–$C_4$-alkyl or $C_1$–$C_4$-alkoxy; $A'$ is —O—; —C(=O)—; —O—C(=O)—; —C(=O)—O—; —S—; —S(=O)—; —O—S—(=O)—; —S(=O)—O—; —S(=O)$_2$—; —O—S(=O)$_2$—; —S—(=O)$_2$—O—; —NR$^e$—; —O—NR$^e$—; —NR$^e$—C(=O)—; —C(=O)—NR$^e$—; —NR$^e$—C(=O)—NR$^f$; —NR$^3$—S(=O)—; —S(=O)—NR$^e$—; —NR$^e$S(=O)—NR $^f$—; —NR$^e$—S(=O)$_2$—; —S(=O)$_2$—NR$^e$—; —NR$^e$—S(=O)$_2$—NR$^f$—; —N=N—; —NR$^e$—NR$^f$—; —NR$^e$—NR$^f$—C(=O)—; —C(=O)—NR$^e$—NR$^f$—; —NR$^e$—NR$^f$—S(=O)—; NR$^f$—S(=O)—; —S—(=O)$_2$—NR$^e$—NR$^f$; —NR$^e$—NR$^f$—S(=O)$_2$—; —S(=O)$_2$—NR$^e$—NR$^f$—; —O—(C$_2$–C$_4$-alkylene)—O—; —C(=O)—O—(C$_2$–C$_4$-alkylene)—O—; —O—C(=O)—(C $_2$–C$_4$-alkylene)—O—; —C(=O)—O—(C $_2$–C$_4$-alkylene)—O—; —S—(C$_2$–C$_4$-alkylene)—O—; —S(=O)$_2$—(C$_2$–C$_4$-alkylene)—O—; —O—S(=O)$_2$—(C$_2$–C$_4$-alkylene)—O—; —S—(=O)$_2$—O—(C $_2$–C$_4$-alkylene)—O—; —NR$^e$—(C$_2$–C$_4$-alkylene)—O—; —O—NR$^e$—(C$_2$–C$_4$-alkylene)—O—; —NR$^e$—C(=O)—(C$_2$–C$_4$-alkylene)—O—;—C(=O)—NR$^e$(C$_2$–C$_4$-alkylene)—O—; —NR$^e$—C(=O)—NR$^f$—(C$_2$–C$_4$-alkylene)—O—; —N=N—(C $_2$–C$_4$-alkylene)—O—; —NR$^e$—NR$^f$—(C$_2$–C$_4$-alkylene)—O—; —NR$^e$—NR$^f$—C(=O)—(C$_2$–C$_4$-alkylene)—O—; —C(=O)—NR$^3$—NR$^f$—(C $_2$–C$_4$-alkylene)—O—; $C_1$–$C_6$-alkylene, $C_2$–$C_6$-alkenylene or $C_2$–$C_6$-alkynylene, where these carbon chains may carry from one to four radicals selected from the group consisting of $C_1$–$C_4$-alkyl and halogen, and may be interrupted by one of the following groups or bonded to $R^d$ or to the phenyl ring by one of the following groups: —O—, —S—, —NR$^e$—, —C(=O)—, —C(=O)—O—, —O—C(=O)—, —S(=O)—, —S(=O)$_2$—, —S(=O)$_2$—O—, —O—S(=O)$_2$—, —NR$^e$—C(=O)—, —C(=O)—NR$^e$—, —NR$^e$—C(=O)—NR$^f$—, —N=N—, —NR$^e$—NR$^f$—, —NR$^e$—NR$^f$—C(=O)— or —C(=O)—NR$^e$—NR$^f$—; $R^e$ and $R^f$ independently of one another are each hydrogen, $C_1$–$C_4$-alkyl or $C_1$–$C_4$-alkoxy, are suitable for controlling pests. This type of activity for such compounds has not been described in the literature to date.

The α-phenylacrylic acid derivatives of the general formula are obtained by processes similar to those described in the literature cited at the outset.

For example, the compounds I in which W is not a direct bond are advantageously obtained by reacting a phenoxalic acid of the general formula II with a Wittig or Wittig-Horner reagent of the general formula IIIa or IIIb in a conventional manner in an inert organic solvent in the presence of a base.

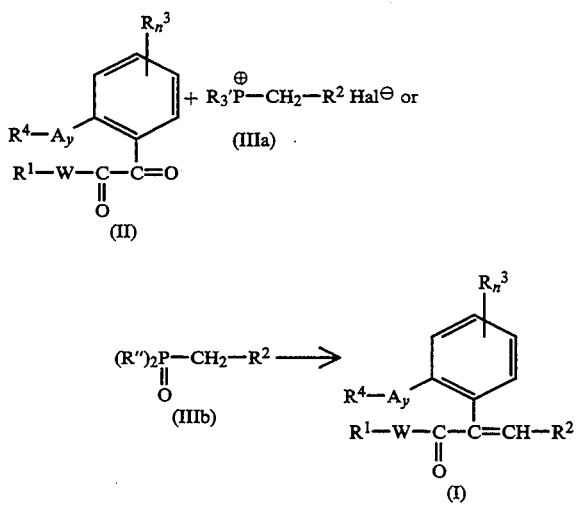

In the formula IIIa, R' is phenyl.

In the formula IIIa, Hal is halogen, such as fluorine, chlorine, bromine or iodine.

In the formula IIIb, R" is alkoxy, preferably $C_1$–$C_4$-alkoxy, in particular $C_1$- or $C_2$-alkoxy.

The reaction is carried out as a rule at from $-20°$ to $60°$ C., preferably from $-10°$ to $30°$ C.

Suitable solvents are aliphatic hydrocarbons, such as pentane, hexane, cyclohexene and petroleumether, aromatic hydrocarbons, such as toluene and o-, m- and p-xylene, halohydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile, propionitrile, alcohols, such as methanol, ethanol, n-propanol, isopropanol, n-butanol and tert-butanol, and dimethyl sulfoxide and dimethylformamide, tetrahydrofuran, dimethyl sulfoxide, dimethylformamide and diethyl ether being particularly preferred.

It is also possible to use mixtures of the stated solvents.

Suitable bases are in general inorganic compounds, for example alkali metal and alkaline earth metal hydroxides, such as lithium hydroxide, sodium hydroxide, potassium hydroxide and calcium hydroxide, alkali metal and alkaline earth metal oxides, such as lithium oxide, sodium oxide, calcium oxide and magnesium oxide, alkali metal and alkaline earth metal hydrides, such as lithium hydride, sodium hydride, potassium hydride and calcium hydride, alkali metal amides, such as lithium amide, sodium amide and potassium amide, alkali metal and alkaline earth metal carbonates, such as lithium carbonate and calcium carbonate, and alkali metal bicarbonates, such as sodium bicarbonate, organometallic compounds, in particular alkali metal alkyls, such as methyllithium, butyllithium and phenyllithium, alkylmagnesium halides, such as methylmagnesium chloride and alkali metal and alkaline earth metal alcoholates, such as sodium methylate, sodium ethylate, potassium ethylate, potassium tert-butylate and dimethoxymagnesium, as well as organic bases, for example tertiary amines, such as trimethylamine, triethylamine, diisopropylethylamine and N-methylpiperidine, pyridine, substituted pyridines, such as collidine, lutidine and 4-dimethylaminopyridine, and bicyclic amines.

Sodium methylate, potassium tert-butylate, sodium hydride, potassium carbonate and n-butyllithium are particularly preferred.

The bases are used in general in equimolar amounts but may also be used in excess or, if required, as solvents.

The starting materials are usually reacted with one another in stoichiometric amounts. It may be advantageous, for example to increase the yield, if one of the starting materials is used in an excess of from 0.1 to 10, preferably from 0.2 to 1.5, mole equivalents.

The reaction is advantageously carried out at atmospheric pressure or at the autogenous pressure of the particular solvent.

The compounds of the general formula I are furthermore obtained by reacting a phenylacetic acid of the general formula IV with an aldehyde of the general formula V in a conventional manner in an inert organic solvent in the presence of a base.

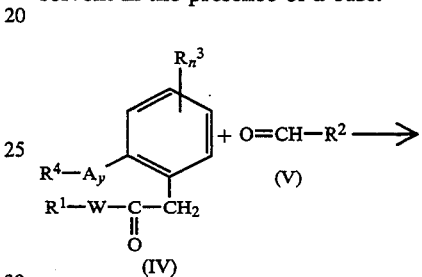

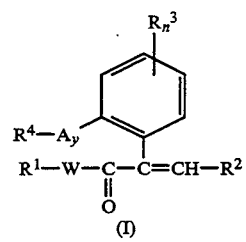

The reaction is carried out as a rule at from $-80°$ to $100°$ C., preferably from $-78°$ to $80°$ C.

Suitable solvents are the aldehydes used or aliphatic hydrocarbons, such as pentane, hexane, cyclohexane and petroleum ether, aromatic hydrocarbons, such as toluene and o-, m- and p-xylene, halohydrocarbons, such as methylene chloride, chloroform and chlorobenzene, ethers, such as diethyl ether, diisopropyl ether, tert-butyl methyl ether, dioxane, anisole and tetrahydrofuran, alcohols, such as methanol, ethanol, n-propanol, isopropanol n-butanol and tert-butanol, and dimethyl sulfoxide and dimethylformamide, the aldehydes V used, toluene, cyclohexane, tetrahydrofuran, dimethylformamide and diethyl ether being particularly preferred.

It is also possible to use mixtures of the stated solvents.

Suitable bases are in general inorganic compounds, for example alkali metal and alkaline earth metal hydroxides, such as lithium hydroxide, sodium hydroxide, potassium hydroxide and calcium hydroxide, alkali metal and alkaline earth metal oxides, such as lithium oxide, sodium oxide, calcium oxide and magnesium oxide, alkali metal and alkaline earth metal hydrides, such as lithium hydride, sodium hydride, potassium hydride and calcium hydride, alkali metal amides, such as lithium amide, sodium amide and potassium amide, alkali metal and alkaline earth metal carbonates, such as lithium carbonate and calcium carbonate, and alkali metal bicarbonates, such as sodium bicarbonate, organometallic compounds, in particular alkali metal alkyls, such as methyllithium, butyllithium, phenyllithium and lithium diisopropylamide, alkylmagnesium halides, such as methylmagnesium chloride and alkali metal and alkaline earth metal alcoholates, such as sodium methylate, sodium ethylate, potassium ethylate, potassium tert-butylate and dimethoxymagnesium, as well as organic bases, for example tertiary amines, such as trimethylamine, triethylamine, diisopropylethylamine and N-methylpiperidine, pyridine, substituted pyridines, such as collidine, lutidine and 4-dimethylaminopyridine, and bicyclic amines.

Sodium methylate, potassium tert-butylate, lithium diisopropylamide and potassium carbonate are particularly preferred.

The bases are used in general in catalytic amounts but may also be used in equimolar amounts, in excess or, if required, as solvents.

The starting materials are usually reacted with one another in stoichiometric amounts. It may be advantageous, for example to increase the yield, if one of the starting materials is used in an excess of from 0.1 to 10, preferably from 0.2 to 1.5, mole equivalents.

To increase the yield, it may be advantageous to carry out the reaction in the presence of phase transfer catalysts. Phase transfer catalysts suitable for this purpose are, for example, quarternary ammonium or phosphonium salts and crown ethers and cryptates, preferably tetrabutylammonium or -phosphonium bromide.

This method too is advantageously carried out at atmospheric pressure or at the autogenous pressure of the particular solvent.

The compounds of the general formula I are also obtained by reacting a phosphonylphenylacetic acid of the general formula VI with an aldehyde of the general formula V in a conventional manner in an inert organic solvent in the presence of a base.

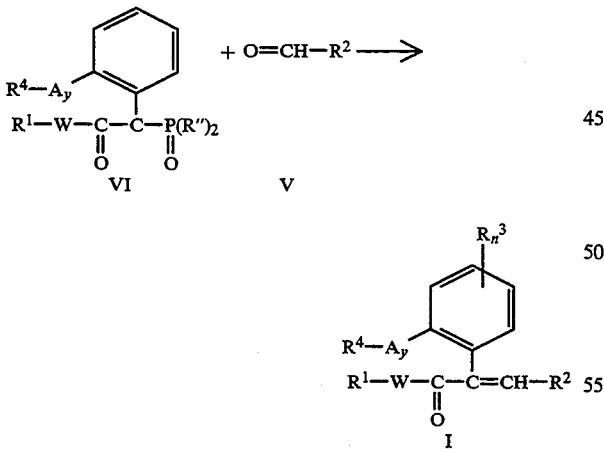

The reaction is carried out as a rule at from −78° to 80° C. preferably from −78° to 60° C.

Suitable solvents are, for example, aliphatic hydrocarbons, such as pentane, hexane, cyclohexane and petroleum ether, aromatic hydrocarbons, such as toluene and o-, m- and p-xylene, halohydrocarbons, such as methylene chloride, chloroform and chlorobenzene, ethers, such as diethyl ether, diisopropyl ether, tert-butyl methyl ether, dioxane, anisole and tetrahydrofuran, alcohols, such as methanol, ethanol, n-propanol, isopropanol, n-butanol and tert-butanol, and dimethyl sulfoxide and dimethylformamide, tetrahydrofuran, dimethylformamide and diethyl ether being particularly preferred.

It is also possible to use mixtures of the stated solvents.

Suitable bases are in general inorganic compounds, for example alkali metal and alkaline earth metal hydroxides, such as lithium hydroxide, sodium hydroxide, potassium hydroxide and calcium hydroxide, alkali metal and alkaline earth metal oxides, such as lithium oxide, sodium oxide, calcium oxide and magnesium oxide, alkali metal and alkaline earth metal hydrides, such as lithium hydride, sodium hydride, potassium hydride and calcium hydride, alkali metal amides, such as lithium amide, lithium diisopropylamide, sodium amide and potassium amide, alkali metal and alkaline earth metal carbonates, such as lithium carbonate and calcium carbonate, and alkali metal bicarbonates, such as sodium bicarbonate, organometallic compounds, in particular alkali metal alkyls, such as methyllithium, butyllithium and phenyllithium, alkylmagnesiumhalides, such as methylmagnesium chloride and alkali metal and alkaline earth metal alcoholates, such as sodium methylate, sodium ethylate, potassium ethylate, potassium tert-butylate and dimethoxymagnesium, as well as organic bases, for example tertiary amines, such as trimethylamine, triethylamine, diisopropylethylamine and N-methylpiperidine, pyridine, substituted pyridines, such as collidine, lutidine and 4-dimethylaminopyridine, and bicyclic amines.

Sodium methylate, potassium tert-butylate, lithium diisopropylamide, potassium carbonate and n-butyllithium are particularly preferred.

The bases are used in general in excess or, if required, as solvents.

The starting materials are usually reacted with one another in stoichiometric amounts. It may be advantageous, for example to increase the yield, if one of the starting materials is used in an excess of from 0.1 to 10, preferably from 0.2 to 1.5, mole equivalents.

This method too is advantageously carried out at atmospheric pressure or at the autogenous pressure of the particular solvent.

The intermediates of the general formula II which are required for the abovementioned reactions and in which W is not a direct bond (IIa) can be obtained starting from phenyl derivatives of the general formula VII. The side chain of the subsequent structure $R^4$—$A_y$— is denoted by R* for greater clarity:

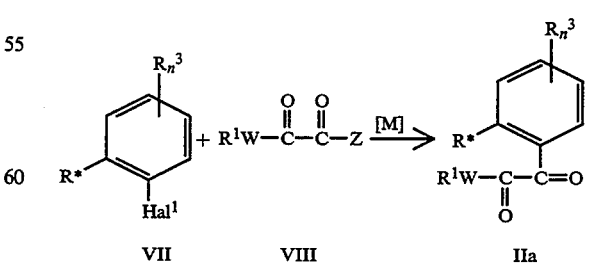

In the formula VII, $Hal^1$ is halogen, such as fluorine, chlorine, bromine or iodine, preferably chlorine or bromine, in particular bromine.

In the formula VIII, Z is halogen, as stated for $Hal^1$, or $C_1$-$C_4$-alkoxy, such as methoxy, ethoxy, propoxy, 1-methylethoxy, butoxy, 1-methylpropoxy, 2-methylpropoxy or 1,1-dimethylethoxy, preferably methoxy.

The reaction is carried out as a rule at from −30° to 80° C. preferably from −10° to 50° C.

Suitable solvents are aliphatic hydrocarbons, such as pentane, hexane, cyclohexane and petroleumether, aromatic hydrocarbons, such as toluene and o-, m- and p-xylene, halohydrocarbons, such as methylene chloride, chloroform and chlorobenzene, ethers, such as diethyl ether, diisopropyl ether, tert-butyl methyl ether, dioxane, anisole and tetrahydrofuran and dimethyl sulfoxide and dimethylformamide, particularly preferably diethyl ether and tetrahydrofuran.

It is also possible to use mixtures of the stated solvents.

Metals, such as magnesium, or metal organyls, such as methyllithium, butyllithium and phenyllithium, may be used as reagent [M].

Magnesium and butyllithium are particularly preferred.

The reagent is used in general in stoichiometric/-catalytic amounts. It is preferably used in amounts of from 1 mole equivalent/mol % to 2 mole equivalents/mol %, in particular from 1 mole equivalent/mol % to 1.3 mole equivalents/mol %, based on the phenyl derivative VII.

The starting materials are usually reacted with one another in stoichiometric amounts. It may be advantageous, for example to increase the yield, if one of the starting materials is used in an excess of from 0.1 to 10, preferably from 0.2 to 1.5, mole equivalents.

The preparation of the intermediates IIa is also advantageously carried out at atmospheric pressure or at the autogenous pressure of the particular solvent.

The compounds IIa in which $R^1$—W— is methoxy can be derivatized by generally known methods:

A. Compounds of the formula I in which A is oxygen (—O—), sulfur (—S—) or —C≡C— and y is 1 can be prepared as described in Scheme 1.

-continued
Scheme 1

Hal = chlorine, bromine or iodine

The known α-ketocarboxylic acid derivatives of the general formula 1 (cf. European Patent 207,101 and U.S. Pat. No. 3,622,569) can be converted by a Wittig or Wittig-Horner reaction [cf. European Patent 348,766] in a conventional manner into the α-alkylacrylic acid derivative of the formula 2, from which the compounds of the general formula I in which A and W are each oxygen (—O—) or sulfur (—S—) and y is 1 are obtained in a conventional manner by an Ullmann reaction [cf. 1) Russ. Chum. Rev. 45 (1974), 679–689; 2) J. Org. Chem. 29 (1964), 977, 3624].

The compounds of the general formula I in which A is —C≡C—, y is 1 and W is oxygen (—O—) or sulfur (—S—) can be obtained starting from α-alkylacrylic acid derivatives of the general formula 2, in which Hal is, in particular, iodine or bromine, in a similar manner by a Stephens-Castro coupling [cf. J. Org. Chem. 28 (1963), 2163].

B. Compounds of the formula I in which $A_y$ is —OCH$_2$—, —SCH$_2$— or —N(alkyl)—CH$_2$— can be prepared as described in Scheme 2.

For greater clarity, the group

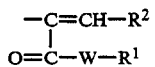

is abbreviated to R*.

Scheme 2

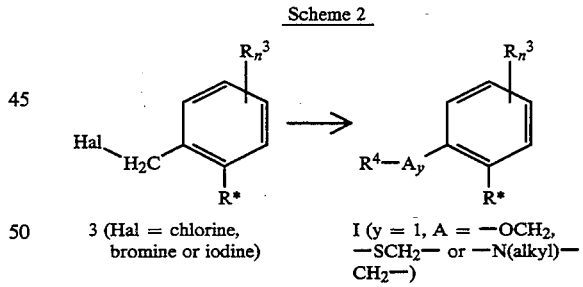

3 (Hal = chlorine, bromine or iodine)    I (y = 1, A = —OCH$_2$—, —SCH$_2$— or —N(alkyl)—CH$_2$—)

Benzyl halides of the formula 3 can be converted into the products of the formula I in which y is 1 and A is —OCH$_2$—, —SCH$_2$— or —N(alkyl)—CH$_2$— by reacting them with alkali metal, alkaline earth metal, silver or ammonium salts of the formula R$^4$-cation, where R$^4$ has the above-mentioned meanings, in a solvent, such as acetone, toluene, dimethylformamide or tetrahydrofuran, with the addition of a catalyst, for example from 0.01 to 10% by weight of potassium iodide or tetramethyldiamine.

The benzyl halides of the general formula 3 can be prepared, for example, as described in the reaction scheme below (Scheme 3).

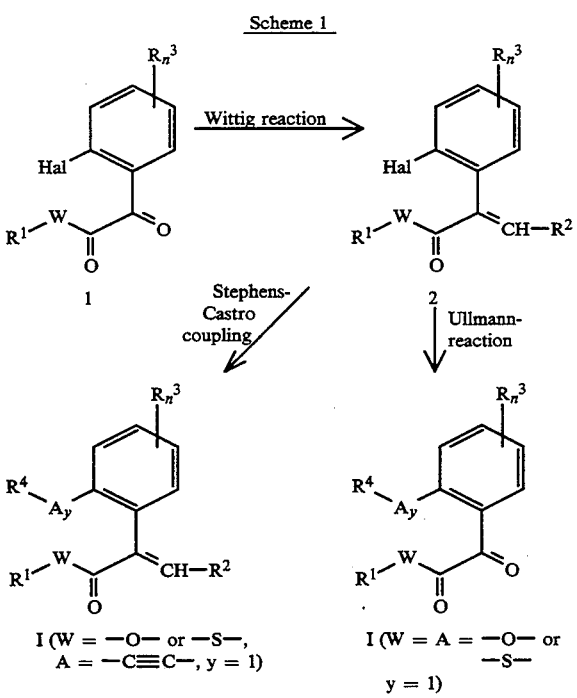

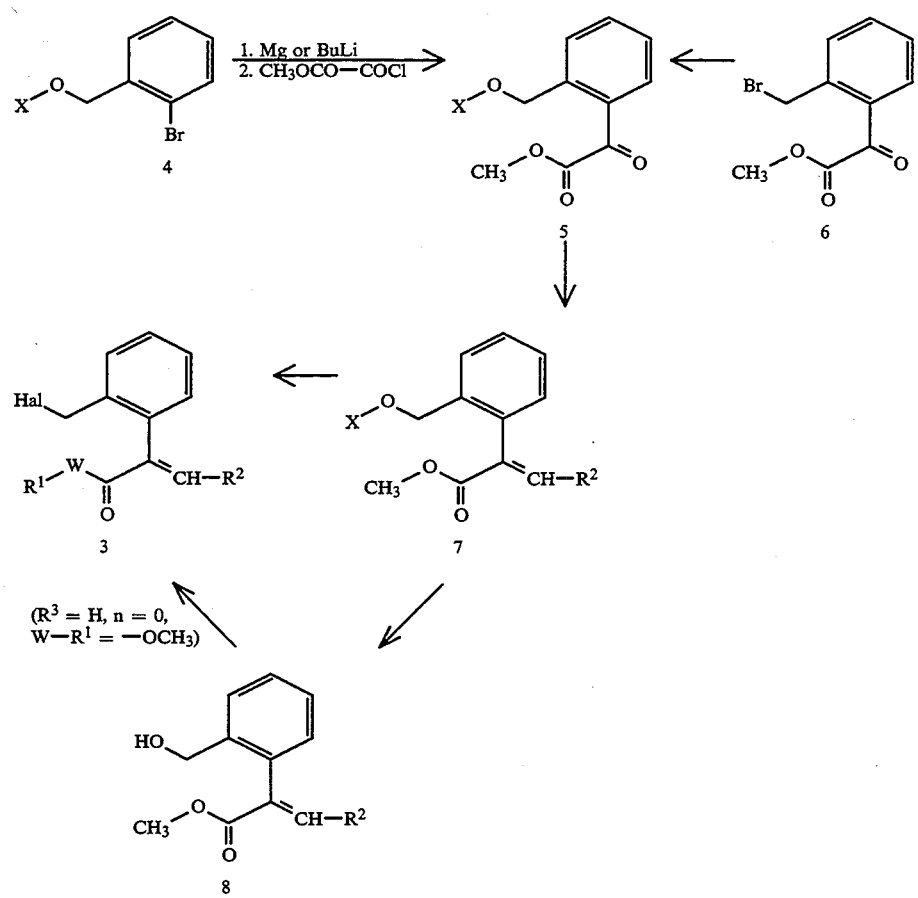

Starting from bromobenzene derivatives of the formula 4 or from methyl o-bromomethylphenylglyoxylate (6) known from the literature (European Patent 342,459), it is possible, by methods known from the literature [cf. 1) J. Org. Chem. 4.6 (1981), 211–213; 2) European Patent 53,213; 3) Synthetic Comm. 11 (1981), 343; 4) European Patent 342,459], to prepare the intermediates of the general formula 5, in which X is an alcohol protective group, eg. methyl, ethyl, phenyl or acetyl (cf. T. W. Greene, Protective Groups in Organic Synthesis, J. Wiley and Sons, 1981, pages 10–86), which, after introduction of the α-alkyl acrylate group, are then converted either directly with the aid of boron trihalide reagents of the formula B(Hal)$_3$ (cf. Synthesis 1983, 249 et seq.) or by the free benzyl alcohols of the formula 8 into the benzyl halides of the general formula 3.

The benzyl halides of the general formula 3 can be prepared, for example, as described in reaction scheme 4 below.

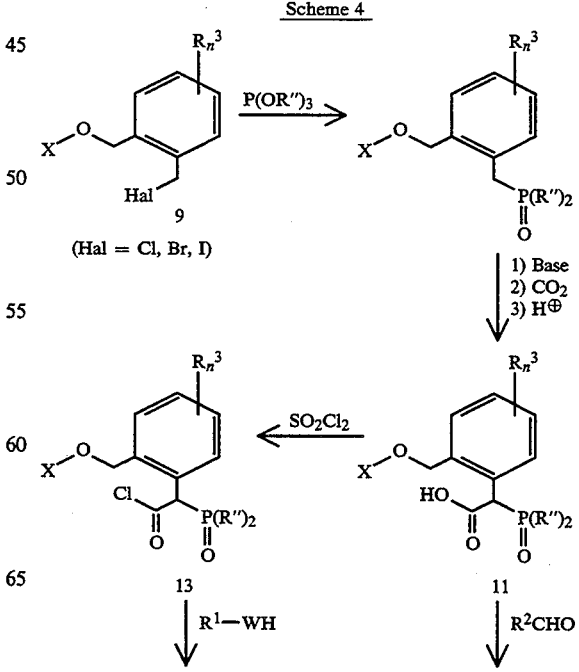

13

-continued
Scheme 4

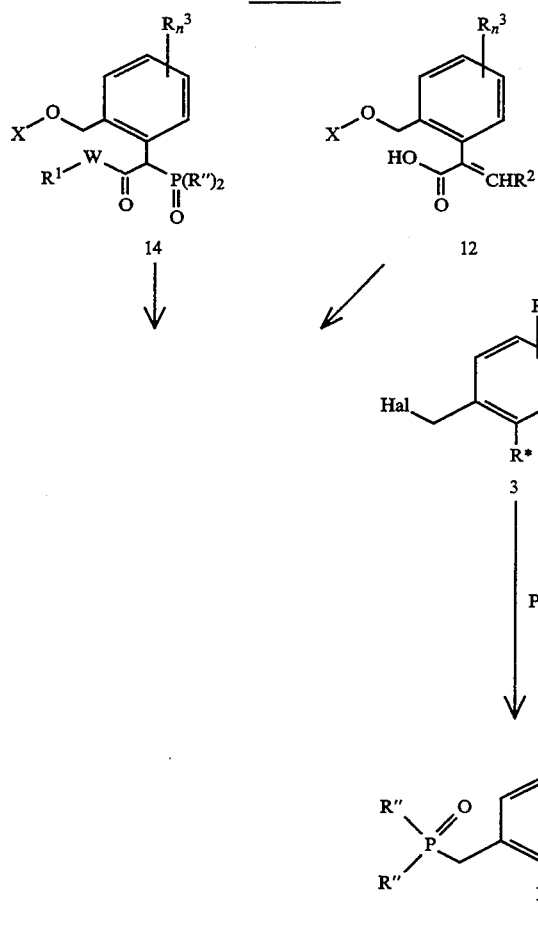

C. Compounds of the general formula I in which $A_y$ is —CH=CH— can be prepared as described in Scheme 5. For greater clarity, the group

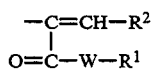

is abbreviated to R*.

Scheme 5

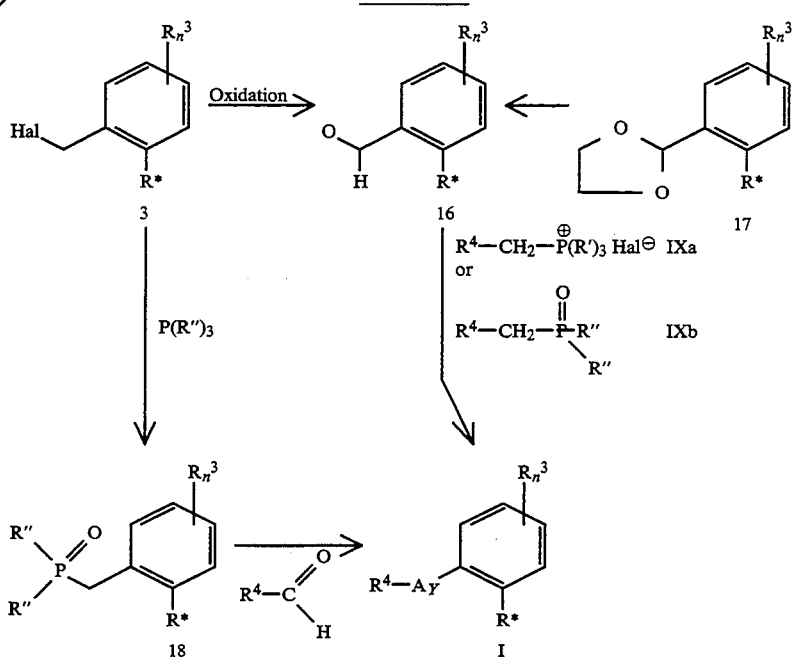

$(A = -CH=CH-, y = 1)$

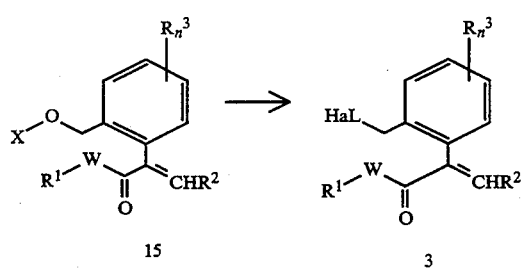

The benzyl phosphonates can be prepared starting from the benzyl halides, for example via a Michaelis-Arbuzov reaction (cf. Houben-Weyl, 4th Edition, Vol. XII/1, page 433 et seq.). After deprotonation by means of a strong base and an addition reaction with carbon dioxide, carboxymethanephosphonates are obtained (cf. Synthesis (1986) 661–664). As shown in the scheme, the phosphonates can be converted directly or after modification of the carboxyl terminal group (cf. Scheme 7) with aldehydes $R^2$CHO into $\alpha,\beta$-unsaturated carbonyl derivatives (cf. Synthesis (1986), 790–792). These can be converted into benzyl halides as described in Scheme 3.

The preparation of the compounds of the formula I in which $A_y$ is —CH=CH— is carried out by reacting 2-formyl-α-alkylacrylic acid derivatives of the general formula 16 with a phosphonate of the general formula IXb or with a phosphonium salt of the formula IXa. The reaction is carried out in a known manner [cf. J. Am. Chem. Soc. 83 (1961), 1733]. The starting materials are usually used in a stoichiometric ratio. An excess of up to 10% by weight of one of the two reactants over and above the stoichiometric amount is possible. The reaction is carried out in an inert solvent or diluent (eg. diethyl ether, tetrahydrofuran or toluene) in the presence of an equivalent amount of a base (eg. sodium hydride, sodium amide, potassium tert-butylate, sodium methylate, butyllithium or sodium bistrimethylsilylamide). The reactions usually take place at from $-70°$ to $+30°$ C. Since in some cases they take place with evolution of heat, it may be advantageous to use a means of cooling.

A second method is available for the preparation of the novel compounds of the formula I in which $A_y$ is —CH=CH—. In this method, aldehydes of the formula $R^4$—CHO are reacted with the benzylphosphonates of the formula 18 [cf. J. Am. Chem. Soc. 83 (1964), 1733].

The 2-formyl-2-alkylacrylic acid compounds of the formula 16 are prepared, for example, in a simple manner by oxidizing the benzyl halides 3, for example with methylmorpholine-N-oxide monohydrate (cf. European Patent 393 428) or with dimethyl sulfoxide (similarly to J. Chem. Soc. 1964, 520).

D. Compounds of the formula I in which $A_y$ is —NH— can be prepared, for example, as described in Scheme 6.

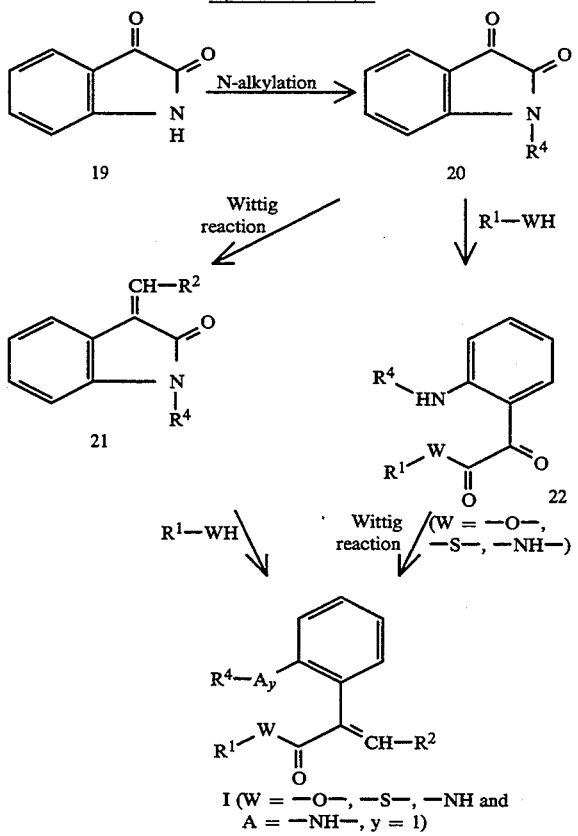

The N-alkylated isatin 20 is prepared starting from isatin (19) by methods known from the literature cf. 1) J. Heterocyclic Chem. 24. (1987), 1249-1251; 2) Liebigs Ann. Chem. (1982), 794-804; 3) Chem. Ber. (1966), 3060-3062] and is then converted into the products of the general formula I (A=NH— and W=—O—, —S— or —NH—) either directly or after introduction of the α-alkyl acrylate group by methods which are likewise known, in an nucleophilic ring cleavage reaction [cf. 1) Chem. Ber. (1966), 3060-3062; 2) Zh. Org. Khim. 22 (1986), 11, 2409-2420; 3) Liebigs Ann. Chem. (1982), 794-804].

E. Compounds of the general formula I where $R^4$ is a group

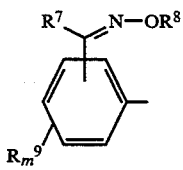

and $A_y$ is —OCH$_2$— can be prepared, for example, by reacting a substituted oxime ether of the formula 23 with a benzyl halide of the formula 3.

For greater clarity, the group

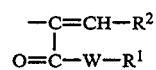

is abbreviated to R*.

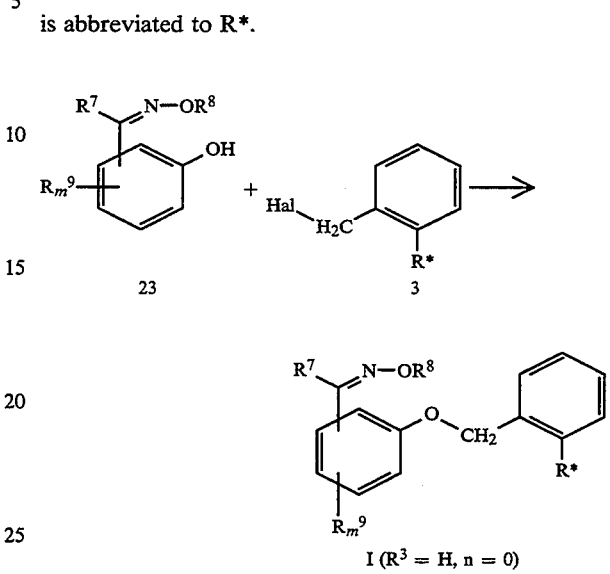

The reaction described can be carried out, for example, in an inert solvent or diluent (eg. acetone, acetonitrile, dimethyl sulfoxide, dimethylformamide, N-methylpyrrolidone, N,N'-dimethylpropyleneurea or pyridine) using a base (eg. sodium carbonate or potassium carbonate).

Alternatively, it is also possible to adopt a procedure in which the compounds of the general formula 23 are first converted with a base (eg. sodium hydroxide, potassium hydroxide or sodium methylate) into the corresponding sodium or potassium phenolates and the latter are then reacted with the substituted benzyl compounds of the general formula 3 in an inert solvent or diluent (eg. dimethylformamide) to give the novel compounds of the formula I.

The novel compounds of the formula I where $R^4$, y, A and R* have the abovementioned meanings can also be prepared by a method in which the novel substituted carbonyl compounds of the general formula 25 are reacted with a hydroxylamine of the general formula 26 or with an acid addition salt (eg. hydrochloride or hydrobromide) of 26.

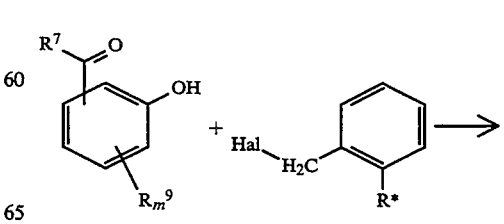

Hal = chlorine, bromine or iodine

-continued

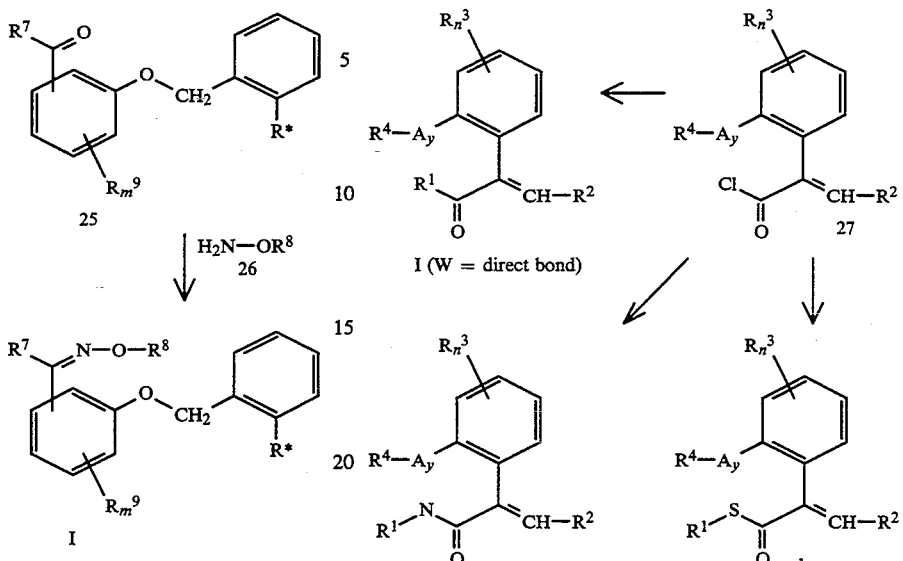

The novel substituted carbonyl compounds of the formula 25 are obtained by reacting the substituted benzyl compounds of the general formula 3 where Hal is chlorine, bromine or iodine with substituted carbonyl compounds of the formula 24. The compounds of the formula 26 are either known or can be prepared by generally conventional processes and methods (cf. EP-A 386,561).

The reaction below with a substituted-hydroxylamine of the formula 26 can be carried out in an inert solvent or diluent (eg. methanol, ethanol or toluene) or in a two-phase system (eg. toluene/water). It may also be advantageous to add a base (eg. triethylamine, sodium carbonate, potassiumcarbonate or potassiumhydroxide) to the reaction mixture (cf. EP-A 386,561).

F. Compounds of the general formula I where W is —S—, NH—, —N(alkyl)—, —N(alkoxy)— or a chemical bond can be prepared as described in Scheme 7.

Scheme 7

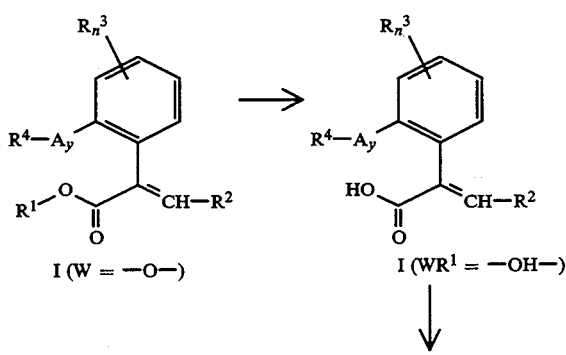

-continued
Scheme 7

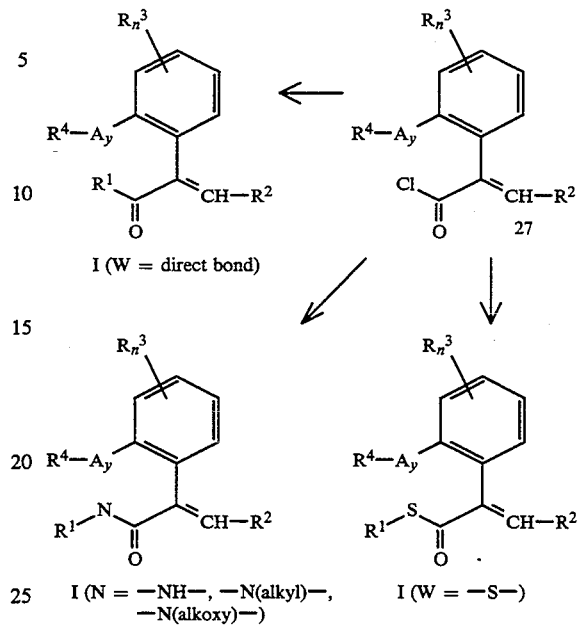

Compounds of the general formula I where W is a direct bond are obtained from acyl chlorides of the formula 27 by reaction with metal organyls of the type $[M]R_x$; $(Hal)_z$, where x is 1 or 2, Z is 0 or 1, [M] is a metal, eg. lithium, magnesium, zinc, cadmium or mercury, in particular zinc or magnesium, and Hal is chlorine, bromine or iodine, in particular chlorine or bromine.

The starting materials are usually reacted with one another in stoichiometric amounts. It may be advantageous, for example in order to increase the yield, to use one of the starting materials in an excess of from 0.1 to 10, preferably from 0.2 to 1.5, mole equivalents.

The reaction is carried out as a rule at from −30° to 80° C., preferably from −10° to 60° C.

Suitable solvents are aliphatic hydrocarbons, such as pentane, hexane, cyclohexane and petroleum ether, aromatic hydrocarbons, such as toluene and o-, m- and p-xylene, halohydrocarbons, such as methylene chloride, chloroform and chlorobenzene, ethers, such as diethyl ether, diisopropyl ether, tert-butyl methyl ether, dioxane, anisole and tetrahydrofuran, and dimethyl sulfoxide and dimethylformamide, particularly preferably diethyl ether and tetrahydrofuran. It is also possible to use mixtures of the stated solvents (cf. Houben-Weyl, Vol. VII/2a, 558 et seq. (1973)).

Compounds of the general formula I, where W is sulfur (—S—) are obtained, for example, from the acyl chlorides 27 by a method similar to that described in Houben-Weyl, Vol. E 5, page 861 et seq. (1985).

Alternatively, the abovementioned compounds of the general formula I can also be prepared from carboxylic acids of the formula I ($WR^1$=—OH) (cf. Houben-Weyl, Vol. E 5, page 855 et seq., (1985)).

Compounds of the general formula I where W is —NH—, —N(Alkyl)— or —N(Alkoxy)— can be prepared in a conventional manner from the acyl chlorides 27 by a method similar to that described in Organikum 16th Edition, page 412 (1985).

The intermediates of the general formula I ($WR^1$=—OH) which are required for the abovementioned reactions can be obtained starting from compounds of the general formula I (W=—O—) by methods known from the literature (cf. Organikum 16th Edition, pages 415 and 622 (1985)).

The acyl chlorides 27 can be prepared from the resulting carboxylic acids I (WR$^1$=—OH) in a conventional manner (cf. Organikum 16th Edition, page 423 et seq. (1985), and Houben-Weyl, Vol. VIII, 464 et seq.).

Because of their biological activity for controlling harmful fungi, suitable compounds I are those in which the indices and the substituents have the following meanings:

n is 0, 1, 2, 3 or 4 and the radicals R$^3$ may be different when n is 2, 3 or 4; n is preferably 0, 1 or 2, in particular 0 or 1;

y is 0 or 1;

R$^1$ is hydrogen;

$C_1$–$C_{15}$-alkyl, in particular $C_1$–$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, propyl or 1-methylethyl, in particular methyl or ethyl;

$C_3$–$C_{15}$-alkenyl, in particular $C_3$–$C_6$-alkenyl, Such as 1-propenyl, 2-propenyl, 1-methylethenyl, 1-butenyl, 2-butenyl, 3-butenyl, 1-methyl-1-propenyl, 2-methyl-1propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl- 2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl- 1-butenyl, 2,3-dimethyl-2-butenyl, 2,3-dimethyl-3-butenyl, 3,3-dimethyl-1-butenyl, 3,3 -dimethyl -2-butenyl, 1-ethyl-1-butenyl, 1-ethyl-2-butenyl, 1-ethyl-3-butenyl, 2-ethyl-1-butenyl, 2-ethyl-2ethyl-2-butenyl, 2-ethyl-3-butenyl, 1,1,2-trimethyl-2propenyl, 1-ethyl- 1-methyl-2 -propenyl, 1-ethyl-2 -methyl-1-propenyl or 1-ethyl-2-methyl-2-propenyl, preferably 2-propenyl, 2-butenyl or 3-methyl-2-butenyl, in particular 2-propenyl;

$C_3$–$C_8$-alkynyl, in particular $C_3$–$C_6$-alkynyl$^1$, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-buytynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl- 1-pentynyl, 3 -methyl-4 -pentynyl, 4-methyl- 1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl or 1-ethyl-1-methyl-2-propynyl, preferably 2-propynyl or 2-butynyl, in particular 2-propynyl;

or $C_3$–$C_8$-cycloalkyl, such as cyclopropyl, cyclobutyl, cyclopentyl, cyclohexyl, cycloheptyl or cyclooctyl, preferably cyclopropyl, cyclopentyl or cyclohexyl, in particular cyclopropyl, where these hydrocarbon groups may carry from one to five halogen atoms, such as fluorine, chlorine, bromine or iodine, preferably fluorine, chlorine or bromine, in particular fluorine or chlorine;

R$^1$ may also be vinyl or ethynyl when W is a direct bond;

R$^2$ is cyano; $C_2$–$C_4$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl or 2-methyl-2-propenyl, preferably $C_2$- or $C_3$-alkenyl, in particular ethenyl or 1-propenyl;

$C_2$–$C_4$-alkynyl, such as ethynyl, 1-propynyl, 2-propynyl, 1-butynyl, 2-butynyl, 3-butynyl or 1-methyl-2-butynyl, preferably ethynyl or 2-propynyl;

a 3-membered to 6-membered, saturated or partially or completely unsaturated cyclic radical which, in addition to carbon atoms, may contain one or two hetero atoms selected from the group consisting of nitrogen, oxygen and sulfur, which in the case of oxygen and-/or sulfur must not be adjacent to one another, such as cyclopropyl, cyclobutyl, cyclopentyl, cyclohexyl, epoxidyl, 2-tetrahydrofuranyl, 3-tetrahydrofuranyl, 2-tetrahydrothienyl, 3-tetrahydrothienyl, 2,3-dihydrofur-2-yl, 2,3-dihydrofur-3-yl, 2,5-dihydrofur-2-yl, 2,5-dihydrofur-3-yl, 2,3-dihydrothien-2-yl, 2,3-dihydrothien-3-yl, 2,5-dihydrothien-2-yl, 2,5-dihydrothien-3-yl, 2-tetrahydropyranyl, 2-tetrahydrothianyl, 1,3-dioxolan-2-yl, 1,3-dithiolan-2-yl, N-morpholinyl or N-pyrrolidinyl, preferably cyclopropyl or epoxidyl, in particular cyclopropyl, where the cyclic structure may additionally carry from one to three of the following radicals: halogen as stated above, preferably fluorine or chlorine, or $C_1$–$C_4$-alkyl as stated above in general, preferably $C_1$- or $C_2$-alkyl; $C_1$–$C_4$-alkyl, such as methyl, ethyl, propyl, 1-methylethyl, butyl, 1-methylpropyl, 2-methylpropyl or 1,1-dimethylethyl, preferably $C_1$–$C_3$-alkyl, in particular methyl or ethyl, where these groups may be partially or completely halogenated by halogen atoms, such as fluorine, chlorine, bromine or iodine, preferably fluorine or chlorine, R$^2$ is also $C_1$- or $C_2$-alkyl, which may carry one of the following groups:

$C_1$–$C_4$-alkoxy, such as methoxy, ethoxy, propoxy, 1-methylethoxy, butoxy, 1-methylpropoxy, 2-methylpropoxy or 1,1-dimethylethoxy, preferably $C_1$–$C_3$-alkoxy, in particular methoxy or ethoxy;

$C_1$–$C_4$-alkylthio, such as methylthio, ethylthio, propylthio, 1-methylethylthio, butylthio, 1-methylpropylthio, 2-methylpropylthio or 1,1-dimethylethylthio, preferably $C_1$–$C_3$-alkylthio, in particular methylthio or ethylthio; or a 3-membered to 6-membered, saturated or partially or completely unsaturated cyclic radical which, in addition to carbon atoms, may contain one or two hetero atoms selected from the group consisting of nitrogen, oxygen and sulfur, which in the case of oxygen and/or sulfur must not be adjacent to one another, such as cyclopropyl, cyclobutyl, cyclopentyl, cyclohexyl, epoxidyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,5-dihydrofur-2-yl, 2,5-dihydrofur-3-yl, 2,3-dihydrothien-2-yl, 2,3-dihydrothien-3-yl, 2,5-dihydrothien-2-yl, 2,5-dihydrothien-3-yl, 2,3-pyrrolin-2-yl 2,3-pyrrolin-3-yl, 2,5-pyrrolin-2-yl, 2,5-pyrrolin-3-yl, 2,3-isoxazolin-3-yl, 3,4-isoxazolin-3-yl, 4,5-isoxazolin-3-yl, 2,3-isoxazolin-4-yl, 3,4-isoxazolin-4-yl, 4,5-isoxazolin-4-yl, 2,3-isoxazolin-5-yl, 3,4-isoxazolin-5-yl, 4,5-isoxazolin-5-yl,2,3-isothiazolin-3-yl,3,4-isothiazolin-3-yl, 4,5-isothiazolin-3-yl, 2,3-isothiazolin-4-yl, 3,4-isothiazolin-4-yl, 4,5-isothiazolin-4-yl, 2,3-isothiazolin- 5-yl, 3,4-isothiazolin-5-yl, 4,5-isothiazolin-5-yl, 2,3-dihydropyrazol-1-yl,2,3-dihydropyrazol-2-yl, 2,3-dihydropyrazol-3-yl, 2,3-dihydropyrazol-4-yl, 2,3-dihydropyrazol-5-yl, 4,5-dihydropyrazol-1-yl, 4,5-dihydropyrazol- 3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 2-piperidinyl, 3-piperidinyl, 4-piperidinyl, 3-tetrahydropyridazinyl, 1-tetrahydropyridazinyl, 2-tetrahydropyrimidinyl, 4-tetrahydropyrimidinyl, 1-tetrahydropyrimidinyl, 2-tetrahydropyrazinyl, 1,3,5-tetrahydrotriazin-2-yl or 1,2,4-tetrahydrotriazin-3-yl, 1,3-dihydrooxazin-2-yl, 1,3-dithian-2-yl, oxazol-2-in-2-yl, 2-tetrahydropyranyl, 1,3-dioxolan-2-yl, thiazol-2-in-2-yl, 3,4,5,6-tetrahydropyridin-2-yl, 4H-1,3-thiazin-2-yl, 4H-3,1-benzothiazin-2-yl, 1,1-dioxo-2,3,4,5-tetrahydrothien-2yl, 2H-1,4-benzothiazin-3-yl, 2H-1,4-benzoxazin-3-yl, 1,3-dihydrooxazin-2-yl, N-morpholinyl or dihydroquinazolinyl, in particular 2-oxazolidinyl, 1,3-dihydrooxazin-2-yl, oxazol-2-in-2-yl, oxiranyl, 1,3-dithian-2-yl, 2-tetrahydropyranyl or 1,3-dioxolan-2-yl, preferably cyclopropyl, 1,3-dioxolan-2-yl or 1,3-dithiolan-2-yl, in particular cyclopropyl, where the cyclic structure may additionally carry from one to three of the following radicals: halogen as stated above, preferably fluorine or chlorine, or $C_1$–$C_4$-alkyl as stated above in general, preferably $C_1$- or $C_2$-alkyl;

$R^3$ is hydrogen; nitro; cyano;

halogen, such as fluorine, chlorine, bromine or iodine, preferably fluorine, chlorine or bromine, in particular fluorine or chlorine;

branched or straight-chain $C_1$–$C_4$-alkyl, such as methyl, ethyl, propyl, 1-methylethyl, butyl, 1-methylpropyl, 2-methylpropyl or 1,1-dimethylethyl, preferably methyl, ethyl, 1-methylethyl or 1,1-dimethylethyl, in particular methyl or 1,1-dimethylethyl;

$C_1$–$C_4$-alkoxy, such as methoxy, ethoxy, propoxy, 1-methylethoxy, butoxy, 1-methylpropoxy, 2-methylpropoxy or 1,1-dimethylethoxy, preferably methoxy, ethoxy or 1,1-dimethylethoxy, in particular methoxy;

partially or completely halogenated $C_1$–$C_4$-alkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, preferably dichloromethyl, trichloromethyl or trifluoromethyl, in particular trifluoromethyl;

partially or completely halogenated $C_1$–$C_4$-alkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2difluoroethoxy, 2,2-dichloro-2-fluoroethoxy, 2,2,2-trichloroethoxy, 1,1,2,2-tetrafluoroethoxy or pentafluoroethoxy, preferably trichloromethoxy, difluoromethoxy, trifluoromethoxy, chlorodifluoromethoxy or 1,1,2,2-tetrafluoroethoxy, in particular difluoromethoxy or 1,1,2,2-tetrafluoroethoxy;

or $C_1$–$C_4$-alkylthio, such as methylthio, ethylthio, propylthio, 1-methylethyl, butylthio, 1-methylpropylthio, 2-methylpropylthio or 1,1-dimethylethylthio, preferably methylthio or ethylthio, in particular methylthio; or, where n is 2, 3 or 4, 1,3-butadiene-1,4-diyl which may carry from one to four halogen atoms, such as fluorine, chlorine, bromine or iodine, preferably fluorine or chlorine, in particular chlorine, and/or one or two of the following groups:

nitro, cyano, straight-chain or branched $C_1$–$C_4$-alkyl, such as methyl, ethyl, propyl, 1-methylethyl, butyl, 1-methylpropyl, 2-methylpropyl or 1,1-dimethylethyl, preferably methyl or ethyl, in particular methyl, $C_1$–$C_4$-alkoxy, such as methoxy, ethoxy, propoxy, 1-methylethoxy, butyloxy, 1-methylpropoxy, 2-methylpropoxy or 1,1-dimethylethoxy, preferably methoxy or ethoxy, in particular methoxy, partially or completely halogenated $C_1$–$C_4$-alkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, preferably trifluoromethyl;

partially or completely halogenated $C_1$–$C_4$-alkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy, preferably difluoromethoxy or 1,1,2,2-tetrafluoroethoxy, in particular difluoromethoxy, or $C_1$–$C_4$-alkylthio, such as methylthio, ethylthio, propylthio, 1-methylethyl, butylthio, 1-methylpropylthio, 2-methylpropylthio or 1,1-dimethylethylthio, preferably methylthio;

$R^4$ is hydrogen; CHO; alkyl, alkenyl or alkynyl, each of which is unsubstituted or substituted;

an unsubstituted or substituted saturated or mono- or diunsaturated 3-membered to 6-membered cyclic structure which, in addition to carbon atoms, may contain from one to three hetero atoms selected from the group consisting of oxygen, sulfur and nitrogen as ring members;

$R'_3P—$, $R'_2P(=O)$ or $R''_2P(=O)$, where $R'$ is phenyl and $R''$ is $C_1$–$C_4$-alkoxy as stated above, in particular methoxy or ethoxy;

or an unsubstituted or substituted mononuclear to trinuclear aromatic system which, in addition to carbon atoms, may contain from one to four nitrogen atoms or from one to three hetero atoms selected from the group consisting of two nitrogen atoms and one oxygen or sulfur atom;

W is a direct bond, oxygen, sulfur or nitrogen which may carry hydrogen, $C_1$–$C_4$-alkyl, such as methyl, ethyl, propyl, 1-methylethyl, butyl, 1-methylpropyl, 2-methylpropyl or 1,1-dimethylethyl, preferably methyl, ethyl or propyl, in particular methyl or ethyl, or $C_1$–$C_4$-alkoxy, such as methoxy, ethoxy, propoxy, 1-methylethoxy, butoxy, 1-methylpropoxy, 2-methylpropoxy or 1,1-dimethylethoxy, preferably methoxy, ethoxy or propoxy, in particular methoxy;

A is —O—; —C(=O)—; —O—C(=O)—; —C(=O)—O—; —S—; —S(=O)—; —O—S(=O)—; —S(=O)—O—; —S(=O)$_2$—; —O—S(=O)$_2$—; —S(=O)$_2$—O—; $NR^5$—; —$NR^5$—; —$NR^5$—C(=O)—; —C(=O)—$NR^5$—; —$NR^5$—C(=O)—$NR^6$; —S(=O)—$NR^5$—; —$NR^5$—S(=O)$_2$—; —S(=O)$_2$—$NR^5$—; —N=N—; —$NR^5$—$NR^6$—; —$NR^5$—$NR^6$—C(=O)—; —C(=O)—$NR^5$—$NR^6$—; —$NR^5$—$NR^6$—S(=O)$_2$—; —S(=O)$_2$—$NR^5$—$NR^6$—; —O—($C_2$-$C_4$-alkylene)—O—; —C(=O)—($C_2$-$C_4$alkylene)—O—; —O—C(=O)—($C_2$-$C_4$-alkylene)—O—; —C(=O)—O—($C_2$-$C_4$-alkylene)—O—; —S—($C_2$-$C_4$-alkylene)—O—; —S(=O)$_2$—($C_2$-$C_4$-alkylene)—O—; —O—S(=O)$_2$—($C_2$-$C_4$-alkylene)—O—; —S(=O)$_2$—O—($C_2$-$C_4$-alkylene)—O—; —$NR^5$—($C_2$-$C_4$-alkylene)—O—; —O—$NR^5$—($C_2$-$C_4$-alkylene)—O—; —$NR^5$—C(=O)—($C_2$-$C_4$-alkylene)—O—; —C(=O)—$NR^5$—($C_2$-$C_4$-alkylene)—O—; —$NR^4$—C(=O)—$NR^6$—($C_2$-$C_4$-alkylene)—O—; —$NR^5$—$NR^6$—($C_2$-$C_4$-alkylene)—O—; —$NR^5$—$NR^6$—C(=O)—($C_2$-$C_4$-alkylene)—O—; —C(=O)—$NR^5$—$NR^6$—($C_2$-$C_4$-alkylene)—O—; in the groups stated above for A, $R^5$ and $R^6$ independently of one another are each hydrogen, straight-chain or branched $C_1$-$C_4$-alkyl as stated above in general, preferably methyl, ethyl or 1-methylethyl, or $C_1$-$C_4$-alkoxy as stated above in general, preferably methoxy, ethoxy or 1-methylethoxy, and $C_2$-$C_4$-alkylene is ethylene, 1-methylethylene, 2-methylethylene, 1,2-dimethylethylene, propylene or butylene;

A may furthermore be $C_1$-$C_6$-alkylene, such as methylene, ethylene, 1-methylmethylene, propylene, 1-methylethylene, 2-methylethylene, butylene, 1-methylpropylene, 2-methylpropylene, 3-methylpropylene, 1-ethylethylene, 2-ethylethylene, 1,1-dimethylethylene, 1,2-dimethylethylene, 2,2-dimethylethylene, pentylene, 1-methylbutylene, 2-methylbutylene, 3-methylbutylene, 4-methylbutylene, 1,1-dimethylpropylene, 1,2-dimethylpropylene, 1,3-dimethylpropylene, 2,2-dimethylpropylene, 2,3-dimethylpropylene, 1-ethylpropylene, 2-ethylpropylene, 3-ethylpropylene, 1-ethyl-1-methylethylene, 1-ethyl-2-methylethylene, 2-ethyl-1-methylethylene, 2-ethyl-2-methylethylene, 1,1,2-trimethylethylene, 1,2,2-trimethylethylene, hexylene, 1-methylpentylene, 2-methylpentylene, 3-methylpentylene, 4-methylpentylene, 5-methylpentylene, 1,1-dimethylbutylene, 1,2-dimethylbutylene, 1,3-dimethylbutylene, 1,4-dimethylbutylene, 2,2-dimethylbutylene, 2,3-dimethylbutylene, 2,4-dimethylbutylene, 3,3-dimethylbutylene, 3,4-dimethylbutylene, 1-ethylbutylene, 2-ethylbutylene, 3-ethylbutylene, 4-ethylbutylene, 1,1,2-trimethylpropylene, 1,1,3-trimethylpropylene, 1,2,2-trimethylpropylene, 1,2,3-trimethylpropylene, 2,2,3-trimethylpropylene, 2,3,3-trimethylpropylene, 1,3,3-trimethylpropylene, 1-ethyl-1-methylpropylene, 2-ethyl-1-methylpropylene, 3-ethyl-1-methylpropylene, 1-ethyl-2-methylpropylene, 2-ethyl-2-methylpropylene, 3-ethyl-2-methylpropylene, 1-ethyl-3-methylpropylene, 2-ethyl-3-methylpropylene, 3-ethyl-3-methylpropylene, 1,1-diethylethylene, 1,2-diethylethylene, 2,2-diethylethylene or 1,1,2,2-tetramethylethylene, preferably methylene, ethylene, propylene, 1-methylethylene, 2-methylethylene or butylene, in particular methylene or ethylene; $C_2$-$C_6$-alkenylene, such as ethenylene, 1-propenylene, 2-propenylene, 1-methylethenylene, 2-methylethylene, 1-butenylene, 2-butenylene, 3-butenylene, 1-methyl-1-propenylene, 2-methyl-1-propenylene, 3-methyl-1-propenylene, 1-methyl-2-propenylene, 2-methyl-2-propenylene, 3-methyl-2-propenylene, 1-ethylethenylene, 2-ethylethenylene, 1,2-dimethylethenylene, 1-pentenylene, 2-pentenylene, 3-pentenylene, 4-pentenylene, 1-methyl-1-butenylene, 2-methyl-1-butenylene, 3-methyl-1-butenylene, 4-methyl-1-butenylene, 1-methyl-2-butenylene, 2-methyl-2-butenylene, 3-methyl-2-butenylene, 4-methyl-2-butenylene, 1-methyl-3-butenylene, 2-methyl-3-butenylene, 3-methyl-3-butenylene, 4-methyl-3-butenylene, 1,2-dimethyl-1-propenylene, 1,3-dimethyl-1-propenylene, 2,3-dimethyl-1-propenylene, 3,3-dimethyl-1-propenylene, 1,1-dimethyl-2-propenylene-1,2-dimethyl-2-propenylene, 1,3-dimethyl-2-propenylene, 2,3-dimethyl-2-propenylene, 1-ethyl-1-propenylene, 2-ethyl-2-propenylene, 3-ethyl-1-propenylene, 1-ethyl-2-propenylene, 2-ethyl-2-propenylene, 3-ethyl-2-propenylene, 1-ethyl-2-methylethenylene, 2-ethyl-1-methylethenylene, 1-hexenylene, 2-hexenylene, 3-hexenylene, 4-hexenylene, 5-hexenylene, 1-methyl-1-pentenylene, 2-methyl-1-pentenylene, 3-methyl-1-pentenylene, 4-methyl-1-pentenylene, 5-methyl-1-pentenylene, 1-methyl-2-pentenylene, 2-methyl-2-pentenylene, 3-methyl-2-pentenylene, 4-methyl-2-pentenylene, 5-methyl-2-pentenylene, 1-methyl-3-pentenylene, 2-methyl-3-pentenylene, 3-methyl-3-pentenylene, 4-methyl-3-pentenylene, 5-methyl-3-pentenylene, 1-methyl-4-pentenylene, 2-methyl-4-pentenylene, 3-methyl-4-pentenylene, 4-methyl-4-pentenylene, 5-methyl-4-pentenylene, 1-ethyl-1-butenylene, 2-ethyl-1-butenylene, 3-ethyl-1-butenylene, 4-ethyl-1-butenylene, 1-ethyl-2-butenylene, 2-ethyl-2-butenylene, 3-ethyl-2-butenylene, 4-ethyl-2-butenylene, 1-ethyl-3-butenylene, 2-ethyl-3-butenylene, 3-ethyl-3-butenylene, 4-ethyl-3-butenylene, 1,1-dimethyl-2-butenylene, 1,1-dimethyl-3-butenylene, 1,2-dimethyl-1-butenylene, 1,2-dimethyl-2-butenylene, 1,2-dimethyl-3-butenylene, 1,3-dimethyl-1-butenylene, 1,3-dimethyl-2-butenylene, 1,3-dimethyl-3-butenylene, 1,4-dimethyl-1-butenylene, 1,4-dimethyl-2-butenylene, 1,4-dimethyl-3-butenylene, 2,2-dimethyl-3-butenylene, 2,3-dimethyl-1-butenylene, 2,3-dimethyl-2-butenylene, 2,3-dimethyl-3-butenylene, 2,4-dimethyl-1-butenylene, 2,4-dimethyl-2-butenylene, 2,4-dimethyl-3-butenylene, 3,3-dimethyl-1-butenylene, 3,4-dimethyl-1-butenylene, 3,4-dimethyl-2-butenylene, 3-4-dimethyl-3-butenylene, 3,3-dimethyl-1-butenylene, 4,4-dimethyl-1-butenylene, 4,4-dimethyl-2-butenylene, 1-ethyl-1-butenylene, 1-ethyl-2-butenylene, 1-ethyl-3-butenylene, 2-ethyl-1-butenylene, 2-ethyl-2-butenylene, 2-ethyl-3-butenylene, 3-ethyl-1-butenylene, 3-ethyl-2-butenylene, 3-ethyl-3-butenylene, 4-ethyl-1-butenylene, 4-ethyl-2-butenylene, 4-ethyl-3-butenylene, 1,1,2-trimethyl-2-propenylene, 1,1,3-trimethyl-2-propenylene, 1,2,3-trimethyl-2-propenylene, 1,3,3-trimethyl-2-propenylene, 1-ethyl-1-methyl-2-propenylene, 1-ethyl-2-methyl-1-propenylene, 1-ethyl-2-methyl-2-propenylene, 1-ethyl-3-methyl-1-propenylene, 1-ethyl-3-methyl-2-propenylene, 2-ethyl-1-methyl-2-propenylene, 2-ethyl-3-methyl-1-propenylene, 2-ethyl-3-methyl-2-propenylene, 3-ethyl-1-methyl-1-propenylene, 3-ethyl-1-methyl-2-propenylene, 3-ethyl-2-methyl-1-propenylene, 3-ethyl-2-methyl-2-propenylene, 3-ethyl-3-methyl-1-propenylene, or 1,2-diethylethenylene, preferably ethenylene, 1-propenylene, 2,propenylene or 2-butenylene, in particular ethenylene; or $C_2$-$C_6$-alkynylene, such as ethynylene, 1-propynylene, 2-propynylene, 1-butynylene, 2-butynylene, 3-butynylene, 1-methyl-2-propynylene, 3-methyl-1-propynylene, 1-pentynylene, 2-pentynylene, 3-pentynylene, 4-pentynylene, 3-methyl-1-butynylene, 4-methyl-1-butynylene, 1-methyl-2-butynylene, 4-methyl-2-butynylene, 1-methyl-3-butynylene, 2-methyl-3-butynylene, 1,1-dimethyl-2-3,3-dimethyl-1-propynylene, 1-ethyl-2-propynylene, 3-ethyl-1-propynylene, 1-hexynylene, 2-propynylene, 2-hexynylene, 3-hexynylene, 4-hexynylene, 5-hexynylene, 3-methyl-1-pentynylene, 4-methyl-1-pentynylene, 5-methyl-1-pentynylene, 1-methyl-2-pentynylene, 4-methyl-2-pentynylene, 5-methyl-2-pentynylene, 1-methyl-3-pentynylene, 2-methyl-3-pentynylene, 5-methyl-3-pentynylene, 1-methyl-4-pentynylene, 2-methyl-4-pentynylene, 3-methyl-4-pentynylene, 3,3-dimethyl-1-butynylene, 3,4-dimethyl-1-butynylene, 4,4-dimethyl-1-butynylene, 1,1-dimethyl-2-butynylene, 1,4-dimethyl-2-butynylene, 4,4-dimethyl-2-butynylene, 1,1-dimethyl-3-butynylene, 1,2-dimethyl-3-butynylene, 2,2-dimethyl-3-butynylene, 3-dimethyl-1-butynylene, 4-ethyl-1-butynylene, 1-ethyl-2-butynylene, 4-ethyl-2-butynylene, 1-ethyl-3-butynylene, 2-ethyl-3-butynylene, 3-ethyl-3-methyl-1-propynylene or 1-ethyl-1-methyl-2-propynylene, preferably ethynylene or 2-propynylene, in particular ethynylene, where these carbon chains may carry from one to four halogen atoms, such as fluorine, chlorine, bromine or iodine, preferably fluorine or chlorine, and may be interrupted by one of the following groups or may be bonded to $R^4$ or to the phenyl ring by one of the following groups: —O—, —S—, —$NR^5$—, —C(=O)—, —C(=O)—O—, —O—C(=O)—, —S(=O)—, —S(=O)$_2$—, —S(=O)$_2$—O—, —O—S(=O)$_2$—, —$NR^5$—C(=O)—, —C(=O)—$NR^513$, —$NR^5$—C(=O)—$NR^6$—, —N=N—, —$NR^5$—$NR^6$—, —$NR^5$—$NR^6$—C(=O)— or —C(=O)—$NR^5$—$NR^6$—; where n is not 0 or $R^1$ is not $C_1$-$C_5$-alkyl or W is not oxygen when $R^4$ is unsubstituted or substituted phenyl and —$A_y$— is one of the following chains: —O—, —$CH_2$O—, —O$CH_2$—, —$CH_2CH_2$— —CH=CH—, —C≡C—, —oxy-$C_2$-$C_{12}$-alkyleneoxy, —thio-$C_2$-$C_{12}$-alkyleneoxy or methyleneoxy-$C_2$-$C_{12}$-alkyleneoxy, or where n is not 0 or $R^1$ is not $C_1$-$C_5$-alkyl or W is not oxygen when —$A_y$— is one of the following chains: —C(=O)—$CH_2$—, —O—C(=O)—$CH_2$—, —$C_1$-$C_{12}$-alkylene—C(=O)—$CH_2$—, —oxy-$C_1$-$C_{12}$-alkylene—C(=O)—$CH_2$—, —$C_1$-$C_{12}$-alkylene—C(=O)—$CH_2$—or oxy-$C_1$-$C_{12}$-alkenylene—C(=O)—$CH_2$—, where the alkylene and the alkenylene groups may carry halogen atoms or hydroxyl groups.

Because of their biological activity for controlling pests, suitable compounds I' are those in which the indices and the substituents have the following meanings:

n is as stated above in general and in particular for n;
c is as stated above in general and in particular for y;
$R^a$ is as stated above in general and in particular for $R^1$;
$R^b$ is as stated above in general and in particular for $R^2$;
$R^c$ is as stated above in general and in particular for $R^3$;
$R^d$ is as stated above in general and in particular for $R^4$;
W' is as stated above in general and in particular for W and
A' is as stated above in general and in-particular for A.

Unsubstituted or substituted alkyl radicals $R^4$ or $R^d$ in the general formulae I and I', respectively, are straight-chain or branched alkyl of not more than 12 carbon atoms, in particular $C_1$-$C_6$-alkyl as stated above, and straight-chain $C_7$-$C_{12}$-alkyl, in particular $C_1$-$C_4$-alkyl, n-decyl or n-dodecyl, where these groups may be partially or completely halogenated.

Among the partially or completely halogenated alkyl groups, preferred ones are those which carry from one to four halogen atoms as stated above, preferably fluorine, chlorine or bromine, in particular chlorine or bromine.

The stated alkyl groups $R^4$ may furthermore carry from one to four of the following radicals:
cyano; cyanato; thiocyanato; nitro; amino; hydroxyl; carboxyl;
straight-chain or branched $C_1$-$c_6$-alkoxy, such as methoxy, ethoxy, n-propoxy, 1-methylethoxy, n-butoxy, 1-methylpropoxy, 2-methylpropoxy, 1,1-dimethylpropoxy, n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexyloxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,1,2-trimethylpropoxy, 1-ethyl-1-methylpropoxy or 1-ethyl-2-methylpropoxy, preferably $C_1$-$C_4$-alkoxy, in particular $C_1$- or $C_2$-alkoxy;
straight-chain or branched $C_1$-$C_6$-alkylthio, such as methylthio, ethylthio, n-propylthio, 1-methylethylthio, n-butylthio, 1-methylpropylthio, 2-methylpropylthio, 1,1-dimethylethylthio, n-pentylthio, 1-methylbutylthio, 2methylbutylthio, 3-methylbutylthio, 2,2-dimethylpropylthio, 1-ethylpropylthio, n-hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio, preferably $C_1$- or $C_2$-alkylthio, in particular methylthio;

$C_3$-$C_6$-cycloalkyl, such as cyclopropyl, cyclobutyl, cyclopentyl, cyclohexyl, cycloheptyl or cyclooctyl, preferably cyclopropyl, cyclopentyl or cyclohexyl, in particular cyclopropyl;

straight-chain or branched $C_1$-$C_6$-alkylamino, such as methylamino, ethylamino, propylamino, 1-methylethylamino, butylamino, 1-methylpropylamino, 2-methylpropylamino, 1,1-dimethylethylamino, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino, 3,3-dimethylbutylamino, 1-ethylbutylamino, 2-ethylbutylamino, 1,1,2-trimethylpropylamino, 1,2,2-trimethylpropylamino, 1-ethyl-1-methylpropylamino or 1-ethyl-2-methylpropylamino, preferably methylamino or ethylamino, in particular methylamino; straight-chain or branched di-($C_1$-$C_6$)-alkylamino, in particular di-($C_1$-$C_4$)-alkylamino, such as N,N-dimethylamino, N,N-diethylamino, N,N-dipropylamino, N,N-di-(1-methylethyl)-amino, N,N-dibutylamino, N,N-di-(1-methylpropyl)-amino, N,N-di-(2-methylpropyl)-amino, N,N-di-(1,1-dimethylethyl)-amino, N-ethyl-N-methylamino, N-methyl-N-propylamino, N-methyl-N-(1-methylethyl)-amino, N-butyl-N-methylamino, N-methyl-N-(1-methylpropyl)-amino, N-methyl-N-(2-methylpropyl)-amino, N-(1,1-dimethylethyl)-N-methylamino, N-ethyl-N-propylamino, N-ethyl-N-(1-methylethyl)-amino, N-butyl-N-ethylamino, N-ethyl-N-(1-methylpropyl)-amino, N-ethyl-N-(2-methylpropyl)-amino, N-ethyl-N-(1,1-dimethylethyl)-amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)-amino, N-(1-methylethyl)-N-(2-methylpropyl)-amino, N-(1,1-dimethylethyl)-N-(1-methylethyl)-amino, N-butyl-N-(1-methylpropyl)-amino, N-butyl-N-(2-methylpropyl)-amino, N-butyl-N-(1,1-dimethylethyl)-amino, N-(1-methylpropyl)-N(2-methylpropyl)-amino, N-(1,1-dimethylethyl)-N-(1-methylpropyl)-amino or N-(1,1-dimethylethyl)-N-(2-methylpropyl)-amino, preferably dimethylamino or diethylamino, in particular dimethylamino;

straight-chain or branched $C_1$-$C_6$-alkylcarbonyl, such as methylcarbonyl, ethylcarbonyl, propylcarbonyl, 1-methylethylcarbonyl, butylcarbonyl, 1-methylpropylcarbonyl, 2-ethylpropylcarbonyl, 1,1-dimethylethylcarbonyl, pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methylpropylcarbonyl, preferably methylcarbonyl or ethylcarbonyl, in particular methylcarbonyl; straight-chain or branched $C_1$-$C_6$-alkoxycarbonyl, such as methoxycarbonyl, ethoxycarbonyl, propoxycarbonyl, 1-methylethoxycarbonyl, butoxycarbonyl, 1-methylpropoxycarbonyl, 2-methylpropoxycarbonyl, 1,1-dimethylethoxycarbonyl, pentoxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, hexyloxycarbonyl, 1,1-dimethoxypropoxycarbonyl, 1,2-dimethylpropoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl or 1-ethyl-2-methylpropoxycarbonyl, preferably $C_1$-$C_4$-alkoxycarbonyl, in particular methoxycarbonyl or 1,1-dimethylethoxycarbonyl; phenyl, phenoxy, phenylthio or phenylamino.

The abovementioned phenyl radicals may in turn carry from one to three substituents selected from the group consisting of:

halogen as stated above, preferably fluorine, chlorine or bromine, in particular fluorine or chlorine; cyano; nitro;

straight-chain or branched $C_1$-$C_4$-alkyl, such as methyl, ethyl, propyl, 1-methylethyl, butyl, 1-methylpropyl, 2-methylpropyl or 1,1-dimethylethyl, in particular methyl or 1,1-dimethylethyl;

partially or completely halogenated $C_1$-$C_4$-alkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, in particular trifluoromethyl;

$C_1$-$C_4$-alkoxy, such as methoxy, ethoxy, propoxy, 1-methylethoxy, butoxy, 1-methylpropoxy, 2-methylpropoxy or 1,1-dimethylethoxy, in particular methoxy;

and the phenyl radicals may additionally carry a number of halogen atoms as stated above, in particular fluorine or chlorine, such that the total number of their substituents is 4 or 5.

Unsubstituted or substituted alkenyl radicals $R^4$ or $R^d$ in general formulae I and I', respectively, are straight-chain or branched alkenyl of not more than 12 carbon atoms, preferably $C_2$-$C_6$-alkenyl as stated above, and n-alkenyl of 7 to 12 carbon atoms, where these groups may carry from one to three halogen atoms as stated above, preferably fluorine, chlorine or bromine, in particular fluorine or chlorine, and/or one or two of the following radicals:

cyano; cyanato; thiocyanato; nitro; carboxyl;

$C_1$–$C_6$-alkoxy as stated above in general and in particular;

$C_1$–$C_6$-alkylthio as stated above in general and in particular;

$C_3$–$C_8$-cycloalkyl as stated above in general and in particular;

$C_1$–$C_6$-alkylamino as stated above in general and in particular;

di-$C_1$–$C_6$-alkylamino as stated above in general and in particular;

$C_1$–$C_6$-alkylcarbonyl as stated above in general and in particular;

$C_1$–$C_6$-alkoxycarbonyl as stated above in general and in particular;

phenyl, phenoxy, phenylthio or phenylamino.

The abovementioned phenyl radicals may in turn carry from one to five halogen atoms as stated above, preferably fluorine, chlorine or bromine, in particular fluorine or chlorine, and/or from one to three of the following groups:

cyano; nitro;

straight-chain or branched $C_1$–$C_4$-alkyl as stated above in general and in particular;

partially or completely halogenated $C_1$–$C_4$-alkyl as stated above in general and in particular;

or $C_1$–$C_4$-alkoxy as stated above in general and in particular.

Unsubstituted or substituted alkynyl radicals $R^4$ or $R^d$ in the general formulae I and I', respectively, are straight-chain or branched alkynyl of not more than 10 carbon atoms, in particular $C_2$–$C_6$-alkynyl as stated above, and straight-chain $C_7$–$C_{10}$-alkynyl, where these groups may carry from one to three halogen atoms as stated above, preferably fluorine, chlorine or bromine, in particular fluorine or bromine, and/or from one to three of the following radicals:

cyano; cyanato, thiocyanato; nitro; carboxyl;

$C_1$–$C_6$-alkoxy as stated above in general and in particular;

$C_1$–$C_6$-alkylthio as stated above in general and in particular;

$C_3$–$C_8$-cycloalkyl as stated above in general and in particular;

$C_1$–$C_6$-alkylamino as stated above in general and in particular;

di-$C_1$–$C_6$-alkylamino as stated above in general and in particular;

$C_1$–$C_6$-alkylcarbonyl as stated above in general and in particular;

$C_1$–$C_6$-alkoxycarbonyl as stated above in general and in particular;

phenyl, phenoxy, phenylthio or phenylamino.

The abovementioned phenyl radicals may in turn carry from one to three substituents selected from a group consisting of halogen as stated above, preferably fluorine, chlorine or bromine, in particular fluorine or chlorine;

cyano; nitro;

straight-chain or branched $C_1$–$C_4$-alkyl as stated above in general and in particular;

partially or completely halogenated $C_1$–$C_4$-alkyl as stated above in general and in particular;

or $C_1$–$C_4$-alkoxy as stated above in general and in particular, and the phenyl radicals may additionally carry a number of halogen atoms as stated above, preferably fluorine, chlorine or bromine, in particular fluorine or chlorine, such that the number of their substituents is 4 or 5.

Unsubstituted or substituted, saturated or mono- or diunsaturated cyclic structures $R^4$ or $R^d$ of the general formulae I and I', respectively, which in addition to carbon atoms may contain from one to three hetero atoms as ring members, selected from a group consisting of two nitrogen atoms and one oxygen or sulfur atom, include saturated or mono- or diunsaturated, non-aromatic ring systems of not more than eight ring members, in particular $C_3$–$C_8$-cycloalkyl as stated above in general and in particular;

$C_5$–$C_8$-cycloalkenyl, such as cyclopent-1-enyl, cyclopent-2-enyl, cylcopent-3-enyl, cyclohex-1-enyl, cyclohex-2-enyl, cyclohex-3-enyl, cyclohept-1-enyl, cyclohept-2-enyl, cyclohept-3-enyl, cyclohept-4-enyl, cyclooct-1-enyl, cyclooct-2-enyl, cyclooct-3-enyl or cyclooct-4-enyl, preferably cyclopent-1-enyl, cyclopent-3-enyl or cyclohex-1-enyl, in particular cyclopent-3-enyl; $C_5$–$C_8$-cycloalkadienyl, such as cyclopenta-1,3-dien-1-yl, cylcopenta-1,3-dien-2-yl, cyclopent-1,3-dien-5-yl, cyclohexa-1,3-dien-1-yl, cylcohexa-1,3-dien-2-yl, cyclohexa-1,3-dien-5-yl, cyclohexa-1,4-dien-1-yl, cyclohexa-1,4-dien-3-yl, cyclhepta-1,3-dien-1-yl, cyclohepta-1,3-dien-2-yl, cyclohepta-1,3-dien-5-yl, cyclohepta-1,3-dien-6-yl, cylcohepta-1,4-dien-1-yl, cyclohepta-1,4-dien-2-yl, cyclohepta-1,4-dien-3-yl, cyclohepta-1,4-dien-6-yl, cyclooca-1,3-dien-1-yl, cyclooca-1,3-dien-2-yl, cyclooca-1,3-dien-5-yl, cyclooca-1,3-dien-6-yl, cyclooca-1,4-dien-1-yl, cyclooca-1,4-dien-2-yl, cyclooca-1,4-dien-3-yl, cyclooca-1,4-dien-6-yl, cyclooca-1,4-dien-7-yl, cyclooca-1,4-dien-1-yl or cyclooca-1,4-dien-3-yl, preferably cyclopenta-1,3-dien-5-yl;

3-membered to 6-membered, saturated or partially unsaturated heterocyclic structures containing from one to three nitrogen atoms or from one to three hetero atoms, selected from a group consisting of two nitrogen, two oxygen and two sulfur atoms or from the group consisting of three oxygen and sulfur atoms, Such as epoxidyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-2-yl, 1,2,4-triazolidin-3-yl, 1,3,4-oxadiazolidin-2-yl, 1,3,4-thiadiazolidin-1-yl, 1,3,4-triazolidin-2-yl, 2,3-dihydrofur-2-yl, 2,3-dihydrofur-3-yl, 2,5-dihydrofur-2-yl, 2,5-dihydrofur-3-yl, 2,3-dihydrothien-2-yl, 2,3-dihydrothien-3-yl, 2,5-dihydrothien-2-yl, 2,5-dihydrothien-3-yl, 2,3-pyrrolin-2-yl 2,3-pyrrolin-3-yl, 2,4-pyrrolin-2-yl, 2,5-pyrrolin-3-yl, 2,3-isoxazolin-3-yl, 3,4-isoxazolin-3-yl, 4,5-isoxazolin-3-yl, 2,3-isoxazolin-4-yl, 3,4-isoxazolin-4-yl, 4,5-isoxazolin-4-yl, 2,3-isoxazolin-5-yl, 3,4-isoxazolin-5-yl, 4,5-isoxazolin-5-yl, 2,3-isothiazolin-3-yl, 3,4-isothiazolin-3-yl, 4,5-isothiazolin-3-yl, 2,3-isothiazolin-4-yl, 3,4-isothiazolin-4-yl, 4,5-isothiazolin-4-yl, 2,3-isothiazolin-5-yl, 3,4-isothiazolin-5-yl, 4,5-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 2-piperidinyl, 3-piperidinyl, 4-piperidinyl, 3-tetrahydropyridazinyl, 4-tetrahydropyridazinyl, 2-tetrahydropyrimidinyl, 4-tetahydropyrimidinyl, 5-tetrahydropyrimidinyl, 2-tetrahydropyrazinyl, 1,3,5-tetrahydrotriazin-2-yl or 1,2,4-tetrahydrotriazin-3-yl, 1,3-dihydrooxazin-2-yl, 1,3-dithian-2-yl, oxazol-2-in-2-yl, 2-tetrahydropyranyl, 1,3-dioxolan-2-yl, thiazol-2-in-2-yl, 3,4,5,6-tetrahydropyridin-2-yl, 4H-1,3-thiazin-2-yl, 4H-3,1-benzothiazin-2-yl, 1,1-dioxo-2,3,4,5-tetrahydrothien-2-yl, 2H-1,4-benzothiazin-3-yl, 2H-1,4-benzooxazin-3-yl, 1,3-dihydrooxazin-2-yl, N-morpholinyl or dihydroquinazolinyl, in particular 2-oxazolidinyl, 1,3-dihydrooxazin-2-yl, oxazol-2-in-2-yl, oxiranyl, 1,3-dithian-2-yl, 2-tetrahydropyranyl or 1,3-dioxolan-2-yl, where these groups may furthermore carry from one to three radicals selected from a group consisting of halogen as stated above, in particular fluorine, chlorine or bromine, in particular fluorine or chlorine, cyano; nitro;

straight-chain or branched $C_1$-$C_6$-alkyl as stated above in general and in particular;

$C_1$-$C_6$-alkoxy as stated above in general and in particular;

$C_1$-$C_6$-alkylthio as stated above general and in particular;

$C_1$-$C_6$-alkylthio as stated above general and in particular;

$C_3$-$C_8$-cycloalkyl as stated above general and in particular;

$C_1$-$C_6$-alkylamino as stated above general and in particular;

di-($C_1$-$C_6$)-alkoxy as stated above in general and in particular;

phenyl, phenoxy, phenylthio or phenylamino, and where the heterocyclic structures additionally contain a number of halogen atoms as stated above, preferably fluorine, chlorine or bromine, in particular fluorine or or chlorine, such that the total number of radicals is 4 or 5.

The abovementioned phenyl, phenoxy, phenylthio and phenylamino radicals may in turn carry from one to five halogen atoms as stated above, preferably fluorine, chlorine or bromine, in particular fluorine or chlorine, and/or from one to three of the following groups: cyano; nitro;

$C_1$-$C_4$-alkyl as stated above in general and in particular; partially or completely halogenated $C_1$-$C_4$-alkyl as stated above in general and in particular;

$C_1$-$C_4$-alkoxy as stated above in general and in particular; or $C_1$-$C_4$-alkylthio as stated above in general and in particular.

Unsubstituted or substituted mononuclear to trinuclear aromatic systems $R^4$ or $R^d$ in the general formulae I and I', respectively, which in addition to carbon atoms may contain from one to four nitrogen atoms or one or two nitrogen atoms and one oxygen or sulfur atom, include aromatic and heteroaromatic ring systems having not more than 14 ring members, in particular phenyl, 1-naphthyl, 2-naphthyl, 1-anthranyl, 2-anthranyl, 9-anthranyl, 9-fluorenyl or 2-fluorenyl, in particular phenyl, heteroaromatic structures having a five-membered ring and containing from one to three hetero atoms selected from a group consisting of three nitrogen atoms and one oxygen or sulfur atom, such as 2-furyl, 3-furyl, 2-thienyl, 3-thienyl, 1-pyrrolyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 1-pyrazolyl, 3-pyrazolyl, 4pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-triazol-2-yl, 1,3,4-oxadiazol-2-yl, 1,3,4-thiadiazol-2-yl, 1,3,4-triazol-2-yl, 1,2,3-oxadiazol-4-yl, 1,2,3-oxadiazol-5-yl, 1,2,5-triazol-3-yl, 1,2,3-triazol-4-yl, 1,2,3-triazol-5-yl, 1,2,3-triazol-4-yl, 5-tetrazolyl, 1,2,3,4-thiatriazol-5-yl, or 1,2,3,4-oxatriazol-5-yl, in particular 3-pyrrolyl, 3-isoxazolyl, 5-isoxazolyl, 4-oxazolyl, 4-thiazolyl, 4-pyrazolyl, 5-pyrazolyl- 1,3,4-oxadizol-2-yl or 1,3,4-thiadiazol-2-yl, heteroaromatic structures having a six-membered ring and containing from one to four nitrogen atoms as hetero atoms, such as 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl or 1,2,4,5-tetrazin-3-yl, in particular 2-pyridinyl, 3-pyridinyl, 2-pyrimidinyl, 4-pyrimidinyl or 1,3,5-triazin-2-yl, and furthermore other heteroaromatic systems, such as 1-indolyl, 2-indolyl, 3-indolyl, 1-indazolyl, 1H-indazol-3-yl, 1-isoquinolyl, 3-isoquinolyl, 4-isoquinolyl, 2-quinoxalyl, 2-benzothienyl, 3-benzothienyl, 1-benzotriazolyl, 1,2-benzisoxazol, 3-yl, 1,2-benzisothiazol-3-yl, benzopyrazol-3-yl, isoindol-2-yl, thiazolpyrimidin- 2-yl, benzimidazol-2-yl, benzoxazol-2-yl, imidazopyrimidin-2-yl, oxazolopyrimidin-2-yl, benzofuran-2-yl, benzofuran-3-yl, quinol-2-yl, quninol-3-yl, quinol-4-yl, quinazolin-2-yl, quinazolin-4-yl, benzothiazol-2-yl, cinnolin-3-yl, cinnolin-4-yl, 1,5-naphthylidin-2-yl, 1,8-naphthylidin-2-yl, phthalazin-1-yl, pteridin-2-yl, pteridin-4-yl, isobenzofuran-1-yl or 7-purinyl, in particular 2-benzimidazolyl, 2-benzoxazolyl or 2-benzothiazolyl, where these groups may carry from one to five halogen atoms as stated above, preferably fluorine, chlorine or bromine, in particular fluorine or chlorine, and/or from one to four of the following radicals: cyano; cyanato; thiocyanato; nitro; amino; hydroxyl; carboxyl;

$C_1$-$C_6$-alkyl as stated above in general and in particular;

partially or completely halogenated C-$C_4$-alkyl as stated above in general and in particular;

$C_1$-$C_6$-alkoxy as stated above in general and in particular;

partially or completely halogenated $C_1$-$C_4$-alkoxy as stated above in general and in particular;

$C_1$-$C_6$-alkylthio as stated above in general and in particular;

$C_5$-$C_{15}$-alkenyloxy, such as 3-methylbut-2-en-1-yloxy, 3,7-dimethylocta-2,6-dien-1-yloxy or 3,7,11-trimethyldodeca-2,6,10-trien-1-yloxy;

$C_3$-$C_8$-cycloalkyl as stated above in general and in particular;

$C_5$-$C_6$-cycloalkenyl, such as cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl, cyclohept-4-enyl, cyclooct-1-enyl, cyclooct-2-enyl, cyclooct-3-enyl or cyclooct-4-enyl;

$C_3$-$C_8$-cylcoalkoxy, such as cyclopropoxy, cyclobutoxy, cyclopentoxy, cyclohexyloxy, cycloheptyloxy or cyclooctyloxy;

$C_1$-$C_6$-alkylamino as stated above in general and in particular;

di-$C_1$–$C_6$-alkylamino as stated above in general and in particular;

$C_1$–$C_6$-alkylcarbonyl as stated above in general, preferably $C_1$–$C_4$-alkylcarbonyl;

$C_1$–$C_6$-alkoxycarbonyl as stated above in general, preferably $C_1$–$C_4$-alkoxycarbonyl;

$C_1$–$C_6$-alkylaminocarbonyl as stated above in general and in particular;

di-($C_1$–$C_6$)-alkylaminocarbonyl, in particular di-($C_1$–$C_4$)-alkylaminocarbonyl, such as N,N-dimethylaminocarbonyl, N,N-diethylaminocarbonyl, N,N-dipropylaminocarbonyl, N,N-di-(1-methylethyl)-aminocarbonyl, N,N-dibutylaminocarbonyl, N,N-di-(1-methylpropyl)-aminocarbonyl, N,N-di-(2-methylpropyl)-aminocarbonyl, N,N-di-(1,1-dimethylethyl)-aminocarbonyl, N-ethyl-N-methylaminocarbonyl, N-methyl-N-propylaminocarbonyl, N-methyl-N-(1-methylethyl)-aminocarbonyl, N-butyl-N-methylaminocarbonyl, N-methyl-N-(1-methylpropyl)-aminocarbonyl, N-methyl-N-(2-methylpropyl)-aminocarbonyl, N-(1,1-dimethylethyl)-N-methylaminocarbonyl, N-ethyl-N-propylaminocarbonyl, N-ethyl-N-(1-methylethyl)-aminocarbonyl, N-butyl-N-ethylaminocarbonyl, N-ethyl-N-(1-methylpropyl)-aminocarbonyl, N-ethyl-N-(2-methylpropyl)-aminocarbonyl, N-ethyl-N-(1,1-dimethylethyl)-aminocarbonyl, N-(1-methylethyl)-N-propylaminocarbonyl, N-butyl-N-propylaminocarbonyl, N-(1-methylpropyl)-N-propylaminocarbonyl, N-(2-methylpropyl)-N-propylaminocarbonyl, N-(1,1-dimethylethyl)-N-propylaminocarbonyl, N-butyl-N-(1-methylethyl)aminocarbonyl, N-(1-methylethyl)-N-(1-methylpropyl)-aminocarbonyl, N-(1-methylethyl)-N-(2-methylpropyl)-aminocarbonyl, N-(1,1-dimethylethyl)-N-(1-methyethyl)-aminocarbonyl, N-butyl-N-(1-methylpropyl)-aminocarbonyl, N-butyl-N-(2-methylpropyl)-aminocarbonyl, N-butyl-N-(1,1-dimethylethyl)-aminocarbonyl, N-(1-methylpropyl)-N-(2-methylpropyl)-aminocarbonyl, N-(1,1-dimethylethyl)-N-(1-methylpropyl)-aminocarbonyl or N-(1,1-dimethylethyl)-N-( 2-methylpropyl)-aminocarbonyl, preferably di-($C_1$–$C_4$)-alkylaminocarbonyl, in particular di-($C_1$–$C_2$)-alkylaminocarbonyl;

$C_1$–$C_6$-alkylcarboxyl, such as methylcarboxyl, ethylcarboxyl, propylcarboxyl, 1-methylethylcarboxyl, butylcarboxyl, 1-methylpropylcarboxyl, 2-methylpropylcarboxyl, 1,1-dimethylethylcarboxyl, pentylcarboxyl, 1-methylbutylcarboxyl, 2-methylbutylcarboxyl, 3-methylbutylcarboxyl, 1,1-dimethylpropylcarboxyl, 1,2-dimethylpropylcarboxyl, 2,2-dimethylpropylcarboxyl, 1-ethylpropylcarboxyl, hexylcarboxyl, 1-methylpentylcarboxyl, 2-methylpentylcarboxyl, 3-methylpentylcarboxyl, 4-methylpentylcarboxyl, 1,1-dimethylbutylcarboxyl, 1,2-dimethylbutylcarboxyl, 1,3-dimethylbutylcarboxyl, 2,2-dimethylbutylcarboxyl, 2,3-dimethylbutylcarboxyl, 3,3-dimethylbutylcarboxyl, 1-ethylbutylcarboxyl, 2-ethylbutylcarboxyl, 1,1,2-trimethylpropylcarboxyl, 1,2,2-trimethylpropylcarboxyl, 1-ethyl-1-methylpropylcarboxyl or 1-ethyl-2-methylpropylcarboxyl, preferably $C_1$–$C_4$-alkylcarboxyl, in particular $C_1$- or $C_2$-alkylcarboxyl;

methyl or ethyl which is substituted in the 1- or 2-position by $C_1$–$C_4$-alkoxy as stated above or by $C_1$–$C_4$-alkylthio as stated above;

phenyl, phenoxy, phenylthio, phenylamino, $C_1$–$C_4$-alkyl as stated above, preferably methyl or ethyl, which is substituted by phenyl, phenoxy, phenylthio or phenylamino;

$C_1$–$C_4$-alkoxy as stated above, preferably methoxy or ethoxy, which is substituted by phenyl, phenoxy, phenylthio or phenylamino.

The abovementioned phenyl radicals may in turn carry from one to three substituents selected from the group consisting of halogen as stated above in general and in particular, cyano; nitro;

$C_1$–$C_4$-alkyl as stated above in general and in particular;

partially or completely halogenated $C_1$–$C_4$-alkyl as stated above in general and in particular;

$C_1$–$C_4$-alkoxy as stated above in general and in particular;

partially or completely halogenated $C_1$–$C_4$-alkoxy as stated above in general and in particular;

or $C_1$–$C_4$-alkylthio as stated above in general and in particular, and the abovementioned phenyl radicals may additionally carry a number of halogen atoms, as stated above in general and in particular, such that the total number of radicals is 4 or 5.

The abovementioned aromatic or heteroaromatic systems $R^4$ or $R^d$ in the general formulae I and I', respectively, may, in addition to the abovementioned radicals, also carry a radical of the structure —$C(R^7)$=$NOR^8$, where $R^7$ is hydrogen;

straight-chain or branched $C_1$–$C_6$-alkyl as stated above in general and in particular;

aryl, such as phenyl, 1-naphthyl, 2-naphthyl, 1-anthranyl or 2-anthranyl, preferably phenyl, where the aromatic radicals may furthermore carry from one to three substituents selected from the group consisting of halogen as stated above in general and in particular, cyano; cyanato; thiocyanato; nitro; amino; hydroxyl; carboxyl;

straight-chain or branched $C_1$–$C_4$-alkyl as stated above in general and in particular;

partially or completely halogenated $C_1$–$C_4$-alkyl as stated above in general and in particular, $C_1$–$C_4$-alkoxy as stated above in general and in particular;

partially or completely halogenated $C_1$–$C_4$-alkoxy as stated above in general and in particular;

$C_1$–$C_4$-alkylthio as stated above in general and in particular, or partially or completely halogenated $C_1$–$C_4$-alkylthio as stated above in general and in particular, and where the aromatic radicals may additionally contain a number of halogen atoms, as stated above in general and in particular, such that the total number of their substituents is 4 or 5.

$R^8$ is straight-chain or branched $C_1$–$C_6$-alkyl as stated above in general and in particular, $C_2$–$C_6$-alkenyl or $C_2$–$C_6$-alkynyl as stated above in general, where these groups may furthermore carry from one to three of the substituents selected from the group consisting of halogen as stated above in general and in particular, cyano; nitro;

straight-chain or branched $C_1$–$C_6$-alkoxy as stated above in general and in particular;

partially or completely halogenated $C_1$–$C_6$-alkyl as stated above in general and in particular;

$C_1$–$C_6$-alkylthio as stated above in general and in particular;

partially or completely halogenated $C_1$–$C_6$-alkylthio as stated above in general and in particular;

$C_1$–$C_6$-cycloalkyl as stated above in general and in particular, 5-membered or 6-membered aromatic or heteroaromatic systems as stated above, preferably phenyl, where the cyclic radicals in turn may carry from one to five halogen atoms as stated above in general and in particular, and/or from one to three of the following groups:

cyano; nitro;

straight-chain or branched $C_1$–$C_4$-alkyl as stated above in general and in particular;

partially or completely halogenated $C_1$–$C_4$-alkyl as stated above in general and in particular, $C_1$–$C_4$-alkoxy as stated above in general and in particular; partially or completely halogenated $C_1$–$C_4$-alkoxy as stated above in general and in particular;

or $C_1$–$C_4$-alkylthio as stated above in general and in particular, and where the alkyl, alkenyl and alkynyl groups $R^8$ may carry a number of halogen atoms, as stated above in general and in particular, such that the total number of the substituents is 4 or 5.

Because of their biological activity against pests, particularly preferred compounds I' are those in which the substructure —$A'_c$— is one of the following groups:

one of the following groups: fluorine, chlorine, methyl, 1,1-dimethylethyl, methoxy, nitro or trifluoromethyl.

Because of the biological activity against pests, preferred compounds I' are those in which the substructure $R^1$—$W'$— is one of the groups B*.1, B*.3 or B*.5 and $R^b$ is one of the groups C*.1, C*.2, C*.4, C*.8, C*.9, C*.10 or C*.11.

Other preferred compounds of the formula I' are those in which the substructure $R^a$—$W'$— is one of the groups B*.1, B*.3, $R^b$ is one of the groups C*.1, C*.2, C*.4, C*.8, C*.10 or C*.11 and $A'_c$ is one of the groups A*.7, A*.8, A*.11, A*.13 or A*.14.

Because of their biological activity against pests, other preferred compounds I' are those in which $R^d$ is one of the unsubstituted or substituted mono- to trinuclear aromatic or heteroaromatic structures defined above.

Because of their biological activity against harmful fungi, particularly preferred compounds I are those in which the substructure —$A_y$— is one of the following groups:

| A*.1 | —O— | A*.2 | —S— | A*.3 | —NH— |
|---|---|---|---|---|---|
| A*.4 | —CH$_2$O— | A*.5 | —CH$_2$S— | A*.6 | —CH$_2$NH— |
| A*.7 | —OCH$_2$— | A*.8 | —SCH$_2$— | A*.9 | —NHCH$_2$— |
| A*.10 | —CH$_2$CH$_2$— | A*.11 | —CH=CH— | A*.12 | —C≡C— |
| A*.17 | —O—CH=CH— | A*.18 | —S—CH=CH— | A*.19 | —OCH$_2$CH=CH— |
| A*.20 | —S—CH$_2$CH=CH— | A*.21 | —CH$_2$CH=CH— | | |
| A*.22 | —CH=CH—O— | A*.23 | —CH=CH—S— | | |

Because of their biological activity against harmful fungi, other preferred compounds I are those in which n is 0 or 1.

Because of their biological activity against harmful fungi, further preferred compounds I are those in which the substructure $R^1$—W— is one of the following groups:

| A*.1 | —O— | A*.2 | —S— | A*.3 | —NH— |
|---|---|---|---|---|---|
| A*.4 | —CH$_2$O— | A*.5 | —CH$_2$S— | A*.6 | —CH$_2$NH— |
| A*.7 | —OCH$_2$— | A*.8 | —SCH$_2$— | A*.9 | —NHCH$_2$— |
| A*.10 | —CH$_2$CH$_2$— | A*.11 | —CH=CH— | A*.12 | —C≡C— |
| A*.13 | —C(=O)OCH$_2$— | A*.14 | —OCH$_2$CH$_2$O— | A*.15 | —NHCH$_2$CH$_2$O |
| A*.16 | —C(=O)NHCH$_2$CH$_2$O— | A*.17 | —O—CH=CH— | A*.18 | —S—CH=CH— |
| A*.19 | —O—CH$_2$CH=CH— | A*.20 | —S—CH$_2$CH=CH— | A*.21 | —C(=O)NH—. |

Because of their biological activity against pests, other preferred compounds I' are those in which a is 0 or 1.

Because of their biological activity against pests, further suitable compounds I' are those in which the substructure $R^1$—$W'$— is one of the following groups:

| B*.1 | OCH$_3$ | B*.2 | OCH$_2$CH$_3$ | B*.3 | NHCH$_3$ |
|---|---|---|---|---|---|
| B*.4 | NHCH$_2$CH$_3$ | B*.5 | CH$_3$ | B*.6 | CH$_2$CH$_3$ |
| B*.7 | CH(CH$_3$)$_2$ | | | | |

Because of their biological activity against harmful fungi, other preferred compounds I are those in which $R^2$ is one of the following groups:

| C*.1 | CH$_3$ | C*.2 | CH$_2$CH$_3$ | C*.3 | (CH$_2$)$_2$CH$_3$ |
|---|---|---|---|---|---|
| C*.4 | CH$_2$Cl | C*.5 | CH$_2$Br | C*.6 | CH$_2$CN |
| C*.7 | CH(CH$_3$)$_2$ | C*.8 | CH$_2$OCH$_3$ | C*.9 | CH$_2$SCH$_3$ |
| C*.13 | CF$_3$ | | | | |

Because of their biological activity against harmful fungi, further preferred compounds I are those in which $R^3$ is one of the following groups:

hydrogen, fluorine, chlorine, bromine, methyl, 1-methylethyl, 1,1-dimethylethyl, cyano, nitro, methoxy or trifluoromethyl.

Because of their biological activity against pests, other preferred compounds I' are those in which $R^b$ is one of the following groups:

| C*.1 | CH$_3$ | C*.2 | CH$_2$CH$_3$ | C*.3 | (CH$_2$)$_2$CH$_3$ |
|---|---|---|---|---|---|
| C*.4 | CH$_2$Cl | C*.5 | CH$_2$Br | C*.6 | CH$_2$CN |
| C*.7 | CH(CH$_3$)$_2$ | C*.8 | CH$_2$OCH$_3$ | C*.9 | CH$_2$SCH$_3$ |
| C*.10 | Cyclopropyl | C*.11 | CN | C*.12 | CH=CH$_2$ |
| C*.13 | CF$_3$ | C*.14 | C≡CH | | |

Because of their biological activity against pests, further preferred compounds I' are those in which $R^c$ is Because of their biological activity against harmful fungi, other preferred compounds I are those in which $R^4$ is an unsubstituted or substituted saturated or mono- or diunsaturated cyclic structure which, in addition to carbon atoms, may contain from one to three hetero atoms selected from the group consisting of oxygen, sulfur and nitrogen as ring members, as stated above in general and in particular, or is an unsubstituted or substituted mono- or dinuclear aromatic system which, in addition to carbon atoms, may contain from one to four nitrogen atoms or one or two nitrogen atoms and/or one oxygen or sulfur atom.

Particularly preferred compounds I are also those in which the aromatic or heteroaromatic radicals $R^4$ carry one or more radicals of the substructure —C($R^7$)=NO—$R^8$ as stated above in general and in particular.

Because of the fungical activity, compounds of the general formula Ia

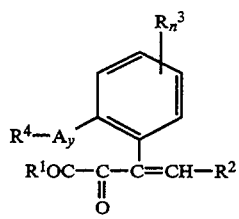

where n is 0 or 1 and —$A_y$— is one of the groups A*.1, A*.2, A*.7, A*.8, A*.10 or A*.11, are preferred.

Because of the fungical activity, other preferred compounds are those of the general formula Ib

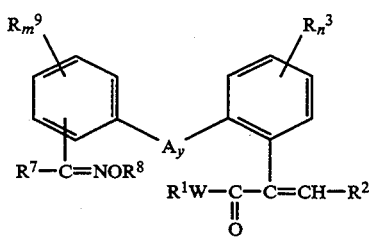

where
n is 0 or 1,
m is 0, 1 or 2, and the radicals $R^9$ may be different when m is 2,
—$A_y$— is A*.1, A*.2, A*.7 or A*.8,
$R^7$ is hydrogen;
$C_1$-$C_6$-alkyl as stated above in general and in particular; aryl, such as phenyl, 1-naphthyl, 2-naphthyl, 1-anthranyl or 2-anthranyl, preferably phenyl, where the aromatic radicals may furthermore carry from one to three substituents selected from the group consisting of halogen as stated above in general and in particular, cyano; cyanato; thiocyanato; nitro; amino; hydroxyl; carboxyl;
straight-chain or branched $C_1$-$C_4$-alkyl as stated above in general and in particular;
partially or completely halogenated $C_1$-$C_4$-alkyl as stated above in general and in particular,
$C_1$-$C_4$-alkoxy as stated above in general and in particular;
partially or completely halogenated $C_1$-$C_4$-alkoxy as stated above in general and in particular;
$C_1$-$C_4$-alkylthio as stated above in general and in particular,
or partially or completely halogenated $C_1$-$C_4$-alkylthio as stated above in general and in particular, and where the aromatic radicals may additionally carry a number of halogen atoms, as stated above in general and in particular, such that the total number of their substituents is 4 or 5,
$R^8$ is $C_1$-$C_6$-alkyl as stated above in general and in particular, $C_2$-$C_6$-alkenyl or $C_2$-$C_6$-alkynyl as stated above in general, where these groups may carry from one to five halogen atoms as stated above in general and in particular and/or from one to three of the following radicals:
cyano; nitro;
$C_1$-$C_6$-alkoxy as stated above in general and in particular; partially or completely halogenated $C_1$-$C_6$-alkoxy as stated above in general and in particular;
$C_1$-$C_6$-alkylthio as stated above in general and in particular;
$C_3$-$C_6$-cycloalkyl as stated above in general and in particular;
a 5-membered or 6-membered aromatic or heteroaromatic system as stated above, preferably phenyl, where the cyclic radicals in turn may carry from one to three substituents selected from a group consisting of halogen as stated above in general and in particular, cyano; nitro;
straight-chain or branched $C_1$-$C_4$-alkyl as stated above in general and in particular;
partially or completely halogenated $C_1$-$C_4$-alkyl as stated above in general and in particular,
$C_1$-$C_4$-alkoxy as stated above in general and in particular; partially or completely halogenated $C_1$-$C_4$-alkoxy as stated above in general and is particular;
or $C_1$-$C_4$-alkylthio as stated above in general and in particular, where the cyclic radicals in turn may additionally carry a number of halogen atoms, as stated above in general and in particular, such that the total number of their substituents is 4 or 5; and
$R^9$ is cyano, halogen, $C_1$-$C_4$-alkyl, $C_1$-$C_4$-haloalkyl or $C_1$-$C_4$-alkoxy.

Because of the fungicidal activity, other preferrred compounds are those of the general formula Ic

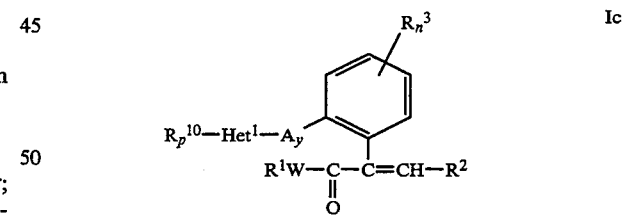

where
n is 0 or 1,
p is 0, 1, 2 or 3, and the radicals $R^{10}$ may be different when p is equal to or greater than 2, and —$A_y$— is one of the groups A*.1, A*.2, A,.7, A*.8, A*.10 or A*.11;
$Het^1$ is a 5-membered or 6-membered, saturated or partially unsaturated heterocyclic structure which may contain from one to three nitrogen atoms or one or two nitrogen atoms and one or two oxygen and/or sulfur atoms or one or two oxygen and/or sulfur atoms;
a mono- or dinuclear heteroaromatic system, which in addition to carbon atoms contains from one to four nitrogen atoms or one or two hydrogen atoms and one oxygen or sulfur atom;

$R^{10}$ is cyano, nitro, amino, hydroxyl, carboxyl, halogen, $C_1$–$C_4$-alkyl, partially or completely halogenated $C_1$–$C_4$-alkyl, $C_1$–$C_4$-alkoxy, partially or completely halogenated $C_1$–$C_4$-alkoxy, $C_1$–$C_4$-alkylthio, partially or completely halogenated $C_1$–$C_4$-alkylthio, $C_3$–$C_6$-cycloalkyl or a mononuclear aromatic or heteroaromatic ring system which is bonded directly or via an oxygen or sulfur bridge to the heterocylic structure Het$^1$ and which, in addition to carbon ring members, may contain one or two nitrogen atoms or one or two nitrogen atoms and one oxygen or sulfur atom as ring members, and where this ring system may furthermore carry from one to three radicals selected from the group consisting of halogen, cyano, nitro, $C_1$–$C_4$-alkyl, partially or completely halogenated $C_1$–$C_4$-alkyl, $C_1$–$C_4$-alkoxy and $C_1$–$C_4$-alkylthio and may additionally carry a number of halogen atoms such that the total number of the radicals is 4.

Because of the fungicidal activity, compounds of the general formula Id

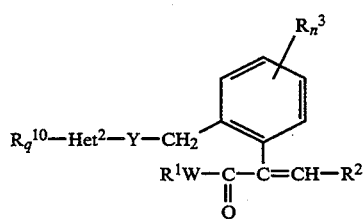

where
n is 0 or 1,
q is 0, 1 or 2 and the radicals $R^{10}$ may be different when q is 2,
Y is oxygen or sulfur and Het$^2$ is a 6-membered heteroaromatic system which, in addition to carbon ring members, contains from one to three nitrogen atoms as ring members, are also preferred.

Because of the fungicidal activity, other preferred compounds of the general formula Id are those in which $R^{10}$ is one of the following groups:
$C_1$–$C_6$-alkyl, partially or completely halogenated $C_1$–$C_4$-alkyl, $C_1$–$C_4$-alkoxy, partially or completely halogenated $C_1$–$C_4$-alkoxy, $C_1$–$C_4$-alkylthio, $C_3$–$C_6$-cycloalkyl or methyl or ethyl which is substituted by $C_1$–$C_4$-alkoxy or by $C_1$–$C_4$-alkylthio.

Because of the fungicidal activity, compounds of the general formula Ie

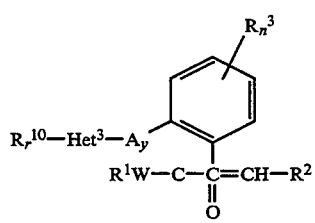

where
n is 0 or 1,
r is 0, 1 or 2, and the radicals $R^{10}$ may be different when r is 2,
—A$_y$— is one of the groups A*.1, A*.2, A*.7, A,.8, A*.10 or A*.11 and
Het$^3$ is a 5-membered heteroaromatic system which addition to carbon ring members contains from one to three nitrogen atom or one or two nitrogen atoms and one oxygen or one sulfur atom as ring members, are also preferred.

Because of the fungicidal activity, compounds of the general formula If

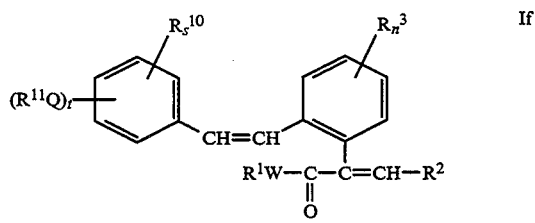

where
n is 0 or 1,
s is 0, 1 or 2, and the radicals $R^{10}$ may be different when s is 2,
t is 0, 1 or 2 and the radicals $R^{11}$Q may be different when t is 2,
Q is a direct bond, oxygen, sulfur or an —NH group and $R^{11}$ is a mono- or dinuclear heteroaromatic system which, in addition to carbon atoms, contains from one to three nitrogen atoms or one or two nitrogen atoms and one oxygen or sulfur atom, and the (hetero)aromatic system may carry from one to three radicals selected from a group consisting of halogen, cyano, nitro, amino, hydroxyl, $C_1$–$C_4$-alkyl, partially or completely halogenated $C_1$–$C_4$-alkyl, $C_1$–$C_4$-alkoxy, partially or completely halogenated $C_1$–$C_4$-alkoxy, $C_1$–$C_4$-alkylthio and partially or completely halogenated $C_1$–$C_4$-alkylthio, and where the (hetero) aromatic system may additionally carry a number of halogen atoms such that the total number of the radicals is 4, are also preferred.

Because of the Ifungicidal activity, compounds of the general formula Ig

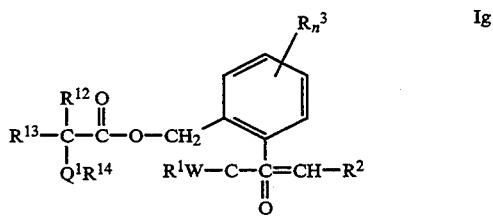

where
n is 0 or 1,
$Q^1$ is a direct bond, $C_1$–$C_6$-alkylene, $C_1$–$C_6$-alkyleneoxy, $C_1$–$C_6$-alkylenethio, oxy-$C_1$–$C_6$-alkylene, thio-$C_1$–$C_6$-alkylene, $C_2$–$C_6$-alkenylene, oxygen or sulfur,
$R_{12}$ and $R^{13}$ independently of one another are each hydrogen or $C_1$–$C_4$-alkyl which may carry from one to three halogen atoms, or, together with the carbon atoms to which they are bonded, form $C_3$–$C_8$-cycloalkyl, which may carry from one to three of the following radicals: halogen, $C_1$–$C_4$-alkyl, partially or completely halogenated $C_1$–$C_4$-alkyl or $C_1$–$C_4$-alkoxy,
$R^{14}$ is a mono- or dinuclear aromatic or heteroaromatic system which, in addition to carbon atoms, may contain from one to four nitrogen atoms or one or two nitrogen atoms and one oxygen or sulfur atom, where the (hetero)aromatic system may additionally carry from one to three of the radicals selected from a group consisting of halogen, cyano, nitro, amino, hydroxyl, carboxyl, $C_1-C_4$-alkyl, partially or completely halogenated $C_1-C_4$-alkyl, $C_1-C_4$-alkoxy, partially or completely halogenated $C_1-C_4$-alkoxy and $C_1-C_4$-alkylthio, and where the (hetero)aromatic system may furthermore carry a number of halogen atoms such that the total number of the radicals is 4 or 5, are also preferred.

Because of the activity against pests, compounds of the general formula I'a

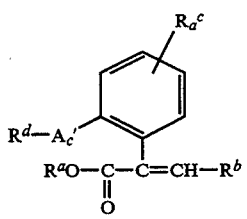

where
a is 0 or 1,
and —$A'_c$— is one of the groups A*.1, A*.2, A*.7, A*.8, A*.10, A*.11, A*.12, A*.13 or A*.14, are preferred.

Because of the activity against pests, compounds of the general formula I'b

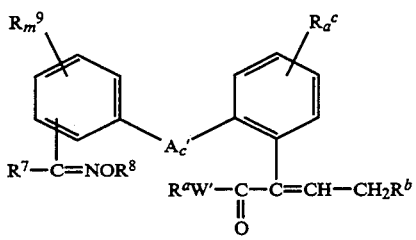

where
a is 0 or 1,
m is 0, 1 or 2 and the radicals $R^9$ may be different when m is 2;
—$A'_c$— is one of the groups A*.1, A*.7, A*.8, A*.10, A*.11 or A*.14,
$R^7$ is hydrogen;
$C_1-C_6$-alkyl as stated above in general and in particular;
aryl, such as phenyl, 1-naphthyl, 2-naphthyl, 1-anthranyl or 2-anthranyl, preferably phenyl, where the aromatic radical may furthermore carry from one to three substituents selected from a group consisting of halogen as stated above in general and in particular; cyano, cyanato; thiocyanato; nitro; amino; hydroxyl; carboxyl;
straight-chain of branched $C_1-C_4$-alkyl as stated above in general and in particular;
partially or complete if halogenated $C_1-C_4$-alkyl as stated above in general and in particular;
$C_1-C_4$-alkoxy as stated above in general and in particular; partially or completely halogenated $C_1-C_4$-alkoxy as stated above in general and in particular;
$C_1-C_4$-alkylthio as stated above in general and in particular;
or partially or completely halogenated $C_1-C_4$-alkylthio as stated above in general and in particular, and where the aromatic radicals may furthermore carry a number of halogen atoms, as stated above in general and in particular, such that the total number of their substituents is 4 or 5;

$R^8$ is straight-chain or branched $C_1-C_6$-alkyl as stated above in general and in particular, $C_2-C_6$-alkenyl or $C_2-C_6$-alkynyl as stated above in general, where these groups may furthermore carry from one to three substituents selected from a group consisting of halogen as stated above in general and in particular; cyano; nitro;

$C_1-C_6$-alkoxy as stated above in general and in particular; partially or completely halogenated $C_1-C_6$-alkoxy as stated above in general and in particular;

$C_1-C_6$-alkylthio as stated above in general and in particular;

partially or completely halogenated $C_1-C_6$-alkylthio as stated above in general and in particular;

$C_3-C_6$-cycloalkyl as stated above in general and in particular, where the alkyl, alkenyl and alkynyl groups may furthermore carry a number of halogen atoms, as stated above in general and in particular, such that the total number of their substituents is 4 or 5;

a 5-membered or 6-membered aromatic or heteroaromatic system as stated above, preferably phenyl, where the cyclic radicals in turn may furthermore carry from one to three substituents selected from a group consisting of halogen as stated above in general and in particular; cyano; nitro;

straight-chain or branched $C_1-C_4$-alkyl as stated above in general and in particular;

partially or completely halogenated $C_1-C_4$-alkyl as stated above in general and in particular;

$C_1-C_4$-alkoxy as stated above in general and in particular; partially or completely halogenated $C_1-C_4$-alkoxy as stated above in general and in particular;

or $C_1-C_4$-alkylthio as stated above in general and in particular, where the cyclic radicals may additionally carry a number of halogen atoms, as stated above in general and in particular, such that the total number of their substituents is 4 or 5, and $R^9$ is cyano, halogen, $C_1-C_4$-alkyl, partially or completely halogenated $C_1-C_4$-alkyl or $C_1-C_4$-alkoxy, are also preferred.

Particularly preferred compounds I'b are those in which the substructure $R^a$—W'— is one of the groups B,.1 or B*.3.

Because of the activity against pests, compounds of the general formula I'c

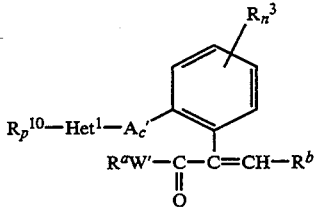

where
a is 0 or 1;
p is 0, 1, 2 or 3 and the radicals $R^{10}$ may be different when p is equal to or greater than 2;
—$A'_c$— is one of the groups A* 1, A*.2, A*.4, A*.7, A*.8, A*.10, A*.11, A*.12, A*.13 or A*.14;
$Het^1$ is a 5-membered or 6-membered, saturated or partially unsaturated heterocyclic structure which contains from one to three nitrogen atoms or one or two nitrogen atoms and one or two oxygen and/or sulfur atoms or one or two oxygen and/or sulfur atoms, where two oxygen atoms and/or two sulfur atoms must not be adjacent to one another; a mono- or dinuclear heteroaromatic system which, in addition to carbon atoms, contains from one to four nitrogen atoms or one or two nitrogen atoms and one oxyen or sulfur atom; and $R^{10}$ is cyano, cyanato, thiocyanato, nitro, amino, hydroxyl, carboxyl, halogen, $C_1$–$C_6$-alkyl, partially or completely halogenated $C_1$–$C_4$-alkyl, $C_1$–$C_4$-alkoxy, partially or completely halogenated $C_1$–$C_4$-alkoxy, $C_1$–$C_4$-alkylthio, partially or completely halogenated $C_1$–$C_4$-alkylthio, $C_1$–$C_4$-alkoxycarbonyl, $C_1$–$C_4$-alkylamino, di-($C_1$–$C_4$)-alkylamino, or methyl or ethyl which is substituted by $C_1$–$C_4$-alkoxy or by $C_1$–$C_4$-alkylthio, or a mononuclear aromatic or heteroaromatic ring system which is bonded directly or via a methylene bridge and which, in addition to carbon ring members, may contain from one to three nitrogen atoms or one oxygen or one sulfur atom or one or two nitrogen atoms and one oxygen or one sulfur atom, and which furthermore may carry from one to three substituents selected from a group consisting of halogen, cyano, nitro, $C_1$–$C_4$-alkyl, partially or completely halogenated $C_1$–$C_4$-alkyl, $C_1$–$C_4$-alkoxy, $C_1$–$C_4$-alkylthio or di-($C_1$–$C_4$)-alkylamino, where the (hetero)aromatic ring system may additionally carry a number of halogen atoms such that the total number of its substituents is 4, are also preferred.

Because of the activity against pests, compounds of the general formula I'd

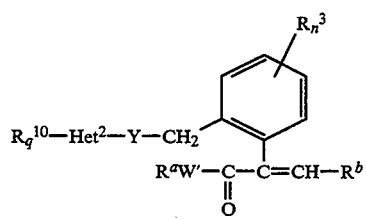

where
a is 0 or 1;
q is 0, 1, 2 or 3 and the radicals $R^{10}$ may be different when q is 2 or 3;
Y is oxygen or sulfur; and
$Het^2$ is a 6-membered heteroaromatic system which, in addition to carbon ring members, contains from one to three nitrogen atoms as ring members, are likewise preferred.

Because of their activity against pests, particularly preferred compounds of the formula I'd are those in which $R^{10}$ is $C_1$–$C_6$-alkyl, partially or completely halogenated $C_1$–$C_4$-alkyl, $C_1$–$C_4$-alkoxy, partially or completely halogenated $C_1$–$C_4$-alkoxy, $C_1$–$C_4$-alkylthio, $C_3$–$C_8$-cycloalkyl, or methyl or ethyl which is substituted by $C_1$–$C_4$-alkoxy or by $C_1$–$C_4$-alkylthio.

Because of the activity against pests, compounds of the general formula I'e

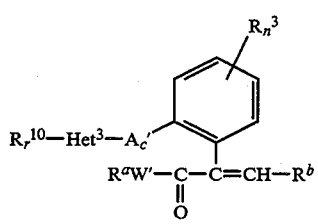

where
a is 0 or 1;
r is 0, 1 or 2 and the radicals $R^{10}$ may be different when r is 2;
—$A'_c$— is one of the groups A*.1, A*.7, A*.8, A*.10, A*.11 or A*.12; and
$Het^3$ is a 5-membered heteroaromatic system which, in addition to carbon ring members, contains from one to three nitrogen atoms or one or two nitrogen atoms and one oxygen or one sulfur atom or an O or S atom as ring members, are also preferred.

Because of their activity against pests, particularly preferred compounds of the general formula I'e are those in which $R^{10}$ is phenyl which may be substituted by from one to three of the following groups:
halogen, cyano, nitro, dimethylamino, $C_1$–$C_4$-alkyl, partially or completely halogenated $C_1$–$C_4$-alkyl or $C_1$–$C_4$-alkoxy.

Because of the activity against pests, compounds of the general formula I'f

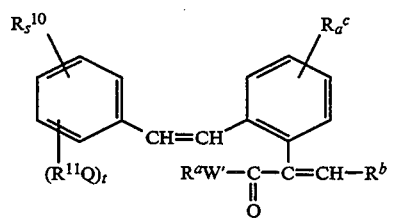

where
a is 0 or 1;
s is 0, 1 or 2 and the radicals $R^{10}$ may be different when s is 2;
t is 0, 1 or 2 and the radicals $R^{11}Q$ may be different when t is 2;
Q is a direct bond, oxygen, sulfur or —NH—;
$R^{11}$ is a mononuclear aromatic ring system which, in addition to carbon atoms, contains from one to three nitrogen atoms or one or two nitrogen atoms and one oxygen or sulfur atom, where these aromatic systems may furthermore carry from one to three radicals selected from the group consisting of halogen, cyano, nitro, amino, hydroxyl, $C_1$–$C_4$-alkyl, partially or completely halogenated $C_1$–$C_4$-alkyl, $C_1$–$C_4$-alkoxy, partially or completely halogenated $C_1$–$C_4$-alkoxy, $C_1$–$C_4$-alkylthio and partially or completely halogenated $C_1$–$C_4$-alkylthio, and where the aromatic systems may additionally carry a number of halogen atoms such that the total number of their radicals is 4, are also preferred.

Because of the activity against pests, particularly preferred compounds of the formula I'f are those in which $R^{10}$ is hydrogen, halogen, cyano, nitro, $C_1$–$C_4$-alkyl, partially or completely halogenated $C_1$–$C_4$-alkyl or $C_1$–$C_4$-alkoxy.

Because of the activity against pests, compounds of the general formula I'g

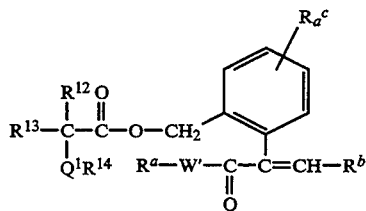

where
a is 0 or 1;
$Q^1$ is a direct bond, $C_1-C_6$-alkylene, $C_1-C_6$-alkyleneoxy, $C_1-C_6$-alkylenethio, oxy-$C_1-C_6$-alkylene, thio-$C_1-C_6$-alkylene, $C_2-C_6$-alkenylene, $C_2-C_6$-alkenylene, oxygen or sulfur; $R^{12}$ and $R^{13}$ independently of one another are each hydrogen or $C_1-C_4$-alkyl which may carry from one to three of the following radicals: halogen and $C_1-C_4$-alkoxy, or together with the carbon atom to which they are bonded may form $C_3-C_8$-cycloalkyl, which may carry from one to three of the following radicals: halogen, $C_1-C_4$-alkyl or partially or completely halogenated $C_1-C_4$-alkyl; and $R^{14}$ is a mono- or dinuclear aromatic or heteroaromatic system which, in addition to carbon atoms, may contain from one to four nitrogen atoms or one or two nitrogen atoms or one oxygen or sulfur atom, where the (hetero)aromatic ring systems may additionally carry from one to three radicals selected from a group consisting of halogen, cyano, nitro, amino, hydroxyl, carboxyl, $C_1-C_4$-alkyl, partially or completely halogenated $C_1-C_4$-alkyl, $C_1-C_4$-alkoxy, partially or completely halogenated $C_1-C_4$-alkoxy and $C_1-C_4$-alkylthio, and where the (hetero)aromatic systems may additionally carry a number of halogen atoms such that the total number of the radicals is 4 or 5 are also preferred, The indices m (in the formulae Ib and I'b), q (in the formulae Id and I'd), r (in the formulae Ie and I'e) and s and t (in the formulae If and I'f) independently of one another are each 0, 1 or 2, preferably 1 or 2.

The index p (in the formulae Ic and I'c) is 0, 1, 2 or 3, preferably 1 or 2.

$R^9$ in the formulae Ib and I'b is cyano; nitro;
halogen as stated above in general and in particular; straight-chain or branched $C_1-C_4$-alkyl as stated above in general and in particular;
partially or completely halogen $C_1-C_4$-alkyl as stated above in general and in particular; or
$C_1-C_4$-alkoxy as stated above in general and in particular.

$R^{10}$ in the formulae Ic, Id, Ie, If, I'c, I'd, I'e and I'f is cyano; cyanato; thiocyanato; nitro; amino; hydroxyl; halogen as stated above, preferably fluorine, chlorine or bromine, in particular fluorine or bromine; straight-chain or branched $C_1-C_6$-alkyl as stated above, preferably $C_1-C_4$-alkyl;
partially or completely halogenated $C_1-C_4$-alkyl as stated above, preferably chloromethyl or trifluoromethyl, in particular trifluoromethyl;
$C_1-C_4$-alkoxy as stated above, in particular methoxy or ethoxy;
partially or completely halogenated $C_1-C_4$-alkoxy, as stated above, in particular difluoromethoxy or 1,1,2,2-tetrafluoroethoxy;

$C_1-C_4$-alkylthio as stated above, in particular methylthio; partially or completely halogenated $C_1-C_4$-alkylthio as stated above in general and in particular;
$C_3-C_6$-cycloalkyl as stated above in general and in particular,
or $C_1-C_4$-alkoxy- or $C_1-C_4$-alkylthio-substituted methyl or ethyl as stated above in general and in particular.

$R^{11}$ in the formulae If and I'f is a mononuclear aromatic system which, in addition to carbon atoms, contains from one to three nitrogen atoms or one or two nitrogen atoms and one oxygen or sulfur atom, as stated above, preferably phenyl, 2-pyridyl, 3-pyridyl, 4-pyridyl, 2-pyrimidyl, 2-thienyl, 1-pyrrolyl, 1-pyrazolyl or 3-isoxazolyl, where these aromatic systems may furthermore carry from one to three radicals selected from a group consisting of halogen as stated above in general and in particular; cyano; nitro; amino; hydroxyl;
straight-chain or branched $C_1-C_4$-alkyl as stated above in general and in particular;
partially or completely halogenated $C_1-C_4$-alkyl as stated above in general and in particular;
$C_1-C_4$-alkoxy as stated above in general and in particular; partially or completely halogenated $C_1-C_4$-alkoxy as stated above in general and in particular;
$C_1-C_4$-alkylthio as stated above in general and in particular;
or partially or completely halogenated $C_1-C_4$-alkylthio as stated above in general and in particular,
where the aromatic systems may additionally carry a number of halogen atoms, as stated above in general and in particular, such that the total number of the radicals is 4.

$R^{12}$ and $R^{13}$ in the formulae If, Ig, I'f and I'g independently of one another are each hydrogen or straight-chain or branched $C_1-C_4$-alkyl as stated above in general and in particular, which may furthermore carry from one to three of the following radicals:
halogen as stated above in general and in particular or $C_1-C_4$-alkoxy as stated above in general and in particular; or $R^{12}$ and $R^{13}$ together with the carbon atom to which they are bonded, form $C_3-C_8$-cycloalkyl as stated above in general and in particular, which may furthermore carry from one to three of the following radicals:
halogen as stated above in general and in particular; straight-chain of branched $C_1-C_4$-alkyl as stated above in general and in particular;
or partially or completely halogenated $C_1-C_4$-alkyl as stated above in general and in particular.

$R^{14}$ in the formulae Ig and I'g is a mono- or dinuclear aromatic or heteroaromatic system which, in addition to carbon atoms, may contain from one to four nitrogen atoms or one or two nitrogen atoms and one oxygen or sulfur atom, as stated above, preferably phenyl, 1-naphthyl, 2-naphthyl or 3-pyridyl, in particular phenyl, where these (hetero)aromatic systems may carry from one to three radicals selected from the group consisting of halogen as stated above in general and in particular; cyano; cyanato; thiocyanato; nitro; amino; hydroxyl; carboxyl;
straight-chain or branched $C_1-C_4$-alkyl as stated above in general and in particular;
partially or completely halogenated $C_1-C_4$-alkyl as stated above in general and in particular;
$C_1-C_4$-alkoxy as stated above in general and in particular; partially or completely halogenated $C_1-C_4$-alkoxy as stated above in general and in particular;

and $C_1$–$C_4$-alkylthio as stated above in general and in particular, where the (hetero)aromatic systems may additionally carry a number of halogen atoms, as stated above in general and in particular, such that the total number of the radicals is 4 or 5.

Het[1] in the formulae Ic and I'c is a 5-membered or 6-membered, saturated or partially unsaturated heterocyclic structure which contains from one to three nitrogen atoms or one or two nitrogen atoms and one or two oxygen and/or sulfur atoms or from one to three oxygen and/or sulfur atoms, as stated above in general and in particular;

a mono- or dinuclear heteroaromatic system which, in addition to carbon atoms, contains from one to four nitrogen atoms or one or two nitrogen atoms and/or one oxygen or sulfur atom, as stated above in general and in particular.

Het[2] in the formulae Id and I'd is a 6-membered heteroaromatic system which, in addition to carbon ring members, contains from one to three nitrogen atoms as ring members, as stated above, preferably 2-pyridyl, 3-pyridyl, 2-pyrimidyl or 4-pyrimidyl, in particular 2-pyridyl or 4-pyrimidyl.

Het[3] in the formulae Ie and I'e is a 5-membered heteroaromatic system which, in addition to carbon ring members, contains from one to three nitrogen atoms or one or two nitrogen atoms and one oxygen or one sulfur atom as ring members, as stated above in general and in particular.

Q in the formulae If and I'f is a direct bond, oxygen, sulfur or —NH—, preferably a direct bond or oxygen.

$Q^1$ in the formulae Ig and I'g is a direct bond;

C–$C_6$-alkylene as stated above, preferably methylene, ethylene or propylene, in particular methylene; $C_1$–$C_6$-alkyleneoxy, such as methyleneoxy, ethyleneoxy, 1-methylmethyleneoxy, propyleneoxy, 1-methylethyleneoxy, 2-methylethyleneoxy, butyleneoxy, 1-methylpropyleneoxy, 2-methylpropyleneoxy, 3-methylpropyleneoxy, 1-ethyl-ethyleneoxy, 2-ethylethyleneoxy, 1,1-dimethylethyleneoxy, 1,2-dimethylethyleneoxy, 2,2-dimethylethyleneoxy, pentyleneoxy, 1-methylbutyleneoxy, 2-methylbutyleneoxy, 3-methylbutyleneoxy, 4-methylbutyleneoxy, 1,1-dimethylpropyleneoxy, 1,2-dimethylpropyleneoxy, 1,3-dimethylpropyleneoxy, 2,2-dimethylpropyleneoxy, 2,3-dimethylpropyleneoxy, 1-ethylpropyleneoxy, 2-ethylpropyleneoxy, 3-ethylpropyleneoxy, 1-ethyl-1-methylethyleneoxy, 1-ethyl-2-methylethyleneoxy, 2-ethyl-1-methylethyleneoxy, 2-ethyl-2-methylethyleneoxy, 1,1,2-trimethylethyleneoxy, 1,2,2-trimethylethyleneoxy, hexyleneoxy, 1-methylpentyleneoxy, 2-methylpentyleneoxy, 3-methylpentyleneoxy, 3-methylpentyleneoxy, 4-methylpentyleneoxy, 5-methylpentenyleneoxy, 1,1-dimethylbutyleneoxy, 1,2-dimethylbutyleneoxy, 1,3-dimethylbutyleneoxy, 1,4-dimethylbutyleneoxy, 2,2-dimethylbutyleneoxy, 2,3-dimethylbutyleneoxy, 2,4-dimethylbutyleneoxy, 3,3.dimethylbutyleneoxy, 3,4-dimethylbutyleneoxy, 1-ethylbutyleneoxy, 2-ethylbutyleneoxy, 3-ethylbutyleneoxy, 4-ethylbutyleneoxy, 1,1,2-trimethylpropyleneoxy, 1,1,3-trimethylpropyleneoxy, 1,2,2-trimethylpropyleneoxy, 1,2,3-trimethylpropyleneoxy, 2,2,3-trimethylpropyleneoxy, 2,3,3-trimethylpropyleneoxy, 1,3,3-trimethylpropyleneoxy, 1-ethyl-1-methylpropyleneoxy, 2-ethyl-1-methylpropyleneoxy, 3-ethyl-1-methylpropyleneoxy, 1-ethyl-2-methylpropyleneoxy, 2-ethyl-2-methylpropyleneoxy, 3-ethyl-2-methylpropyleneoxy, 1-ethyl-3-methylpropyleneoxy, 2-ethyl-3-methylpropyleneoxy, 3-ethyl-3-methylpropyleneoxy, 1,1-diethylethyleneoxy, 1,2-diethylethyleneoxy, 2,2-diethylethyleneoxy or 1,1,2,2-tetramethylethyleneoxy, preferably methyleneoxy; $C_1$–$C_6$-alkylenethio, such as methylenethio, ethylenethio, 1-methylmethylenethio, propylenethio, 1-methylethylenethio, 2-methylethylenethio, butylenethio, 1-methylpropylenethio, 2-methylpropylenethio, 3-methylpropylenethio, 1-ethylethylenethio, 2-ethylethylenethio, 1,1-dimethylethylenethio, 1,2-dimethylethylenethio, 2,2-dimethylethylenethio, pentylenethio, 1-methylbutylenethio, 2-methylbutylenethio, 3-methylbutylenethio, 4-methylbutylenethio, 1,1-dimethylpropylenethio, 1,2-dimethylpropylenethio, 1,3-dimethylpropylenethio, 2,2-dimethylpropylenethio, 2,3-dimethylpropylenethio, 1-ethylpropylenethio, 2-ethylpropylenethio, 3-ethylpropylenethio, 1-ethyl-1-methylethylenethio, 1-ethyl-2-methylethylenethio, 2-ethyl-1-methylethylenethio, 2-ethyl-2methylethylenethio, 1,1,2-methylethylenethio, 1,2,2-trimethylethylenethio, hexylenethio, 1-methylpentylenethio, 2-methylpentylenethio, 3-methylpentylenethio, 4-methylpentylenethio, 5-methylpentylenethio, 1,1-dimethylbutylenethio, 1,2-dimethylbutylenethio, 1,3-dimethylbutylenethio, 1,4-dimethylbutylenethio, 2,2-dimethylbutylenethio, 2,3-dimethylbutylenethio, 2,4-dimethylbutylenethio, 3,3-dimethylbutylenethio, 3,4-dimethylbutylenethio, 1-ethylbutylenethio, 2-ethylbutylenethio, 3-ethylbutylenethio, 4-ethylbutylenethio, 1,1,2-trimethylpropylenethio, 1,1,3-trimethylpropylenethio, 1,2,2-trimethylpropylenethio, 1,2,3-trimethylpropylenethio, 2,2,3-trimethylpropylenethio, 2,3,3-trimethylpropylenethio, 1,3,3-trimethylpropylenethio, 1-ethyl-1-methylpropylenethio, 2-ethyl-1-methylpropylenethio, 3-ethyl-1-methylpropylenethio, 1-ethyl-2-methylpropylenethio, 2-ethyl-2-methylpropylenethio, 3-ethyl-2-methylpropylenethio, 1-ethyl-3-methylpropylenethio, 2-ethyl-3-methylpropylenethio, 3-ethyl-3-methylpropylenethio, 1,1-diethylethylenethio, 1,2-diethylethylenethio, 2,2-diethylethylenethio or 1,1,2,2-tetramethylethylenethio, preferably methylenethio;

oxy-$C_1$–$C_6$-alkylene, such as oxymethylene, oxyethylene, oxy-1-methylmethylene, oxypropylene, oxy-1-methylethylene, oxy-2-methylethylene, oxybutylene, oxy-1-methylpropylene, oxy-2-methylpropylene, oxy-3-methylpropylene, oxy-1-ethylethylene, oxy-2-ethylethylene, oxy-1,1-dimethylethylene, oxy-1,2-dimethylethylene, oxy-2,2-dimethylethylene, oxypentylene, oxy-1-methylbutylene, oxy-2-methylbutylene, oxy-3-methylbutylene, oxy-4-methylbutylene, oxy-1,1-dimethylpropylene, oxy-1,2-dimethylpropylene, oxy-1,3-dimethylpropylene, oxy-2,2-dimethylpropylene, oxy-2,3-dimethylpropylene, oxy-1-ethylpropylene, oxy-2-ethylpropylene, oxy-3-ethylpropylene, oxy-1-ethyl-1-methylethylene, oxy-1-ethyl-2-methylethylene, oxy-2-ethyl-1-methylethylene, oxy-2-ethyl-2-methylethylene, oxy-1,1,2-trimethylethylene, oxy-1,2,2-trimethylethylene, oxyhexylene, oxy-1-methylpentylene, oxy-2-methylpentylene, , oxy-3-methylpentylene, oxy-4-methylpentylene, oxy-5-methylpentylene, oxy-1,1-dimethylbutylene, oxy-1,2-dimethylbutylene, oxy-1,3-dimethylbutylene, oxy-1,4-dimethylbutylene, oxy-2,2-dimethylbutylene, oxy-2,3-dimethylbutylene, oxy-2,4-dimethylbutylene, oxy-3,3-dimethylbutylene, oxy-3,4-dimethylbutylene, oxy-1-ethylbutylene, oxy-2-ethylbutylene, oxy-3-ethylbutylene, oxy-4-ethylbutylene, oxy-1,1,2-trimethylpropylene, oxy-1,1,3-trimethylpropylene, oxy-1,2,2-trimethylpropylene, oxy-1,2,3-trimethylpropylene, oxy-2,2,3-trimethylpropylene, oxy-2,3,3-trimethylpropylene, oxy-1,3,3-trimethylpropylene, oxy-1-ethyl-1-methylpropylene, oxy-2-ethyl-1-methylpropylene, oxy-3-ethyl-1-methylpropylene, oxy-1-ethyl-2-methylpropylene, oxy-2-ethyl-2-methylpropylene, oxy-3-ethyl-2-methylpropylene, oxy-1-ethyl-3-methylpropylene, oxy-2-ethyl-3-methylpropylene, oxy-3-ethyl-3-methylpropylene, oxy-1,1-diethylethylene, oxy-1,2-diethylethylene, oxy-2,2-diethylethylene or oxy-1,1,2,2-tetramethylethylene, preferably oxymethylene;

thio-$C_1$–$C_6$-alkylene, such as thiomethylene, thioethylene, thio-1-methylmethylene, thiopropylene, thio-1-methylethylene, thio-2-methylethylene, thiobutylene, thio-1-methylpropylene, thio-2-methylpropylene, thio-3-methylpropylene, thio-1-ethylethylene, thio-2-ethylethylene, thio-1,1-dimethylethylene, thio-1,2-dimethylethylene, thio-2,2-dimethylethylene, oxypentylene, thio-1-methylbutylene, thio-2-methylbutylene, thio-3-methylbutylene, thio-4-methylbutylene, thio-1,1-dimethylpropylene, thio-1,2-dimethylpropylene, thio-1,3-dimethylpropylene, thio-2,2-dimethylpropylene, thio-2,3-dimethylpropylene, thio-1-ethylpropylene, thio-2-ethylpropylene, thio-3-ethylpropylene, thio-1-ethyl-1-methylethylene, thio-1-ethyl-2-methylethylene, thio-2-ethyl-1-methylethylene, thio-2-ethyl-2-methylethylene, thio-1,1,2-trimethylethylene, thio-1,2,2-trimethylethylene, oxyhexylene, thio-1-methylpentylene, thio-2-methylpentylene, thio-3-methylpentylene, thio-4-methylpentylene, thio-5-methylpentylene, thio-1,1-dimethylbutylene, thio-1,2-dimethylbutylene, thio-1,3-dimethylbutylene, thio-1,4-dimethylbutylene, thio-2,2-dimethylbutylene, thio-2,3-dimethylbutylene, thio-2,4-dimethylbutylene, thio-3,3-dimethylbutylene, thio-3,4-dimethylbutylene, thio-1-ethylbutylene, thio-2-ethylbutylene, thio-3-ethylbutylene, thio-4-ethylbutylene, thio-1,1,2-trimethylpropylene, thio-1,1,3-trimethylpropylene, thio-1,2,2-trimethylpropylene, thio-1,2,3-trimethylpropylene, thio-2,2,3-trimethylpropylene, 2,3,3-trimethylpropylene, thio-1,3,3-trimethylpropylene, thio-1-ethyl-1-methylpropylene, thio-2-ethyl-1-methylpropylene, thio-3-ethyl-1-methylpropylene, thio-1-ethyl-2-methylpropylene, thio-2-ethyl-2-methylpropylene, thio-3-ethyl-2-methylpropylene, thio-1-ethyl-3-methylpropylene, thio-2-ethyl-3-methylpropylene, thio-3-ethyl-3-methylpropylene, thio-1,1-diethylethylene, thio-1,2-diethylethylene, thio-2,2-diethylethylene or thio-1,1,2,2-tetramethylethylene, preferably thiomethylene; $C_2$–$C_6$-alkenylene as stated above, preferably ethenylene or propenylene; oxygen or sulfur.

Examples of α-phenylacrylic acid derivatives I and I' which are particularly preferred because of their biological activity against harmful fungi and pests are summarized in Tables 1 to 66 below.

TABLE I

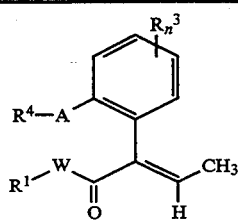 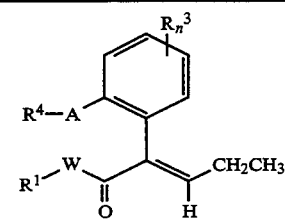 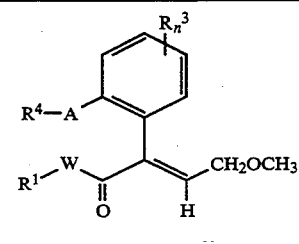

I.1  I.2  I.3

| $R^4$ | A | $R^1$—W | $R^3_n$ |
|---|---|---|---|
| 2-Pyridyl | —SCH$_2$ | CH$_3$O | H |
| 2-Pyridyl | —OCH$_2$ | CH$_3$O | H |
| 6-Methyl-2-pyridyl | —OCH$_2$ | CH$_3$O | H |
| 6-Methyl-2-pyridyl | —SCH$_2$ | CH$_3$O | H |
| 6-Ethyl-2-pyridyl | —OCH$_2$ | CH$_3$O | H |
| 6-Ethyl-2-pyridyl | —SCH$_2$ | CH$_3$O | H |
| 6-n-Propyl-2-pyridyl | —OCH$_2$ | CH$_3$O | H |
| 6-n-Propyl-2-pyridyl | —SCH$_2$ | CH$_3$O | H |
| 6-iso-Propyl-2-pyridyl | —OCH$_2$ | CH$_3$O | H |
| 6-iso-Propyl-2-pyridyl | —SCH$_2$ | CH$_3$O | H |
| 6-n-Butyl-2-pyridyl | —OCH$_2$ | CH$_3$O | H |
| 6-n-Butyl-2-pyridyl | —SCH$_2$ | CH$_3$O | H |
| 6-tert.-Butyl-2-pyridyl | —OCH$_2$ | CH$_3$O | H |
| 6-tert.-Butyl-2-pyridyl | —SCH$_2$ | CH$_3$O | H |
| 6-n-Pentyl-2-pyridyl | —OCH$_2$ | CH$_3$O | H |
| 6-n-Pentyl-2-pyridyl | —SCH$_2$ | CH$_3$O | H |
| 6-n-Hexyl-2-pyridyl | —OCH$_2$ | CH$_3$O | H |
| 6-n-Hexyl-2-pyridyl | —SCH$_2$ | CH$_3$O | H |
| 6-Phenyl-2-pyridyl | —OCH$_2$ | CH$_3$O | H |
| 6-Phenyl-2-pyridyl | —SCH$_2$ | CH$_3$O | H |
| 6-Benzyl-2-pyridyl | —OCH$_2$ | CH$_3$O | H |
| 6-Benzyl-2-pyridyl | —SCH$_2$ | CH$_3$O | H |
| 6-Trifluoromethyl-2-pyridyl | —OCH$_2$ | CH$_3$O | H |
| 6-Trifluoromethyl-2-pyridyl | —SCH$_2$ | CH$_3$O | H |
| 6-Methoxy-2-pyridyl | —OCH$_2$ | CH$_3$O | H |
| 6-Methoxy-2-pyridyl | —SCH$_2$ | CH$_3$O | H |
| 6-Chloro-2-pyridyl | —OCH$_2$ | CH$_3$O | H |
| 6-Chloro-2-pyridyl | —SCH$_2$ | CH$_3$O | H |
| 3,6-Dimethyl-2-pyridyl | —OCH$_2$ | CH$_3$O | H |

TABLE I-continued

I.1, I.2, I.3 structures with R⁴—A— substituent on phenyl ring bearing Rₙ³, connected to CH variants: =CH-CH₃ (I.1), =CH-CH₂CH₃ (I.2), =CH-CH₂OCH₃ (I.3), with R¹—W—C(=O)— group.

| R⁴ | A | R¹—W | R³n |
|---|---|---|---|
| 3,6-Dimethyl-2-pyridyl | —SCH₂ | CH₃O | H |
| 3,6-Diethyl-2-pyridyl | —OCH₂ | CH₃O | H |
| 3,6-Diethyl-2-pyridyl | —SCH₂ | CH₃O | H |
| 4,6-Dimethyl-2-pyridyl | —OCH₂ | CH₃O | H |
| 4,6-Dimethyl-2-pyridyl | —SCH₂ | CH₃O | H |
| 5,6-Dimethyl-2-pyridyl | —OCH₂ | CH₃O | H |
| 5,6-Dimethyl-2-pyridyl | —SCH₂ | CH₃O | H |
| 4-Phenyl-6-methyl-2-pyridyl | —OCH₂ | CH₃O | H |
| 4-Phenyl-6-methyl-2-pyridyl | —SCH₂ | CH₃O | H |
| 4,6-Diphenyl-2-pyridyl | —OCH₂ | CH₃O | H |
| 4,6-Diphenyl-2-pyridyl | —SCH₂ | CH₃O | H |
| 3,4-Dichloro-6-methyl-2-pyridyl | —OCH₂ | CH₃O | H |
| 3,4-Dichloro-6-methyl-2-pyridyl | —SCH₂ | CH₃O | H |
| 3,4,5-Trichloro-6-phenyl-2-pyridyl | —OCH₂ | CH₃O | H |
| 3,4,5-Trichloro-6-phenyl-2-pyridyl | —SCH₂ | CH₃O | H |
| 4-Trifluoromethyl-6-methyl-2-pyridyl | —OCH₂ | CH₃O | H |
| 4-Trifluoromethyl-6-methyl-2-pyridyl | —SCH₂ | CH₃O | H |
| 3-Acetyl-4,6-dimethyl-2-pyridyl | —OCH₂ | CH₃O | H |
| 3-Acetyl-4,6-dimethyl-2-pyridyl | —SCH₂ | CH₃O | H |
| 3-Cyano-6-methyl-2-pyridyl | —OCH₂ | CH₃O | H |
| 3-Cyano-6-methyl-2-pyridyl | —SCH₂ | CH₃O | H |
| 3-Cyano-6-ethyl-2-pyridyl | —OCH₂ | CH₃O | H |
| 3-Cyano-6-ethyl-2-pyridyl | —SCH₂ | CH₃O | H |
| 3-Cyano-6-n-propyl-2-pyridyl | —OCH₂ | CH₃O | H |
| 3-Cyano-6-n-propyl-2-pyridyl | —SCH₂ | CH₃O | H |
| 3-Cyano-iso-propyl-2-pyridyl | —OCH₂ | CH₃O | H |
| 3-Cyano-iso-propyl-2-pyridyl | —SCH₂ | CH₃O | H |
| 3-Cyano-6-cyclo-propyl-2-pyridyl | —OCH₂ | CH₃O | H |
| 3-Cyano-6-cyclo-propyl-2-pyridyl | —SCH₂ | CH₃O | H |
| 3-Cyano-6-n-butyl-2-pyridyl | —OCH₂ | CH₃O | H |
| 3-Cyano-6-n-butyl-2-pyridyl | —SCH₂ | CH₃O | H |
| 3-Cyano-6-tert.-butyl-2-pyridyl | —OCH₂ | CH₃O | H |
| 3-Cyano-6-tert.-butyl-2-pyridyl | —SCH₂ | CH₃O | H |
| 3-Cyano-6-cyclo-hexyl-2-pyridyl | —OCH₂ | CH₃O | H |
| 3-Cyano-6-cyclo-hexyl-2-pyridyl | —SCH₂ | CH₃O | H |
| 3-Cyano-6-phenyl-2-pyridyl | —OCH₂ | CH₃O | H |
| 3-Cyano-6-phenyl-2-pyridyl | —SCH₂ | CH₃O | H |
| 3-Methyloxycarbonyl-6-iso-propyl-2-pyridyl | —OCH₂ | CH₃O | H |
| 3-Methyloxycarbonyl-6-iso-propyl-2-pyridyl | —SCH₂ | CH₃O | H |
| 3-Ethyloxycarbonyl-6-iso-propyl-2-pyridyl | —OCH₂ | CH₃O | H |
| 3-Ethyloxycarbonyl-6-iso-propyl-2-pyridyl | —SCH₂ | CH₃O | H |
| 3-Cyano-4,6-dimethyl-2-pyridyl | —OCH₂ | CH₃O | H |
| 3-Cyano-4,6-dimethyl-2-pyridyl | —SCH₂ | CH₃O | H |
| 3,5,6-Trichloro-2-pyridyl | —OCH₂ | CH₃O | H |
| 3,5,6-Trichloro-2-pyridyl | —SCH₂ | CH₃O | H |
| 5-Trifluoromethyl-2-pyridyl | —OCH₂ | CH₃O | H |
| 5-Trifluoromethyl-2-pyridyl | —SCH₂ | CH₃O | H |
| 3-Chloro-5-trifluoromethyl-2-pyridyl | —OCH₂ | CH₃O | H |
| 3-Chloro-5-trifluoromethyl-2-pyridyl | —SCH₂ | CH₃O | H |
| 6-Cyclopropyl-2-pyridyl | —OCH₂ | CH₃O | H |
| 6-Cyclopropyl-2-pyridyl | —SCH₂ | CH₃O | H |
| 6-Bromo-2-pyridyl | —OCH₂ | CH₃O | H |
| 4-Trifluoromethyl-2-pyridyl | —OCH₂ | CH₃O | H |
| 4-Trifluoromethyl-5-chlor-2-pyridyl | —OCH₂ | CH₃O | H |
| 4-tert.butyl-2-pyridyl | —OCH₂ | CH₃O | H |
| 3,6-Bis(trifluoromethyl)-2-pyridyl | —OCH₂ | CH₃O | H |
| 5-Trifluoromethyl-2-pyridyl | —OCH₂ | CH₃O | H |
| 3-Fluoro-2-pyridyl | —OCH₂ | CH₃O | H |
| 3-Chloro-2-pyridyl | —OCH₂ | CH₃O | H |
| 4-Brom-2-pyridyl | —OCH₂ | CH₃O | H |
| 5-Methyl-2-pyridyl | —OCH₂ | CH₃O | H |
| 3-Fluor-5-trifluormethyl-2-pyridyl | —OCH₂ | CH₃O | H |
| 3,6-Dichlor-5-trifluormethyl-2-pyridyl | —OCH₂ | CH₃O | H |
| 6-Chlor-4-cyano-2-pyridyl | —OCH₂ | CH₃O | H |
| 3-Cyano-5-nitro-2-pyridyl | —OCH₂ | CH₃O | H |
| 4,6-Difluor-2-pyridyl | —OCH₂ | CH₃O | H |
| 3,5-Dichlor-6-fluor-2-pyridyl | —OCH₂ | CH₃O | H |
| 6-Methoxy-3-nitro-2-pyridyl | —OCH₂ | CH₃O | H |

TABLE I-continued

| | I.1 | I.2 | I.3 |
|---|---|---|---|
| | (R⁴-A, Rₙ³ on phenyl, W=O, CH=CH-CH₃) | (CH=CH-CH₂CH₃) | (CH=CH-CH₂OCH₃) |

| $R^4$ | A | $R^1$—W | $R^3{}_n$ |
|---|---|---|---|
| 4-Cyano-6-fluor-2-pyridyl | —OCH$_2$ | CH$_3$O | H |
| 4-Cyano-3,5,6,-trifluor-2-pyridyl | —OCH$_2$ | CH$_3$O | H |
| 6-Chlor-5-nitro-2-pyridyl | —OCH$_2$ | CH$_3$O | H |
| 4,6-Dicyano-2-pyridyl | —OCH$_2$ | CH$_3$O | H |
| 5-Trichlormethyl-2-pyridyl | —OCH$_2$ | CH$_3$O | H |
| 5-Cyano-2-pyridyl | —OCH$_2$ | CH$_3$O | H |
| 5-Brom-4-trifluormethyl-2-pyridyl | —OCH$_2$ | CH$_3$O | H |
| 3-Nitro-5-trifluormethyl-2-pyridyl | —OCH$_2$ | CH$_3$O | H |
| 5-Formamido-2-pyridyl | —OCH$_2$ | CH$_3$O | H |
| 5-Amino-2-pyridyl | —OCH$_2$ | CH$_3$O | H |
| 5-Nitro-2-pyridyl | —OCH$_2$ | CH$_3$O | H |
| 4-Methyl-5-nitro-2-pyridyl | —OCH$_2$ | CH$_3$O | H |
| 5-Difluormethyl-2-pyridyl | —OCH$_2$ | CH$_3$O | H |
| 5-Fluormethyl-2-pyridyl | —OCH$_2$ | CH$_3$O | H |
| 5-Methoxycarbonyl-2-pyridyl | —OCH$_2$ | CH$_3$O | H |
| 5-Chlor-6-methoxy-2-pyridyl | —OCH$_2$ | CH$_3$O | H |
| 5,6-Dichlor-2-pyridyl | —OCH$_2$ | CH$_3$O | H |
| 6-Brom-5-chlor-2-pyridyl | —OCH$_2$ | CH$_3$O | H |
| 5-Chlor-6-acetoxy-2-pyridyl | —OCH$_2$ | CH$_3$O | H |
| 5-Brom-6-fluor-2-pyridyl | —OCH$_2$ | CH$_3$O | H |
| 5-Brom-6-cyano-2-pyridyl | —OCH$_2$ | CH$_3$O | H |
| 5-Brom-6-hydroxy-2-pyridyl | —OCH$_2$ | CH$_3$O | H |
| 5-Brom-6-methoxy-2-pyridyl | —OCH$_2$ | CH$_3$O | H |
| 5,6-Dibrom-2-pyridyl | —OCH$_2$ | CH$_3$O | H |
| 6-Phenoxy-2-pyridyl | —OCH$_2$ | CH$_3$O | H |
| 4-Phenyl-2-pyridyl | —OCH$_2$ | CH$_3$O | H |
| 4-Phenoxy-2-pyridyl | —OCH$_2$ | CH$_3$O | H |
| 6-Hydroxy-2-pyridyl | —OCH$_2$ | CH$_3$O | H |
| 6-Ethoxy-2-pyridyl | —OCH$_2$ | CH$_3$O | H |
| 6-Benzyloxy-2-pyridyl | —OCH$_2$ | CH$_3$O | H |
| 4-Benzyloxy-2-pyridyl | —OCH$_2$ | CH$_3$O | H |
| 4,6-Bis(trifluormethyl)-2-pyridyl | —OCH$_2$ | CH$_3$O | H |
| 5-Formyl-2-pyridyl | —OCH$_2$ | CH$_3$O | H |
| 6-Amino-2-pyridyl | —OCH$_2$ | CH$_3$O | H |
| 4-Amino-2-pyridyl | —OCH$_2$ | CH$_3$O | H |
| 4-Carboxy-2-pyridyl | —OCH$_2$ | CH$_3$O | H |
| 3-Brom-5-trifluormethyl-2-pyridyl | —OCH$_2$ | CH$_3$O | H |
| 6-Methyl-3-nitro-2-pyridyl | —OCH$_2$ | CH$_3$O | H |
| 3-Nitro-2-pyridyl | —OCH$_2$ | CH$_3$O | H |
| 3-Fluor-5-trifluormethyl-2-pyridyl | —OCH$_2$ | CH$_3$O | H |
| 3-Pyridyl | —OCH$_2$ | CH$_3$O | H |
| 3-Pyridyl | —SCH$_2$ | CH$_3$O | H |
| 2-Fluor-3-pyridyl | —OCH$_2$ | CH$_3$O | H |
| 4-Trifluormethyl-3-pyridyl | —OCH$_2$ | CH$_3$O | H |
| 5-Methyl-3-pyridyl | —OCH$_2$ | CH$_3$O | H |
| 6-Methoxy-3-pyridyl | —OCH$_2$ | CH$_3$O | H |
| 4-Cyano-2,5,6-trifluor-3-pyridyl | —OCH$_2$ | CH$_3$O | H |
| 4-Pyridyl | —OCH$_2$ | CH$_3$O | H |
| 4-Pyridyl | —SCH$_2$ | CH$_3$O | H |
| 2-Chlor-4-pyridyl | —OCH$_2$ | CH$_3$O | H |
| 3-Trifluormethyl-4-pyridyl | —OCH$_2$ | CH$_3$O | H |
| 2-Chlor-6-fluor-4-pyridyl | —OCH$_2$ | CH$_3$O | H |
| 2,3,5,6-Tetrafluor-4-pyridyl | —OCH$_2$ | CH$_3$O | H |
| 2-Pyrimidinyl | —OCH$_2$ | CH$_3$O | H |
| 2-Pyrimidinyl | —SCH$_2$ | CH$_3$O | H |
| 4,6-Dimethyl-2-pyrimidinyl | —OCH$_2$ | CH$_3$O | H |
| 4,6-Dimethyl-2-pyrimidinyl | —SCH$_2$ | CH$_3$O | H |
| 4-Trifluormethyl-2-pyrimidinyl | —OCH$_2$ | CH$_3$O | H |
| 4-Trifluormethyl-2-pyrimidinyl | —SCH$_2$ | CH$_3$O | H |
| 4,5,6-Trimethyl-2-pyrimidinyl | —OCH$_2$ | CH$_3$O | H |
| 4,5,6-Trimethyl-2-pyrimidinyl | —SCH$_2$ | CH$_3$O | H |
| 4-Benzyl-6-methyl-2-pyrimidinyl | —OCH$_2$ | CH$_3$O | H |
| 4-Benzyl-6-methyl-2-pyrimidinyl | —SCH$_2$ | CH$_3$O | H |
| 4-Methyl-6-phenyl-2-pyrimidinyl | —OCH$_2$ | CH$_3$O | H |
| 4-Methyl-6-phenyl-2-pyrimidinyl | —SCH$_2$ | CH$_3$O | H |
| 4,6-Dimethyl-5-chlor-2-pyrimidinyl | —OCH$_2$ | CH$_3$O | H |
| 4,6-Dimethyl-5-chlor-2-pyrimidinyl | —SCH$_2$ | CH$_3$O | H |
| 4-Fluor-2-pyrimidinyl | —OCH$_2$ | CH$_3$O | H |

TABLE I-continued

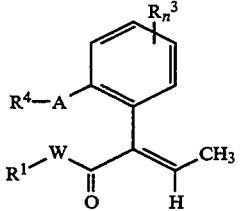

| R⁴ | A | R¹—W | R³n |
|---|---|---|---|
| 5-Methyl-2-pyrimidinyl | —OCH₂ | CH₃O | H |
| 4,6-Difluor-2-pyrimidinyl | —OCH₂ | CH₃O | H |
| 5-Phenyl-2-pyrimidinyl | —SCH₂ | CH₃O | H |
| 4-Hydroxy-5-methyl-6-propyl-2-pyrimidinyl | —SCH₂ | CH₃O | H |
| 4-Methyl-2-pyrimidinyl | —SCH₂ | CH₃O | H |
| 4-Pyrimidinyl | —OCH₂ | CH₃O | H |
| 4-Pyrimidinyl | —SCH₂ | CH₃O | H |
| 2,6-Dimethyl-4-pyrimidinyl | —OCH₂ | CH₃O | H |
| 2,6-Dimethyl-4-pyrimidinyl | —SCH₂ | CH₃O | H |
| 2,6-Bis-(trifluormethyl)-4-pyrimidinyl | —OCH₂ | CH₃O | H |
| 2,6-Bis-(trifluormethyl)-4-pyrimidinyl | —SCH₂ | CH₃O | H |
| 2-Chloromethyl-6-methyl-4-pyrimidinyl | —OCH₂ | CH₃O | H |
| 2-Chloromethyl-6-methyl-4-pyrimidinyl | —SCH₂ | CH₃O | H |
| 2-Methyl-6-chloromethyl-4-pyrimidinyl | —OCH₂ | CH₃O | H |
| 2-Methyl-6-chloromethyl-4-pyrimidinyl | —SCH₂ | CH₃O | H |
| 2-iso-Propyl-6-methyl-4-pyrimidinyl | —OCH₂ | CH₃O | H |
| 2-iso-Propyl-6-methyl-4-pyrimidinyl | —SCH₂ | CH₃O | H |
| 2-iso-Propyl-6-chloromethyl-4-pyrimidinyl | —OCH₂ | CH₃O | H |
| 2-iso-Propyl-6-chloromethyl-4-pyrimidinyl | —SCH₂ | CH₃O | H |
| 2-cyclo-Propyl-6-chloromethyl-4-pyrimidinyl | —OCH₂ | CH₃O | H |
| 2-cyclo-Propyl-6-chloromethyl-4-pyrimidinyl | —SCH₂ | CH₃O | H |
| 2-cyclo-Propyl-6-methyl-4-pyrimidinyl | —OCH₂ | CH₃O | H |
| 2-cyclo-Propyl-6-methyl-4-pyrimidinyl | —SCH₂ | CH₃O | H |
| 2-Methyl-6-methoxymethyl-4-pyrimidinyl | —OCH₂ | CH₃O | H |
| 2-Methyl-6-methoxymethyl-4-pyrimidinyl | —SCH₂ | CH₃O | H |
| 2-iso-Propyl-6-methoxymethyl-4-pyrimidinyl | —OCH₂ | CH₃O | H |
| 2-iso-Propyl-6-methoxymethyl-4-pyrimidinyl | —SCH₂ | CH₃O | H |
| 2-Phenyl-4-pyrimidinyl | —OCH₂ | CH₃O | H |
| 2-Phenyl-4-pyrimidinyl | —SCH₂ | CH₃O | H |
| 2,5-Dimethyl-4-pyrimidinyl | —OCH₂ | CH₃O | H |
| 2,5-Dimethyl-4-pyrimidinyl | —SCH₂ | CH₃O | H |
| 2-Methylthio-6-trifluoromethyl-4-pyrimidinyl | —OCH₂ | CH₃O | H |
| 2-Methylthio-6-trifluoromethyl-4-pyrimidinyl | —SCH₂ | CH₃O | H |
| 2-Methylthio-5-chloro-6-trifluoromethyl-4-pyrimidinyl | —OCH₂ | CH₃O | H |
| 2-Methylthio-5-chloro-6-trifluoromethyl-4-pyrimidinyl | —SCH₂ | CH₃O | H |
| 2-Methylthio-5-n-octyl-6-methyl-4-pyrimidinyl | —OCH₂ | CH₃O | H |
| 2-Methylthio-5-n-octyl-6-methyl-4-pyrimidinyl | —SCH₂ | CH₃O | H |
| 2-Methyl-6-trifluoromethyl-4-pyrimidinyl | —OCH₂ | CH₃O | H |
| 2-Methyl-6-trifluoromethyl-4-pyrimidinyl | —SCH₂ | CH₃O | H |
| 2-n-Propyl-6-trifluoromethyl-4-pyrimidinyl | —OCH₂ | CH₃O | H |
| 2-n-Propyl-6-trifluoromethyl-4-pyrimidinyl | —SCH₂ | CH₃O | H |
| 2-iso-Propyl-6-trifluoromethyl-4-pyrimidinyl | —OCH₂ | CH₃O | H |
| 2-iso-Propyl-6-trifluoromethyl-4-pyrimidinyl | —SCH₂ | CH₃O | H |
| 2-n-Propyl-6-methyl-4-pyrimidinyl | —OCH₂ | CH₃O | H |
| 2-n-Propyl-6-methyl-4-pyrimidinyl | —SCH₂ | CH₃O | H |
| 2-tert.-Butyl-6-trifluoromethyl-4-pyrimidinyl | —OCH₂ | CH₃O | H |
| 2-tert.-Butyl-6-trifluoromethyl-4-pyrimidinyl | —SCH₂ | CH₃O | H |
| 2-Methyl-5-chloro-6-trifluoromethyl-4-pyrimidinyl | —OCH₂ | CH₃O | H |
| 2-Methyl-5-chloro-6-trifluoromethyl-4-pyrimidinyl | —SCH₂ | CH₃O | H |
| 2-n-Propyl-5-chloro-6-trifluoromethyl-4-pyrimidinyl | —OCH₂ | CH₃O | H |
| 2-n-Propyl-5-chloro-6-trifluoromethyl-4-pyrimidinyl | —SCH₂ | CH₃O | H |
| 2-iso-Propyl-5-chloro-6-trifluoromethyl-4-pyrimidinyl | —OCH₂ | CH₃O | H |
| 2-iso-Propyl-5-chloro-6-trifluoromethyl-4-pyrimidinyl | —SCH₂ | CH₃O | H |
| 2-tert.-Butyl-5-chloro-6-trifluoromethyl-4-pyrimidinyl | —OCH₂ | CH₃O | H |
| 1-tert.-Butyl-5-chloro-6-trifluoromethyl-4-pyrimidinyl | —SCH₂ | CH₃O | H |
| 2-Chlor-4-pyrimidinyl | —OCH₂ | CH₃O | H |
| 5-Methoxy-4-pyrimidinyl | —OCH₂ | CH₃O | H |
| 6-Trifluormethyl-4-pyrimidinyl | —OCH₂ | CH₃O | H |
| 2-Chlor-6-trichlormethyl-4-pyrimidinyl | —OCH₂ | CH₃O | H |
| 2,6-Dichlor-4-pyrimidinyl | —OCH₂ | CH₃O | H |
| 2-Phenyl-6-trifluormethyl-4-pyrimidinyl | —OCH₂ | CH₃O | H |
| 2-Phenyl-6-trifluormethyl-4-pyrimidinyl | —SCH₂ | CH₃O | H |
| 2-Methylthio-6-difluormethoxy-4-pyrimidyl | —OCH₂ | CH₃O | H |
| 2-Methylthio-6-difluormethoxy-4-pyrimidyl | —SCH₂ | CH₃O | H |
| 2-Ethyl-6-trifluormethyl-4-pyrimidinyl | —OCH₂ | CH₃O | H |
| 2-Ethyl-6-trifluormethyl-4-pyrimidinyl | —SCH₂ | CH₃O | H |
| 2-Cyclo-propyl-6-trifluormethyl-4-pyrimidinyl | —OCH₂ | CH₃O | H |
| 2-Cyclo-propyl-6-trifluormethyl-4-pyrimidinyl | —SCH₂ | CH₃O | H |

TABLE I-continued

Structures I.1, I.2, I.3: phenyl ring with $R_n^3$ substituent and $R^4-A$ group, attached to an acrylate-type moiety with $R^1-W-C(=O)-$ and =CH- bearing CH₃ (I.1), CH₂CH₃ (I.2), or CH₂OCH₃ (I.3).

| R⁴ | A | R¹—W | R³n |
|---|---|---|---|
| 2-Phenyl-6-trifluormethyl-4-pyrimidinyl | —OCH₂ | CH₃O | H |
| 2-Phenyl-6-trifluormethyl-4-pyrimidinyl | —SCH₂ | CH₃O | H |
| 2-Methylthio-5-chloro-6-methoxy-4-pyrimidinyl | —OCH₂ | CH₃O | H |
| 2-Methylthio-5-chloro-6-methoxy-4-pyrimidinyl | —SCH₂ | CH₃O | H |
| 2-Dimethylamino-5-n-butyl-6-methyl-4-pyrimidinyl | —OCH₂ | CH₃O | H |
| 2-Dimethylamino-5-n-butyl-6-methyl-4-pyrimidinyl | —SCH₂ | CH₃O | H |
| 2-Dimethylamino-5-nitro-6-methyl-4-pyrimidinyl | —OCH₂ | CH₃O | H |
| 2-Dimethylamino-5-nitro-6-methyl-4-pyrimidinyl | —SCH₂ | CH₃O | H |
| 2-Quinolyl | —OCH₂ | CH₃O | H |
| 2-Quinolyl | —SCH₂ | CH₃O | H |
| 3-Methyl-2-quinolyl | —OCH₂ | CH₃O | H |
| 3-Methyl-2-quinolyl | —SCH₂ | CH₃O | H |
| 4-Methyl-2-quinolyl | —OCH₂ | CH₃O | H |
| 4-Methyl-2-quinolyl | —SCH₂ | CH₃O | H |
| 4-Ethyl-2-quinolyl | —OCH₂ | CH₃O | H |
| 4-Ethyl-2-quinolyl | —SCH₂ | CH₃O | H |
| 4-Phenyl-2-quinolyl | —OCH₂ | CH₃O | H |
| 4-Phenyl-2-quinolyl | —SCH₂ | CH₃O | H |
| 6-Methyl-2-quinolyl | —OCH₂ | CH₃O | H |
| 6-Methyl-2-quinolyl | —SCH₂ | CH₃O | H |
| 6-Chloro-2-quinolyl | —OCH₂ | CH₃O | H |
| 6-Chloro-2-quinolyl | —SCH₂ | CH₃O | H |
| 8-Methyl-2-quinolyl | —OCH₂ | CH₃O | H |
| 8-Methyl-2-quinolyl | —SCH₂ | CH₃O | H |
| 8-Chloro-2-quinolyl | —OCH₂ | CH₃O | H |
| 8-Chloro-2-quinolyl | —SCH₂ | CH₃O | H |
| 4-Ethoxycarbonyl-2-quinolyl | —OCH₂ | CH₃O | H |
| 4-Ethoxycarbonyl-2-quinolyl | —SCH₂ | CH₃O | H |
| 3,4-Dimethyl-2-quinolyl | —OCH₂ | CH₃O | H |
| 3,4-Dimethyl-2-quinolyl | —SCH₂ | CH₃O | H |
| 4-Methyl-8-methoxy-2-quinolyl | —OCH₂ | CH₃O | H |
| 4-Methyl-8-methoxy-2-quinolyl | —SCH₂ | CH₃O | H |
| 4-Phenyl-8-ethoxy-2-quinolyl | —OCH₂ | CH₃O | H |
| 4-Phenyl-8-ethoxy-2-quinolyl | —SCH₂ | CH₃O | H |
| 4-Methyl-8-chloro-2-quinolyl | —OCH₂ | CH₃O | H |
| 4-Methyl-8-chloro-2-quinolyl | —SCH₂ | CH₃O | H |
| 4-Methyl-8-fluoro-2-quinolyl | —OCH₂ | CH₃O | H |
| 4-Methyl-8-fluoro-2-quinolyl | —SCH₂ | CH₃O | H |
| 4-Chinolyl | —OCH₂ | CH₃O | H |
| 4-Chinolyl | —SCH₂ | CH₃O | H |
| 2-Methyl-4-quinolyl | —OCH₂ | CH₃O | H |
| 2-Methyl-4-quinolyl | —SCH₂ | CH₃O | H |
| 2-Trichloromethyl-4-quinolyl | —OCH₂ | CH₃O | H |
| 2-Trichloromethyl-4-quinolyl | —SCH₂ | CH₃O | H |
| 2-Trifluoromethyl-2-quinolyl | —OCH₂ | CH₃O | H |
| 2-Trifluoromethyl-2-quinolyl | —SCH₂ | CH₃O | H |
| 2-iso-Propyl-4-quinolyl | —OCH₂ | CH₃O | H |
| 2-iso-Propyl-4-quinolyl | —SCH₂ | CH₃O | H |
| 2-n-Pentyl-4-quinolyl | —OCH₂ | CH₃O | H |
| 2-n-Pentyl-4-quinolyl | —SCH₂ | CH₃O | H |
| 2-Phenyl-4-quinolyl | —OCH₂ | CH₃O | H |
| 2-Phenyl-4-quinolyl | —SCH₂ | CH₃O | H |
| 2-Methoxycarbonyl-4-quinolyl | —OCH₂ | CH₃O | H |
| 2-Methoxycarbonyl-4-quinolyl | —SCH₂ | CH₃O | H |
| 2,6-Dimethyl-4-quinolyl | —OCH₂ | CH₃O | H |
| 2,6-dimethyl-4-quinolyl | —SCH₂ | CH₃O | H |
| 2-Methyl-6-chloro-4-quinolyl | —OCH₂ | CH₃O | H |
| 2-Methyl-6-chloro-4-quinolyl | —SCH₂ | CH₃O | H |
| 2-Methyl-6-fluoro-4-quinolyl | —OCH₂ | CH₃O | H |
| 2-Methyl-6-fluoro-4-quinolyl | —SCH₂ | CH₃O | H |
| 8-Quinolyl | —OCH₂ | CH₃O | H |
| 8-Quinolyl | —SCH₂ | CH₃O | H |
| 2-Methyl-8-quinolyl | —OCH₂ | CH₃O | H |
| 2-Methyl-8-quinolyl | —SCH₂ | CH₃O | H |
| 5,7-Dichloro-8-quinolyl | —OCH₂ | CH₃O | H |
| 5,7-Dichloro-8-quinolyl | —SCH₂ | CH₃O | H |
| 2-Pyrazinyl | —OCH₂ | CH₃O | H |
| 2-Pyrazinyl | —SCH₂ | CH₃O | H |

TABLE I-continued

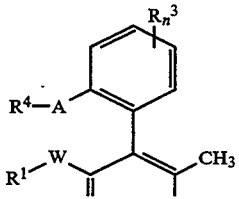 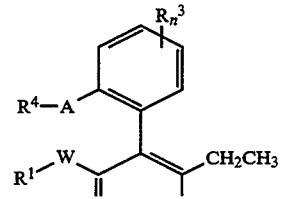 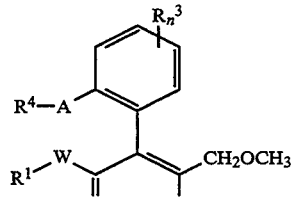

I.1        I.2        I.3

| $R^4$ | A | $R^1$—W | $R^3n$ |
|---|---|---|---|
| 6-Chlor-2-pyrazinyl | —OCH$_2$ | CH$_3$O | H |
| 6-Chlor-2-pyrazinyl | —SCH$_2$ | CH$_3$O | H |
| 5-Methyl-2-pyrazinyl | —OCH$_2$ | CH$_3$O | H |
| 5-Methyl-2-pyrazinyl | —SCH$_2$ | CH$_3$O | H |
| 3-Pyridazinyl | —OCH$_2$ | CH$_3$O | H |
| 3-Pyridazinyl | —SCH$_2$ | CH$_3$O | H |
| 5-Chlor-3-pyridazinyl | —OCH$_2$ | CH$_3$O | H |
| 5-Chlor-3-pyridazinyl | —SCH$_2$ | CH$_3$O | H |
| 2-Thienyl | —OCH$_2$ | CH$_3$O | H |
| 2-Thienyl | —SCH$_2$ | CH$_3$O | H |
| 3-Thienyl | —OCH$_2$ | CH$_3$O | H |
| 3-Thienyl | —SCH$_2$ | CH$_3$O | H |
| 4-Chlor-3-thienyl | —OCH$_2$ | CH$_3$O | H |
| 4-Chlor-3-thienyl | —SCH$_2$ | CH$_3$O | H |
| 2-Chlor-3-thienyl | —OCH$_2$ | CH$_3$O | H |
| 2-Chlor-3-thienyl | —SCH$_2$ | CH$_3$O | H |
| 5-Chlor-3-thienyl | —OCH$_2$ | CH$_3$O | H |
| 5-Chlor-3-thienyl | —SCH$_2$ | CH$_3$O | H |
| 4-Chlor-2-thienyl | —OCH$_2$ | CH$_3$O | H |
| 4-Chlor-2-thienyl | —SCH$_2$ | CH$_3$O | H |
| 5-Chlor-2-thienyl | —OCH$_2$ | CH$_3$O | H |
| 5-Chlor-2-thienyl | —SCH$_2$ | CH$_3$O | H |
| 2-Chinoxalinyl | —OCH$_2$ | CH$_3$O | H |
| 2-Chinoxalinyl | —SCH$_2$ | CH$_3$O | H |
| 3-Methyl-2-chinoxalinyl | —OCH$_2$ | CH$_3$O | H |
| 3-Methyl-2-chinoxalinyl | —SCH$_2$ | CH$_3$O | H |
| 7,8-Dimethyl-2-chinoxalinyl | —OCH$_2$ | CH$_3$O | H |
| 7,8-Dimethyl-2-chinoxalinyl | —SCH$_2$ | CH$_3$O | H |
| 7,8-Dichlor-2-chinoxalinyl | —OCH$_2$ | CH$_3$O | H |
| 7,8-Dichlor-2-chinoxalinyl | —SCH$_2$ | CH$_3$O | H |
| 7-Methyl-2-chinoxalinyl | —OCH$_2$ | CH$_3$O | H |
| 7-Methyl-2-chinoxalinyl | —SCH$_2$ | CH$_3$O | H |
| 8-Methyl-2-chinoxalinyl | —OCH$_2$ | CH$_3$O | H |
| 8-Methyl-2-chinoxalinyl | —SCH$_2$ | CH$_3$O | H |
| 7-Methoxy-2-chinoxalinyl | —OCH$_2$ | CH$_3$O | H |
| 7-Methoxy-2-chinoxalinyl | —SCH$_2$ | CH$_3$O | H |
| 3-Phenyl-5-isoxazolyl | —OCH$_2$ | CH$_3$O | H |
| 3-Phenyl-5-isoxazolyl | —SCH$_2$ | CH$_3$O | H |
| 2-Benzoxazolyl | —OCH$_2$ | CH$_3$O | H |
| 2-Benzoxazolyl | —SCH$_2$ | CH$_3$O | H |
| 2-Benzthiazolyl | —OCH$_2$ | CH$_3$O | H |
| 2-Benzthiazolyl | —SCH$_2$ | CH$_3$O | H |
| 2-Benzimidazolyl | —SCH$_2$ | CH$_3$O | H |
| 6-Ethoxy-2-benzthiazolyl | —SCH$_2$ | CH$_3$O | H |
| 5-MeCO-2-benzthiazolyl | —SCH$_2$ | CH$_3$O | H |
| 5-Trifluormethyl-2-benzthiazolyl | —SCH$_2$ | CH$_3$O | H |
| 6-Chlor-4-methyl-2-benzthiazolyl | —SCH$_2$ | CH$_3$O | H |
| 5-Amino-2-benzthiazolyl | —SCH$_2$ | CH$_3$O | H |
| 4-Chlor-2-benzthiazolyl | —SCH$_2$ | CH$_3$O | H |
| 5-Methyl-2-benzthiazolyl | —SCH$_2$ | CH$_3$O | H |
| 7-Chlor-2-benzthiazolyl | —SCH$_2$ | CH$_3$O | H |
| 6-Chlor-2-benzthiazolyl | —SCH$_2$ | CH$_3$O | H |
| 5-Brom-2-benzthiazolyl | —SCH$_2$ | CH$_3$O | H |
| 7-Chlor-4-methoxy-2-benzthiazolyl | —SCH$_2$ | CH$_3$O | H |
| 4,6,7-Trichlor-2-benzthiazolyl | —SCH$_2$ | CH$_3$O | H |
| 6-Propyl-2-benzthiazolyl | —SCH$_2$ | —CH$_3$O | H |
| 6-Phenoxy-2-benzthiazolyl | —SCH$_2$ | CH$_3$O | H |
| 5-PhCONH-2-benzthiazolyl | —SCH$_2$ | CH$_3$O | H |
| 6-PhCH=N-2-benzthiazolyl | —SCH$_2$ | CH$_3$O | H |
| 5-MeCONH-2-benzthiazolyl | —SCH$_2$ | CH$_3$O | H |
| 5-Methyl-2-benzoxazolyl | —SCH$_2$ | CH$_3$O | H |
| 5-Chlor-2-benzoxazolyl | —SCH$_2$ | CH$_3$O | H |
| 5-Nitro-2-benzoxazolyl | —SCH$_2$ | CH$_3$O | H |
| 5-tert.-Butyl-2-benzoxazolyl | —SCH$_2$ | CH$_3$O | H |
| 5,7-Dimethyl-2-benzoxazolyl | —SCH$_2$ | CH$_3$O | H |
| 6-Methyl-2-benzoxazolyl | —SCH$_2$ | CH$_3$O | H |
| 5-Chlor-2-benzthiazolyl | —SCH$_2$ | CH$_3$O | H |
| 5-Trifluormethyl-2-benzimidazolyl | —SCH$_2$ | CH$_3$O | H |

TABLE I-continued

Structures I.1, I.2, I.3 (from left to right): phenyl ring bearing $R^3_n$ substituents and $R^4$–A group, connected to an acrylate moiety $R^1$–W–C(=O)–C=CH–X, where X = CH$_3$ (I.1), CH$_2$CH$_3$ (I.2), or CH$_2$OCH$_3$ (I.3).

| R⁴ | A | R¹—W | R³n |
|---|---|---|---|
| 5,6-Dichlor-2-benzimidazolyl | —SCH₂ | CH₃O | H |
| 1-Propyl-2-benzimidazolyl | —SCH₂ | CH₃O | H |
| 1-Methyl-5-methylthio-2-benzimidazolyl | —SCH₂ | CH₃O | H |
| 1-iso-Propyl-2-benzimidazolyl | —SCH₂ | CH₃O | H |
| 5-Brom-2-benzimidazolyl | —SCH₂ | CH₃O | H |
| 5-Chlor-2-benzimidazolyl | —SCH₂ | CH₃O | H |
| 5-Chlor-1-methyl-2-benzimidazolyl | —SCH₂ | CH₃O | H |
| 5-Ethylthio-1-methyl-2-benzimidazolyl | —SCH₂ | CH₃O | H |
| 1-Methyl-2-imidazolyl | —SCH₂ | CH₃O | H |
| 4-tert.-Butyl-2-imidazolyl | —SCH₂ | CH₃O | H |
| 1-Phenyl-5-tetrazolyl | —SCH₂ | CH₃O | H |
| 1-(3-NO2—Ph)-5-tetrazolyl | —SCH₂ | CH₃O | H |
| 5-Phenyl-2-thiazolyl | —SCH₂ | CH₃O | H |
| 4-(4-Cl—Ph)-2-thiazolyl | —SCH₂ | CH₃O | H |
| 4-(4-Me—Ph)-2-thiazolyl | —SCH₂ | CH₃O | H |
| 4-Phenyl-1-thiazolyl | —SCH₂ | CH₃O | H |
| 5-Methyl-4-phenyl-2-thiazolyl | —SCH₂ | CH₃O | H |
| 4-Methyl-5-phenyl-2-thiazolyl | —SCH₂ | CH₃O | H |
| 1-Phenyl-1,2,4-triazol-4-yl | —SCH₂ | CH₃O | H |
| 3-Phenyl-1,2,4-thiadiazol-5-yl | —SCH₂ | CH₃O | H |
| 5-Propargylthio-1,3,4-thiadiazol-2-yl | —SCH₂ | CH₃O | H |
| 6-Chlor-oxazolo[4,5-b]pyridin-2-yl | —SCH₂ | CH₃O | H |
| 2-H-1,4-benzoxazin-3-yl | —SCH₂ | CH₃O | H |
| 2-H-1,4-benzthiazin-3-yl | —SCH₂ | CH₃O | H |
| 1,2,4-Triazin-3-yl | —SCH₂ | CH₃O | H |
| 5-Phenyl-1,2,4-triazin-2-yl | —SCH₂ | CH₃O | H |
| 4-Oxo-3,4-dihydropyrimidin-2-yl | —SCH₂ | CH₃O | H |
| 4-Oxo-3,4-dihydrochinazolin-2-yl | —SCH₂ | CH₃O | H |
| 4,5-Dimethyl-2-thiazolyl | —SCH₂ | CH₃O | H |
| 5-Phenyl-1,3,4-thiadiazol-2-yl | —SCH₂ | CH₃O | H |
| 5-Phenyl-1,3,4-thiadiazol-2-yl | —SCH₂ | CH₃O | H |
| 5-Phenyl-1,3,4-oxadiazol-2-yl | —SCH₂ | CH₃O | H |
| 1-Phenyl-pyrazol-4-yl | —OCH₂ | CH₃O | H |
| 2-n-Propyl-6-methyl-4-pyrimidinyl | —OCH₂ | CH₃O | H |
| 2-n-Propyl-6-methyl-4-pyrimidinyl | —SCH₂ | CH₃O | H |
| 2-Cyclopentyl-6-trifluormethyl-4-pyrimidyl | —OCH₂ | CH₃O | H |
| 2-Cyclopentyl-6-trifluormethyl-4-pyrimidyl | —SCH₂ | CH₃O | H |
| 2-Cyclohexyl-6-triflormethyl-4-pyrimidyl | —OCH₂ | CH₃O | H |
| 2-Cyclohexyl-6-triflormethyl-4-pyrimidyl | —SCH₂ | CH₃O | H |
| 2-Cyclohexyl-5-chlor-6-methyl-4-pyrimidyl | —OCH₂ | CH₃O | H |
| 2-Cyclohexyl-5-chlor-6-methyl-4-pyrimidyl | —SCH₂ | CH₃O | H |
| 2-n-Propyl-5-chlor-6-methyl-4-pyrimidyl | —OCH₂ | CH₃O | H |
| 2-n-Propyl-5-chlor-6-methyl-4-pyrimidyl | —SCH₂ | CH₃O | H |
| 1,2,3-Triazin-6-yl | —SCH₂ | CH₃O | H |
| 1,2,3-Triazin-5-yl | —SCH₂ | CH₃O | H |
| 1,2,4-Triazin-6-yl | —SCH₂ | CH₃O | H |
| 1,3,5-Triazin-2-yl | —SCH₂ | CH₃O | H |
| 1,2,4,5-Tetrazin-2-yl | —SCH₂ | CH₃O | H |
| 1-Benzothiophen-3-yl | —SCH₂ | CH₃O | H |
| 6-Chlorchinazolin-2-yl | —SCH₂ | CH₃O | H |
| Pyrazol-1-yl | —OCH₂ | CH₃O | H |
| 5-Chlorpyrazol-1-yl | —OCH₂ | CH₃O | H |
| 3,5-Dimethylpyrazol-1-yl | —OCH₂ | CH₃O | H |
| 1,2-Benzisoxazol-3-yl | —OCH₂ | CH₃O | H |
| 1-(4-Chlorphenyl)-pyrazol-4-yl | —OCH₂ | CH₃O | H |
| 1-(4-Methylphenyl)-pyrazol-4-yl | —OCH₂ | CH₃O | H |
| 1-Phenylpyrazol-4-yl | —OCH₂ | CH₃O | H |
| 5-Chlor-2-benzthiazolyl | —SCH₂ | CH₃O | H |
| 5-Methyl-1,3,4-thiadiazol-2-yl | —SCH₂ | CH₃O | H |
| 2-Thiazolin-2-yl | —SCH₂ | CH₃O | H |
| 1-Methyl-3-trifluormethylpyrazol-5-yl | —OCH₂ | CH₃O | H |
| 1-(4-Fluorphenyl)-pyrazol-4-yl | —OCH₂ | CH₃O | H |
| 5-Phenylisoxazol-3-yl | —OCH₂ | CH₃O | H |
| Benztriazol-1-yl | —OCH₂ | CH₃O | H |

TABLE 2

Structures I.1, I.2, I.3 (aromatic ring with $R_n^3$, $R^4-A$ substituent, and acrylate with $CH_3$, $CH_2CH_3$, $CH_2OCH_3$ groups respectively, $R^1-W-C(=O)-$)

| R⁴ | A | R¹-W | R³n |
|---|---|---|---|
| 3-Fluoropyridin-2-yl | O | CH₃O | H |
| 3-Fluoropyridin-2-yl | S | CH₃O | H |
| 3-Chloropyridin-2-yl | O | CH₃O | H |
| 2-Chloropyridin-2-yl | S | CH₃O | H |
| 3-Bromopyridin-2-yl | O | CH₃O | H |
| 3-Bromopyridin-2-yl | S | CH₃O | H |
| 3-Methylpyridin-2-yl | O | CH₃O | H |
| 3-Methylpyridin-2-yl | S | CH₃O | H |
| 3-Trifluoromethylpyridin-2-yl | O | CH₃O | H |
| 3-Trifluoromethylpyridin-2-yl | S | CH₃O | H |
| 3-Methoxypyridin-2-yl | O | CH₃O | H |
| 3-Methoxypyridin-2-yl | S | CH₃O | H |
| 4-Fluoropyridin-2-yl | O | CH₃O | H |
| 4-Fluoropyridin-2-yl | S | CH₃O | H |
| 4-Chloropyridin-2-yl | O | CH₃O | H |
| 4-Chloropyridin-2-yl | S | CH₃O | H |
| 4-Bromopyridin-2-yl | O | CH₃O | H |
| 4-Bromopyridin-2-yl | S | CH₃O | H |
| 4-Methylpyridin-2-yl | O | CH₃O | H |
| 4-Methylpyridin-2-yl | S | CH₃O | H |
| 4-Trifluoromethylpyridin-2-yl | O | CH₃O | H |
| 4-Trifluoromethylpyridin-2-yl | S | CH₃O | H |
| 4-Methoxypyridin-2-yl | O | CH₃O | H |
| 4-Methoxypyridin-2-yl | S | CH₃O | H |
| 5-Fluoropyridin-2-yl | O | CH₃O | H |
| 5-Fluoropyridin-2-yl | S | CH₃O | H |
| 5-Chloropyridin-2-yl | O | CH₃O | H |
| 5-Chloropyridin-2-yl | S | CH₃O | H |
| 5-Bromopyridin-2-yl | O | CH₃O | H |
| 5-Bromopyridin-2-yl | S | CH₃O | H |
| 5-Methylpyridin-2-yl | O | CH₃O | H |
| 5-Methylpyridin-2-yl | S | CH₃O | H |
| 5-Methoxypyridin-2-yl | O | CH₃O | H |
| 5-Methoxypyridin-2-yl | S | CH₃O | H |
| 6-Fluoropyridin-2-yl | O | CH₃O | H |
| 6-Fluoropyridin-2-yl | S | CH₃O | H |
| 6-Chloropyridin-2-yl | O | CH₃O | H |
| 6-Chloropyridin-2-yl | S | CH₃O | H |
| 6-Bromopyridin-2-yl | O | CH₃O | H |
| 6-Bromopyridin-2-yl | S | CH₃O | H |
| 6-Methylpyridin-2-yl | O | CH₃O | H |
| 6-Methylpyridin-2-yl | S | CH₃O | H |
| 6-Trifluoromethylpyridin-2-yl | O | CH₃O | H |
| 6-Trifluoromethylpyridin-2-yl | S | CH₃O | H |
| 6-Methoxypyridin-2-yl | O | CH₃O | H |
| 6-Methoxypyridin-2-yl | S | CH₃O | H |
| 2-Fluoropyridin-3-yl | O | CH₃O | H |
| 2-Fluoropyridin-3-yl | S | CH₃O | H |
| 2-Chloropyridin-3-yl | O | CH₃O | H |
| 2-Chloropyridin-3-yl | S | CH₃O | H |
| 2-Bromopyridin-3-yl | O | CH₃O | H |
| 2-Bromopyridin-3-yl | S | CH₃O | H |
| 2-Methylpyridin-3-yl | O | CH₃O | H |
| 2-Methylpyridin-3-yl | S | CH₃O | H |
| 2-Trifluoromethylpyridin-3-yl | O | CH₃O | H |
| 2-Trifluoromethylpyridin-3-yl | S | CH₃O | H |
| 3-Methoxypyridin-3-yl | O | CH₃O | H |
| 3-Methoxypyridin-3-yl | S | CH₃O | H |
| 4-Fluoropyridin-3-yl | O | CH₃O | H |
| 4-Fluoropyridin-3-yl | S | CH₃O | H |
| 4-Chloropyridin-3-yl | O | CH₃O | H |
| 4-Chloropyridin-3-yl | S | CH₃O | H |
| 4-Bromopyridin-3-yl | O | CH₃O | H |
| 4-Bromopyridin-3-yl | S | CH₃O | H |
| 4-Methylpyridin-3-yl | O | CH₃O | H |
| 4-Methylpyridin-3-yl | S | CH₃O | H |
| 4-Trifluoromethylpyridin-3-yl | O | CH₃O | H |
| 4-Trifluoromethylpyridin-3-yl | S | CH₃O | H |

TABLE 2-continued

| R⁴ | A | R¹-W | R³n |
|---|---|---|---|
| 4-Methoxypyridin-3-yl | O | CH₃O | H |
| 4-Methoxypyridin-3-yl | S | CH₃O | H |
| 5-Fluoropyridin-3-yl | O | CH₃O | H |
| 5-Fluoropyridin-3-yl | S | CH₃O | H |
| 5-Chloropyridin-3-yl | O | CH₃O | H |
| 5-Chloropyridin-3-yl | S | CH₃O | H |
| 5-Bromopyridin-3-yl | O | CH₃O | H |
| 5-Bromopyridin-3-yl | S | CH₃O | H |
| 5-Methylpyridin-3-yl | O | CH₃O | H |
| 5-Methylpyridin-3-yl | S | CH₃O | H |
| 5-Trifluoromethylpyridin-3-yl | O | CH₃O | H |
| 5-Trifluoromethylpyridin-3-yl | S | CH₃O | H |
| 5-Methoxypyridin-3-yl | O | CH₃O | H |
| 5-Methoxypyridin-3-yl | S | CH₃O | H |
| 6-Fluoropyridin-3-yl | O | CH₃O | H |
| 6-Fluoropyridin-3-yl | S | CH₃O | H |
| Pyridin-2-yl | O | CH₃O | H |
| Pyridin-2-yl | S | CH₃O | H |
| Pyridin-3-yl | O | CH₃O | H |
| Pyridin-3-yl | S | CH₃O | H |
| Pyridin-4-yl | O | CH₃O | H |
| Pyridin-4-yl | S | CH₃O | H |
| 6-Chloropyridin-3yl | O | CH₃O | H |
| 6-Chloropyridin-3-yl | S | CH₃O | H |
| 6-Bromopyridin-3-yl | O | CH₃O | H |
| 6-Bromopyridin-3-yl | S | CH₃O | H |
| 6-Methylpyridin-3-yl | O | CH₃O | H |
| 6-Methylpyridin-3-yl | S | CH₃O | H |
| 6-Trifluoromethylpyridin-3-yl | O | CH₃O | H |
| 6-Trifluoromethylpyridin-3-yl | S | CH₃O | H |
| 6-Methoxypyridin-3-yl | O | CH₃O | H |
| 6-Methoxypyridin-3-yl | S | CH₃O | H |
| 2-Fluoropyridin-4-yl | O | CH₃O | H |
| 2-Fluoropyridin-4-yl | S | CH₃O | H |
| 2-Chloropyridin-4-yl | O | CH₃O | H |
| 6-Chloropyridin-4-yl | S | CH₃O | H |
| 2-Bromopyridin-4-yl | O | CH₃O | H |
| 2-Bromopyridin-4-yl | S | CH₃O | H |
| 2-Methylpyridin-4-yl | O | CH₃O | H |
| 2-Methylpyridin-4-yl | S | CH₃O | H |
| 2-Trifluoromethylpyridin-4-yl | O | CH₃O | H |
| 2-Trifluoromethylpyridin-4-yl | S | CH₃O | H |
| 2-Methoxypyridin-4-yl | O | CH₃O | H |
| 2-Methoxypyridin-4-yl | S | CH₃O | H |
| 3-Fluoropyridin-4-yl | O | CH₃O | H |
| 3-Fluoropyridin-4-yl | S | CH₃O | H |
| 3-Chloropyridin-4-yl | O | CH₃O | H |
| 3-Chloropyridin-4-yl | S | CH₃O | H |
| 3-Bromopyridin-4-yl | O | CH₃O | H |
| 3-Bromopyridin-4-yl | S | CH₃O | H |
| 3-Methylpyridin-4-yl | O | CH₃O | H |
| 3-Methylpyridin-4-yl | S | CH₃O | H |
| 3-Trifluoromethylpyridin-4-yl | O | CH₃O | H |
| 3-Trifluoromethylpyridin-4-yl | S | CH₃O | H |
| 3-Methoxypyridin-4-yl | O | CH₃O | H |
| 3-Methoxypyridin-4-yl | S | CH₃O | H |
| 4-Fluoropyrimidin-2-yl | O | CH₃O | H |
| 4-Fluoropyrimidin-2-yl | S | CH₃O | H |
| 4-Chloropyrimidin-2-yl | O | CH₃O | H |
| 4-Chloropyrimidin-2-yl | S | CH₃O | H |
| 4-Bromopyrimidin-2-yl | O | CH₃O | H |
| 4-Bromopyrimidin-2-yl | S | CH₃O | H |
| 4-Methylpyrimidin-2-yl | O | CH₃O | H |
| 4-Methylpyrimidin-2-yl | S | CH₃O | H |
| 4-Trifluoromethylpyrimidin-2-yl | O | CH₃O | H |
| 4-Trifluoromethylpyrimidin-2-yl | S | CH₃O | H |
| 4-Methoxypyrimidin-2-yl | O | CH₃O | H |
| 4-Methoxypyrimidin-2-yl | S | CH₃O | H |

TABLE 2-continued

Structures I.1, I.2, I.3 with R⁴—A substituent on benzene ring bearing R³ₙ, and vinyl group with CH₃ (I.1), CH₂CH₃ (I.2), or CH₂OCH₃ (I.3) and R¹-W-C(=O)- group.

| R⁴ | A | R¹-W | R³n |
|---|---|---|---|
| 5-Fluoropyrimidin-2-yl | O | CH₃O | H |
| 5-Fluoropyrimidin-2-yl | S | CH₃O | H |
| 5-Chloropyrimidin-2-yl | O | CH₃O | H |
| 5-Chloropyrimidin-2-yl | S | CH₃O | H |
| 5-Bromopyrimidin-2-yl | O | CH₃O | H |
| 5-Bromopyrimidin-2-yl | S | CH₃O | H |
| 5-Methylpyrimidin-2-yl | O | CH₃O | H |
| 5-Methylpyrimidin-2-yl | S | CH₃O | H |
| 5-Trifluoromethylpyrimidin-2-yl | O | CH₃O | H |
| 5-Trifluoromethylpyrimidin-2-yl | S | CH₃O | H |
| 5-Methoxypyrimidin-2-yl | O | CH₃O | H |
| 5-Methoxypyrimidin-2-yl | S | CH₃O | H |
| 2-Fluoropyrimidin-4-yl | O | CH₃O | H |
| 2-Fluoropyrimidin-4-yl | S | CH₃O | H |
| 2-Chloropyrimidin-4-yl | O | CH₃O | H |
| 2-Chloropyrimidin-4-yl | S | CH₃O | H |
| 2-Bromopyrimidin-4-yl | O | CH₃O | H |
| 2-Bromopyrimidin-4-yl | S | CH₃O | H |
| 2-Methylpyrimidin-4-yl | O | CH₃O | H |
| 2-Methylpyrimidin-4-yl | S | CH₃O | H |
| 2-Trifluoromethylpyrimidin-4-yl | O | CH₃O | H |
| 2-Trifluoromethylpyrimidin-4-yl | S | CH₃O | H |
| 2-Methoxypyrimidin-4-yl | O | CH₃O | H |
| 2-Methoxypyrimidin-4-yl | S | CH₃O | H |
| 5-Fluropyrimidin-4-yl | O | CH₃O | H |
| 5-Fluropyrimidin-4-yl | S | CH₃O | H |
| 5-Chloropyrimidin-4-yl | O | CH₃O | H |
| 5-Chloropyrimidin-4-yl | S | CH₃O | H |
| 5-Bromopyrimidin-4-yl | O | CH₃O | H |
| 5-Bromopyrimidin-4-yl | S | CH₃O | H |
| 5-Methoxypyrimidin-4-yl | O | CH₃O | H |
| 5-Methoxypyrimidin-4-yl | S | CH₃O | H |
| 5-Trifluoromethylpyrimidin-4-yl | O | CH₃O | H |
| 5-Trifluoromethylpyrimidin-4-yl | S | CH₃O | H |
| 5-Methoxypyrimidin-4-yl | O | CH₃O | H |
| 5-Methoxypyrimidin-4-yl | S | CH₃O | H |
| 6-Fluoropyrimidin-4-yl | O | CH₃O | H |
| 6-Fluoropyrimidin-4-yl | S | CH₃O | H |
| 6-Chloropyrimidin-4-yl | O | CH₃O | H |
| 6-Chloropyrimidin-4-yl | S | CH₃O | H |
| 6-Bromopyrimidin-4-yl | O | CH₃O | H |
| 6-Bromopyrimidin-4-yl | S | CH₃O | H |
| 6-Methylpyrimidin-4-yl | O | CH₃O | H |
| 6-Methylpyrimidin-4-yl | S | CH₃O | H |
| 6-Trifluoromethylpyrimidin-4-yl | O | CH₃O | H |
| 6-Trifluoromethylpyrimidin-4-yl | S | CH₃O | H |
| 6-Methoxypyrimidin-4-yl | O | CH₃O | H |
| 6-Methoxypyrimidin-4-yl | S | CH₃O | H |
| 2-Fluoropyrimidin-5-yl | O | CH₃O | H |
| 2-Fluoropyrimidin-5-yl | S | CH₃O | H |
| 2-Chlorpyrimidin-5-yl | O | CH₃O | H |
| 2-Chlorpyrimidin-5-yl | S | CH₃O | H |
| 2-Bromopyrimidin-5-yl | O | CH₃O | H |
| 2-Bromopyrimidin-5-yl | S | CH₃O | H |
| 2-Methylpyrimidin-5-yl | O | CH₃O | H |
| 2-Methylpyrimidin-5-yl | S | CH₃O | H |
| 2-Trifluoromethylpyrimidin-5-yl | O | CH₃O | H |
| 2-Trifluoromethylpyrimidin-5-yl | S | CH₃O | H |
| 2-Methoxypyrimidin-5-yl | O | CH₃O | H |
| 2-Methoxypyrimidin-5-yl | S | CH₃O | H |
| 4-Fluoropyrimidin-5-yl | O | CH₃O | H |
| 4-Fluoropyrimidin-5-yl | S | CH₃O | H |
| 4-Chloropyrimidin-5-yl | O | CH₃O | H |
| 4-Chloropyrimidin-5-yl | S | CH₃O | H |
| 4-Bromopyrimidin-5-yl | O | CH₃O | H |
| 4-Bromopyrimidin-5-yl | S | CH₃O | H |
| 4-Methylpyrimidin-5-yl | O | CH₃O | H |
| 4-Methylpyrimidin-5-yl | S | CH₃O | H |

TABLE 2-continued

Structures:
- I.1: R⁴—A—(phenyl with R³ₙ)—C(=C(H)CH₃)—C(=O)—W—R¹
- I.2: R⁴—A—(phenyl with R³ₙ)—C(=C(H)CH₂CH₃)—C(=O)—W—R¹
- I.3: R⁴—A—(phenyl with R³ₙ)—C(=C(H)CH₂OCH₃)—C(=O)—W—R¹

| R⁴ | A | R¹-W | R³n |
|---|---|---|---|
| 4-Trifluoromethylpyrimidin-5-yl | O | CH₃O | H |
| 4-Trifluoromethylpyrimidin-5-yl | S | CH₃O | H |
| 4-Methoxypyrimidin-5-yl | S | CH₃O | H |
| 4-Fluoro-5-trifluoromethylpyridin-2yl | O | CH₃O | H |
| 3,6-Dichloro-5-trifluoromethylpyridin-2-yl | O | CH₃O | H |
| 5,6-Dichloro-3-trifluoromethylpyridin-2-yl | O | CH₃O | H |
| 5-Chloro-3-trifluoromethylpyridin-2-yl | O | CH₃O | H |
| 3-Chloro-5-trifluoromethylpyridin-2-yl | O | CH₃O | H |
| 6-Chloro-4-cyanopyridin-2-yl | O | CH₃O | H |
| 3-Cyano-5nitropyridin-2-yl | O | CH₃O | H |
| 2-Chloro-6-fluoropyridin-4-yl | O | CH₃O | H |
| 6-Chloro-4-fluoropyridin-2-yl | O | CH₃O | H |
| 4,6-Difluoropyridin-2-yl | O | CH₃O | H |
| 3,5-Dichloro-6-fluoropyridin-2-yl | O | CH₃O | H |
| 6-Methoxy-3-nitropyridin-2-yl | O | CH₃O | H |
| 4-Cyano-6-fluoropyridin-2-yl | O | CH₃O | H |
| 6-Chloro-5-cyanopyridin-2-yl | O | CH₃O | H |
| 6-Chloro-3-cyanopyridin-2-yl | O | CH₃O | H |
| 4-Cyano-3,5,6-trifluoropyridin-2-yl | O | CH₃O | H |
| 6-Chloro-5-nitropyridin-2-yl | O | CH₃O | H |
| 6-Chloro-3-nitropyridin-2-yl | O | CH₃O | H |
| 5-Cyano-6-fluoropyridin-2-yl | O | CH₃O | H |
| 3-Cyano-6-fluoropyridin-2-yl | O | CH₃O | H |
| 4,6-Dicyanopyridin-2-yl | O | CH₃O | H |
| 5-Trichloromethylpyridin-2-yl | O | CH₃O | H |
| 5-Cyanopyridin-2-yl | O | CH₃O | H |
| 5-Bromo-4-trifluoromethylpyridin-2-yl | O | CH₃O | H |
| 3-Nitro-5-trifluoromethylpyridin-2-yl | O | CH₃O | H |
| 5-Formamidopyridin-2-yl | O | CH₃O | H |
| 5-Aminopyridin-2-yl | O | CH₃O | H |
| 2,3,5,6-Tetrafluoropyridin-4-yl | O | CH₃O | H |
| 5-Nitropyridin-2-yl | O | CH₃O | H |
| 4-Methyl-5-nitroypridin-2-yl | O | CH₃O | H |
| 5-Difluoromethylpyridin-2-yl | O | CH₃O | H |
| 5-Fluoromethylpyridin-2-yl | O | CH₃O | H |
| 4,6-Difluoropyrimidin-2-yl | O | CH₃O | H |
| 2,6-Difluoropyrimidin-4-yl | O | CH₃O | H |
| 2-Chloro-6-trichloromethylpyrimidin-4-yl | O | CH₃O | H |
| 2,6-Dichloropyrimidin-4-yl | O | CH₃O | H |
| 5-Methoxycarbonylpyrdin-2-yl | O | CH₃O | H |
| 5-Chloro-6-fluoropyridin-2-yl | O | CH₃O | H |
| 5-Chloro-6-hydroxypyridin-2-yl | O | CH₃O | H |
| 5-Chloro-6methoxypyridin-2-yl | O | CH₃O | H |
| 5-Chloro-6-cyanopyridin-2-yl | O | CH₃O | H |
| 5,6-Dichloropyridin-2-yl | O | CH₃O | H |
| 6-Bromo-5-chloropyridin-2-yl | O | CH₃O | H |
| 5-Chloro-6-acetoxypyridin-2-yl | O | CH₃O | H |
| 5-Bromo-6-fluoropyridin-2-yl | O | CH₃O | H |
| 5-Bromo-6-chloropyridin-2-yl | O | CH₃O | H |
| 5-Bromo-6-cyanopyridin-2-yl | O | CH₃O | H |
| 5-Bromo-6-hydroxypyridin-2-yl | O | CH₃O | H |
| 5-Bromo-6-methoxypyridin-2-yl | O | CH₃O | H |
| 5,6-Dibromopyridin-2-yl | O | CH₃O | H |
| 4-Cyanopyridin-2-yl | O | CH₃O | H |
| 6-Cyanopyridin-2-yl | O | CH₃O | H |
| 5-Chloropyridin-2-yl | O | CH₃O | H |
| 5-Chloropyridin-2-yl | S | CH₃O | H |
| 4-Chloro-6-methylpyrimidin-2-yl | O | CH 3O | H |
| 2-Choro-6-fluoropyridin-4-yl | O | CH₃O | H |
| 5-Bromo-4-trifluoromethylpyridin-2-yl | O | CH₃O | H |
| 4,5-Dichlorpyridin-2-yl | O | CH₃O | H |
| 4,5-Dibromopyridin-2-yl | O | CH₃O | H |
| 5,6-Dichlorpyridin-2-yl | O | CH₃O | H |
| 4,6-Dichloropyridin-2-yl | O | CH₃O | H |
| 4,6-Dibromopyridin-2-yl | O | CH₃O | H |
| 5,6-Dibromopyridin-2-yl | O | CH₃O | H |
| 4-Bromo-5-chloropyridin-2-yl | O | CH₃O | H |
| 6-Bromo-5-chloropyridin-2-yl | O | CH₃O | H |

TABLE 2-continued

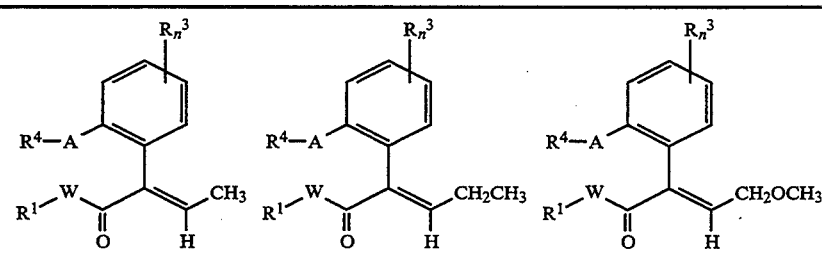

| R⁴ | A | R¹-W | R³n |
|---|---|---|---|
| 5-Bromo-4-chloropyridin-2-yl | O | CH₃O | H |
| 5-Bromo-4-chloropyridin-2-yl | O | CH₃O | H |
| 6-Bromo-4-chloropyridin-2-yl | O | CH₃O | H |
| 4-Bromo-6-chloropyridin-2-yl | O | CH₃O | H |
| 6-Chloro-4-methoxypyridin-2-yl | O | CH₃O | H |
| 6-Bromo-4-methoxypyridin-2-yl | O | CH₃O | H |
| 6-Chlorchinazolin-2-yl | O | CH₃O | H |
| Chinazolin-2-yl | O | CH₃O | H |
| 5-Benzyloxycarbonylpyridin-2-yl | O | CH₃O | H |
| 4-Fomylpyridin-2-yl | O | CH₃O | H |
| 5-Fomylpyridin-2-yl | O | CH₃O | H |
| 6-Fomylpyridin-2-yl | O | CH₃O | H |
| 4-Cyanopyridin-2-yl | O | CH₃O | H |
| 6-Cyanopyridin-2-yl | O | CH₃O | H |
| 5-Hydroxymethylpyridin-2-yl | O | CH₃O | H |
| 6-Chloro-4-trifluoromethylpyridin-2-yl | O | CH₃O | H |
| 6-Chloro-4-trifluoromethylpyridin-2-yl | O | CH₃O | H |
| 6-Chloro-4-methylpyridin-2-yl | O | CH₃O | H |
| 2,5-Dichloro-6-cyanopyridin-2-yl | O | CH₃O | H |
| 2,5-Dichloro-6-carboxypyridin-2-yl | O | CH₃O | H |
| 2,5-Dichloro-6-methoxycarbonyl-pyridin-2-yl | O | CH₃O | H |
| 4-Cyanopyridin-2-yl | O | CH₃O | H |
| 6-Trifluoromethylpyridin-2-yl | O | CH₃O | H |
| 6-Methoxycarbonylpyridin-2-yl | O | CH₃O | H |
| 6-Carboxypyridin-2-yl | O | CH₃O | H |
| 4-Phenoxypyridin-2-yl | O | CH₃O | H |
| 5-Phenoxypyridin-2-yl | O | CH₃O | H |
| 6-Phenoxypyridin-2-yl | O | CH₃O | H |
| 6-Chloropyridin-3-yl | O | CH₃O | H |
| 1-Phenoxypyrimidin-4-yl | O | CH₃O | H |
| 1-(4-Methylphenoxy)pyrimidin-4-yl | O | CH₃O | H |
| 4-Phenoxypyrimidin-2-yl | O | CH₃O | H |
| 4-(2-Fluorphenoxy)-pyrimidin-2-yl | O | CH₃O | H |
| 4-Phenoxypyrimidin-6-yl | O | CH₃O | H |
| 4-(4-Chlorphenoxy)pyrimidin-6-yl | O | CH₃O | H |
| 4-(2-Pyridyloxy)pyrimidin-6-yl | O | CH₃O | H |
| 4-(6-Chlor-2-pyridyloxy)pyrimidin-6-yl | O | CH₃O | H |
| 4-(3-Pyridyloxy)pyrimidin-6-yl | O | CH₃O | H |
| 4-(2-Methyl-3-pyridyloxy)pyrimidin-6-yl | O | CH₃O | H |
| 4-(4-Pyridyloxy)pyrimidin-6-yl | O | CH₃O | H |
| 2-Furanyl | O | CH₃O | H |
| 2-Furanyl | S | CH₃O | H |
| 3-Furanyl | O | CH₃O | H |
| 3-Furanyl | S | CH₃O | H |
| 2-Thienyl | O | CH₃O | H |
| 2-Thienyl | S | CH₃O | H |
| 4-Chlor-2-thienyl | O | CH₃O | H |
| 4-Chlor-2-thienyl | S | CH₃O | H |
| 5-Chlor-2-thienyl | O | CH₃O | H |
| 5-Chlor-2-thienyl | S | CH₃O | H |
| 5-Brom-2-thienyl | O | CH₃O | H |
| 5-Brom-2-thienyl | S | CH₃O | H |
| 5-Nitro-2-thienyl | O | CH₃O | H |
| 5-Nitro-2-thienyl | S | CH₃O | H |
| 3-Thienyl | O | CH₃O | H |
| 3-Thienyl | S | CH₃O | H |
| 2-Chlor-3-thienyl | O | CH₃O | H |
| 2-Chlor-3-thienyl | S | CH₃O | H |
| 2-Brom-3-thienyl | O | CH₃O | H |
| 2-Brom-3-thienyl | S | CH₃O | H |
| 1-Methyl-3-pyrrolyl | O | CH₃O | H |
| 1-Methyl-3-pyrrolyl | S | CH₃O | H |
| 1-Methyl-2-pyrrolyl | O | CH₃O | H |
| 1-Methyl-2-pyrrolyl | S | CH₃O | H |
| 1-Benzofuran-2-yl | O | CH₃O | H |
| 1-Benzofuran-2-yl | S | CH₃O | H |
| 1-Benzofuran-3-yl | O | CH₃O | H |
| 1-Benzofuran-3-yl | S | CH₃O | H |

TABLE 2-continued

Structures I.1, I.2, I.3 with substituents $R^3_n$, $R^4$–A, $R^1$–W, CH$_3$/CH$_2$CH$_3$/CH$_2$OCH$_3$

| R$^4$ | A | R$^1$-W | R$^3$n |
|---|---|---|---|
| 1-Benzothiophen-2-yl | O | CH$_3$O | H |
| 1-Benzothiophen-2-yl | S | CH$_3$O | H |
| 1-Benzothiophen-3-yl | O | CH$_3$O | H |
| 1-Benzothiophen-3-yl | S | CH$_3$O | H |
| 3-Pyrrolyl | O | CH$_3$O | H |
| 3-Pyrrolyl | S | CH$_3$O | H |
| 2-Pyrrolyl | O | CH$_3$O | H |
| 2-Pyrrolyl | S | CH$_3$O | H |
| 3-Indolyl | O | CH$_3$O | H |
| 3-Indolyl | S | CH$_3$O | H |
| 2-Indolyl | O | CH$_3$O | H |
| 2-Indolyl | S | CH$_3$O | H |
| 1-Methyl-3-Indolyl | O | CH$_3$O | H |
| 1-Methyl-3-Indolyl | S | CH$_3$O | H |
| 1-Methyl-2-Indolyl | O | CH$_3$O | H |
| 1-Methyl-2-Indolyl | S | CH$_3$O | H |
| 1-Methylpyrazol-4-yl | O | CH$_3$O | H |
| 1-Methylpyrazol-4-yl | S | CH$_3$O | H |
| 1-Methylpyrazol-3-yl | O | CH$_3$O | H |
| 1-Methylpyrazol-3-yl | S | CH$_3$O | H |
| 1-Methylpyrazol-5-yl | O | CH$_3$O | H |
| 1-Methylpyrazol-5-yl | S | CH$_3$O | H |
| Isoxazol-3-yl | O | CH$_3$O | H |
| Isoxazol-3-yl | S | CH$_3$O | H |
| Isoxazol-4-yl | O | CH$_3$O | H |
| Isoxazol-4-yl | S | CH$_3$O | H |
| Isoxazol-5-yl | O | CH$_3$O | H |
| Isoxazol-5-yl | S | CH$_3$O | H |
| Isothiazol-3-yl | O | CH$_3$O | H |
| Isothiazol-3-yl | S | CH$_3$O | H |
| Isothiazol-4-yl | O | CH$_3$O | H |
| isothiazol-4-yl | S | CH$_3$O | H |
| Isothiazol-5-yl | O | CH$_3$O | H |
| Isothiazol-5-yl | S | CH$_3$O | H |
| Oxazol-2-yl | O | CH$_3$O | H |
| Oxazol-2-yl | S | CH$_3$O | H |
| Oxazol-5-yl | O | CH$_3$O | H |
| Oxazol-5-yl | S | CH$_3$O | H |
| Oxazol-4-yl | O | CH$_3$O | H |
| Oxazol-4-yl | S | CH$_3$O | H |
| Thiazol-4-yl | O | CH$_3$O | H |
| Thiazol-4-yl | S | CH$_3$O | H |
| Thiazol-5-yl | O | CH$_3$O | H |
| Thiazol-5-yl | S | CH$_3$O | H |
| Thiazol-2-yl | O | CH$_3$O | H |
| Thiazol-2-yl | S | CH$_3$O | H |
| 1-Methylimidazol-4-yl | O | CH$_3$O | H |
| 1-Methylimidazol-4-yl | S | CH$_3$O | H |
| 1-Methylimidazol-5-yl | O | CH$_3$O | H |
| 1-Methylimidazol-5-yl | S | CH$_3$O | H |
| 1-Methylimidazol-2-yl | O | CH$_3$O | H |
| 1-Methylimidazol-2-yl | S | CH$_3$O | H |
| 1,2-Benzisoxazol-3-yl | O | CH$_3$O | H |
| 1,2-Benzisoxazol-3-yl | S | CH$_3$O | H |
| 1,2-Benzisothiazol-3-yl | O | CH$_3$O | H |
| 1,2-Benzisothiazol-3-yl | S | CH$_3$O | H |
| 1-Methylindazol-3-yl | O | CH$_3$O | H |
| 1-Methylindazol-3-yl | S | CH$_3$O | H |
| Benzoxazol-2-yl | O | CH$_3$O | H |
| Benzoxazol-2-yl | S | CH$_3$O | H |
| 5-Chlorbenzoxazol-2-yl | O | CH$_3$O | H |
| 5-Chlorbenzoxazol-2-yl | S | CH$_3$O | H |
| 6-Fluorbenzoxazol-2-yl | O | CH$_3$O | H |
| 6-Fluorbenzoxazol-2-yl | S | CH$_3$O | H |
| Benzthiazol-2-yl | O | CH$_3$O | H |
| Benzthiazol-2-yl | S | CH$_3$O | H |
| 5-Fluorbenzthiazol-2-yl | O | CH$_3$O | H |
| 5-Fluorbenzthiazol-2-yl | S | CH$_3$O | H |

TABLE 2-continued

| R⁴ | A | R¹-W | R³n |
|---|---|---|---|
| 6-Fluorbenzthiazol-2-yl | O | CH₃O | H |
| 6-Fluorbenzthiazol-2-yl | S | CH₃O | H |
| Pyrido[3,2-dthiazol-2-yl | O | CH₃O | H |
| Pyrido[3,2-dthiazol-2-yl | S | CH₃O | H |
| (6-Chlor-pyrido)[3,2-dthiazol-2-yl | O | CH₃O | H |
| (6-Chlor-pyrido)[3,2-dthiazol-2-yl | S | CH₃O | H |
| 1-Methyl-1,2,3-triazol-5-yl | O | CH₃O | H |
| 1-Methyl-1,2,3-triazol-5-yl | S | CH₃O | H |
| 1-Methyl-1,2,3-triazol-4-yl | O | CH₃O | H |
| 1-Methyl-1,2,3-triazol-4-yl | S | CH₃O | H |
| 1-Methyl-1,2,4-triazol-5-yl | O | CH₃O | H |
| 1-Methyl-1,2,4-triazol-5-yl | S | CH₃O | H |
| 1-Methyl-1,2,4-triazol-3-yl | O | CH₃O | H |
| 1-Methyl-1,2,4-triazol-3-yl | S | CH₃O | H |
| 1-Methyl-1,2,3,4-tetrazol-5-yl | O | CH₃O | H |
| 1-Methyl-1,2,3,4-tetrazol-5-yl | S | CH₃O | H |
| 2-Methyl-1,2,3,4-tetrazol-5-yl | O | CH₃O | H |
| 2-Methyl-1,2,3,4-tetrazol-5-yl | S | CH₃O | H |
| 5-Trifluormethyl-1,3,4-thiadiazol-2-yl | O | CH₃O | H |
| 5-Trifluormethyl-1,3,4-thiadiazol-2-yl | S | CH₃O | H |
| 6-Chlorbenzoxazol-2-yl | O | CH₃O | H |
| 6-Chlorbenzoxazol-2-yl | S | CH₃O | H |
| 5-Fluorbenzoxazol-2-yl | O | CH₃O | H |
| 5-Fluorbenzoxazol-2-yl | S | CH₃O | H |
| 5-Nitrothiazol-2-yl | O | CH₃O | H |
| 5-Nitrothiazol-2-yl | S | CH₃O | H |

TABLE 3

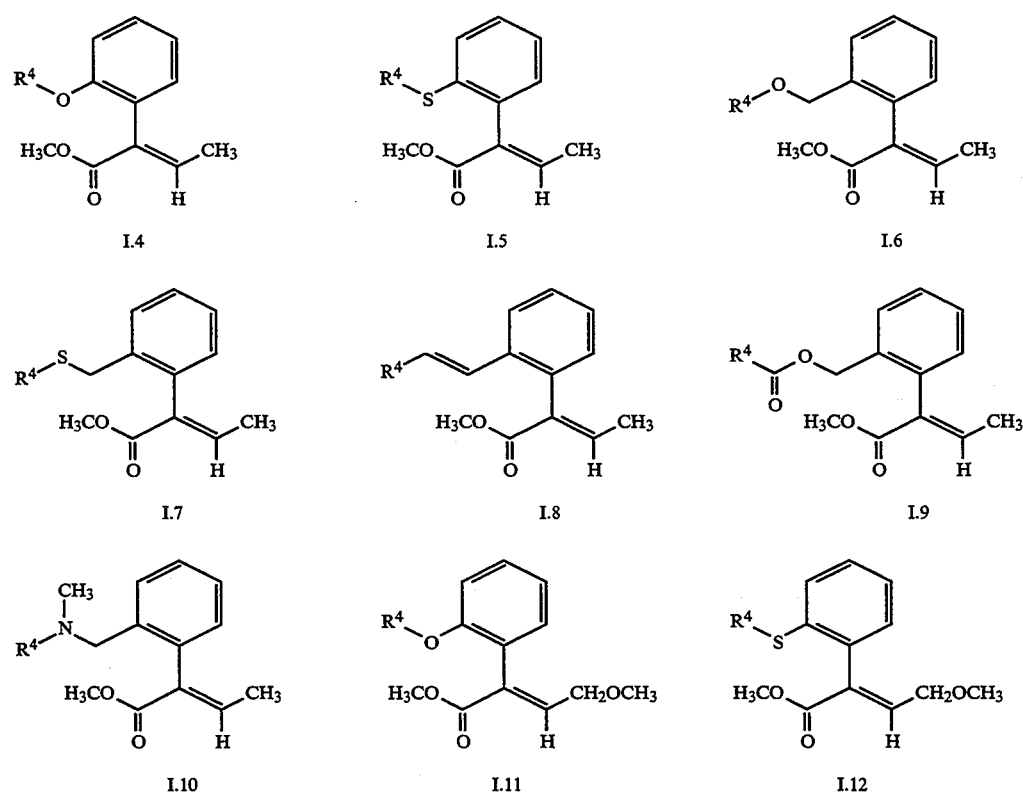

TABLE 3-continued

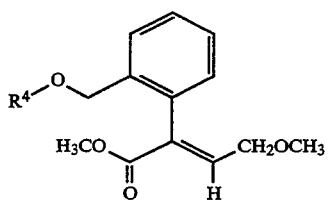
I.13

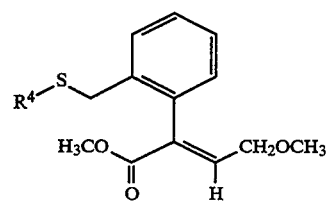
I.14

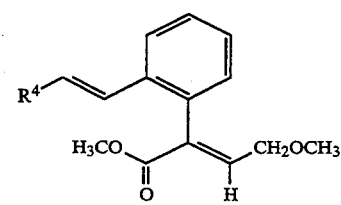
I.15

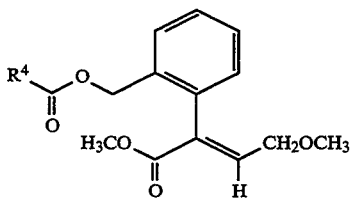
I.16

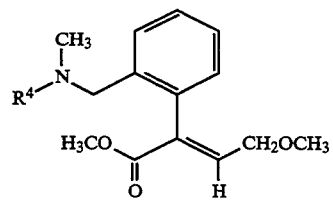
I.17

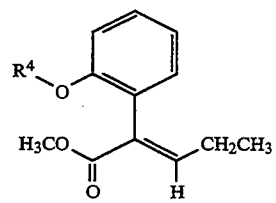
I.18

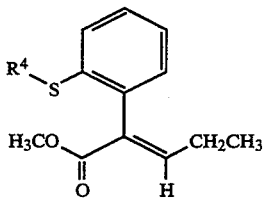
I.19

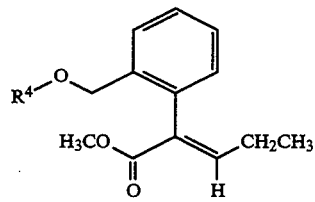
I.20

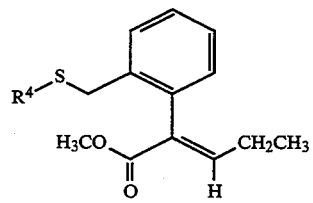
I.21

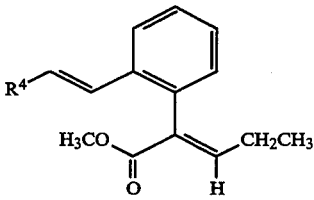
I.22

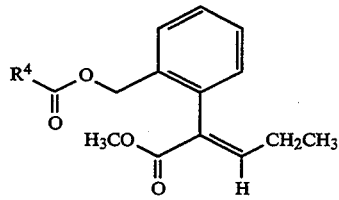
I.23

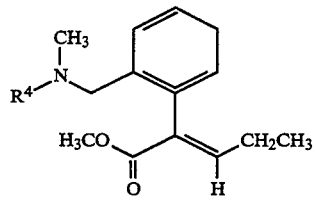
I.24

| $R^4$ | $R^4$ | $R^4$ |
|---|---|---|
| Phenyl | 2,5-Dichlorphenyl | 2-Brom-4-chlorphenyl |
| 2-Fluorphenyl | 3,4-Dichlorphenyl | 2-Brom-4-fluorphenyl |
| 3-Fluorphenyl | 3,5-Dichlorphenyl | 3-Brom-4-chlorphenyl |
| 4-Fluorphenyl | 2,3,4-Trichlorphenyl | 3-Chlor-4-fluorphenyl |
| 2-Chlorphenyl | 2,3,5-Trichlorphenyl | 3-Fluor-4-chlorphenyl |
| 2-Chlor-4-fluorphenyl | 2,3,6-Trichlorphenyl | 2-Cyanophenyl |
| 2-Chlor-5-fluorphenyl | 3,4,5-Trichlorphenyl | 4-Cyanophenyl |
| 2-Chlor-6-fluorphenyl | 2-Bromphenyl | 2-Nitrophenyl |
| 2-Ethylphenyl | 3-Bromphenyl | 2-Methylphenyl |
| 3-Ethylphenyl | 4-Bromphenyl | 3-Methylphenyl |
| 3,5-Diethylphenyl | 2,4-Dibromphenyl | 4-Methylphenyl |
| 2-n-Propylphenyl | 3-Brom-4-fluorphenyl | 2,4-Dimethylphenyl |
| 3-Chlorphenyl | 3-Brom-4-methoxyphenyl | 2,6-Dimethylphenyl |
| 4-Chlorphenyl | 2-Iodphenyl | 3,4-Diemthylphenyl |
| 2,4-Dichlorphenyl | 2-Chlor-4-bromphenyl | 3,5-Diemthylphenyl |
| 2,3,4-Trimethylphenyl | 2-Methyl-4-phenoxyphenyl | 3-n-Hexoxyphenyl |
| 2,3,5-Trimethylphenyl | 2-Methyl-4-benzyloxyphenyl | 4-n-Hexoxyphenyl |
| 2,3,6-Trimethylphenyl | 2-Methyl-3-chlorphenyl | 3-Allyoxyphenyl |
| 2,4,5-Trimethylphenyl | 2-Methyl-4-chlorphenyl | 4-iso-Propoxyphenyl |
| 2,4,6-Trimethylphenyl | 2-Methyl-5-chlorphenyl | 2-Phenylphenyl |
| 3,4,5-Trimethylphenyl | 2-Methyl-6-chlorphenyl | 3-Phenylphenyl |
| 3-n-Propylphenyl | 2-Methyl-4-fluorphenyl | 4-Phenylphenyl |
| 4-n-Propylphenyl | 2-Methyl-3-bromphenyl | 2-Phenoxyphenyl |
| 2-iso-Propylphenyl | 2-Methyl-4-methoxyphenyl | 4-Phenoxyphenyl |
| 3-iso-Propylphenyl | 2-Methyl-5-methoxyphenyl | 1-Naphthyl |
| 4-iso-Propylphenyl | 2-Methyl-6-methoxyphenyl | 2-Naphthyl |
| 2,3-Di-isopropylphenyl | 2-Methyl-4-isopropoxyphenyl | 9-Anthryl |
| 3,5-Di-isopropylphenyl | 2-Methyl-2,5-dimethoxyphenyl | 2-Fluor-4-phenoxyphenyl |
| 4-n-Butylphenyl | 2-Methoxyphenyl | 3-Fluor-4-phenoxyphenyl |

TABLE 3-continued

| | | |
|---|---|---|
| 4-sec.-ButylphenyL | 3-Methoxyphenyl | |
| 4-iso-Butylphenyl | 4-Fluor-4-phenoxyphenyl | 2-Chlor-4-phenoxyphenyl |
| 2-tert.-Butylphenyl | 4-Methoxyphenyl | 3-Chlor-4-phenoxyphenyl |
| 2-Methyl-4-tert.-butylphenyl | 2-Chlor-4-methylphenyl | 4-Chlor-4-phenoxyphenyl |
| 2-Methyl-6-tert.-butylphenyl | 2-Chlor-5-methylphenyl | 2-Brom-4-phenoxyphenyl |
| 2-Methyl-4-isopropylphenyl | 2-Chlor-4-isopropylphenyl | 3-Brom-4-phenoxyphenyl |
| 2-Methyl-4-cyclohexylphenyl | 3-n-Propoxyphenyl | 4-Brom-4-phenoxyphenyl |
| 2-Methyl-4-phenylphenyl | 3-n-Butoxyphenyl | 3-Methyl-4-phenoxyphenyl |
| 2-Methyl-4-benzylphenyl | 3-iso-Butoxyphenyl | 4-Methyl-4-phenoxyphenyl |
| 3-tert.-Butyl-4-phenoxyphenyl | 3-n-Pentoxyphenyl | |
| 2-Methoxy-4-phenoxyphenyl | 4-(Imidazol-1'-yl)phenyl | |
| 3-Methoxy-4-phenoxyphenyl | 4-(Piperazin-1'-yl)phenyl | |
| 4-Methoxy-4-phenoxyphenyl | 4-(Morpholin-1'-yl)phenyl | |
| 3-5-Dichlor-4-phenoxyphenyl | 4-(Piperidin-1'-yl)phenyl | |
| 3-4-Dichlor-4-phenoxyphenyl | 4-(Pyridyl-2'-oxy)phenyl | |
| 4-Ethyl-4-phenoxyphenyl | 2-Cyclopropylphenyl | |
| 4-iso-Propyl-4-phenoxyphenyl | 3-Cyclopropylphenyl | |
| 2,4-Dimethoxyphenyl | 3-Cyclohexylphenyl | |
| 2,5-Dimethoxyphenyl | 4-Cyclohexylphenyl | |
| 3,6-Dimethoxyphenyl | 4-Oxiranylphenyl | |
| 2,3,4-Trimethoxyphenyl | 4-(Pyrid-2-yl)phenyl | |
| 2-Ethoxyphenyl | 3-(Pyrid-2-yl)phenyl | |
| 2-iso-Propoxyphenyl | 4-(Pyrid-3-yl)phenyl | |
| 2-Methyl-3-isopropylphenyl | 3-(Pyrid-3-yl)phenyl | |
| 2-Methyl-5-isopropylphenyl | 3-(Pyrimid-2-yl)phenyl | |
| 2-Benzyloxyphenyl | 3-Phenoxyphenyl | |
| 3-Benzyloxyphenyl | 2-Fluor-3-phenoxyphenyl | |
| 4-Benzyloxyphenyl | 2-Methyl-3-phenoxyphenyl | |

TABLE 4

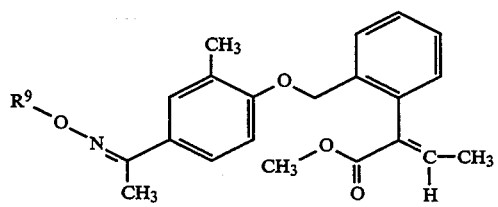

I.25

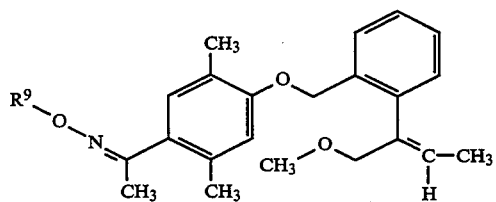

I.26

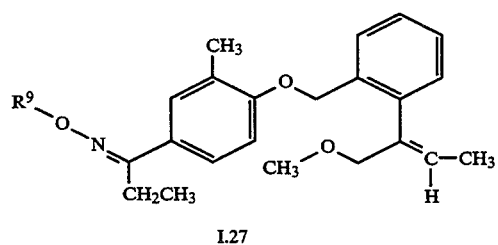

I.27

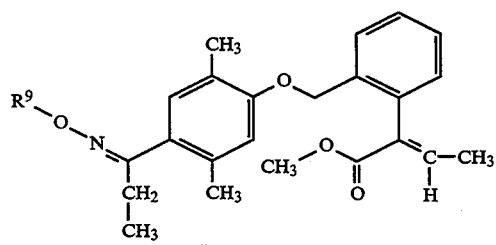

I.28

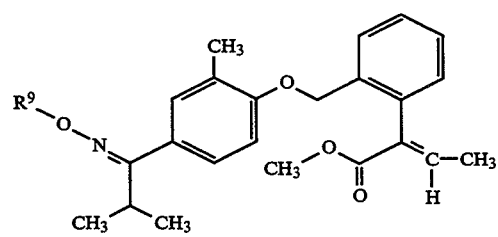

I.29

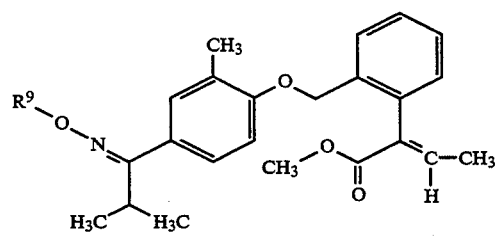

I.30

TABLE 4-continued
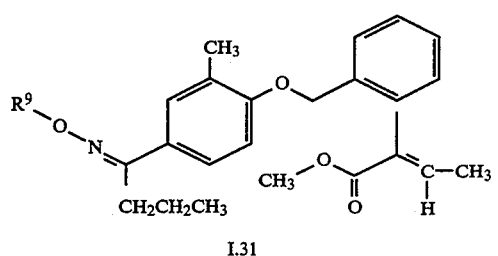
I.31
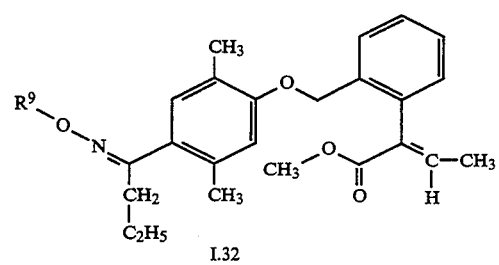
I.32
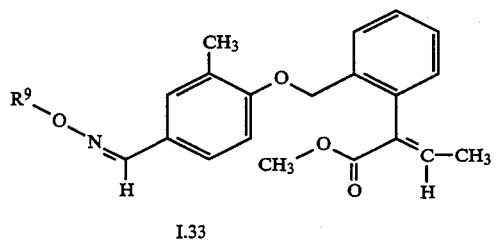
I.33
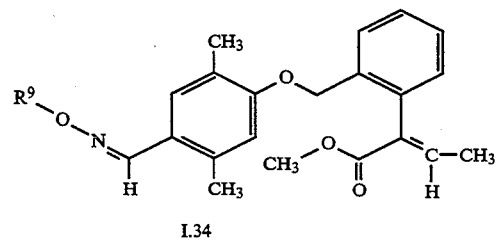
I.34
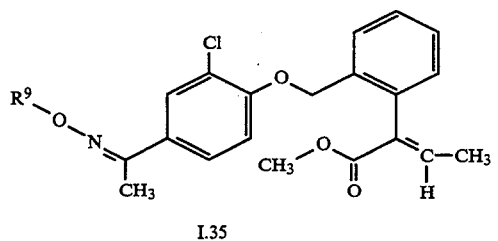
I.35
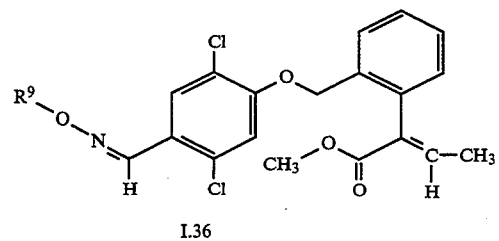
I.36
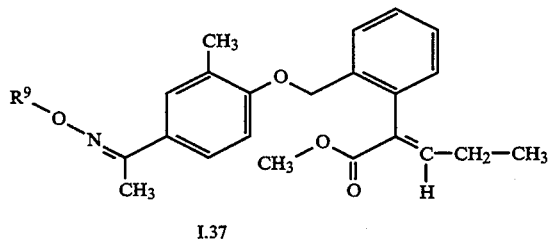
I.37
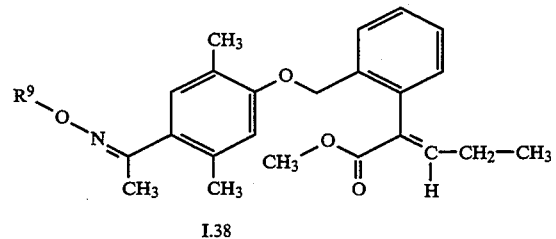
I.38
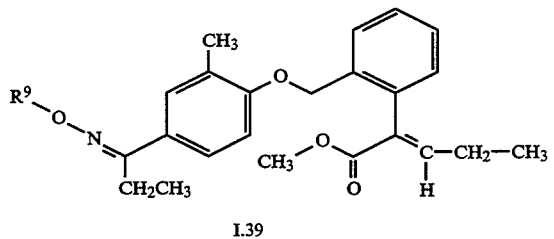
I.39
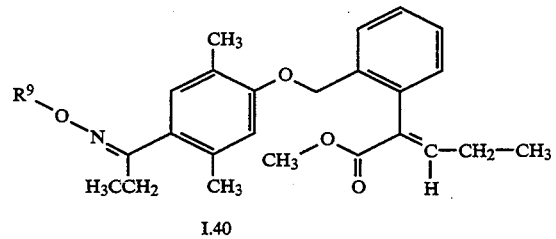
I.40
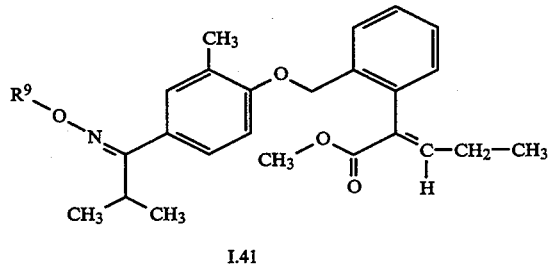
I.41
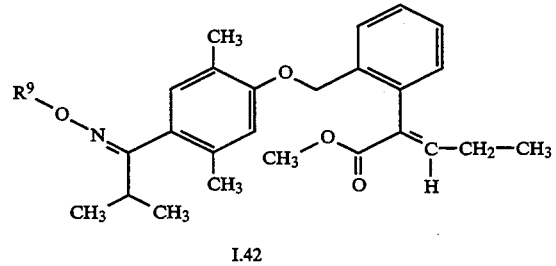
I.42

TABLE 4-continued
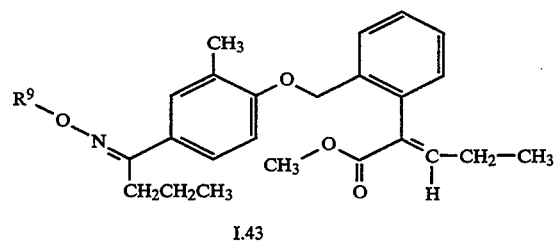
I.43
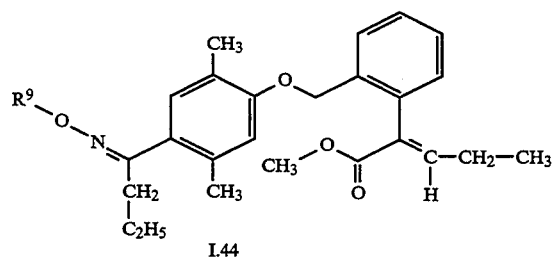
I.44
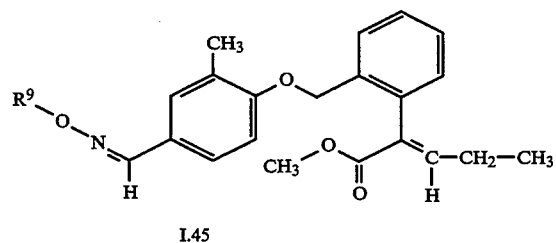
I.45
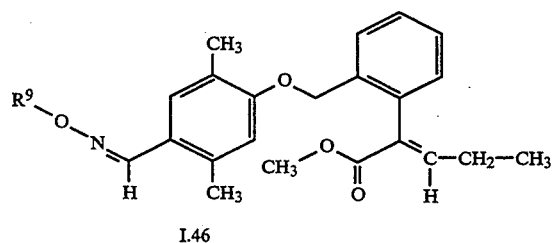
I.46
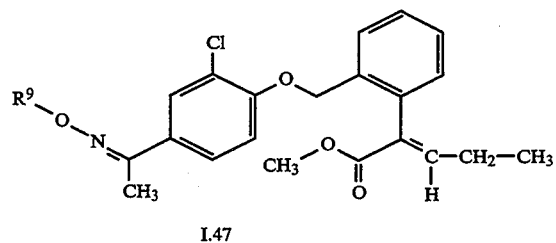
I.47
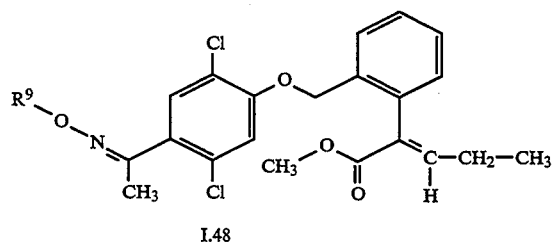
I.48
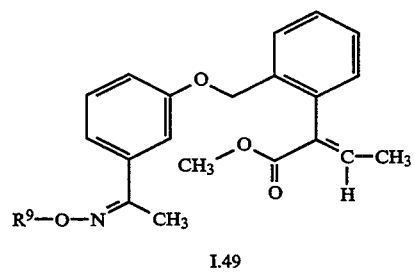
I.49
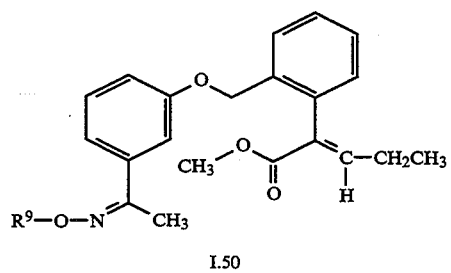
I.50
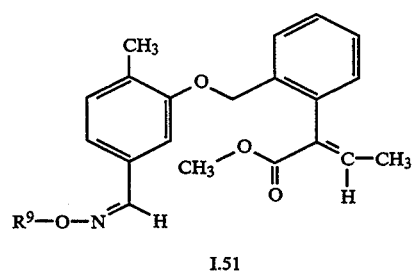
I.51
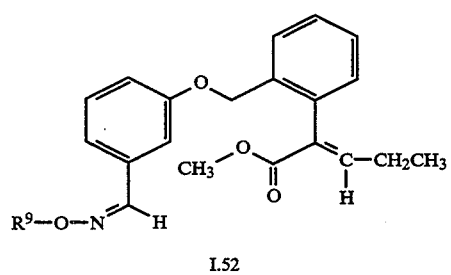
I.52
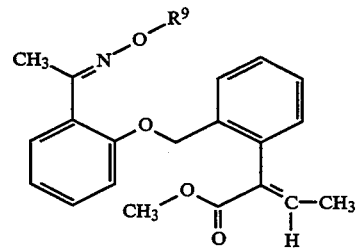
I.53
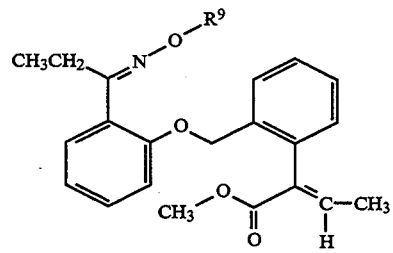
I.54

TABLE 4-continued

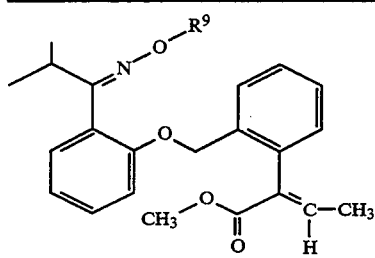
I.55

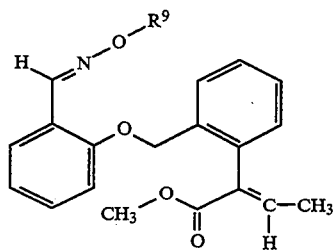
I.56

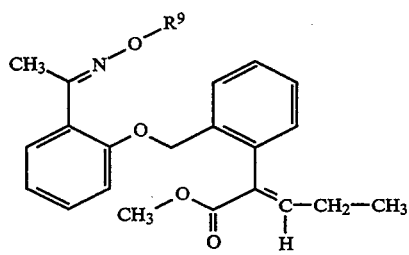
I.57

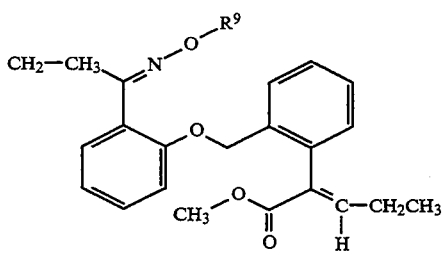
I.58

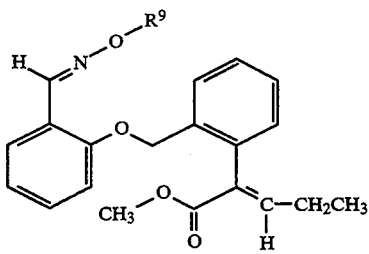
I.59

| $R^9$ | $R^9$ |
|---|---|
| H | 2-Cl—C$_6$H$_4$—CH$_2$ |
| CH$_3$ | 3-Cl—C$_6$H$_4$—CH$_2$ |
| CH$_3$CH$_2$ | 4-Cl—C$_6$H$_4$—CH$_2$ |
| CH$_3$CH$_2$CH$_2$ | 2,5-Cl$_2$—C$_6$H$_3$—CH$_2$ |
| CH$_3$CH(CH$_3$) | 2-CH$_3$—C$_6$H$_4$—CH$_2$ |
| (CH$_3$)$_3$C | 3-CH$_3$—C$_6$H$_4$—CH$_2$ |
| CH$_2$=CH—CH$_2$ | 4-CH$_3$—C$_6$H$_4$—CH$_2$ |
| HC≡C—CH$_2$ | 2,3-(CH$_3$)$_2$—C$_6$H$_3$—CH$_2$ |
| CH$_3$OCH$_2$CH$_2$ | 2,4-(CH$_3$)$_2$—C$_6$H$_3$—CH$_2$ |
| Cyclopropyl-CH$_2$ | 2,5-(CH$_3$)$_2$—C$_6$H$_3$—CH$_2$ |
| CH$_2$=CH—CH$_2$—CH$_2$ | 2,4,6-(CH$_3$)$_3$—C$_6$H$_2$—CH$_2$ |
| CH$_3$—CH=CH—CH$_2$ | 2-CF$_3$—C$_6$H$_4$—CH$_2$ |
| CH$_3$—(CH$_2$)$_3$ | 3-CF$_3$—C$_6$H$_4$—CH$_2$ |
| CH$_3$—(CH$_2$)$_4$ | 4-CF$_3$—C$_6$H$_4$—CH$_2$ |
| CH$_3$—(CH$_2$)$_5$ | 2-CF$_3$-5-CH$_3$—C$_6$H$_3$—CH$_2$ |
| Cyclohexyl | 2-CH$_3$-5-CF$_3$—C$_6$H$_3$—CH$_2$ |
| 2-CH$_3$-Cyclohexyl | 2-Br-C$_6$H$_4$—CH$_2$ |
| CH$_3$—CH$_2$—C(CH$_3$)$_2$ | 2-(iso-Propyl)-C$_6$H$_4$—CH$_2$ |
| CH$_3$—CH(CH$_3$)—CH$_2$ | 2-(iso-Propyl-3-Cl-C$_6$H$_3$—CH$_2$ |
| CH$_3$—CH(CH$_3$)—CH$_2$—CH$_2$ | 2-CH$_3$-5-t-C$_4$H$_9$—C$_6$H$_3$—CH$_2$ |
| CH$_2$=C(CH$_3$)—CH$_2$ | 2-CH$_3$-5-t-C$_4$H$_9$—C$_6$H$_3$—CH$_2$ |
| HC≡C—C(CH$_3$)=CH—CH$_2$ | 3-CH$_3$-5-t-C$_4$H$_9$—C$_6$H$_3$—CH$_2$ |
| Cl(CH$_3$)—C=CH | 2-Cl-5-t-C$_4$H$_9$—C$_6$H$_3$—CH$_2$ |
| CH$_2$=C(Cl)—CH$_2$— | 3-Cl-5-t-C$_4$H$_9$—C$_6$H$_3$—CH$_2$ |
| ClHC=CH—CH$_2$— | 2-OCH$_3$—C$_6$H$_4$—CH$_2$ |
| C$_6$H$_5$—CH$_2$ | 3-OCH$_3$—C$_6$H$_4$—CH$_2$ |
| 2-F—C$_6$H$_4$—CH$_2$ | 2-CH$_3$-5-OCH$_3$—C$_6$H$_3$—CH$_2$ |
| 3-F—C$_6$H$_4$—CH$_2$ | 3-CH$_3$-5-OCH$_3$—C$_6$H$_3$—CH$_2$ |
| 4-F—C$_6$H$_4$—CH$_2$ | 2-Cl-5-OCH$_3$—C$_6$H$_3$—CH$_2$ |

TABLE 5
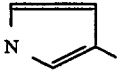
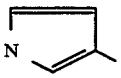
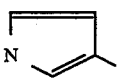
| R$_H$ | position of R$_H$ on Het | Het |
|---|---|---|
| —CH$_3$ | 1 |  |
| —CH(CH$_3$)$_2$ | 1 |  |
| —C(CH$_3$)$_2$ | 1 |  |
| -Cyclo-C$_3$H$_5$ | 1 |  |
| —C$_6$H$_5$ | 1 | 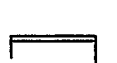 |
| 4-CH$_3$—C$_6$H$_4$ | 1 |  |
| 3-CH$_3$—C$_6$H$_4$ | 1 | 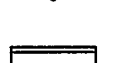 |
| 2-CH$_3$—C$_6$H$_4$ | 1 |  |
| 4-CH$_3$—C$_6$H$_4$— | 1 |  |
TABLE 5-continued
| | | |
|---|---|---|
| 3-CH$_3$O—C$_6$H$_4$— | 1 | 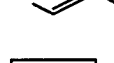 |
| 4-NO$_2$—C$_6$H$_4$— | 1 | 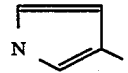 |
| 3-NO$_2$—C$_6$H$_4$— | 1 | 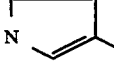 |
| 4-CN—C$_6$H$_4$— | 1 | 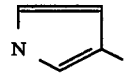 |
| 3-CN—C$_6$H$_4$— | 1 | 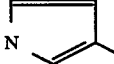 |
| 4-CF$_3$—C$_6$H$_4$— | 1 | 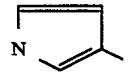 |
| 3-CF$_3$—C$_6$H$_4$— | 1 | 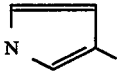 |
| 4-(C(CH$_3$)$_3$)—C$_6$H$_4$— | 1 |  |
| 4-(C$_6$H$_4$)—C$_6$H$_4$— | 1 | 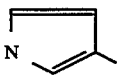 |
| 4-Cl—C$_6$H$_4$— | 1 |  |
| 3-Cl—C$_6$H$_4$— | 1 |  |
| 2-Cl—C$_6$H$_4$— | 1 |  |
| 4-Br—C$_6$H$_4$— | 1 | 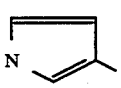 |
| 3-Br—C$_6$H$_4$— | 1 | 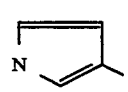 |
| 2-Br—C$_6$H$_4$— | 1 |  |
| 4-F—C$_6$H$_4$— | 1 | 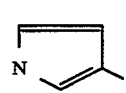 |

TABLE 5-continued

| | | |
|---|---|---|
| 3-F—C$_6$H$_4$— | 1 | pyrrol-3-yl |
| 2-F—C$_6$H$_4$— | 1 | pyrrol-3-yl |
| 3,4-Cl$_2$—C$_6$H$_3$— | 1 | pyrrol-3-yl |
| 2,4-Cl$_2$—C$_6$H$_3$— | 1 | pyrrol-3-yl |
| 3,4-F$_2$—C$_6$H$_3$— | 1 | pyrrol-3-yl |
| 2,4-F$_2$—C$_6$H$_3$— | 1 | pyrrol-3-yl |
| 2,6-F$_2$—C$_6$H$_3$— | 1 | pyrrol-3-yl |
| 5-Cl-2-CH$_3$O—C$_6$H$_3$ | 1 | pyrrol-3-yl |
| —CH$_3$ | 1 | pyrrol-2-yl |
| —CH(CH$_3$)$_2$ | 1 | pyrrol-2-yl |
| —C(CH$_3$)$_2$ | 1 | pyrrol-2-yl |
| -Cyclo-C$_3$H$_5$ | 1 | pyrrol-2-yl |
| —C$_6$H$_5$ | 1 | pyrrol-2-yl |
| 4-CH$_3$—C$_6$H$_4$ | 1 | pyrrol-2-yl |
| 3-CH$_3$—C$_6$H$_4$ | 1 | pyrrol-2-yl |
| 2-CH$_3$—C$_6$H$_4$ | 1 | pyrrol-2-yl |

TABLE 5-continued

| | | |
|---|---|---|
| 4-CH$_3$O—C$_6$H$_4$— | 1 | pyrrol-2-yl |
| 3-CH$_3$O—C$_6$H$_4$— | 1 | pyrrol-2-yl |
| 4-NO$_2$—C$_6$H$_4$— | 1 | pyrrol-2-yl |
| 3-NO$_2$—C$_6$H$_4$ | 1 | pyrrol-2-yl |
| 4-CN—C$_6$H$_4$— | 1 | pyrrol-2-yl |
| 3-CN—C$_6$H$_4$— | 1 | pyrrol-2-yl |
| 4-CF$_3$—C$_6$H$_4$— | 1 | pyrrol-2-yl |
| 3-CF$_3$—C$_6$H$_4$— | 1 | pyrrol-2-yl |
| 4-(C(CH$_3$)$_3$)—C$_6$H$_4$— | 1 | pyrrol-2-yl |
| 4-(C$_6$H$_4$)—C$_6$H$_4$— | 1 | pyrrol-2-yl |
| 4-Cl—C$_6$H$_4$— | 1 | pyrrol-2-yl |
| 3-Cl—C$_6$H$_4$— | 1 | pyrrol-2-yl |
| 2-Cl—C$_6$H$_4$— | 1 | pyrrol-2-yl |
| 4-Br—C$_6$H$_4$— | 1 | pyrrol-2-yl |
| 3-Br—C$_6$H$_4$— | 1 | pyrrol-2-yl |

TABLE 5-continued

| | | |
|---|---|---|
| 2-Br—C$_6$H$_4$— | 1 | 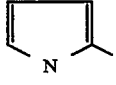 |
| 4-F—C$_6$H$_4$— | 1 | 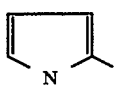 |
| 3-F—C$_6$H$_4$— | 1 | 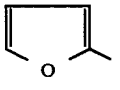 |
| 2-F—C$_6$H$_4$— | 1 | 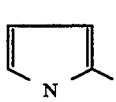 |
| 3,4-Cl$_2$—C$_6$H$_3$— | 1 | 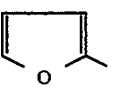 |
| 2,4-Cl$_2$—C$_6$H$_3$— | 1 |  |
| 3,4-F$_2$—C$_6$H$_3$— | 1 | 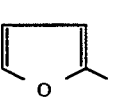 |
| 2,4-F$_2$—C$_6$H$_3$— | 1 | 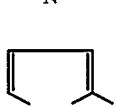 |
| 2,6-F$_2$—C$_6$H$_3$— | 1 | 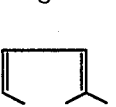 |
| 5-Cl-2-CH$_3$O—C$_6$H$_3$ | 1 | 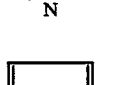 |
| —CH$_3$ | 5 | 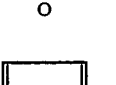 |
| —CH(CH$_3$)$_2$ | 5 | 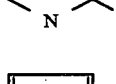 |
| —C(CH$_3$)$_2$ | 5 | 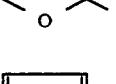 |
| -Cyclo-C$_3$H$_5$ | 5 | 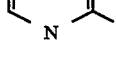 |
| —C$_6$H$_5$ | 5 | 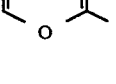 |

TABLE 5-continued

| | | |
|---|---|---|
| 4-CH$_3$—C$_6$H$_4$ | 5 | 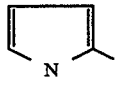 |
| 3-CH$_3$—C$_6$H$_4$ | 5 | 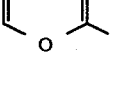 |
| 2-CH$_3$—C$_6$H$_4$ | 5 | 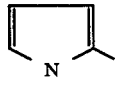 |
| 4-CH$_3$O—C$_6$H$_4$— | 5 | 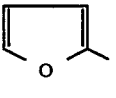 |
| 3-CH$_3$O—C$_6$H$_4$— | 5 | 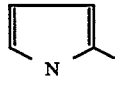 |
| 4-NO$_2$—C$_6$H$_4$— | 5 | 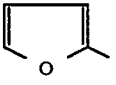 |
| 3-NO$_2$—C$_6$H$_4$— | 5 | 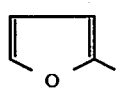 |
| 4-CN—C$_6$H$_4$— | 5 | 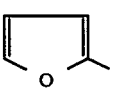 |
| 3-CN—C$_6$H$_4$— | 5 | 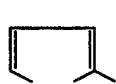 |
| 4-CF$_3$—C$_6$H$_4$— | 5 | 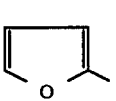 |
| 3-CF$_3$—C$_6$H$_4$— | 5 | 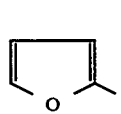 |
| 4-(C(CH$_3$)$_3$)—C$_6$H$_4$— | 5 |  |
| 4-(C$_6$H$_4$)—C$_6$H$_4$— | 5 |  |
| 4-Cl—C$_6$H$_4$— | 5 |  |
| 3-Cl—C$_6$H$_4$— | 5 | 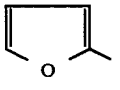 |

TABLE 5-continued
| | | |
|---|---|---|
| 2-Cl—C6H4— | 5 | 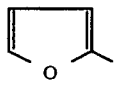 |
| 4-Br—C6H4— | 5 | 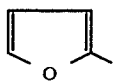 |
| 3-Br—C6H4— | 5 | 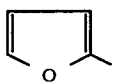 |
| 2-Br—C6H4— | 5 | 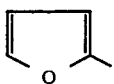 |
| 4-F—C6H4— | 5 | 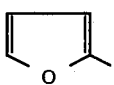 |
| 3-F—C6H4— | 5 | 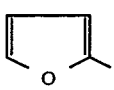 |
| 2-F—C6H4— | 5 | 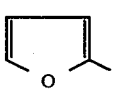 |
| 3,4-Cl2—C6H3— | 5 | 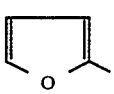 |
| 2,4-Cl2—C6H3— | 5 | 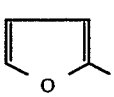 |
| 3,4-F2—C6H13— | 5 | 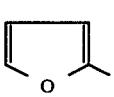 |
| 2,4-F2—C6H3— | 5 | 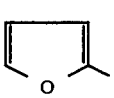 |
| 2,6-F2—C6H3— | 5 | 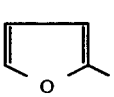 |
| 5-Cl-2-CH3O—C6H3 | 5 | 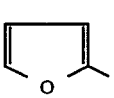 |
| —CH3 | 4 | 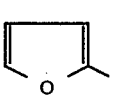 |
| —CH(CH3)2 | 4 | 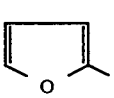 |
TABLE 5-continued
| | | |
|---|---|---|
| —C(CH3)3 | 4 | 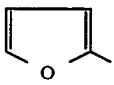 |
| -Cyclo-C3H5 | 4 | 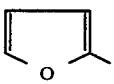 |
| —C6H5 | 4 | 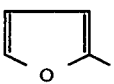 |
| 4-CH3—C6H4 | 4 | 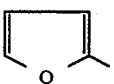 |
| 3-CH3—C6H4 | 4 | 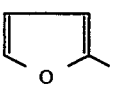 |
| 2-CH3—C6H4 | 4 | 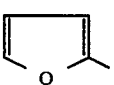 |
| 4-CH3O—C6H4— | 4 | 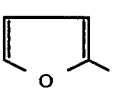 |
| 3-CH3O—C6H4— | 4 | 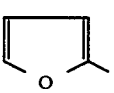 |
| 4-NO2—C6H4— | 4 | 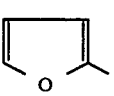 |
| 3-NO2—C6H4— | 4 | 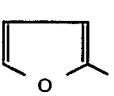 |
| 4-CN—C6H4— | 4 | 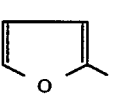 |
| 3-CN—C6H4— | 4 | 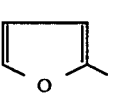 |
| 4-CF3—C6H4— | 4 | 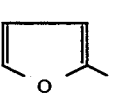 |
| 3-CF3—C6H4— | 4 | 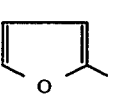 |
| 4-(C(CH3)3)—C6H4— | 4 | |

5,416,068
TABLE 5-continued
| | | |
|---|---|---|
| 4-(C₆H₄)—C₆H₄— | 4 | 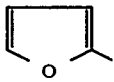 |
| 4-Cl—C₆H₄— | 4 | 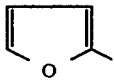 |
| 3-Cl—C₆H₄— | 4 | 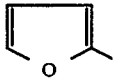 |
| 2-Cl—C₆H₄— | 4 | 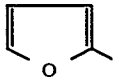 |
| 4-Br—C₆H₄— | 4 | 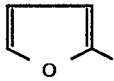 |
| 3-Br—C₆H₄— | 4 | 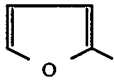 |
| 2-Br—C₆H₄— | 4 | 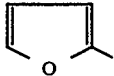 |
| 4-F—C₆H₄— | 4 | 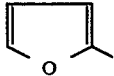 |
| 3-F—C₆H₄— | 4 | 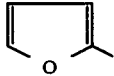 |
| 2-F—C₆H₄— | 4 | 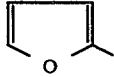 |
| 3,4-Cl₂—C₆H₃— | 4 | 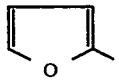 |
| 2,4-Cl₂—C₆H₃— | 4 | 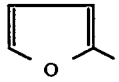 |
| 3,4-F₂—C₆H₃— | 4 | 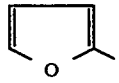 |
| 2,4-F₂—C₆H₃— | 4 | 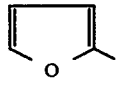 |
| 2,6-F₂—C₆H₃— | 4 | 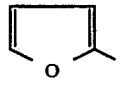 |
TABLE 5-continued
| | | |
|---|---|---|
| 5-Cl-2-CH₃O—C₆H₃ | 4 | 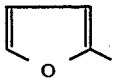 |
| —CH₃ | 5 | 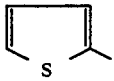 |
| —CH(CH₃)₂ | 5 | 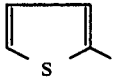 |
| —C(CH₃)₂ | 5 | 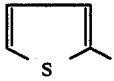 |
| -Cyclo-C₃H₅ | 5 | 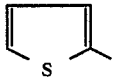 |
| —C₆H₅ | 5 | 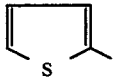 |
| 4-CH₃—C₆H₄ | 5 | 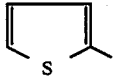 |
| 3-CH₃—C₆H₄ | 5 | 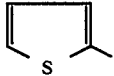 |
| 2-CH₃—C₆H₄ | 5 | 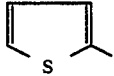 |
| 4-CH₃O—C₆H₄— | 5 | 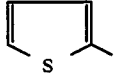 |
| 3-CH₃O—C₆H₄— | 5 | 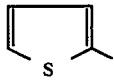 |
| 4-NO₂—C₆H₄— | 5 | 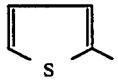 |
| 3-NO₂—C₆H₄— | 5 | 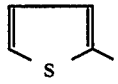 |
| 4-CN—C₆H₄— | 5 | 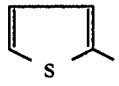 |
| 3-CN—C₆H₄— | 5 | 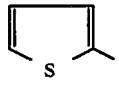 |

TABLE 5-continued

| | | |
|---|---|---|
| 4-CF₃—C₆H₄— | 5 | 2-thienyl-CH(CH₃)— |
| 3-CF₃—C₆H₄— | 5 | 2-thienyl-CH(CH₃)— |
| 4-(C(CH₃)₃)—C₆H₄— | 5 | 2-thienyl-CH(CH₃)— |
| 4-(C₆H₄)—C₆H₄— | 5 | 2-thienyl-CH(CH₃)— |
| 4-Cl—C₆H₄— | 5 | 2-thienyl-CH(CH₃)— |
| 3-Cl—C₆H₄— | 5 | 2-thienyl-CH(CH₃)— |
| 2-Cl—C₆H₄— | 5 | 2-thienyl-CH(CH₃)— |
| 4-Br—C₆H₄— | 5 | 2-thienyl-CH(CH₃)— |
| 3-Br—C₆H₄— | 5 | 2-thienyl-CH(CH₃)— |
| 2-Br—C₆H₄— | 5 | 2-thienyl-CH(CH₃)— |
| 4-F—C₆H₄— | 5 | 2-thienyl-CH(CH₃)— |
| 3-F—C₆H₄— | 5 | 2-thienyl-CH(CH₃)— |
| 2-F—C₆H₄— | 5 | 2-thienyl-CH(CH₃)— |
| 3,4-Cl₂—C₆H₃— | 5 | 2-thienyl-CH(CH₃)— |
| 2,4-Cl₂—C₆H₃— | 5 | 2-thienyl-CH(CH₃)— |

TABLE 5-continued

| | | |
|---|---|---|
| 3,4-F₂—C₆H₃— | 5 | 2-thienyl-CH(CH₃)— |
| 2,4-F₂—C₆H₃— | 5 | 2-thienyl-CH(CH₃)— |
| 2,6-F₂—C₆H₃— | 5 | 2-thienyl-CH(CH₃)— |
| 5-Cl-2-CH₃O—C₆H₃ | 5 | 2-thienyl-CH(CH₃)— |
| —CH₃ | 4 | 2-thienyl-CH(CH₃)— |
| —CH(CH₃)₂ | 4 | 2-thienyl-CH(CH₃)— |
| —C(CH₃)₂ | 4 | 2-thienyl-CH(CH₃)— |
| -Cyclo-C₃H₅ | 4 | 2-thienyl-CH(CH₃)— |
| —C₆H₅ | 4 | 2-thienyl-CH(CH₃)— |
| 4-CH₃—C₆H₄ | 4 | 2-thienyl-CH(CH₃)— |
| 3-CH₃—C₆H₄ | 4 | 2-thienyl-CH(CH₃)— |
| 2-CH₃—C₆H₄ | 4 | 2-thienyl-CH(CH₃)— |
| 4-CH₃O—C₆H₄— | 4 | 2-thienyl-CH(CH₃)— |
| 3-CH₃O—C₆H₄— | 4 | 2-thienyl-CH(CH₃)— |
| 4-NO₂—C₆H₄— | 4 | 2-thienyl-CH(CH₃)— |

TABLE 5-continued
| | | |
|---|---|---|
| 3-NO2—C6H4— | 4 | 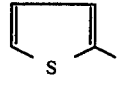 |
| 4-CN—C6H4— | 4 | 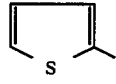 |
| 3-CN—C6H4— | 4 | 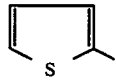 |
| 4-CF3—C6H4— | 4 | 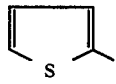 |
| 3-CF3—C6H4— | 4 | 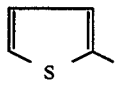 |
| 4-(C(CH3)3)—C6H4— | 4 | 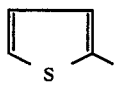 |
| 4-(C6H4)—C6H4— | 4 | 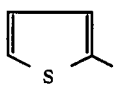 |
| 4-Cl—C6H4— | 4 | 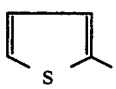 |
| 3-Cl—C6H4— | 4 | 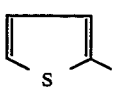 |
| 2-Cl—C6H4— | 4 | 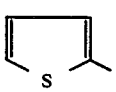 |
| 4-Br—C6H4— | 4 | 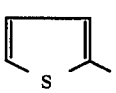 |
| 3-Br—C6H4— | 4 | 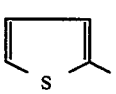 |
| 2-Br—C6H4— | 4 | 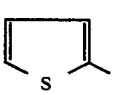 |
| 4-F—C6H4— | 4 | 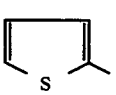 |
| 3-F—C6H4— | 4 | 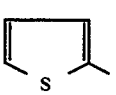 |
TABLE 5-continued
| | | |
|---|---|---|
| 2-F—C6H4— | 4 | 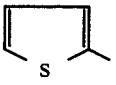 |
| 3,4-Cl2—C6H3— | 4 | 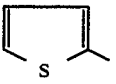 |
| 2,4-Cl2—C6H3— | 4 | 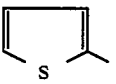 |
| 3,4-F2—C6H3— | 4 | 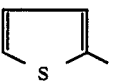 |
| 2,4-F2—C6H3— | 4 | 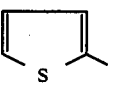 |
| 2,6-F2—C6H3— | 4 | 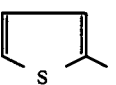 |
| 5-Cl-2-CH3O—C6H3 | 4 | 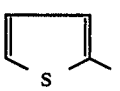 |
| —CH3 | 5 | 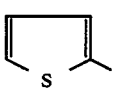 |
| —CH(CH3)2 | 5 | 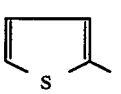 |
| —C(CH3)2 | 5 | 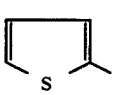 |
| -Cyclo-C3H5 | 5 | 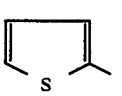 |
| —C6H5 | 5 | 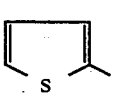 |
| 4-CH3—C6H4 | 5 | 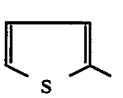 |
| 3-CH3—C6H4 | 5 | 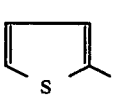 |
| 2-CH3—C6H4 | 5 | 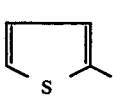 |

TABLE 5-continued

| | | |
|---|---|---|
| 4-CH₃O—C₆H₄— | 5 | 2-thienyl |
| 3-CH₃O—C₆H₄— | 5 | 2-thienyl |
| 4-NO₂—C₆H₄— | 5 | 2-thienyl |
| 3-NO₂—C₆H₄— | 5 | 2-thienyl |
| 4-CN—C₆H₄— | 5 | 2-thienyl |
| 3-CN—C₆H₄— | 5 | 2-thienyl |
| 4-CF₃—C₆H₄— | 5 | 2-thienyl |
| 3-CF₃—C₆H₄— | 5 | 2-thienyl |
| 4-(C(CH₃)₃)—C₆H₄— | 5 | 2-thienyl |
| 4-(C₆H₄)—C₆H₄— | 5 | 2-thienyl |
| 4-Cl—C₆H₄— | 5 | 2-thienyl |
| 3-Cl—C₆H₄— | 5 | 2-thienyl |
| 2-Cl—C₆H₄— | 5 | 2-thienyl |
| 4-Br—C₆H₄— | 5 | 2-thienyl |
| 3-Br—C₆H₄— | 5 | 2-thienyl |

TABLE 5-continued

| | | |
|---|---|---|
| 2-Br—C₆H₄— | 5 | 2-thienyl |
| 4-F—C₆H₄— | 5 | 2-thienyl |
| 3-F—C₆H₄— | 5 | 2-thienyl |
| 2-F—C₆H₄— | 5 | 2-thienyl |
| 3,4-Cl₂—C₆H₃— | 5 | 2-thienyl |
| 2,4-Cl₂—C₆H₃— | 5 | 2-thienyl |
| 3,4-F₂—C₆H₃— | 5 | 2-thienyl |
| 2,4-F₂—C₆H₃— | 5 | 2-thienyl |
| 2,6-F₂—C₆H₃— | 5 | 2-thienyl |
| 5-Cl-2-CH₃O—C₆H₃ | 5 | 2-thienyl |
| —CH₃ | 1 | pyrazolyl |
| —CH(CH₃)₂ | 1 | pyrazolyl |
| —C(CH₃)₂ | 1 | pyrazolyl |
| -Cyclo-C₃H₅ | 1 | pyrazolyl |
| —C₆H₅ | 1 | pyrazolyl |

TABLE 5-continued
| | | |
|---|---|---|
| 4-CH₃—C₆H₄ | 1 | 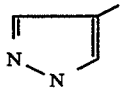 |
| 3-CH₃—C₆H₄ | 1 | 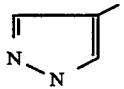 |
| 2-CH₃—C₆H₄ | 1 | 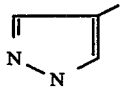 |
| 4-CH₃O—C₆H₄— | 1 | 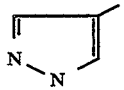 |
| 3-CH₃O—C₆H₄— | 1 | 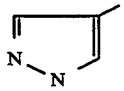 |
| 4-NO₂—C₆H₄— | 1 | 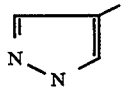 |
| 3-NO₂—C₆H₄— | 1 | 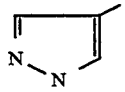 |
| 4-CN—C₆H₄— | 1 | 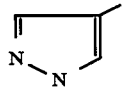 |
| 3-CN—C₆H₄— | 1 | 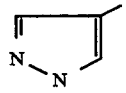 |
| 4-CF₃—C₆H₄— | 1 | 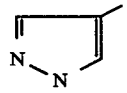 |
| 3-CF₃—C₆H₄— | 1 | 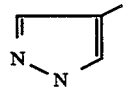 |
| 4-(C(CH₃)₃)—C₆H₄— | 1 | 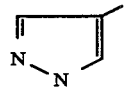 |
| 4-(C₆H₄)—C₆H₄— | 1 | 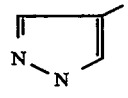 |
| 4-Cl—C₆H₄— | 1 | 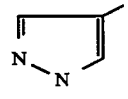 |
TABLE 5-continued
| | | |
|---|---|---|
| 3-Cl—C₆H₄— | 1 | 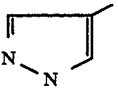 |
| 2-Cl—C₆H₄— | 1 | 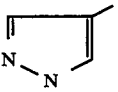 |
| 4-Br—C₆H₄— | 1 | 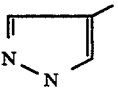 |
| 3-Br—C₆H₄— | 1 | 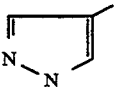 |
| 2-Br—C₆H₄— | 1 | 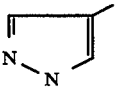 |
| 4-F—C₆H₄— | 1 | 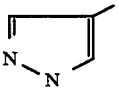 |
| 3-F—C₆H₄— | 1 | 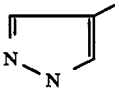 |
| 2-F—C₆H₄— | 1 | 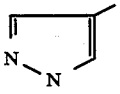 |
| 3,4-Cl₂—C₆H₃— | 1 | 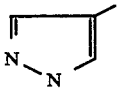 |
| 2,4-Cl₂—C₆H₃— | 1 | 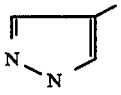 |
| 3,4-F₂—C₆H₃— | 1 | 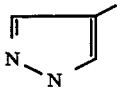 |
| 2,4-F₂—C₆H₃— | 1 | 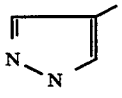 |
| 2,6-F₂—C₆H₃— | 1 | 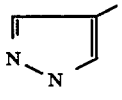 |
| 5-Cl-2-CH₃O—C₆H₃ | 1 | |

TABLE 5-continued
| | | |
|---|---|---|
| —CH₃ | 5 | 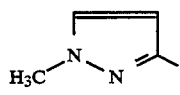 |
| —CH(CH₃)₂ | 5 | 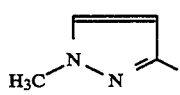 |
| —C(CH₃)₃ | 5 | 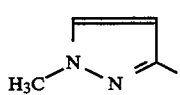 |
| -Cyclo-C₃H₅ | 5 | 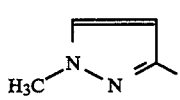 |
| —C₆H₅ | 5 | 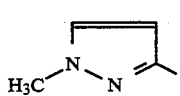 |
| 4-CH₃—C₆H₄ | 5 | 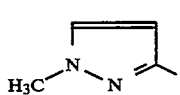 |
| 3-CH₃—C₆H₄ | 5 | 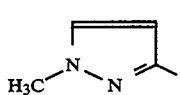 |
| 2-CH₃—C₆H₄ | 5 | 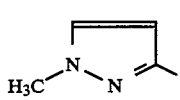 |
| 4-CH₃O—C₆H₄— | 5 | 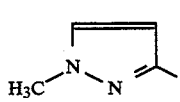 |
| 3-CH₃O—C₆H₄— | 5 | 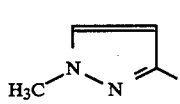 |
| 4-NO₂—C₆H₄— | 5 | 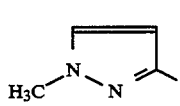 |
| 3-NO₂—C₆H₄— | 5 | 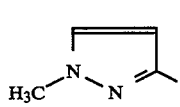 |
| 4-CN—C₆H₄— | 5 | 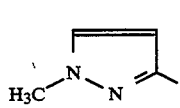 |
| 3-CN—C₆H₄— | 5 | 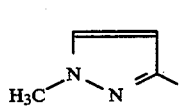 |
| 4-CF₃—C₆H₄— | 5 | 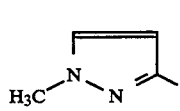 |
TABLE 5-continued
| | | |
|---|---|---|
| 3-CF₃—C₆H₄— | 5 | 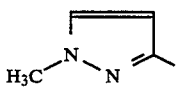 |
| 4-(C(CH₃)₃)—C₆H₄— | 5 | 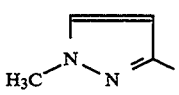 |
| 4-(C₆H₄)—C₆H₄— | 5 | 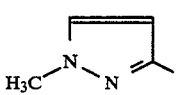 |
| 4-Cl—C₆H₄— | 5 | 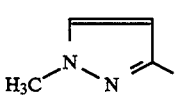 |
| 3-Cl—C₆H₄— | 5 | 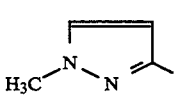 |
| 2-Cl—C₆H₄— | 5 | 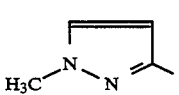 |
| 4-Br—C₆H₄— | 5 | 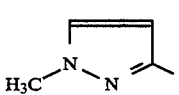 |
| 3-Br—C₆H₄— | 5 | 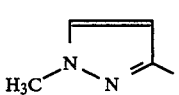 |
| 2-Br—C₆H₄— | 5 | 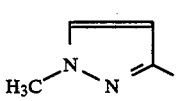 |
| 4-F—C₆H₄— | 5 | 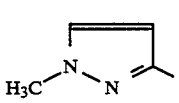 |
| 3-F—C₆H₄— | 5 | 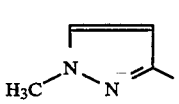 |
| 2-F—C₆H₄— | 5 | 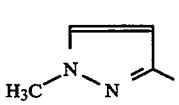 |
| 3,4-Cl₂—C₆H₃— | 5 | 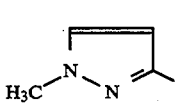 |
| 2,4-Cl₂—C₆H₃— | 5 | 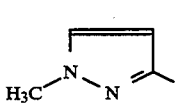 |
| 3,4-F₂—C₆H₃— | 5 | 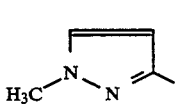 |

TABLE 5-continued

| | | |
|---|---|---|
| 2,4-F$_2$—C$_6$H$_3$— | 5 | 1-methyl-3-pyrazolyl (H$_3$C-N-N=) |
| 2,6-F$_2$—C$_6$H$_3$— | 5 | 1-methyl-3-pyrazolyl |
| 5-Cl-2-CH$_3$O—C$_6$H$_3$ | 5 | 1-methyl-3-pyrazolyl |
| —CH$_3$ | 3 | 5-isoxazolyl (N-O) |
| —CH(CH$_3$)$_2$ | 3 | 5-isoxazolyl |
| —(CH$_3$)$_2$ | 3 | 5-isoxazolyl |
| -Cyclo-C$_3$H$_5$ | 3 | 5-isoxazolyl |
| —C$_6$H$_5$ | 3 | 5-isoxazolyl |
| 4-CH$_3$—C$_6$H$_4$ | 3 | 5-isoxazolyl |
| 3-CH$_3$—C$_6$H$_4$ | 3 | 5-isoxazolyl |
| 2-CH$_3$—C$_6$H$_4$ | 3 | 5-isoxazolyl |
| 4-CH$_3$O—C$_6$H$_4$ | 3 | 5-isoxazolyl |
| 3-CH$_3$O—C$_6$H$_4$ | 3 | 5-isoxazolyl |
| 4-NO$_2$—C$_6$H$_4$— | 3 | 5-isoxazolyl |
| 3-NO$_2$—C$_6$H$_4$— | 3 | 5-isoxazolyl |

TABLE 5-continued

| | | |
|---|---|---|
| 4-CN—C$_6$H$_4$— | 3 | 5-isoxazolyl |
| 3-CN—C$_6$H$_4$— | 3 | 5-isoxazolyl |
| 4-CF$_3$—C$_6$H$_4$— | 3 | 5-isoxazolyl |
| 3-CF$_3$—C$_6$H$_4$— | 3 | 5-isoxazolyl |
| 4-(C(CH$_3$)$_3$)—C$_6$H$_4$— | 3 | 5-isoxazolyl |
| 4-(C$_6$H$_4$)—C$_6$H$_4$— | 3 | 5-isoxazolyl |
| 4-Cl—C$_6$H$_4$— | 3 | 5-isoxazolyl |
| 3-Cl—C$_6$H$_4$— | 3 | 5-isoxazolyl |
| 2-Cl—C$_6$H$_4$— | 3 | 5-isoxazolyl |
| 4-Br—C$_6$H$_4$— | 3 | 5-isoxazolyl |
| 3-Br—C$_6$H$_4$— | 3 | 5-isoxazolyl |
| 2-Br—C$_6$H$_4$— | 3 | 5-isoxazolyl |
| 4-F—C$_6$H$_4$— | 3 | 5-isoxazolyl |
| 3-F—C$_6$H$_4$— | 3 | 5-isoxazolyl |
| 2-F—C$_6$H$_4$— | 3 | 5-isoxazolyl |

TABLE 5-continued
| | | |
|---|---|---|
| 3,4-Cl$_2$—C$_6$H$_3$— | 3 | 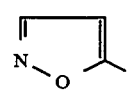 |
| 2,4-Cl$_2$—C$_6$H$_3$— | 3 | 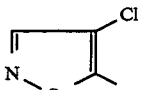 |
| 3,4-F$_2$—C$_6$H$_3$— | 3 | 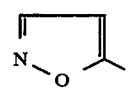 |
| 2,4-F$_2$—C$_6$H$_3$— | 3 | 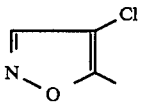 |
| 2,6-F$_2$—C$_6$H$_3$— | 3 | 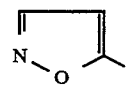 |
| 5-Cl-2-CH$_3$O—C$_6$H$_3$ | 3 |  |
| —CH$_3$ | 3 | 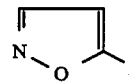 |
| —CH(CH$_3$)$_2$ | 3 |  |
| —C(CH$_3$)$_2$ | 3 | 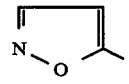 |
| -Cyclo-C$_3$H$_5$ | 3 |  |
| —C$_6$H$_5$ | 3 | 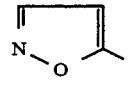 |
| 4-CH$_3$—C$_6$H$_4$ | 3 |  |
| 3-CH$_3$—C$_6$H$_4$ | 3 | 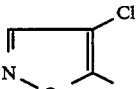 |
| 2-CH$_3$—C$_6$H$_4$ | 3 | 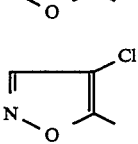 |
| 4-CH$_3$O—C$_6$H$_4$— | 3 |  |
TABLE 5-continued
| | | |
|---|---|---|
| 3-CH$_3$O—C$_6$H$_4$— | 3 |  |
| 4-NO$_2$—C$_6$H$_4$— | 3 | 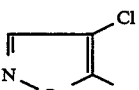 |
| 3-NO$_2$—C$_6$H$_4$— | 3 | 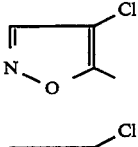 |
| 4-CN—C$_6$H$_4$— | 3 | 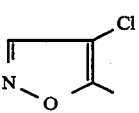 |
| 3-CN—C$_6$H$_4$— | 3 | 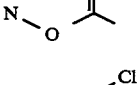 |
| 4-CF$_3$—C$_6$H$_4$— | 3 |  |
| 3-CF$_3$—C$_6$H$_4$— | 3 | 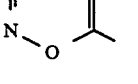 |
| 4-(C(CH$_3$)$_3$)—C$_6$H$_4$— | 3 |  |
| 4-(C$_6$H$_4$)—C$_6$H$_4$— | 3 | 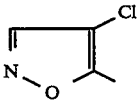 |
| 4-Cl—C$_6$H$_4$— | 3 | 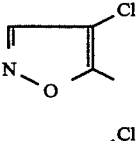 |
| 3-Cl—C$_6$H$_4$— | 3 |  |
| 2-Cl—C$_6$H$_4$— | 3 | 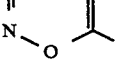 |
| 4-Br—C$_6$H$_4$— | 3 |  |
| 3-Br—C$_6$H$_4$— | 3 | 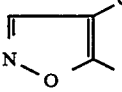 |

TABLE 5-continued
| | | |
|---|---|---|
| 2-Br—C6H4— | 3 | 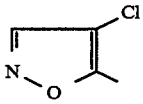 |
| 4-F—C6H4— | 3 | 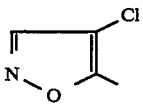 |
| 3-F—C6H4— | 3 | 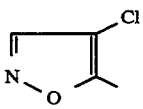 |
| 2-F—C6H4— | 3 | 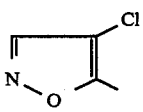 |
| 3,4-Cl2—C6H3— | 3 | 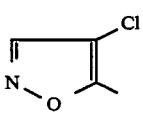 |
| 2,4-Cl2—C6H3— | 3 | 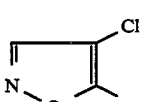 |
| 3,4-F2—C6H3— | 3 | 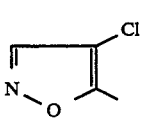 |
| 2,4-F2—C6H3— | 3 |  |
| 2,6-F2—C6H3— | 3 | 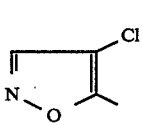 |
| 5-Cl-2-CH3O—C6H3 | 3 |  |
| —CH3 | 5 | 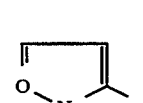 |
| —CH(CH3)2 | 5 | 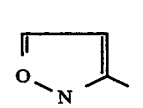 |
| —C(CH3)2 | 5 | 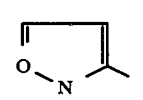 |
| -Cyclo-C3H5 | 5 | 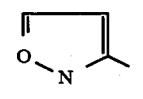 |
TABLE 5-continued
| | | |
|---|---|---|
| —C6H5 | 5 | 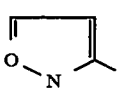 |
| 4-CH3—C6H4 | 5 | 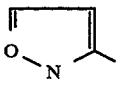 |
| 3-CH3—C6H4 | 5 | 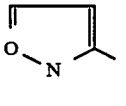 |
| 2-CH3—C6H4 | 5 | 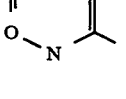 |
| 4-CH3O—C6H4— | 5 | 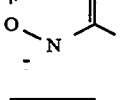 |
| 3-CH3O—C6H4— | 5 | 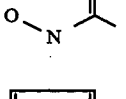 |
| 4-NO2—C6H4— | 5 | 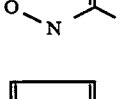 |
| 3-NO2—C6H4— | 5 | 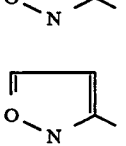 |
| 4-CN—C6H4— | 5 |  |
| 3-CN—C6H4— | 5 | 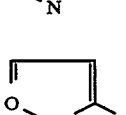 |
| 4-CF3—C6H4— | 5 | 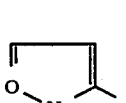 |
| 3-CF3—C6H4— | 5 | 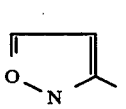 |
| 4-(C(CH3)3)—C6H4— | 5 | 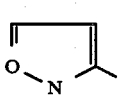 |
| 4-(C6H4)—C6H4— | 5 | 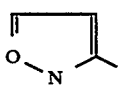 |
| 4-Cl—C6H4— | 5 |  |

TABLE 5-continued
| | | |
|---|---|---|
| 3-Cl—C₆H₄— | 5 | 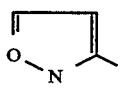 |
| 2-Cl—C₆H₄— | 5 | 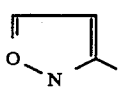 |
| 4-Br—C₆H₄— | 5 | 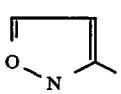 |
| 3-Br—C₆H₄— | 5 | 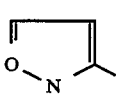 |
| 2-Br—C₆H₄— | 5 | 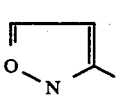 |
| 4-F—C₆H₄— | 5 | 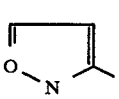 |
| 3-F—C₆H₄— | 5 | 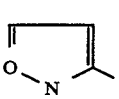 |
| 2-F—C₆H₄— | 5 | 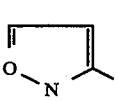 |
| 3,4-Cl₂—C₆H₃— | 5 | 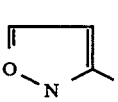 |
| 2,4-Cl₂—C₆H₃— | 5 | 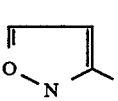 |
| 3,4-F₂—C₆H₃— | 5 | 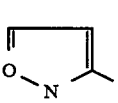 |
| 2,4-F₂—C₆H₃— | 5 | 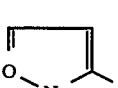 |
| 2,6-F₂—C₆H₃— | 5 | 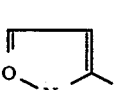 |
| 5-Cl-2-CH₃O—C₆H₃ | 5 | 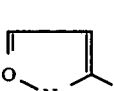 |
| —CH₃ | 3 | 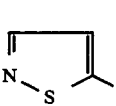 |
| —CH(CH₃)₂ | 3 | 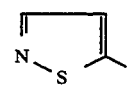 |
| —C(CH₃)₃ | 3 | 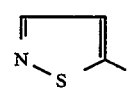 |
| -Cyclo-C₃H₅ | 3 | 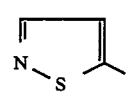 |
| —C₆H₅ | 3 | 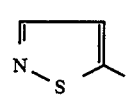 |
| 4-CH₃—C₆H₄— | 3 | 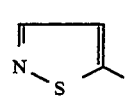 |
| 3-CH₃—C₆H₄— | 3 | 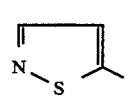 |
| 2-CH₃—C₆H₄— | 3 | 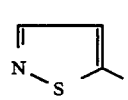 |
| 4-CH₃O—C₆H₄— | 3 | 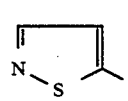 |
| 3-CH₃O—C₆H₄— | 3 | 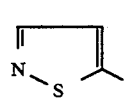 |
| 4-NO₂—C₆H₄— | 3 | 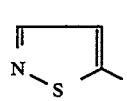 |
| 3-NO₂—C₆H₄— | 3 | 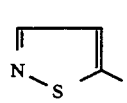 |
| 4-CN—C₆H₄— | 3 | 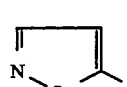 |
| 3-CN—C₆H₄— | 3 | 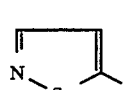 |
| 4-CF₃—C₆H₄— | 3 | 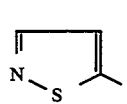 |
| 3-CF₃—C₆H₄— | 3 |  |

TABLE 5-continued

| | | |
|---|---|---|
| 4-(C(CH$_3$)$_3$)—C$_6$H$_4$— | 3 | isothiazole (N-S) |
| 4-(C$_6$H$_4$)—C$_6$H$_4$— | 3 | isothiazole (N-S) |
| 4-Cl—C$_6$H$_4$— | 3 | isothiazole (N-S) |
| 3-Cl—C$_6$H$_4$— | 3 | isothiazole (N-S) |
| 2-Cl—C$_6$H$_4$— | 3 | isothiazole (N-S) |
| 4-Br—C$_6$H$_4$— | 3 | isothiazole (N-S) |
| 3-Br—C$_6$H$_4$— | 3 | isothiazole (N-S) |
| 2-Br—C$_6$H$_4$— | 3 | isothiazole (N-S) |
| 4-F—C$_6$H$_4$— | 3 | isothiazole (N-S) |
| 3-F—C$_6$H$_4$— | 3 | isothiazole (N-S) |
| 2-F—C$_6$H$_4$— | 3 | isothiazole (N-S) |
| 3,4-Cl$_2$—C$_6$H$_3$— | 3 | isothiazole (N-S) |
| 2,4-Cl$_2$—C$_6$H$_3$— | 3 | isothiazole (N-S) |
| 3,4-F$_2$—C$_6$H$_3$— | 3 | isothiazole (N-S) |
| 2,4-F$_2$—C$_6$H$_3$— | 3 | isothiazole (N-S) |
| 2,6-F$_2$—C$_6$H$_3$— | 3 | isothiazole (N-S) |
| 5-Cl-2-CH$_3$O—C$_6$H$_3$ | 3 | isothiazole (N-S) |
| —CH$_3$ | 2 | isoxazole (N-O) |
| —CH(CH$_3$)$_2$ | 2 | isoxazole (N-O) |
| —C(CH$_3$)$_2$ | 2 | isoxazole (N-O) |
| -Cyclo-C$_3$H$_5$ | 2 | isoxazole (N-O) |
| —C$_6$H$_5$ | 2 | isoxazole (N-O) |
| 4-CH$_3$—C$_6$H$_4$ | 2 | isoxazole (N-O) |
| 3-CH$_3$—C$_6$H$_4$ | 2 | isoxazole (N-O) |
| 2-CH$_3$—C$_6$H$_4$ | 2 | isoxazole (N-O) |
| 4-CH$_3$O—C$_6$H$_4$— | 2 | isoxazole (N-O) |
| 3-CH$_3$O—C$_6$H$_4$— | 2 | isoxazole (N-O) |
| 4-NO$_2$—C$_6$H$_4$— | 2 | isoxazole (N-O) |
| 3-NO$_2$—C$_6$H$_4$— | 2 | isoxazole (N-O) |

TABLE 5-continued
| | | |
|---|---|---|
| 4-CN—C6H4— | 2 | 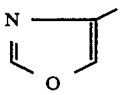 |
| 3-CN—C6H4— | 2 | 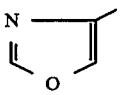 |
| 4-CF3—C6H4— | 2 | 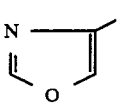 |
| 3-CF3—C6H4— | 2 | 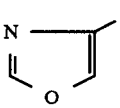 |
| 4-(C(CH3)3)—C6H4— | 2 | 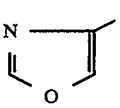 |
| 4-(C6H4)—C6H4— | 2 | 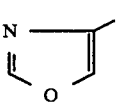 |
| 4-Cl—C6H4— | 2 | 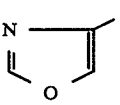 |
| 3-Cl—C6H4— | 2 | 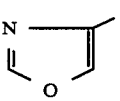 |
| 2-Cl—C6H4— | 2 | 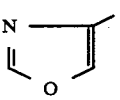 |
| 4-Br—C6H4— | 2 | 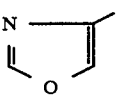 |
| 3-Br—C6H4— | 2 | 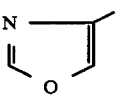 |
| 2-Br—C6H4— | 2 | 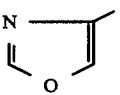 |
| 4-F—C6H4— | 2 | 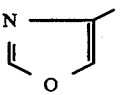 |
| 3-F—C6H4— | 2 | 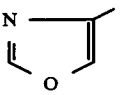 |
| 2-F—C6H4— | 2 | 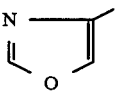 |
| 3,4-Cl2—C6H3— | 2 | 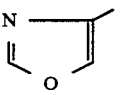 |
| 2,4-Cl2—C6H3— | 2 | 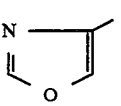 |
| 3,4-F2—C6H3— | 2 | 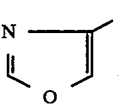 |
| 2,4-F2—C6H3— | 2 | 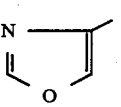 |
| 2,6-F2—C6H3— | 2 | 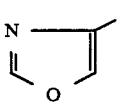 |
| 5-Cl-2-CH3O—C6H3 | 2 | 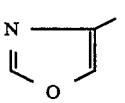 |
| —CH3 | 2 | 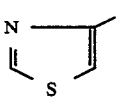 |
| —CH(CH3)2 | 2 | 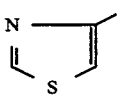 |
| —C(CH3)2 | 2 | 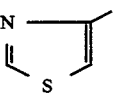 |
| -Cyclo-C3H5 | 2 | 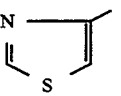 |
| —C6H5 | 2 | 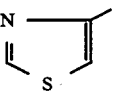 |
| 4-CH3—C6H4 | 2 | 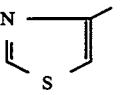 |
| 3-CH3—C6H4 | 2 | 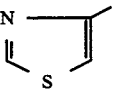 |

TABLE 5-continued
| | | |
|---|---|---|
| 2-CH₃—C₆H₄— | 2 | 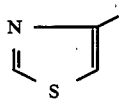 |
| 4-CH₃O—C₆H₄— | 2 | 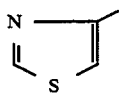 |
| 3-CH₃O—C₆H₄— | 2 | 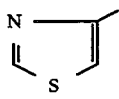 |
| 4-NO₂—C₆H₄— | 2 | 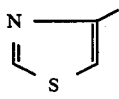 |
| 3-NO₂—C₆H₄— | 2 | 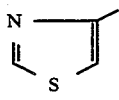 |
| 4-CN—C₆H₄— | 2 | 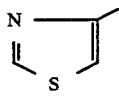 |
| 3-CN—C₆H₄— | 2 | 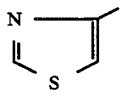 |
| 4-CF₃—C₆H₄— | 2 | 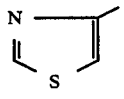 |
| 3-CF₃—C₆H₄— | 2 | 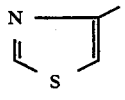 |
| 4-(C(CH₃))—C₆H₄— | 2 | 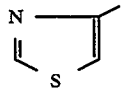 |
| 4-(C₆H₄)—C₆H₄— | 2 | 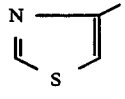 |
| 4-Cl—C₆H₄— | 2 | 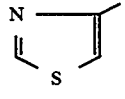 |
| 3-Cl—C₆H₄— | 2 | 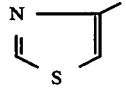 |
| 2-Cl—C₆H₄— | 2 | 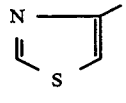 |
TABLE 5-continued
| | | |
|---|---|---|
| 4-Br—C₆H₄— | 2 | 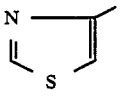 |
| 3-Br—C₆H₄— | 2 | 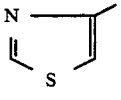 |
| 2-Br—C₆H₄— | 2 | 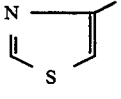 |
| 4-F—C₆H₄— | 2 | 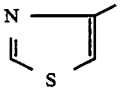 |
| 3-F—C₆H₄— | 2 | 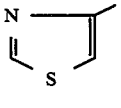 |
| 2-F—C₆H₄— | 2 | 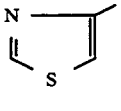 |
| 3,4-Cl₂—C₆H₃— | 2 | 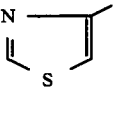 |
| 2,4-Cl₂—C₆H₃— | 2 | 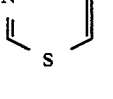 |
| 3,4-F₂—C₆H₃— | 2 | 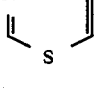 |
| 2,4-F₂—C₆H₃— | 2 | 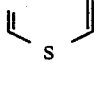 |
| 2,6-F₂—C₆H₃— | 2 | 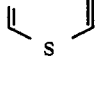 |
| 5-Cl-2-CH₃O—C₆H₃ | 2 | 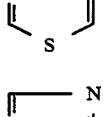 |
| —CH₃ | 3 | 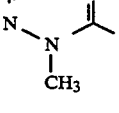 |
| —CH(CH₃)₂ | 3 | 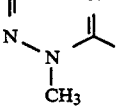 |

TABLE 5-continued

| | | |
|---|---|---|
| —C(CH₃)₂ | 3 | *N-methyl triazolyl ethylidene* |
| -Cyclo-C₃H₅ | 3 | *N-methyl triazolyl ethylidene* |
| —C₆H₅ | 3 | *N-methyl triazolyl ethylidene* |
| 4-CH₃—C₆H₄ | 3 | *N-methyl triazolyl ethylidene* |
| 3-CH₃—C₆H₄ | 3 | *N-methyl triazolyl ethylidene* |
| 2-CH₃—C₆H₄ | 3 | *N-methyl triazolyl ethylidene* |
| 4-CH₃O—C₆H₄— | 3 | *N-methyl triazolyl ethylidene* |
| 3-CH₃O—C₆H₄— | 3 | *N-methyl triazolyl ethylidene* |
| 4-NO₂—C₆H₄— | 3 | *N-methyl triazolyl ethylidene* |
| 3-NO₂—C₆H₄— | 3 | *N-methyl triazolyl ethylidene* |
| 4-CN—C₆H₄— | 3 | *N-methyl triazolyl ethylidene* |
| 3-CN—C₆H₄— | 3 | *N-methyl triazolyl ethylidene* |
| 4-CF₃—C₆H₄— | 3 | *N-methyl triazolyl ethylidene* |
| 3-CF₃—C₆H₄— | 3 | *N-methyl triazolyl ethylidene* |
| 4-(C(CH₃)₃)—C₆H₄— | 3 | *N-methyl triazolyl ethylidene* |
| 4-(C₆H₄)—C₆H₄— | 3 | *N-methyl triazolyl ethylidene* |
| 4-Cl—C₆H₄— | 3 | *N-methyl triazolyl ethylidene* |
| 3-Cl—C₆H₄— | 3 | *N-methyl triazolyl ethylidene* |
| 2-Cl—C₆H₄— | 3 | *N-methyl triazolyl ethylidene* |
| 4-Br—C₆H₄— | 3 | *N-methyl triazolyl ethylidene* |
| 3-Br—C₆H₄— | 3 | *N-methyl triazolyl ethylidene* |
| 2-Br—C₆H₄— | 3 | *N-methyl triazolyl ethylidene* |

TABLE 5-continued

| | | |
|---|---|---|
| 4-F—C₆H₄— | 3 | pyrazole-N-CH₃ |
| 3-F—C₆H₄— | 3 | pyrazole-N-CH₃ |
| 2-F—C₆H₄— | 3 | pyrazole-N-CH₃ |
| 3,4-Cl₂—C₆H₃— | 3 | pyrazole-N-CH₃ |
| 2,4-Cl₂—C₆H₃— | 3 | pyrazole-N-CH₃ |
| 3,4-F₂—C₆H₃— | 3 | pyrazole-N-CH₃ |
| 2,4-F₂—C₆H₃— | 3 | pyrazole-N-CH₃ |
| 2,6-F₂—C₆H₃— | 3 | pyrazole-N-CH₃ |
| 5-Cl-2-CH₃O—C₆H₃ | 3 | pyrazole-N-CH₃ |
| —CH₃ | 5 | oxadiazole |
| —CH(CH₃)₂ | 5 | oxadiazole |
| —C(CH₃)₂ | 5 | oxadiazole |
| -Cyclo-C₃H₅ | 5 | oxadiazole |
| —C₆H₅ | 5 | oxadiazole |
| 4-CH₃—C₆H₄ | 5 | oxadiazole |
| 3-CH₃—C₆H₄ | 5 | oxadiazole |
| 2-CH₃—C₆H₄ | 5 | oxadiazole |
| 4-CH₃O—C₆H₄— | 5 | oxadiazole |
| 3-CH₃O—C₆H₄— | 5 | oxadiazole |
| 4-NO₂—C₆H₄— | 5 | oxadiazole |
| 3-NO₂—C₆H₄— | 5 | oxadiazole |
| 4-CN—C₆H₄— | 5 | oxadiazole |
| 3-CN—C₆H₄— | 5 | oxadiazole |
| 4-CF₃—C₆H₄— | 5 | oxadiazole |
| 3-CF₃—C₆H₄— | 5 | oxadiazole |
| 4-(C(CH₃)₃)—C₆H₄— | 5 | oxadiazole |
| 4-(C₆H₄)—C₆H₄— | 5 | oxadiazole |

TABLE 5-continued
| | | |
|---|---|---|
| 4-Cl—C$_6$H$_4$— | 5 |  |
| 3-Cl—C$_6$H$_4$— | 5 |  |
| 2-Cl—C$_6$H$_4$— | 5 |  |
| 4-Br—C$_6$H$_4$— | 5 |  |
| 3-Br—C$_6$H$_4$— | 5 |  |
| 2-Br—C$_6$H$_4$— | 5 |  |
| 4-F—C$_6$H$_4$— | 5 |  |
| 3-F—C$_6$H$_4$— | 5 |  |
| 2-F—C$_6$H$_4$— | 5 |  |
| 3,4-Cl$_2$—C$_6$H$_3$— | 5 |  |
| 2,4-Cl$_2$—C$_6$H$_3$— | 5 |  |
| 3,4-F$_2$—C$_6$H$_3$— | 5 |  |
| 2,4-F$_2$—C$_6$H$_3$— | 5 |  |
| 2,6-F$_2$—C$_6$H$_3$— | 5 |  |
| 5-Cl-2-CH$_3$O—C$_6$H$_3$ | 5 |  |
TABLE 5-continued
| | | |
|---|---|---|
| —CH$_3$ | 5 | 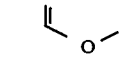 |
| —CH(CH$_3$)$_2$ | 5 | 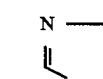 |
| —C(CH$_3$)$_2$ | 5 | 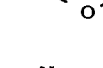 |
| —Cylco—C$_3$H$_5$ | 5 | 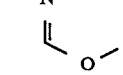 |
| —C$_6$H$_5$ | 5 | 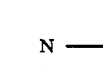 |
| 4-CH$_3$—C$_6$H$_4$ 4 | 5 | 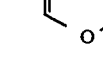 |
| 3-CH$_3$—C$_6$H$_4$ | 5 | 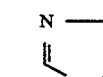 |
| 2-CH$_3$—C$_6$H$_4$ | 5 | 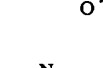 |
| 4-CH$_3$O—C$_6$H$_4$— | 5 | 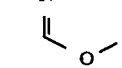 |
| 3-CH$_3$O—C$_6$H$_4$— | 5 | 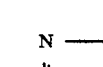 |
| 4-NO$_2$—C$_6$H$_4$— | 5 | 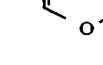 |
| 3-NO$_2$—C$_6$H$_4$— | 5 | 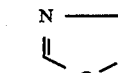 |
| 4-CN—C$_6$H$_4$— | 5 | 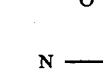 |
| 3-CN—C$_6$H$_4$— | 5 | 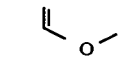 |

TABLE 5-continued
| | | |
|---|---|---|
| 4-CF₃—C₆H₄— | 5 | 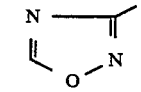 |
| 3-CF₃—C₆H₄— | 5 | 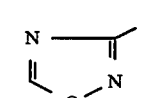 |
| 4-(C(CH₃)₃)—C₆H₄— | 5 | 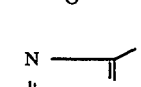 |
| 4-(C₆H₄)—C₆H₄— | 5 | 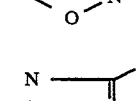 |
| 4-Cl—C₆H₄— | 5 | 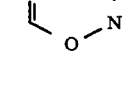 |
| 3-Cl—C₆H₄— | 5 | 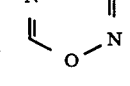 |
| 2-Cl—C₆H₄— | 5 | 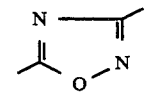 |
| 4-Br—C₆H₄— | 5 | 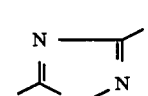 |
| 3-Br—C₆H₄— | 5 | 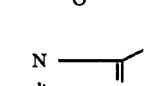 |
| 2-Br—C₆H₄— | 5 | 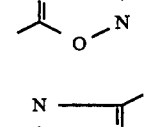 |
| 4-F—C₆H₄— | 5 | 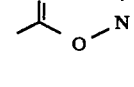 |
| 3-F—C₆H₄— | 5 | 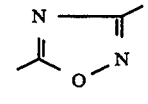 |
| 2-F—C₆H₄— | 5 | 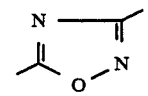 |
| 3,4-Cl₂—C₆H₃— | 5 | 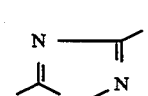 |
TABLE 5-continued
| | | |
|---|---|---|
| 2,4-Cl₂—C₆H₃— | 5 | 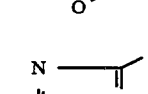 |
| 3,4-F₂—C₆H₃— | 5 | 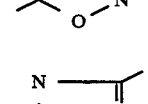 |
| 2,4-F₂—C₆H₃— | 5 | 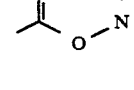 |
| 2,6-F₂—C₆H₃— | 5 |  |
| 5-Cl-2-CH₃O—C₆H₃ | 5 | |
| —CH₃ | 3 | |
| —CH(CH₃)₂ | 3 | |
| —C(CH₃)₂ | 3 | |
| -Cyclo-C₃H₅ | 3 | |
| —C₆H₅ | 3 | |
| 4-CH₃—C₆H₄ | 3 | |
| 3-CH₃—C₆H₄ | 3 | |
| 2-CH₃—C₆H₄ | 3 | |
| 4-CH₃O—C₆H₄— | 3 | |

TABLE 5-continued

| | | |
|---|---|---|
| 3-CH3O—C6H4— | 3 | oxadiazole ring (N=C-C=N-O) |
| 4-NO2—C6H4— | 3 | oxadiazole ring |
| 3-NO2—C6H4— | 3 | oxadiazole ring |
| 4-CN—C6H4— | 3 | oxadiazole ring |
| 3-CN—C6H4— | 3 | oxadiazole ring |
| 4-CF3—C6H4— | 3 | oxadiazole ring |
| 3-CF3—C6H4— | 3 | oxadiazole ring |
| 4-(C(CH3)3)—C6H4— | 3 | oxadiazole ring |
| 4-(C6H4)—C6H4— | 3 | oxadiazole ring |
| 4-Cl—C6H4— | 3 | oxadiazole ring |
| 3-Cl—C6H4— | 3 | oxadiazole ring |
| 2-Cl—C6H4— | 3 | oxadiazole ring |
| 4-Br—C6H4— | 3 | oxadiazole ring |
| 3-Br—C6H4— | 3 | oxadiazole ring |
| 2-Br—C6H4— | 3 | oxadiazole ring |
| 4-F—C6H4— | 3 | oxadiazole ring |
| 3-F—C6H4— | 3 | oxadiazole ring |
| 2-F—C6H4— | 3 | oxadiazole ring |
| 3,4-Cl2—C6H3— | 3 | oxadiazole ring |
| 2,4-Cl2—C6H3— | 3 | oxadiazole ring |
| 3,4-F2—C6H3— | 3 | oxadiazole ring |
| 2,4-F2—C6H3— | 3 | oxadiazole ring |
| 2,6-F2—C6H3— | 3 | oxadiazole ring |
| 5-Cl-2-CH3O—C6H3 | 3 | oxadiazole ring |
| —CH3 | 5 | thiadiazole ring (N=C-C=N-S) |
| —CH(CH3)2 | 5 | thiadiazole ring |
| —C(CH3)2 | 5 | thiadiazole ring |
| -Cyclo-C3H5 | 5 | thiadiazole ring |

TABLE 5-continued

| | | |
|---|---|---|
| —C₆H₅ | 5 | thiadiazole |
| 4-CH₃—C₆H₄ | 5 | thiadiazole |
| 3-CH₃—C₆H₄ | 5 | thiadiazole |
| 2-CH₃—C₆H₄ | 5 | thiadiazole |
| 4-CH₃O—C₆H₄— | 5 | thiadiazole |
| 3-CH₃O—C₆H₄— | 5 | thiadiazole |
| 4-NO₂—C₆H₄— | 5 | thiadiazole |
| 3-NO₂—C₆H₄— | 5 | thiadiazole |
| 4-CN—C₆H₄— | 5 | thiadiazole |
| 3-CN—C₆H₄— | 5 | thiadiazole |
| 4-CF₃—C₆H₄— | 5 | thiadiazole |
| 3-CF₃—C₆H₄— | 5 | thiadiazole |
| 4-(C(CH₃)₃)—C₆H₄— | 5 | thiadiazole |
| 4-(C₆H₄)—C₆H₄— | 5 | thiadiazole |
| 4-Cl—C₆H₄— | 5 | thiadiazole |
| 3-Cl—C₆H₄— | 5 | thiadiazole |
| 2-Cl—C₆H₄— | 5 | thiadiazole |
| 4-Br—C₆H₄— | 5 | thiadiazole |
| 3-Br—C₆H₄— | 5 | thiadiazole |
| 2-Br—C₆H₄— | 5 | thiadiazole |
| 4-F—C₆H₄— | 5 | thiadiazole |
| 3-F—C₆H₄— | 5 | thiadiazole |
| 2-F—C₆H₄— | 5 | thiadiazole |
| 3,4-Cl₂—C₆H₃— | 5 | thiadiazole |
| 2,4-Cl₂—C₆H₃— | 5 | thiadiazole |
| 3,4-F₂—C₆H₃— | 5 | thiadiazole |
| 2,4-F₂—C₆H₃— | 5 | thiadiazole |
| 2,6-F₂—C₆H₃— | 5 | thiadiazole |

TABLE 5-continued

| | | |
|---|---|---|
| 5-Cl-2-CH3O—C6H3 | 5 | N=N, S, N ring (thiadiazole) |
| —CH3 | 3 | N—N, S ring |
| —CH(CH3)2 | 3 | N—N, S ring |
| —C(CH3)2 | 3 | N—N, S ring |
| -Cyclo-C3H5 | 3 | N—N, S ring |
| —C6H5 | 3 | N—N, S ring |
| 4-CH3—C6H4 | 3 | N—N, S ring |
| 3-CH3—C6H4 | 3 | N—N, S ring |
| 2-CH3—C6H4 | 3 | N—N, S ring |
| 4-CH3O—C6H4— | 3 | N—N, S ring |
| 3-CH3O—C6H4— | 3 | N—N, S ring |
| 4-NO2—C6H4— | 3 | N—N, S ring |
| 3-NO2—C6H4— | 3 | N—N, S ring |
| 4-CN—C6H4— | 3 | N—N, S ring |
| 3-CN—C6H4— | 3 | N—N, S ring |
| 4-CF3—C6H4— | 3 | N—N, S ring |
| 3-CF3—C6H4— | 3 | N—N, S ring |
| 4-(C(CH3)3)—C6H4— | 3 | N—N, S ring |
| 4-(C6H4)—C6H4— | 3 | N—N, S ring |
| 4-Cl—C6H4— | 3 | N—N, S ring |
| 3-Cl—C6H4— | 3 | N—N, S ring |
| 2-Cl—C6H4— | 3 | N—N, S ring |
| 4-Br—C6H4— | 3 | N—N, S ring |
| 3-Br—C6H4— | 3 | N—N, S ring |
| 2-Br—C6H4— | 3 | N—N, S ring |
| 4-F—C6H4— | 3 | N—N, S ring |
| 3-F—C6H4— | 3 | N—N, S ring |
| 2-F—C6H4— | 3 | N—N, S ring |
| 3,4-Cl2—C6H3— | 3 | N—N, S ring |
| 2,4-Cl2—C6H3— | 3 | N—N, S ring |

TABLE 5-continued

| | | |
|---|---|---|
| 3,4-F$_2$—C$_6$H$_3$— | 3 | 2-methyl-1,3,4-thiadiazole |
| 2,4-F$_2$—C$_6$H$_3$— | 3 | 2-methyl-1,3,4-thiadiazole |
| 2,6-F$_2$—C$_6$H$_3$— | 3 | 2-methyl-1,3,4-thiadiazole |
| 5-Cl-2-CH$_3$O—C$_6$H$_3$ | 3 | 2-methyl-1,3,4-thiadiazole |
| 3-Br—C$_6$H$_4$— | 3 | 2-methyl-1,3,4-thiadiazole |
| 2-Br—C$_6$H$_4$— | 3 | 2-methyl-1,3,4-thiadiazole |
| 4-F—C$_6$H$_4$— | 3 | 2-methyl-1,3,4-thiadiazole |
| 3-F—C$_6$H$_4$— | 3 | 2-methyl-1,3,4-thiadiazole |
| 2-F—C$_6$H$_4$— | 3 | 2-methyl-1,3,4-thiadiazole |
| 3,4-Cl$_2$—C$_6$H$_3$— | 3 | 2-methyl-1,3,4-thiadiazole |
| 2,4-Cl$_2$—C$_6$H$_3$— | 3 | 2-methyl-1,3,4-thiadiazole |
| 3,4-F$_2$—C$_6$H$_3$— | 3 | 2-methyl-1,3,4-thiadiazole |
| 2,4-F$_2$—C$_6$H$_3$— | 3 | 2-methyl-1,3,4-thiadiazole |
| 2,6-F$_2$—C$_6$H$_3$— | 3 | 2-methyl-1,3,4-thiadiazole |
| 5-Cl-2-CH$_3$O—C$_6$H$_3$ | 3 | 2-methyl-1,3,4-thiadiazole |

TABLE 5-continued

| | | |
|---|---|---|
| C$_6$H$_5$ | 1 | 3,4-dimethylpyrazole |
| 4-CH$_3$—C$_6$H$_4$ | 1 | 3,4-dimethylpyrazole |
| 4-Cl—C$_6$H$_4$ | 1 | 3,4-dimethylpyrazole |
| C$_6$H$_5$ | 1 | 3,4-dimethylpyrazole |
| 4-CH$_3$—C$_6$H$_4$ | 1 | 3,4-dimethylpyrazole |
| 4-Cl—C$_6$H$_4$ | 1 | 3,4-dimethylpyrazole |
| C$_6$H$_5$ | 1 | 4-methylpyrazole (N-linked) |
| 4-CH$_3$—C$_6$H$_4$ | 1 | 4-methylpyrazole (N-linked) |
| 4-Cl—C$_6$H$_4$ | 1 | 4-methylpyrazole (N-linked) |
| C$_6$H$_5$ | 1 | 3-methylpyrazole |
| 4-CH$_3$—C$_6$H$_4$ | 1 | 3-methylpyrazole |
| 4-Cl—C$_6$H$_4$ | 1 | 3-methylpyrazole |
| C$_6$H$_5$ | 5 | 4-ethyl-3-methylisoxazole |
| 4-CH$_3$—C$_6$H$_4$ | 5 | 4-ethyl-3-methylisoxazole |

TABLE 5-continued
| | | |
|---|---|---|
| 4-Cl—C$_6$H$_4$ | 5 | 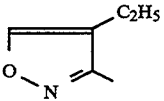 |
| Pyrid-2-yl | 3 | 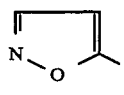 |
| 6-CH$_3$-Pyrid-2-yl | 3 | 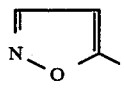 |
| 6-nC$_4$H$_9$-Pyrid-2-yl | 3 | 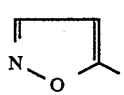 |
| C$_6$H$_5$ | 1 | 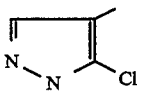 |
| 4-CH$_3$—C$_6$H$_4$ | 1 | 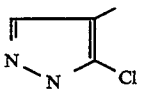 |
| 4-Cl—C$_6$H$_4$ | 1 | 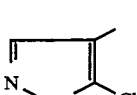 |
| C$_6$H$_5$ | 1 | 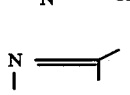 |
| 4-CH$_3$—C$_6$H$_4$ | 1 | 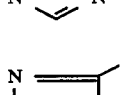 |
| 4-Cl—C$_6$H$_4$ | 1 | 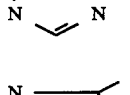 |
| H | — | 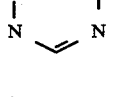 |
| 5-Cl | — | 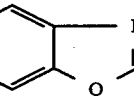 |
| 5-NO$_2$ | — | 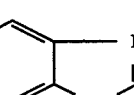 |
| 4,6,7-Cl$_3$ | — | 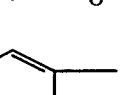 |
TABLE 5-continued
| | | |
|---|---|---|
| 5-NO$_2$, 6-Cl | — | 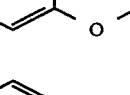 |
| H | — | 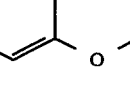 |
| 4-CH$_3$ | — |  |
| 1-CH$_3$ | — |  |
| 1-CH$_3$, 2-Cl | — | 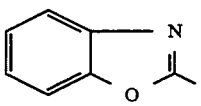 |
| 1-COCH$_3$ | — | 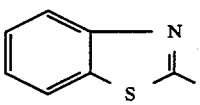 |
| 1-CH$_3$, 2-C$_6$H$_5$ | — | 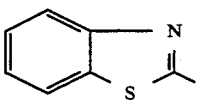 |
| 2-Thienyl | 5 | 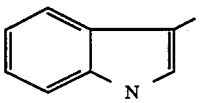 |
| 5-Cl-Thien-2-yl | 5 | 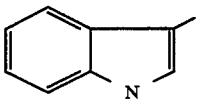 |
| 5-Br-Thien-2-yl | 5 | 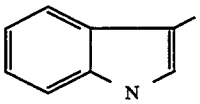 |
| 5-CH$_3$-Thien-2-yl | 5 | 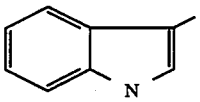 |
| 3-Isoxazolyl | 5 | 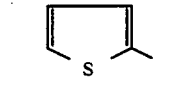 |
| 2,5-Dimethylpyrrolyl | 5 | 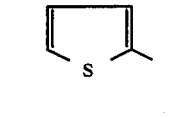 |
| 5-N,N-Dimethylamino-1,3,4-Thiadiazol-2-yl | 5 | 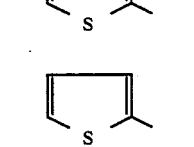 |

TABLE 5-continued

| | | |
|---|---|---|
| 4-Brom-thien-2-yl | 3 | isoxazole ring (N—O, =N, C) |
| 2,4,5-Trichlorthien-2-yl | 3 | isoxazole ring |
| 2-Furanyl | 3 | isoxazole ring |
| 3-[(H₃C)₂CH]-Isoxazol-5-yl | 3 | isoxazole ring |
| 2-Methylpyrazol-4-yl | 3 | isoxazole ring |
| 3-Pyridyl | 3 | isoxazole ring |
| 2,5-Diemthylfuran-2-yl | 5 | oxadiazole ring (N—N, O) |
| 3-Thienyl | 5 | oxadiazole ring |
| 3-Furanyl | 3 | oxazole ring |
| 3-Furanyl | 2 | oxazole ring |
| 1-Pyrryl | 2 | oxazole ring |
| 2,5-Dimethylpyrrl | 2 | isothiazole ring (N—S) |
| 3-[(H₃C)₂CH]-Isoxazol-5-yl | 3 | isoxazole ring (N—O) |
| 1-Methylpyrazol-3-yl | 3 | isoxazole ring (N—O) |

TABLE 6

I

Structure: phenyl ring bearing $R_n^3$ and $R^4$–A substituents, attached to C(=O)(W–R¹)=CH–R² (with H on the alkene terminus).

| R⁴ | A | R² | W–R¹ | $R^3_n$ |
|---|---|---|---|---|
| Phenyl | — | CH₃ | OCH₃ | H |
| H | — | CH₃ | NHCH₃ | H |
| H | — | CH₃ | C₂H₅ | H |
| Phenyl | — | C₂H₅ | OCH₃ | H |
| 4-Methylphenyl | — | CH₃ | OCH₃ | H |
| 4-Chlorphenyl | — | CH₃ | OCH₃ | H |
| H | — | CH₃ | OCH₃ | H |
| 2-n-Propyl-6-trifluormethyl-pyrimidin-4-yl | —OCH₂ | CH₃ | NHCH₃ | H |
| 2-n-Propyl-6-trifluormethyl-pyrimidin-4-yl | —OCH₂ | CH₃ | C₂H₅ | H |
| 5-Trifluormethyl-benzo-thiazol-2-yl | —SCH₂ | CH₃ | NHCH₃ | H |
| 5-Trifluormethyl-benzo-thiazol-2-yl | —SCH₂ | CH₃ | C₂H₅ | H |
| 6-Chlor-benzothiazol-2-yl | —SCH₂ | CH₃ | NHCH₃ | H |
| 6-Chlor-benzothiazol-2-yl | —SCH₂ | CH₃ | C₂H₅ | H |
| 3-Chlor-5-trifluormethyl-pyridin-2-yl | —SCH₂ | CH₃ | NHCH₃ | H |
| 3-Chlor-5-trifluormethyl-pyridin-2-yl | —OCH₂ | CH₃ | C₂H₅ | H |
| 5-Trifluormethylpyridin-2-yl | —SCH₂ | —CH₃ | NHCH₃ | H |
| 5-Trifluormethylpyridin-2-yl | —OCH₂ | —CH₃ | C₂H₅ | H |
| CH₃ | —OCH₂ | Cyclopropyl | OCH₃ | H |
| CH₃ | — | —CH=CH₂ | OCH₃ | H |
| CH₃ | — | —C≡CH | OCH₃ | H |
| CH₃ | — | i-Propyl | OCH₃ | H |
| CH₃ | — | —C≡N | OCH₃ | H |
| 2-Methyl-4-(2-ethoxy-iminoethyl)phenyl | —OCH₂ | CH₃ | C₂H₅ | H |
| 2-Methyl-4-(2-ethoxy-iminoethyl)phenyl | —OCH₂ | CH₃ | NHCH₃ | H |
| 2-Methyl-4-(2-methoxy-iminoethyl)phenyl | —OCH₂ | CH₃ | C₂H₅ | H |
| 2-Methyl-4-(2-methoxy-iminoethyl)phenyl | —OCH₂ | CH₃ | NHCH₃ | H |
| Phenyl | —SCH₂ | CH₃ | C₂H₅ | H |

TABLE 6-continued

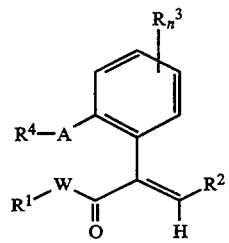

I

| R⁴ | A | R² | W-R¹ | R³ₙ |
|---|---|---|---|---|
| Phenyl | —SCH₂ | CH₃ | NHCH₃ | H |
| Phenyl | O | CH₃ | C₂H₅ | H |
| Phenyl | O | CH₃ | NHCH₃ | H |
| Phenyl | S | CH₃ | C₂H₅ | H |
| Phenyl | S | CH₃ | NHCH₃ | H |
| 1,3-Dioxolan-2-yl | — | —CH₃ | NHCH₃ | H |
| 1,3-Dioxolan-2-yl | — | —C₂H₅ | NHCH₃ | H |
| Phenyl | —CH₂—CH₂— | CH₃ | OCH₃ | H |
| H | —C(=O)— | —CH₃ | —OCH₃ | H |
| BrCH₂— | — | CH₃ | —OCH₃ | H |
| BrCH₂— | — | C₂H₅ | —OCH₃ | H |
| Tetrahydropyran-2-yl | —OCH₂ | CH₃ | —OCH₃ | H |
| Tetrahydropyran-2-yl | —OCH₂ | C₂H₅ | —OCH₃ | H |
| BrCH₂— | — | Cyclopropyl | —OCH₃ | H |
| CH₃ | —OCH₂ | CN | —OCH₃ | H |
| 2-n-Propyl-6-trifluormethyl-pyrimidin-4-yl | —OCH₂ | Cyclopropyl | —OCH₃ | H |
| 3-Phenylisoxazol-5-yl | —CCl=CH— | —CH₃ | —OCH₃ | H |
| 3-Phenylisoxazol-5-yl | —CCl=CH— | —C₂H₅ | —OCH₃ | H |
| 2-Phenyl-1,3,4-Oxadiazol-5-yl | —CCl=CH— | —CH₃ | —OCH₃ | H |
| 1-Phenylpyrazol-4-yl | —CH=CH— | —CH₃ | NHCH₃ | H |
| 1-Phenylpyrazol-4-yl | —CH=CH— | C₂H₅ | NHCH₃ | H |
| 1-Phenylpyrazol-4-yl | —CH=CH— | Cyclopropyl | OCH₃ | H |
| 1-Phenylpyrazol-4-yl | —CH=CH— | Cyclopropyl | NHCH₃ | H |
| 1-Phenylpyrazol-4-yl | —CH=CH— | —CN | OCH₃ | H |
| 1-Phenylpyrazol-4-yl | —CH=CH— | —CN | NHCH₃ | H |
| 1-Phenylpyrryl-3-yl | —CH=CH— | —CH₃ | NHCH₃ | H |
| 1-Phenylpyrryl-3-yl | —CH=CH— | C₂H₅ | NHCH₃ | H |
| 1-Phenylpyrryl-3-yl | —CH=CH— | Cyclopropyl | OCH₃ | H |
| 1-Phenylpyrryl-3-yl | —CH=CH— | Cyclopropyl | NHCH₃ | H |
| 1-Phenylpyrryl-3-yl | —CH=CH— | —CN | OCH₃ | H |
| 1-Phenylpyrryl-3-yl | —CH=CH— | —CN | NHCH₃ | H |
| 3-Phenylisoxazol-5-yl | —CH=CH— | —CH₃ | NHCH₃ | H |
| 3-Phenylisoxazol-5-yl | —CH=CH— | C₂H₅ | NHCH₃ | H |
| 3-Phenylisoxazol-5-yl | —CH=CH— | Cyclopropyl | OCH₃ | H |
| 3-Phenylisoxazol-5-yl | —CH=CH— | Cyclopropyl | NHCH₃ | H |
| 3-Phenylisoxazol-5-yl | —CH=CH— | —CN | OCH₃ | H |
| 3-Phenylisoxazol-5-yl | —CH=CH— | —CN | NHCH₃ | H |
| 2-Phenyloxazol-4-yl | —CH=CH— | —CH₃ | NHCH₃ | H |
| 2-Phenyloxazol-4-yl | —CH=CH— | C₂H₅ | NHCH₃ | H |
| 2-Phenyloxazol-4-yl | —CH=CH— | Cyclopropyl | OCH₃ | H |
| 2-Phenyloxazol-4-yl | —CH=CH— | Cyclopropyl | NHCH₃ | H |
| 2-Phenyloxazol-4-yl | —CH=CH— | —CN | OCH₃ | H |
| 2-Phenyloxazol-4-yl | —CH=CH— | —CN | NHCH₃ | H |
| 1-Phenylpyrazol-4-yl | —OCH₂— | —CH₃ | NHCH₃ | H |
| 1-Phenylpyrazol-4-yl | —OCH₂— | C₂H₅ | NHCH₃ | H |
| 1-Phenylpyrazol-4-yl | —OCH₂— | Cyclopropyl | OCH₃ | H |
| 1-Phenylpyrazol-4-yl | —OCH₂— | Cyclopropyl | NHCH₃ | H |
| 1-Phenylpyrazol-4-yl | —OCH₂— | —CN | OCH₃ | H |
| 1-Phenylpyrazol-4-yl | —OCH₂— | —CN | NHCH₃ | H |
| BrCH₂— | — | —CN | OCH₃ | H |

The ortho-substituted compounds I are suitable as fungicides.

The novel compounds are extremely effective on a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:
Erysiphe graminis in cereals,
Erysiphe cichoracearum and Sphaerotheca fuliginea in cucurbits,
Podosphaera leucotricha in apples,
Uncinula necator in vines,
Puccinia species in cereals,
Rhizoctonia species in cotton and lawns,
Ustilago species in cereals and sugar cane,
Venturia inaequalis (scab) in apples, Helminthosporium species in cereals,
Septoria nodorum in wheat,
Botrytis cinerea (gray mold) in strawberries and grapes,
Cercospora arachidicola in groundnuts,
Pseudocercosporella herpotrichoides in wheat and barley,
Pyricularia oryzae in rice,
Phytophthora infestans in potatoes and tomatoes,
Fusarium and Verticillium species in various plants,
Plasmopara viticola in grapes,
Alternaria species in fruit and vegetables.

The compounds I are applied by spraying or dusting the plants with the active ingredients, or treating the seeds of the plants with the active ingredients. They may be applied before or after infection of the plants, materials or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the ortho-substituted benzyl ester of a cyclopropanecarboxylic acid. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as ligninsulfite waste liquors and methylcellulose.

The fungicides generally contain from 0.1 to 95, and preferably from 0.5 to 90, wt % of active ingredient. The application rates are from 0.02 to 3 kg or more of active ingredient per hectare, depending on the type of effect desired.

When the active ingredients are used for treating seed, amounts of from 0.001 to 50, and preferably from 0.01 to 10, g per kg of seed are usually required.

When the agents according to the invention are used as fungicides, other active ingredients may also be present, e.g., herbicides, insecticides, growth regulators, other fungicides and fertilizers. When the agents are mixed with other fungicides, the fungicidal spectrum is in many cases increased.

The following list of fungicides with which the novel compounds may be combined is intended to illustrate possible combinations but not to impose any restrictions:
sulfur,
dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc N,N'-propylenebisdithiocarbamate and N,N'-polypropylenebis(thiocarbamyl) disulfide;
nitro derivatives, such as
dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and
diisopropyl 5-nitroisophthalate;
heterocyclic substances, such as
2-heptadecylimidazol-2-yl acetate,
2,4-dichloro-6-(o-chloroanilino)-s-triazine,
O,O-diethyl phthalimidophosphonothioate,
5-amino-1-[-bis-(dimethylamino)-phosphinyl]-3-phenyl-1,2,4-triazole,
2,3-dicyano-1,4-dithioanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide,
N-trichloromethylthiophthalimide,
N-dichlorofluoromethylthio-N',N'-dimethyl-N-phenyl-sulfuric acid diamide,
5-ethoxy-3-trichloromethyl-1,2,3-thiadiazole,
2-thiocyanatomethylthiobenzothiazole,
1,4-dichloro-2, 5-dimethoxybenzene,
4-(2-chlorophenylhydrazono)-3-methyl-5-isoxazolone,
2-thiopyridine 1-oxide,
8-hydroxyquinoline and its copper salt,
2,3-dihydro-5-carboxanilido-6-methyl-1,4-oxathiyne,
2,3-dihydro-5-carboxanilido-6-methyl-1,4-oxathiyne 4,4-dioxide,
2-methyl-5,6-dihydro-4H-pyran-3-carboxanilide,
2-methylfuran-3-carboxanilide,
2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-diethylfuran-3-carboxamide,
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide),
1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts,
N-[3-(p-tert.-butylphenyl)-2-methylpropyl]-cis-2,6-dimethylmorpholine,
N-[3-(p-tert.-butylphenyl)-2-methylpropyl]-piperidine,
1-[2-(2,4-dichlorophenyl)-4-ethyl-1,3-dioxolan-2-ylethyl]-1H-1,2,4-triazole,
1-[2-(2,4-dichlorophenyl)-4-n-propyl-1,3-dioxolan-2-ylethyl]-1H-1,2,4-triazole,
N-(n-propyl)-N-(2,4,6-trichlorophenoxyethyl)-N'-imidazolyl-urea,
1-(4-chlorophenoxy)-3,3-dimethyl-1-(1H-1,2,4-triazol-1-yl)-butan-2-one,
1-(4-chlorophenoxy)-3,3-dimethyl-1-(1H-1,2,4-triazol-1-yl)-butan-2-ol,
α-(2-chlorophenyl)-α-(4-chlorophenyl)-5-pyrimidinemethanol, 5-butyl-(2-dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene,
and various fungicides, such as
dodecylguanidine acetate,
3-[3-(3,5-dimethyl-2-oxycyclohexyl)-2-hydroxyethyl]-glutaramide,
hexachlorobenzene,
DL-methyl-N-(2,6-dimethylphenyl)-N-fur-2-yl alanate,
methyl DL-N-(2,6-dimethylphenyl)-N-(2'-methoxyacetyl)-alanate,
N-(2,6-dimethylphenyl)-N'chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3, 5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole,
2,4-difluoro-α-(1H-1,2,4-triazol-1-ylmethyl)-benzhydryl alcohol,
N-(3-chloro-2,6-dinitro-4-trifluoromethylphenyl)-5-trifluoromethyl-3-chloro-2-aminopyridine, and
1-((bis-(4-fluorophenyl)-methylsilyl)-methyl)-1H-1,2,4-triazole.

The compounds of the formula I' are suitable for effectively combating pests such as insects, arachnids and nematodes. They may be used as pesticides in crop protection and in the hygiene, stores protection and veterinary sector.

Examples of injurious insects belonging to the Lepidoptera order are Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholita funebrana, Grapholita molesta, Hellothis armigera, Heliothis virescens, Hellothis zea, Hellula undalis, Hibernia defoliaria, Hyphantria cunea, Hyponomeuta malinellus, Keifferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flamea, Pectinophora gossypiella, Peridroma saucia, Phalera bucephala, Phthorimaea operculella, Phyllocnistis citrella, Pieris brassicae, Plathypena scarbra, Plutella xylostella, Pseudoplusia includens, Phyacionia frustrana, Scrobipalpula absoluta, Sitotroga cerelella, Sparganothis pilleriana, Spodoptera frugiperda, Spodoptera littoralis, Spodoptera litura, Thaumatopoea pityocampa, Tortrix viridana, Trichoplusia ni and Zeiraphera canadensis.

Examples from the Coleoptera order are Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrynchus napi, Chaetocnema tibialis, Conoderus vespertinus, Crioceris asparagi, Diabrotica longicornis, Diabrotica 12-punctata, Diabrotica virgilera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Onlema oryzae, Ortiorrhynchus sulcatus, Ortiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus and Sitophilus granaria.

Examples from the Diptera order are Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossia morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea and Tipula paludosa.

Examples from the Thysanoptera order are Frankliniella fusca, Frankliniella occidentalis, Frankliniella tritici, Scirtothrips citri, Thrips oryzae, Thrips palmi and Thrips tabaci.

Examples from the Hymenoptera order are Athalia rosae, Atta cephalotes, Atta sexdens, Atta texana, Hoplocampa minuta, Hoplocampa testudinea, Monomorium pharaonis, Solenopsis geminata and Solenopsis invicta.

Examples from the Heteroptera order are AcroSternum hilare, Blissus leucopterus, Cyrtopeltis notatus, DySdercus cingulatus, Dysdercus intermedius, Eurygaster integriceps, Euchistus impictiventris, Leptoglossus phyllopus, Lygus lineolaris, Lygus pratensis, Nezara viridula, Piesma quadrata, Solubea insularis and Thyanta perditor.

Examples from the Homoptera order are Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dyasphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla Rhopalomyzus ascalonicus, Rhopalosiphum maudis, Sappaphis mala, Sappaphis mali, Schizaphis graminum, Schizoneura lanuginosa, Trialeurodes vaporariorum and Viteus vitifolii.

Examples from the Isoptera order are Calotermes flavicollis, Leucotermes flavipes, Reticulitermes lucifugus and Termes natalensis.

Examples from the Orthoptera order are Acheta domestica, Blatta orientalis, Blattella germanica, Forficula auricularia, Gryllotalpa gryllotalpa, Locusta migratoria, Melanoplus birittatus, Melanoplus femurrubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus and Tachycines asynamorus.

Examples from the Acarina order are Amblyomma americanum, Amglyomma variegatum, Argas persicus, Boophilus annulatus, Boophilus decoloratus, Boophilus microplus, Brevipalpus phoenicis, Bryobia praetiosa, Dermacentor silvarum, Eotetranychus carping, Eriophyes sheldoni, Hyalomma truncatum, Ixodes ricinus, Ixodes rubicundus, Ornithodorus moubata, Otobins megnini, Paratetranychus pilosus, Permanyssus gallinae, Phyllocaptrata oleivora, Polyphagotarsonemus latus, Psoroptes ovis, Rhipicephalus appendiculatus, Rhipicephalus evertsi, Saccoptes scabiei, Tetranychus cinnabarinus, Tetranychus kanzawai, Tetranychus pacificus, Tetranychus telarius and Tetranychus urticae.

Examples from the nematodes class are root-Knot nematodes, e.g., Meloidogyne hapla, Meloidogyne incognita and Meloidogyne javanica, cyst-forming nematodes, e.g., Globodera rostochiensis, Heterodera avenae, Hetrodera glycinae, Heterodera schachtii and Heterodera trifolii, and stem and leaf eelworms, e.g., Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus and Pratylenchus goodeyi.

The active ingredients may be applied as such, as formulations or application forms prepared therefrom, e.g., as directly sprayable solutions, powders, suspensions, dispersions, emulsions, oil dispersions, pastes, dusts, broadcasting agents or granules by spraying, atomizing, dusting, broadcasting or watering. The application forms depend entirely on the purpose for which the agents are being used; they should at all events ensure as fine a distribution of the active ingredients according to the invention as possible.

The active ingredient concentrations in the finished formulations may vary over a wide range, but are generally from 0.0001 to 10, and preferably from 0.01 to 1,%.

The active ingredients may also be successfully used in the ultra-low-volume method, where it is possible to apply formulations containing more than 95wt % of active ingredient, or even the active ingredient without any additives.

When the active ingredients are applied in the open for combating pests, the application rate is from 0.1 to 2.0, and preferably from 0.2 to 1.0, kg/ha.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as toluene, xylene, paraffin, tetrahydronaphthalene, alkylated naphthalenes and their derivatives, methanol, ethanol, propanol, butanol, cyclohexanol, cyclohexanone, chlorobenzene, isophorone, etc., and strongly polar solvents such as N,N-dimethylformamide, dimethyl sulfoxide, N-methylpyrrolidone, water, etc. are suitable.

Aqueous formulations may be prepared from emulsion concentrates, pastes, oil dispersions, wettable powders or water-dispersible granules by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

The formulations generally contain from 0.01 to 95, and preferably 0.5 to 90,% by weight of active ingredient. The active ingredients are used in a purity of from 90 to 100, and preferably from 95 to 100,% (according to the NMR spectrum).

Examples of formulations are as follows:

I. 5 parts by weight of compound no. 11 is intimately mixed with 95 parts by weight of particulate kaolin. A dust is obtained containing 5% by weight of the active ingredient.

II. 30 parts by weight of compound no. 13 is intimately mixed with a mixture consisting of 92 parts by weight of powdered silica gel and 8 parts by weight of paraffin oil which has been sprayed onto the surface of this silica gel. A formulation of the active ingredient is obtained having good adherence (active ingredient content: 23wt %).

III. 10 parts by weight of compound no. 31 is dissolved in a mixture consisting of 90 parts by weight of xylene, 6 parts by weight of the adduct of 8 to 10 moles of ethylene oxide and I mole of oleic acid-N-monoethanolamide, 2 parts by weight of the calcium salt of dodecylbenzenesulfonic acid, and 2 parts by weight of the adduct of 40 moles of ethylene oxide and 1 mole of castor oil (active ingredient content: 9wt %).

IV. 20 parts by weight of compound no. 32 is dissolved in a mixture consisting of 60 parts by weight of cyclohexanone, 30 parts by weight of isobutanol, 5 parts by weight of the adduct of 7 moles of ethylene oxide and 1 mole of isooctanylphenol, and 5 parts by weight of the adduct of 40 moles of ethylene oxide and 1 mole of castor oil (active ingredient content: 16wt %).

V. 80 parts by weight of compound no. 11 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in .a hammer mill active ingredient content: 80wt %).

VI. 90 parts by weight of compound no. 13 is mixed with 10 parts by weight of N-methyl-alpha-pyrrolidone. A mixture is obtained which is suitable for application in the form of very fine drops (active ingredient content: 90wt %).

VII. 20 parts by weight of compound no. 31 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

VIII. 20 parts by weight of compound no. 32 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

There may be added to the active ingredients oils of various types, herbicides, fungicides, other pesticides and bactericides - if desired, immediately before use (tankmix). These agents may be mixed with the agents according to the invention in a weight ratio of from 1:10 to 10:1.

SYNTHESIS EXAMPLES

The directions given in the synthesis examples below were employed, after appropriate modification of the starting materials, to obtain further compounds I. The compounds thus obtained are given in the following tables with their physical details.

Example 1

Preparation of 1-bromo-2-methoxymethylbenzene

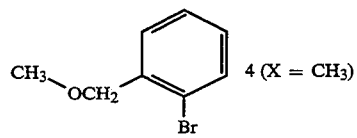

685 g (2.74 mol) of o-bromobenzyl bromide was refluxed with 2.74 mol of a 30% strength sodium methylate solution in methanol for 15 hours. After the mixture had cooled to room temperature it was evaporated down, taken up in ethyl acetate, and washed with water. After the organic phase had been dried over sodium sulfate, it was again evaporated down. There was obtained 478.2 g (87%) of the title substance as a colorless liquid.

$^1$H-NMR (in CDCl$_3$): 3.5 ppm (s,3H), 4.58 ppm (s,2H), 7.08–7.6 ppm (m, 4H).

Example 2

Preparation of methyl 2-methoxymethylphenylglyoxylate

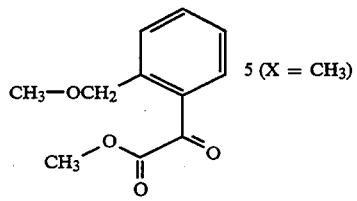

500 ml of an ethereal 1 M zinc chloride solution was dripped into a Grignard solution prepared from 12.0 g (0.46 mol) of magnesium shavings and 99.5 g (0.5 mol) of 1-bromo-2-methoxymethylbenzene in 500 ml of THF. The mixture was then refluxed for 1 hour, and a solution of 61.2 g (0.5 mol) of oxalic acid methyl ester chloride in 100 ml of THF was dripped in at an internal temperature of (−10)° C. After the mixture had been heated to about 20° C. it was stirred for a further 20 hours and then hydrolyzed with saturated ammonium chloride solution. After extraction with ether the combined ether phases were washed with water, dried and evaporated down. There was obtained 60 g of product (57.7%) as a mobile liquid.

$^1$H-NMR (in CDCl$_3$): 3.38 ppm (s,3H), 3.98 ppm (s,3H), 4.8 ppm (s,2H), 7.3–7.7 ppm (m, 4H).

Example 3

Preparation of methyl α-(2-methoxymethylphenyl)-62-methylacrylate

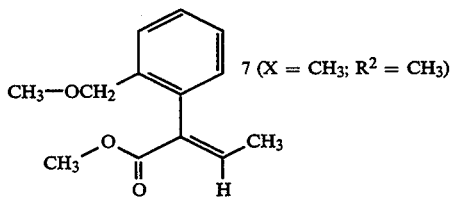

At 5° C., 11.2 g (0.1 mol) of potassium tert-butanolate was added to a A mixture of 37.1 g (100 mmol) of ethyltriphenylphosphonium bromide was added under a nitrogen blanket to 300 ml of absolute tetrahydrofuran. At 5° C., 11.2 g (0.1 mol) of potassium tert-butanolate was added. After the mixture had been stirred for 1 hour at 5° C., 20.8 g (100 mmol) of methyl 2-methoxymethylphenylglyoxylate in 100 ml of tetrahydrofuran was dripped in. The mixture was stirred for 1 hour at 5° C. and for 1 hour at 25° C., 200 ml of water was added and extraction carried out with methylene chloride. After the combined organic phases had been washed with water and dried, the solvent was removed under reduced pressure. The residue was purified chromatographically in a silica gel column (methyl tert-butyl ether/n-hexane=½). There was obtained 17.2 g (78%) of the above-mentioned ester as an oil (Z/E isomer=1/9) (compound no. 25).

$^1$H-NMR (in CDCl$_3$): 1.8 ppm (d,3H), 3.3 ppm (s,3H), 3.7 ppm (s,3H), 4.3 ppm (d,2H), 7.05 ppm (m, 1H), 7.2–7.6 ppm (m, 4H).

Example 4

Preparation of methyl α-(2-bromomethylphenyl)-β-methylacrylate (compound no. 24)

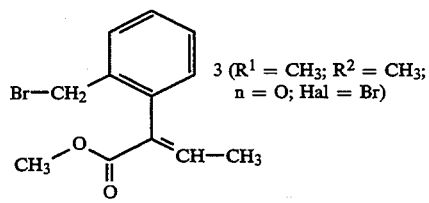

3 (R$^1$ = CH$_3$; R$^2$ = CH$_3$; n = 0; Hal = Br)

At 0° C., 105.3 ml (140 mmol) of a 1.33 M boron tribromide solution in methylene chloride was dripped into 31 g (140 mmol) of methyl α-(2-methoxymethylphenyl)-β-methylacrylate in 500 ml of CH$_2$Cl$_2$, and the mixture was refluxed for 2 hours. 25 ml of methanol was then added, the mixture was stirred for a further 90 minutes at room temperature, hydrolyzed with water while cooling with ice, and washed neutral with 3% strength caustic solution, and the aqueous phase was extracted with methylene chloride. The combined organic phases were washed with water, dried and evaporated down. The crystals which precipitated were separated off, washed with a small amount of n-hexane and dried. The filtrates were evaporated down and purified chromatographically in a silica gel column (cyclohexane/MTBE: 8/1). A total of 31 g of product was obtained in the form of pale yellow crystals.

$^1$H-NMR (in CDCl$_3$): 1.65 ppm (d, 3H) 3.7 ppm (S,3H), 4.28 ppm (d,2H), 7.05 ppm (m, 1H), 7.2–7.6 ppm (m, 4H).

Example 5

Preparation of α-(2-methoxymethylphenyl)-β-methylacrylic acid (compound no. 1)

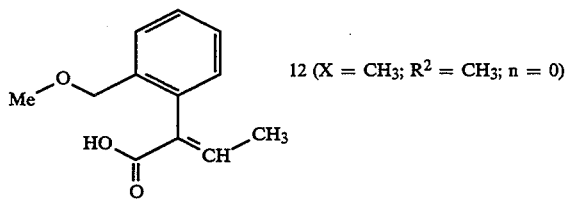

12 (X = CH$_3$; R$^2$ = CH$_3$; n = 0)

4.4 g (20 mmol) of methyl α-(2-methoxymethylphenyl)-β-methylacrylate was stirred in 80 ml of 1N potassium hydroxide solution at 80° C. for 30 minutes. The mixture was cooled to room temperature and extracted twice, each time with 50 ml of methyl tert-butyl ether. The pH of the aqueous phase remaining was adjusted to 1 with 10% strength hydrochloric acid. The mixture was then extracted three times, each time with 50 ml of dichloromethane. The combined dichloromethane extracts were washed three times with water, dried over sodium sulfate and evaporated down.

There was obtained 3.8 g (92%) of the title compound in the form of colorless crystals (m.p.: 67°–69° C.).

IR (cm$^{-1}$): 1687, 1631, 1285, 1112, 968, 772, 754.

Example 6

Preparation of α-(2-methoxymethylphenyl)-β-methylacrylic chloride

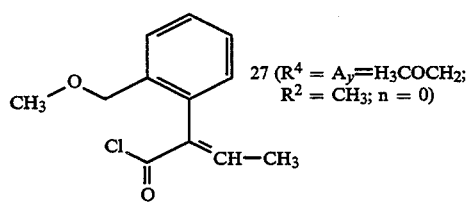

27 (R$^4$ = A$_y$=H$_3$COCH$_2$; R$^2$ = CH$_3$; n = 0)

At 0° to 5° C., 3.7 g of thionyl chloride was dripped into 4.9 g (24 mmol) of α-(2-methoxymethylphenyl)-β-methylacrylic acid and 2.5 g of pyridine in 40 ml of ether. The mixture was stirred for 3 hours at about 20° C. After filtration, the residue was washed with diethyl ether. The filtrate was combined with the ether phase. After removal of the solvent, there was obtained 5.2 g (96.5%) of the title compound as a colorless oil. The crude product can be used for further reactions without any additional purification.

Example 7

Preparation of
α-(2-methoxymethylphenyl)-β-methylacrylic
acid-N-methylamide (comp. no. 22)

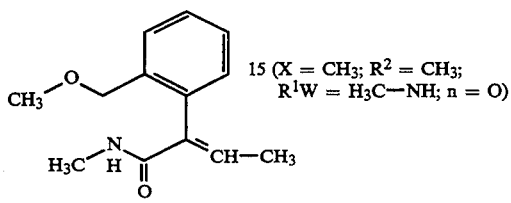

15 (X = CH₃; R² = CH₃;
R¹W = H₃C—NH; n = 0)

1.7 g of methylamine hydrochloride was added to 5.2 g (23 mmol) of α-(2-methoxymethylphenyl)-β-methylacrylic chloride in 30 ml of dichloromethane, and 4 g of pyridine was dripped in at 0° to 5° C. The mixture was stirred for a further 15 hours at about 20° C. The reaction mixture was diluted with 20 ml of dichloromethane and washed with water. The organic phase was dried over sodium sulfate and evaporated down. The crude product was chromatographed on silica gel with methyl tert-butyl ether/cyclohexane (5/1). Removal of the solvent gave 1.5 g (30%) of the title compound in the form of colorless crystals (m.p.: 58° C.).

Example 8

Preparation of dimethyl
2-methoxymethylbenzylphosphonate

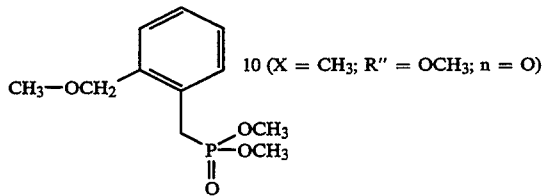

10 (X = CH₃; R″ = OCH₃; n = 0)

At 60° C., a 30% strength sodium methylate solution in methanol was dripped into 332 g of [1,2-bis-(bromomethyl)]-benzene I in 1400 ml of toluene until an optimal ratio of educt, 1-bromomethyl-2-methoxymethylbenzene II and [1,2-bis-(methoxymethyl)]-benzene III had been set up. After cooling to about 20° C., precipitated sodium bromide was filtered off. The filtrate was evaporated down, excess starting material substantially crystallizing out. The supernatant liquid was distilled off. The fraction at 68°–71° C./0.4 mm Hg (156 g) consisted of a mixture of 35% of I, 55% of II and 10% of III. 155 g of this mixture was refluxed in 500 ml of trimethyl phosphit for 5 hours. After excess phosphite had been distilled off, the residue was fractionated under a high vacuum. The fraction in the range of 118°–119° C./0.2 mm Hg (62 g) contained more than 95% of the desired dimethyl 2-methoxymethylbenzylphosphonate.

¹H-NMR (in CDCl₃): 3.35 ppm (d, 2H), 3.4 ppm (s,3H), 3.65 ppm (d,6H), 4.6 ppm (s,3H), 7.2–7.5 ppm (m, 4H)

Example 9

Preparation of
dimethylphosphono-(2-methoxymethylphenyl)-acetic
acid

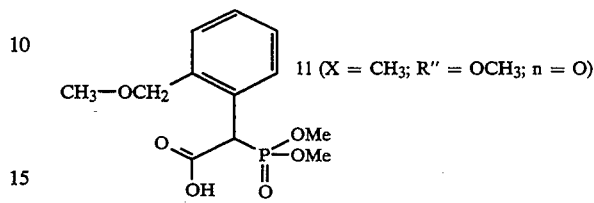

11 (X = CH₃; R″ = OCH₃; n = 0)

165 ml of a 1.6 M solution of n-butyllithium in hexane was added at (−65)° C. to 170 ml of absolute tetrahydrofuran. At this temperature a solution of 61 g of dimethyl 2-methoxymethylbenzylphosphonate (from Example 8) in 100 ml of tetrahydrofuran was dripped in. After 30 minutes the batch was poured into a (−60)° C. cold saturated solution (500 ml) of dry ice and diethyl ether. After the batch had been stirred for 10 minutes it was allowed to heat up to about 20° C. over a period of 4 hours. 300 ml of water was added and the organic phase was separated off and extracted three times, each time with 100 ml of 100 ml of 10% strength sodium carbonate solution. The combined aqueous phases were extracted twice, each time with 150 ml of diethyl ether, and the pH was adjusted to 1 with 2 N sulfuric acid. Extraction was carried out three times, each time with 150 m]of dichloromethane, the organic phases were dried, and the solvent was removed under reduced pressure. There remained 60 g of dimethylphosphone-(2-methoxymethylphenyl)-acetic acid as a yellow ¹H-NMR (in CDCl₃): 3.3 ppm (s,3H), 3.6 ppm (s,3H), 3.75 ppm (s,3H), 4.45 ppm (s, 1H), 4.6 ppm (S, 1H), 4.8 ppm (S, 1H), 7.2–7.35 ppm (m, 3H), 7.8 ppm (d, 1H), 10.3 ppm (broad, 1H).

Example 10

Preparation of methyl
α-(2-bromomethylphenyl)-β-ethylacrylate

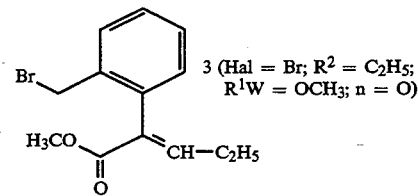

3 (Hal = Br; R² = C₂H₅;
R¹W = OCH₃; n = 0)

17 g of α-(2-methoxymethylphenyl)-β-ethylacrylic acid was reacted with boron tribromide and methanol analogously to Example 4. Yield: 14.5 g.

¹H-NMR (in CDCl₃): 1.0 ppm (t,3H), 2.0 ppm (m, 2H), 3.7 ppm (S,3H), 4.4 ppm (m, 2H), 7.0–7.5 ppm (m, 5H)

Example 11

Preparation of methyl 2-(1,3-dioxolan-2-yl)-phenylglyoxylate

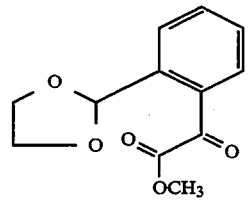

174.5 g of 1-bromo-2-(1,3-dioxolan-2-yl)-benzene was reacted via the zinc-organic compound with 102 g of oxalic acid monomethyl ester chloride, analogously to Example 2. Yield: 41.6 g.

$^1$H-NMR (in CDCl$_3$): 3.8–4.1 ppm (m, 7H), 6.25 ppm (s, 1H), 7.4–7.7 ppm (m, 4H)

Example 12

Preparation of methyl α-[2-(1,3-dioxolan-2-yl)-phenyl]-β-methylacrylate (compound 33)

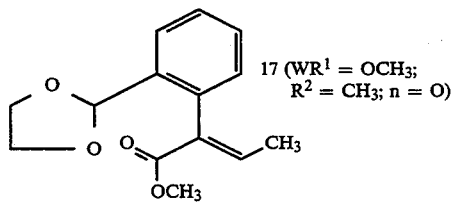

17 (WR$^1$ = OCH$_3$; R$^2$ = CH$_3$; n = 0)

18.0 g of methyl 2-(1,3-dioxolan-2-yl)-phenylglyoxylate was reacted with 33.9 g of ethyltriphenylphosphonium bromide analogously to Example 3. Yield: 9.0 g.

$^1$H-NMR (in CDCl$_3$): 1.6 ppm (d,3H), 3.7 ppm (s,3H), 3.9–4.1 ppm (m, 4H), 5.65 ppm (s, 1H), 7.0–7.7 ppm (m, 5H).

Example 13

Preparation of 2-(β-methyl-α-methoxycarbonylvinyl)-benzaldehyde (compound 42)

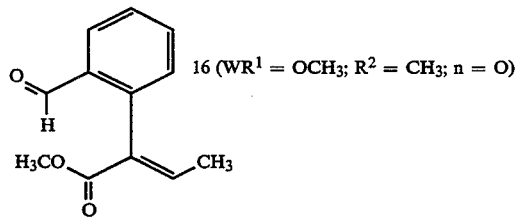

16 (WR$^1$ = OCH$_3$; R$^2$ = CH$_3$; n = 0)

3 ml of 2N hydrochloric acid was added to a solution of 7.0 g of methyl α-[2-(1,3-dioxolan-2-yl)-phenyl]-β-methylacrylate in 30 ml of tetrahydrofuran. The mixture was stirred overnight, the solvent was removed under reduced pressure and the residue was taken up in 100 ml of 5% strength aqueous sodium bicarbonate solution/dichloromethane (1:2, v/v). The organic phase was separated off, washed twice, each time with sodium chloride solution, and dried with sodium sulfate. After removal of the solvent there remained 5.3 g of the aldehyde as an oil.

$^1$H-NMR (in CDCl$_3$): 1.7 ppm (d,3H), 3.65 ppm (s,3H), 7.2–7.7 ppm (m, 4H); 7.95 ppm (d, 1H), 10.0 ppm (s, 1H)

Example 14

Preparation of dimethyl 2-(β-methyl-α-methoxycarbonylvinyl)-benzylphosphonate (compound 36)

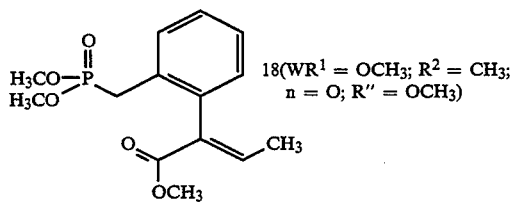

18(WR$^1$ = OCH$_3$; R$^2$ = CH$_3$; n = 0; R" = OCH$_3$)

5 g of methyl α-(2-bromomethylphenyl)-β-methylacrylate was refluxed in 40 ml of trimethyl phosphite for 2 hours. Excess phosphite was distilled off and the remaining residue was taken up in water/dichloromethane (1:1, v/v). The aqueous phase was extracted twice with dichloromethane. The combined organic phases were dried with sodium sulfate. After the solvent had been removed the phosphonate remained as a pale yellow oil.

$^1$H-NMR (in CDCl$_3$): 1.65 ppm (d,3H); 3.1 ppm (m, 2H); 3.65 ppm (d,6h); 3.7 ppm (s,3H), 7.1 ppm (d, 1H); 7.3 ppm (m, 2H); 7.55 ppm (d, 1H).

Example 15

Preparation of methyl α-[2-(5'methyl-1',3',4'-thiadiazol-2'-yl)-thiomethylphenyl ]-β-methylacrylate (compound 9)

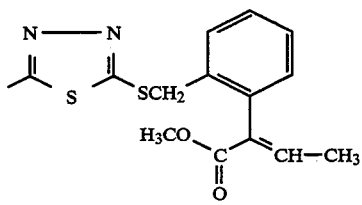

4.04 g (15 mmol) of methyl α-(2-bromomethylphenyl)-β-methylacrylate, 2.08 g (16 mmol) of 5-methyl-2-mercapto-1,3,4-thiadiazole and 3.1 g (22.4 mol) of potassium carbonate were stirred for 3 hours at 60° C. and then for 15 hours at 20° to 25° C. The reaction mixture was taken up in water and extracted with methyl tert-butyl ether. The organic phase was washed twice with saturated sodium bicarbonate solution and twice with water, dried over sodium sulfate and evaporated down. The crude product was chromatographed on silica gel with methyl tert-butyl ether/cyclohexane (1/1). After removal of the solvent there was obtained 4.6 g (96%) of the title compound in the form of colorless crystals (m.p.: 74°–75° C.).

Example 16

Preparation of methyl α-[2-(2',6'-dimethyl-4'-pyrimidinyl)-oxymethylphenyl]-β-methylacrylate (compound 6)

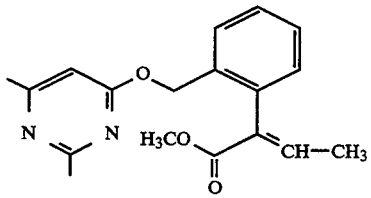

2.05 g (16.5 mmol; 10% excess) of 2,6-dimethyl-4-hydroxypyrimidine and 3.1 g (22.4 mmol) of potassium carbonate were stirred in 35 ml of dimethylformamide for 30 minutes at 60° C. 4.04 g (15 mmol) of methyl α-(2-bromomethyl-phenyl)-β-methylacrylate was then added. The reaction mixture was stirred for 4 hours at 75° C., and then for 15 hours at 20° to 25° C. It was then taken up in water and extracted with methyl tert-butyl ether. The organic phase was washed twice with sodium bicarbonate solution and twice with water, dried over sodium sulfate and evaporated down. The crude produce was purified chromatographically on silica gel with methyl tert-butyl ether/cyclohexane (8/1). There was obtained 3.2 g.(68° /o) of the above compound in the form of pale yellow crystals (m.p.: 56°-58° C.).

Example 17

Preparation of methyl α-[2-methyl-4-(2-methoxyiminoethyl)-phenyloxymethylphenyl]-β-methylacrylate (compound 32)

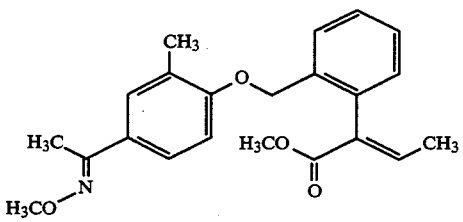

a) 31.8 g (0.21 mol) of 3-methyl-4-hydroxyacetophenone and 57 g (0.21 mol) of methyl α-(2-bromomethyl-phenyl)-β-methylacrylate were dissolved in 800 ml of dimethylformamide, and 58 g (0.42 mol) of potassium carbonate was added. The mixture was stirred for 8 hours at 50° C., hydrolyzed with ice water and extracted with ethyl acetate. The organic phase was washed with water, dried and evaporated down. There was obtained 62 g of methyl α-[2-methyl-4-acetylphenyloxymethylphenyl]-β-methylacrylate in the form of yellowish crystals (compound no. 30).

$^1$H-NMR (in CDCl$_3$) [δ in ppm]: 1.62 (d,3H); 2.3 (s,3H); 3.54 (2,3H); 3.75 (s,3H); 4.98 (2,2H); 6.79 (d,2H); 7.0-7.9 (m, 7H).

b) 22 g (67.4 mmol) of methyl α-[2-methyl-4-acetylphenyloxymethylphenyl]-β-methylacrylate and 11.3 g (0.135 mol) of O-methylhydroxylamine hydrochloride were refluxed in 600 ml of methanol for 6 hours. The mixture was allowed to cool to about 25° C., was hydrolyzed and extracted with ice water. The organic phases were washed with water, dried and evaporated down. There was obtained 18 g of the title compound in the form of pale yellow crystals (m.p.: 55°-60° C.).

$^1$H-NMR (in CDCl$_3$) [δ in ppm]: 1.5 (d, 3H); 2.1 (s,3H); 2.15 (s,3H); 3.7 (s,3H); 3.98 (s,3H); 4.95 (S,2H); 6.7 (d, 1H); 7-7.62 (m, 7H).

Example 18

Preparation of methyl α-(2-[2-(3-[4-chlorophenyl]isoxazol-5-yl)-ethenyl])-β-methylacrylate (compound 46)

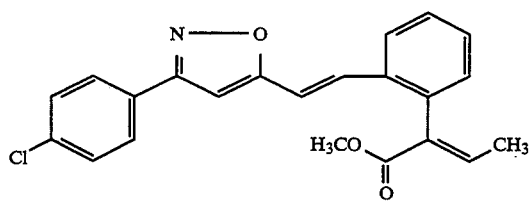

At about 20° C. a solution of 4.6 g of dimethyl (3-(4-chlorophenyl)-isoxazol-5-ylmethylphosphonate in 50 ml of dimethylformamide was dripped into 0.4 g of sodium hydride in 10 ml of anhydrous dimethylformamide. The mixture was stirred for 30 minutes and then dripped into a solution of 2.4 g of 2-(β-methyl-α-methoxycarbonylvinyl)-benzaldehyde in 40 ml of dimethylformamide. The mixture was stirred for 4 hours at room temperature and then worked up as follows. It was poured into 200 ml of ice water and extracted three times with ethyl acetate. The combined organic phases were washed neutral with saturated sodium chloride solution, dried and inerted. The dark brown oil remaining was triturated with methanol, whereupon the E-isomer crystallized out.

Example 19

Preparation of methyl α-(2-[-(3-[4-chlorophenyl]isoxazo15-yl)-2-chloroethenyl])-β-ethylacrylate (compound 47 and 48)

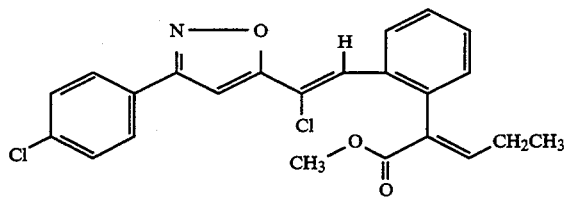

175 ml of a 1.6M solution of n-butyllithium in hexane was dripped into a (−70)° C. solution of 9.0 g of dimethyl 3-(4-chlorophenyl)-isoxazol-5-yl-methylphosphonate in 50 ml of anhydrous tetrahydrofuran. After 30 minutes 4.2 g of tetrachloromethane was added and the mixture stirred for 1 hour at (−70)° C. The temperature was allowed to rise to −30° C., and at this temperature 5.2 g of 2-(β-ethyl-α-methoxycarbonylvinyl)-benzaldehyde in 30 ml of tetrahydrofuran was dripped in. After 1 hour the mixture was allowed to heat up to 20° C. and was stirred overnight. Working up was as in Example 21. When the crude product was triturated with diisopropyl ether, 3 g of colorless crystals was obtained which consisted of about 85%.of the Z-isomer of the desired product. From the mother liquor there was obtained 1.9 g of an oil which consisted of about 95% of the E-isomer.

Example 20

Preparation of
α-(2-(2-methylphenoxy)methylphenyl)-β-methylacrylic acid-N-methylamide (compound no. 76)

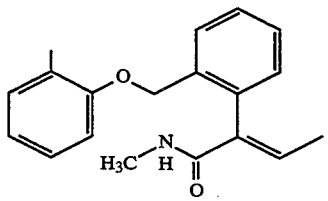

Methyl α-(2-(2-methylphenoxy)-methylphenyl)-β-methylacrylate was reacted analogously to Examples 5 and 6 to α-(2-(2-methylphenoxy)-methylphenyl)-β-methylacrylic acid chloride. At 0° C. a solution of 2,6-methylamine in 35 ml of dichloromethane was dripped into 6.3 g (21 mmol) of this chloride, and the mixture was stirred for 2 hours at room temperature. The reaction mixture was washed with water, dried over sodium sulfate and evaporated down. The crude product was chromatographed over silica gel with cyclohexan/ethyl acetate (1/1). After removal of the solvent there was obtained 4.8 g (78%) of the title compound as a colorless oil.

IR (cm$^{-1}$): 1664, 1626, 1602, 1517, 1495, 1462, 1241, 1191, 1121, 752.

TABLE

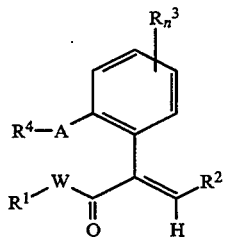

| Comp. No. | $R^4$ | A | $R^2$ | $W-R^1$ | $R_n^3$ | Phys. data [IR (cm$^{-1}$); NMR (ppm); mp (°C.)] |
|---|---|---|---|---|---|---|
| 1 | Methyl | —OCH$_2$— | —CH$_3$ | —OH | H | 1687, 1631, 1285, 1112, 968, 772, 754 |
| 2 | 2-n-Propyl-6-trifluoromethyl-pyrimidin-4-yl | —OCH$_2$— | —CH$_3$ | —OCH$_3$ | H | 1598, 1571, 1420, 1349, 1255, 1184, 1151, 1035 |
| 3 | 2-i-Propyl-6-trifluoromethyl-pyrimidin-4-yl | —OCH$_2$— | —CH$_3$ | —OCH$_3$ | H | 1597, 1570, 1421, 1349, 1257, 1186, 1151, 1036, 1018 |
| 4 | 2-Cyclopropyl-6-trifluoromethyl-pyrimidin-4-yl | —OCH$_2$— | —CH$_3$ | —OCH$_3$ | H | 1597, 1574, 1441, 1417, 1350, 1256, 1186, 1150, 1036 |
| 5 | 2-Methyl-6-trifluoromethyl-pyrimidin-4-yl | —OCH$_2$— | —CH$_3$ | —OCH$_3$ | H | 1438, 1417, 1360, 1351, 1271, 1202, 1151, 1118 |
| 6 | 2,6-Dimethylpyrimidin-4-yl | —OCH$_2$— | —CH$_3$ | —OCH$_3$ | H | 1591, 1561, 1436, 1399, 1341, 1253, 1167, 1070 |
| 7 | 2-i-Propyl-6-methyl-pyrimidin-4-yl | —OCH$_2$— | —CH$_3$ | —OCH$_3$ | H | 1589, 1561, 1431, 1342, 1253, 1163, 1038 |
| 8 | 2-Benzimidazolyl | —SCH$_2$— | —CH$_3$ | —OCH$_3$ | H | 1433, 1401, 1352, 1253, 1231 |
| 9 | 5-Methyl-1,3,4-thiadiazol-2-yl | —SCH$_2$— | —CH$_3$ | —OCH$_3$ | H | 1434, 1381, 1253, 1204, 1188, 1068, 1036 |
| 10 | Methyl | —OCH$_2$— | —C$_2$H$_5$ | —OCH$_3$ | H | NMR (CDCl$_3$): δ = 0.93t, 3.28s, 3.67s, 4.25, 7.0–7.5m |
| 11 | 5-Trifluoromethyl-benzothiazol-2-yl | —SCH$_2$— | —CH$_3$ | —OCH$_3$ | H | 1421, 1333, 1262, 1148, 1119, 1060, 994 |
| 12 | 5-Chlorobenzothiazol-2-yl | —SCH$_2$— | —CH$_3$ | —OCH$_3$ | H | 1455, 1428, 1413, 1258, 1204, 1066, 1035, 1015 |
| 13 | 6-Chlorobenzothiazol-2-yl | —SCH$_2$— | —CH$_3$ | —OCH$_3$ | H | 1459, 1433, 1259, 1253, 1204, 1103, 1037, 1002 |
| 14 | 6-Ethoxybenzothiazol-2-yl | —SCH$_2$— | —CH$_3$ | —OCH$_3$ | H | 1445, 1252, 1221, 1205, 1037, 1000, 938 |
| 15 | Bromomethyl | — | —C$_2$H$_5$ | —OCH$_3$ | H | mp.: 31–32° C. 1709, 1637, 1432, 1267, 1241, 1226, 771, 746 |
| 16 | 2-n-Propyl-6-methyl-pyrimidin-4-yl | —OCH$_2$— | —CH$_3$ | —OCH$_3$ | H | 1436, 1404, 1394, 1341, 1253, 1164, 1036 |
| 17 | 1-(4-Chlorophenyl)pyrazol-4-yl | —OCH$_2$— | —CH$_3$ | —OCH$_3$ | H | 1592, 1579, 1500, 1399, 1357, 1256, 1035, 942 |
| 18 | 2-Benzisoxazolyl | —OCH$_2$— | —CH$_3$ | —OCH$_3$ | H | 1532, 1446, 1351, 1339, 1252, 1232, 917 |
| 19 | 5-Phenylisoxazol-3-yl | —OCH$_2$— | —CH$_3$ | —OCH$_3$ | H | 1623, 1576, 1511, 1455, 1438, 1363, 1255, 1197 |
| 20 | 2-n-Propyl-6-trifluoromethyl-pyrimidin-4-yl | —OCH$_2$— | —C$_2$H$_5$ | —OCH$_3$ | H | 1421, 1350, 1264, 1244, 1184, 1151, 1089 |
| 21 | 2-n-Propyl-6-methyl-pyrimidin-4-yl | —OCH$_2$— | —C$_2$H$_5$ | —OCH$_3$ | H | 1452, 1435, 1342, 1242, 1164, 1038 |
| 22 | Methyl | —OCH$_2$ | —CH$_3$ | —NHCH$_3$ | H | Fp.: 58° C. |
| 23 | 1-Methyl-3-trifluoromethyl-pyrazol-5-yl | —OCH$_2$— | —CH$_3$ | —OCH$_3$ | H | mp.: 69–71° C. |
| 24 | Bromomethyl | — | —CH$_3$ | —OCH$_3$ | H | 1711, 1641, 1434, 1251, 1206, 1042, 1032, 765, 752 |
| 25 | Methyl | —OCH$_2$— | —CH$_3$ | —OCH$_3$ | H | 1718, 1435, 1253, 1195, 110 1090, 1046, 758 |
| 26 | 2-Cyclohexyl-6-trifluoro-methyl-pyrimidin-4-yl | —OCH$_2$— | CH$_3$ | —OCH$_3$ | H | 1596, 1569, 1421, 1347, 1258, 1184, 1150, 1001 |
| 27 | 2-Cyclopentyl-6-trifluoro- | —OCH$_2$— | CH$_3$ | —OCH$_3$ | H | 1597, 1569, 1422, 1349, 1255, 1184, |

TABLE-continued $$R^1-W-C(=O)-C(=CH-R^2)-C_6H_3(R^4-A)(R_n^3)$$

| Comp. No. | R⁴ | A | R² | W-R¹ | $R_n^3$ | Phys. data [IR (cm⁻¹); NMR (ppm); mp (°C.)] |
|---|---|---|---|---|---|---|
|  | methyl-pyrimidin-4-yl |  |  |  |  | 1150, 1104, 1037 |
| 28 | 3-Chlorophenyl | —SCH₂— | —CH₃ | —OCH₃ | H | 1715, 1577, 1461, 1434, 1252, 1204, 1046, 1036, 776, 679 |
| 29 | 4,6-Dimethyl-pyrimidin-2-yl | —SCH₂— | —CH₃ | —OCH₃ | H | 1710, 15823, 1538, 1433, 1240, 1201, 1035, 779, 765 |
| 30 | 2-Methyl-4-acetylphenyl | —OCH₂— | —CH₃ | —OCH₃ | H | 1715, 1675, 1600, 1502, 135, 1261, 1183, 1143, 1130, 10 |
| 31 | 2-Methyl-4-(2-ethoxy-iminoethyl)phenyl | —OCH₂— | —CH₃ | —OCH₃ | H | 1718, 1508, 1269, 1296, 1231, 1039, 950, 770, 765 mp.: 96–100° C. |
| 32 | 2-Methyl-4-(2-methoxy-iminoethyl)phenyl | —OCH₂— | —CH₃ | —OCH₃ | H | 1716, 1505, 1435, 131, 1249, 1180, 1143, 1051, 871, 757 |
| 33 | 1,3-Dioxolan-2-yl | — | —CH₃ | —OCH₃ | H | 1716, 1434, 1255, 1214, 1107, 1072, 1045, 944, 758 |
| 34 | 1,3-Dioxolan-2-yl | — | —C₂H₅ | —OCH₃ | H | 1709, 1433, 1399, 1237, 1214, 1192, 1072, 1048, 943, 771 |
| 35 | Phenyl | — | —CH₃ | —OCH₃ | H | 1429, 1267, 1240, 1197, 1039, 775, 748 |
| 36 | (H₃CO)₂P(=O)— | —CH₂— | —CH₃ | —OCH₃ | H | 1715, 1255, 1203, 1055, 1032, 855 |
| 37 | Methyl | —OCH₂— | Cyclopropyl | —OCH₃ | H | NMR (CDCl₃) δ = 0.6–1.3m, 3.30s, 3.68s, 4.38, 6.45, 7.15–7.5m |
| 38 | Bromomethyl | — | Cyclopropyl | —OCH₃ | H | NMR (CDCl₃) δ = 0.6–1.3m, 3.65s, 4.42, 6.70, 7.1–7.6m |
| 39 | Methyl | —OCH₂— | —CN | —OCH₃ | H | NMR (CDCl₃) δ = 3.42s, 3.77s, 4.40s, 6.56s, 7.2–7.5m |
| 40 | 1,3-Dioxolan-2-yl | — | —CH₃ | —Ot-C₄H₉ | H | 1707, 1366, 1276, 1255, 1165, 1072, 945, 758 |
| 41 | 1,3-Dioxolan-2-yl | — | —C₂H₅ | —Ot-C₄H₉ | H | 1708, 1366, 1276, 1251, 1165, 1074, 944, 758 |
| 42 | Formyl | — | —CH₃ | —OCH₃ | H | 1713, 1698, 1598, 1435, 1273, 1251, 1202, 1035, 770, 760 |
| 43 | Formyl | — | —C₂H₅ | —OCH₃ | H | 1717, 1698, 1597, 1435, 1273, 1243, 1203, 1048, 767 |
| 44 | 3-(4-Chlorophenyl)-isoxazol-5-yl | C(Cl)=CH (H trans to Cl) | —CH₃ | —OCH₃ | H | NMR (CDCl₃) δ = 1.65d, 3.65s, 7.0s, 7.1–7.6m |
| 45 | 3-(4-Chlorophenyl)-isoxazol-5-yl | C(Cl)=CH (H cis to Cl) | —CH₃ | —OCH₃ | H | NMR (CDCl₃) δ = 1.65d, 3.7s, 6.75s, 7.3–8.0m |
| 46 | 3-(4-Chlorophenyl)-isoxazol-5-yl | —CH=CH— E/Z 6:4 | —CH₃ | —OCH₃ | H | NMR (CDCl₃) E compd: δ = 1.65d, 3.7s, 6.55s, 6.95d, 7.1–7.8m Z compd: δ = 1.6d, 3.6s, 6.2s, 6.5d, 6.7d, 7.1–7.6m |
| 47 | 3-(4-Chlorophenyl)-isoxazol-5-yl | C(Cl)=CH (H trans to Cl) | —C₂H₅ | —OCH₃ | H | NMR (CDCl₃) δ = 0.95 6, 1.95m, 3.7s, 6.7s, 7.1–7.95m, |
| 48 | 3-(4-Chlorophenyl)-isoxazol-5-yl | C(Cl)=CH (H cis to Cl) | —C₂H₅ | —OCH₃ | H | NMR (CDCl₃) δ = 0.95t, 2.0m, 3.65s, 6.55s, 7.0–7.7m |
| 49 | Bromomethyl | — | —CN | —OCH₃ | H | NMR (CDCl₃) δ = 3.81s, 4.36s, 6.74s, 7.15–7.55m |
| 50 | 2-n-Propyl-6-trifluoromethyl-pyrimidin-4-yl | —OCH₂— | Cyclopropyl | —OCH₃ | H | 1599, 1571, 1421, 1350, 1248, 1184, 1151, 1028 |
| 51 | 2-Methylthio-5-chloro-6-methoxy-pyrimidin-4-yl | —OCH₂— | —CH₃ | —OCH₃ | H | mp.: 109–111° C. |
| 52 | 2-Cyclohexyl-5-chloro-6-methyl-pyrimidin-4-yl | —OCH₂— | —CH₃ | —OCH₃ | H | 1565, 1542, 1433, 1344, 1252, 1069, 1037 |
| 53 | 2-n-Propyl-5-chloro-6-methyl-pyrimidin-4-yl | —OCH₂— | —CH₃ | —OCH₃ | H | mp.: 71–72° C. |

TABLE-continued

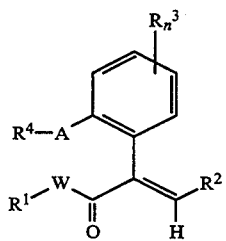

| Comp. No. | R⁴ | A | R² | W-R¹ | $R_n^3$ | Phys. data [IR (cm⁻¹); NMR (ppm); mp (°C.)] |
|---|---|---|---|---|---|---|
| 54 | Pyrazol-1-yl | —OCH₂— | —CH₃ | —OCH₃ | H | 1714, 1642, 1435, 1256, 1210, 1195, 1038, 965, 747 |
| 55 | 2-Dimethylamino-5-n-butyl-6-methyl-pyrimidin-4-yl | —OCH₂— | —CH₃ | —OCH₃ | H | 1594, 1552, 1397, 1345, 1250, 1208, 1125, 1036 |
| 56 | 1-(2,4-Dichlorophenyl)-pyrazol-4-yl | —OCH₂— | —CH₃ | —OCH₃ | H | 1714, 1583, 1493, 1434, 1402, 1356, 1254, 1036, 1017, 942 |
| 57 | 1-(4-Trifluoromethyl)-pyrazol-4-yl | —OCH₂— | —CH₃ | —OCH₃ | H | 1713, 1617, 1403, 1360, 1330, 1264, 1167, 1122, 1110, 1069 |
| 58 | 2-n-Propyl-6-trifluoromethyl-pyrimidin-4-yl | —OCH₂— | —CN | —OCH₃ | H | 1729, 1599, 1573, 1420, 1353, 1257, 1185, 1088, 1027 |
| 59 | Methyl | —OCH₂— | Isopropyl | —OCH₃ | H | NMR (CDCl₃): δ = 1.0m, 2.19m, 3.30s, 3.70s, 4.3, 6.85-7.50m |
| 60 | Bromomethyl | — | Isopropyl | —OCH₃ | H | NMR (CDCl₃): δ = 1.0m, 2.19m, 3.68s, 4.37, 6.93-7.50m |
| 61 | Pyrimidin-2-yl | —SCH₂— | —CH₃ | —OCH₃ | H | 1714, 1565, 1548, 1381, 1253, 1204, 1036, |
| 62 | 6-Chloropyridin-2-yl | —OCH₂— | —CH₃ | —OCH₃ | H | 1715, 1591, 1560, 1439, 1299, 1260, 1160, 785 |
| 63 | 4-Chlorophenyl | —OCH₂— | —CH₃ | —OCH₃ | H | NMR (CDCl₃): δ = 1.6d, 3.9s, 4.92s, 6.9s, 7-7.6m |
| 64 | 2-Methyl-4-(2-methoxy-iminopropyl)phenyl | —OCH₂— | —CH₃ | —OCH₃ | H | 1717, 1504, 1251, 1050, 757 |
| 65 | 2-Methyl-4-(2-ethoxy-iminopropyl)phenyl | —OCH₂— | —CH₃ | —OCH₃ | H | 1717, 1504, 1251, 1050, 1040, 757 |
| 66 | 2-Methyl-4-ethylcarbonyl-phenyl | —OCH₂— | —CH₃ | —OCH₃ | H | NMR (CDCl₃): δ = 1.2t, 1.6d, 2.3s, 3.95q, 3.85s, 5.0s, 6.8d, 7.1-7.8m |
| 67 | 2-Chloro-4-methylphenyl | —OCH₂— | —CH₃ | —OCH₃ | H | 1716, 1490, 1435, 1253, 1177, 1063 |
| 68 | 3-tert.-Butylphenyl | —OCH₂— | —CH₃ | —OCH₃ | H | 1718, 1487, 1435, 1263, 1202, 1036 |
| 69 | 4-Chlorophenyl | —OCH₂— | —CH₃ | —OCH₃ | H | 1716, 1491, 1242, 1036, 825 |
| 70 | 5-Methylisoxazol-3-yl | —OCH₂— | —CH₃ | —OCH₃ | H | NMR (CDCl₃): δ = 1.6d, 2.15s, 3.7s, 5.05s, 5.6s, 7.0-7.6m |
| 71 | 2-(Ethoxyimino)phenyl | —OCH₂— | —CH₃ | —OCH₃ | H | 1716, 1600, 1487, 1451, 1248, 1053, 958, 753 |
| 72 | 2-Methyl-4-iso-propyl-carbonylphenyl | —OCH₂— | —CH₃ | —OCH₃ | H | 1716, 1673, 1599, 1502, 1381, 1251, 1177, 1131, 1036, 758 |
| 73 | Acetyl | —OCH₂— | —CH₃ | —OCH₃ | H | |
| 74 | 2-Methylphenyl | —OCH₂— | Isopropyl | —OCH₃ | H | 1716, 1492, 1309, 1265, 1244, 1228, 1124, 1021, 752 |
| 75 | 2-n-Propyl-6-trifluoro-methylpyrimidin-4-yl | —OCH₂— | Isopropyl | —OCH₃ | H | 2963, 1719, 1599, 1572, 1421, 1350, 1247, 1184, 1152, 1026 |
| 76 | 2-Methylphenyl | —OCH₂— | —CH₃ | —NHCH₃ | H | 1664, 1626, 1602, 1517, 1495, 1462, 1241, 1191, 1121, 752 |
| 77 | 2-Methoxy-6-trifluoro-methylpyrimidin-4-yl | —OCH₂— | —CH₃ | —OCH₃ | H | 1717, 1604, 1579, 14215, 1373, 1347, 1253, 1184, 1150, 1124 |
| 78 | 2-Ethoxy-6-trifluoro-methylpyrimidin-4-yl | —OCH₂— | —CH₃ | —OCH₃ | H | 1718, 1602, 1579, 1437, 1413, 1338, 1266, 1253, 1150, 1133 |
| 79 | 2-i-Propoxy-6-trifluoromethyl-pyrimidin-4-yl | —OCH₂— | —CH₃ | —OCH₃ | H | 1718, 1600, 1436, 1405, 1351, 1325, 1266, 1253, 1150, 1130 |
| 80 | 2-n-Butylthio-6-trifluoromethyl-pyrimidin-4-yl | —OCH₂— | —CH₃ | —OCH₃ | H | 1718, 1589, 1558, 1428, 1406, 1351, 1284, 1267, 1185, 1151 |
| 81 | 2-Dimethylamino-6-trifluoromethyl-pyrimidin-4-yl | —OCH₂— | —CH₃ | —OCH₃ | H | 1717, 1614, 1583, 1424, 1408, 1348, 1246, 1137, 1114, 1016 |
| 82 | 2-Diethylamino-6-trifluoromethyl-pyrimidin-4-yl | —OCH₂— | —CH₃ | —OCH₃ | H | 1718, 1593, 1538, 1437, 1409, 1350, 1253, 1178, 1146, 1111 |
| 83 | 2-Methylquinazolin-4-yl | —OCH₂— | —CH₃ | —OCH₃ | H | 1712, 1620, 1581, 1570, 1496, 1418, 1353, 1317, 1252, 779 |
| 84 | 2-Methyl-4-quinazolon-3-yl | —CH2— | —CH₃ | —OCH₃ | H | 1714, 1683, 1638, 1595, 1474, 1389, 1257, 1035, 778, 762 |
| 85 | 2-Trifluoromethylquinazolin-4-yl | —OCH₂— | —CH₃ | —OCH₃ | H | 85-86° C. |
| 86 | 2-i-Propyl-6-hydroxymethyl-pyrimidin-4-yl | —OCH₂— | —CH₃ | —OCH₃ | H | 73-74° C. |

TABLE-continued

| Comp. No. | R⁴ | A | R² | W-R¹ | $R_n^3$ | Phys. data [IR (cm⁻¹); NMR (ppm); mp (°C.)] |
|---|---|---|---|---|---|---|
| 87 | 2-Cyclopentyl-6-trifluoro-methylpyrimidin-4-yl | —OCH₂— | Cyclo-propyl | —OCH₃ | H | 1714, 1597, 1569, 1423, 1350, 1247, 1184, 1150, 1103, 1028 |
| 88 | 2-Cyclohexyl-6-trifluoromethyl-pyrimidin-4-yl | —OCH₂— | Cyclo-propyl | —OCH₃ | H | 1715, 1596, 1569, 1421, 1347, 1260, 1247, 1184, 1130 |
| 89 | 1-(4-Chlorophenyl)-pyrazol-4-yl | —CH=CH— (E) | Cyclo-propyl | —OCH₃ | H | 1707, 1628, 1497, 1430, 1399, 1248, 1180, 1022, 948, 830 |
| 90 | 3-(4-Chlorophenyl)-isoxazol-5-yl | —CH=CH— (E) | Cyclo-propyl | —OCH₃ | H | 1700, 1427, 1252, 1191, 1180, 1031, 966, 835, 750 |
| 91 | 2-Methyl-6-methoxymethyl-pyrimidin-4-yl | —OCH₂— | —CH₃ | —OCH₃ | H | 1717, 1592, 1567, 1434, 1416, 1342, 1253, 1198, 1117 |
| 92 | 2-i-Propyl-6-methoxymethyl-pyrimidin-4-yl | —OCH₂— | —CH₃ | —OCH₃ | H | 72–73° C. |
| 93 | 3-Chloro-5-trifluoromethyl-2-pyridon-1-yl | —CH2— | —CH₃ | —OCH₃ | H | 1709, 1680, 1640, 1438, 1300, 1251, 1160, 1132, 1116 |
| 94 | 5-Trifluoromethyl-2-pyridon-1-yl | —CH2— | —CH₃ | —OCH₃ | H | 1704, 1678, 1632, 1351, 1336, 1246, 1154, 1114, 1098, 1062 |
| 95 | 2-Dimethylamino-6-methyl-5-nitropyrimidin-4-yl | —OCH₂— | —CH₃ | —OCH₃ | H | 100–101° C. |
| 96 | 2-n-Propyl-6-trifluoromethyl-pyrimidin-4-yl | —OCH₂— | —CH₃ | —OCH₃ | 5-t-Butyl | 2963, 1719, 1598, 1570, 1422, 1395, 1348, 1254, 1183, 1152 |
| 97 | 2-n-Propyl-5-chloro-6-trifluoro-methyl-pyrimidin-4-yl | —OCH₂— | —CH₃ | —OCH₃ | H | 1718, 1555, 1461, 1432, 1399, 1347, 1253, 1190, 1148, 1025 |
| 98 | 4-Fluorophenyl | — | —CH₃ | —OCH₃ | H | 1718, 1511, 1480, 1268, 1241, 1210, 1158, 838, 771, 751 |
| 99 | 3-(3-Fluorophenyl)-isoxazol-5-yl | E (—CH=CH—) | —CH₃ | —OCH₃ | H | NMR (CDCl₃) δ = 1.6d; 3.75s; 6.50s; 6.95d; 7.1–7.7m |
| 100 | 3-(3-Methylphenyl)-isoxazol-5-yl | E (—CH=CH—) | —CH₃ | —OCH₃ | H | NMR (CDCl₃) δ = 1.6d; 2.2s; 3.75s; 6.55s; 6.9d; 7.1–7.8m |
| 101 | 3-(4-Chlorophenyl)-isoxazol-5-yl | E | -oxy)-imino-propyl]-phenyl | | | |
| 112 | 2-Methyl-4-[(1'-methoxyimino-2'-methyl)-propyl]-phenyl | —OCH₂— | —CH₃ | —OCH₃ | H | 1717, 1600, 1502, 1251, 1132, 1035, 757 |
| 113 | 2-Methyl-4-[(1'-ethoxyimino-2'-methyl)-propyl]-phenyl | —OCH₂— | —CH₃ | —OCH₃ | H | 1718, 1502, 1381, 1249, 1132, 1037 |
| 114 | 2-Methyl-4-[(1'-iso-propoxy-imino-2'-methyl)-propyl]-phenyl | —OCH₂— | —CH₃ | —OCH₃ | H | 1718, 1502, 1380, 1249, 1134, 1037, 966 |
| 115 | 2-Methyl-4-[1'-(prop-1-yn-3--oxy)-imino-2'-methyl-propyl]-phenyl | —OCH₂— | —CH₃ | —OCH₃ | H | 1715, 1502, 1251, 1192, 1135, 1036 |
| 116 | 2-Methyl-4-[(1'-n-butoxyimino-2'-methyl)-propyl]-phenyl | —OCH₂— | —CH₃ | —OCH₃ | H | 1714, 1502, 1250, 1134, 1036, 1013 |
| 117 | 2-Methyl-4-[(1'-cyanomethoxy-imino-2'-methyl)-propyl]-phenyl | —OCH₂— | —CH₃ | —OCH₃ | H | 1714, 1502, 1435, 1251, 1034, 1012, 757 |
| 118 | 2-Methyl-4-(n-propoxy-imino-ethy-1'-yl)-phenyl | —OCH₂— | —CH₃ | —OCH₃ | H | 1.0(t, 3H); 1.7(d, 3H); 1.71 (q, 2H); 2.2(s, 3H); 2,3(s, 3H); 3.7(s, 3H); 4.1(t, 2H); 4.9(s, 2H); 6.7(d, 1H); 7.0–7.6(m, 7H) |
| 119 | 2-Methyl-4-(n-butoxyimino-eth-1'-yl)-phenyl | —OCH₂— | —CH₃ | —OCH₃ | H | 1.0(t, 3H); 1.4(q, 2H); 1.7(d, 3H); 1.75(t, 2H); 2.17(s, 3H); 2.23(s, 3H); 3.7(s, 3H); 4.95(s, 2H); 6.7(d, 1H); 7.0–7.6(m, 7H) |
| 120 | 2-Methyl-4-(allyloxyimino-eth-1'-yl)-phenyl | —OCH₂— | —CH₃ | —OCH₃ | H | 1705, 1507, 1249, 1037, 1012, 935, 759 |
| 121 | 2-Methyl-4-(iso-propoxy-imino-eth-1'-yl)-phenyl | —OCH₂— | —CH₃ | —OCH₃ | H | 1718, 1507, 1319, 1247, 1135, 1037, 963, 771 |
| 122 | 2,5-Dimethyl-4-(methoxyimino-eth-1'-yl)-phenyl | —OCH₂— | —CH₃ | —OCH₃ | H | 1717, 1508, 1435, 1325, 1248, 1147, 1049, 875 |
| 123 | 2,5-Dimethyl-4-(ethoxyimino-eth-1'-yl)-phenyl | —OCH₂— | —CH₃ | —OCH₃ | H | 1717, 1509, 1435, 1326, 1249, 1147, 1047 |
| 124 | 2,5-Dimethyl-4-(n-propoxyimino-eth-1'-yl)-phenyl | —OCH₂— | —CH₃ | —OCH₃ | H | 1717, 1509, 1435, 1326, 1249, 1146, 1047, 988 |
| 125 | 2,5-Dimethyl-4-(n-butoxyimino-eth-1'-yl)-phenyl | —OCH₂— | —CH₃ | —OCH₃ | H | 1717, 1509, 1326, 1249, 1147, 1038 |

TABLE-continued

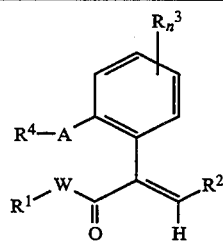

| Comp. No. | R⁴ | A | R² | W-R¹ | $R_n^3$ | Phys. data [IR (cm⁻¹); NMR (ppm); mp (°C.)] |
|---|---|---|---|---|---|---|
| 126 | 2,5-Dimethyl-4-(iso-propoxy-imino-eth-1'-yl)-phenyl | —OCH₂— | —CH₃ | —OCH₃ | H | 1716, 1509, 1367, 1322, 1249, 1157, 1037, 952 |
| 127 | 2,5-Dimethyl-4-(allyloxyimino-eth-1'-yl)-phenyl | —OCH₂— | —CH₃ | —OCH₃ | H | 1716, 1508, 1435, 1249, 1149, 1036, 1002 |
| 128 | 2,5-Dimethyl-4-[1'-(prop-1-yn-3-oxy)-imino-ethyl]-phenyl | —OCH₂— | —CH₃ | —OCH₃ | H | 1715, 1509, 1435, 1326, 1249, 1038, 1005 |
| 129 | 2,5-Dimethyl-4-[1'-(but-2-en-4-oxy)-imino-ethyl]-phenyl | —OCH₂— | —CH₃ | —OCH₃ | H | 1717, 1508, 1435, 1249, 1150, 1037, 967 |
| 130 | 2-Methyl-4-[-(but-2-en-4-oxy)-imino-ethyl]-phenyl | —OCH₂— | —CH₃ | —OCH₃ | H | 1.6(d, 3H); 1.7(d, 3H); 2.19 (s, 3H); 2.3(s, 3H); 3.7(s, 3H); 4.6(m, 2H); 4.9(s, 2H); 6.8(m, 2H); 6.7(d, 1H); 7.0–7.6(m, 7H) |
| 131 | 2-Methyl-4-[1'-(prop-1-yn-oxy)-imino-ethyl]-phenyl | —OCH₂— | —CH₃ | —OCH₃ | H | 1714, 1505, 1435, 1250, 1143, 1042 |
| 132 | 2-Methyl-4-[(1'-cyanomethoxy-imino)-ethyl]-phenyl | —OCH₂— | —CH₃ | —OCH₃ | H | 1713, 1505, 1435, 1320, 1251, 1143, 1059, 1015 |
| 133 | 2,4-Dibromophenyl | —OCH₂— | —CH₃ | —OCH₃ | H | 1714, 1474, 1248, 1046, 758 |
| 134 | 2,6-Dichlorophenyl | —OCH₂— | —CH₃ | —OCH₃ | H | 1716, 1447, 1374, 1250, 1037, 783 |
| 135 | 3-Chlorophenyl | —OCH₂— | —CH₃ | —OCH₃ | H | 1716, 1593, 1477, 1435, 1252, 1036, 766 |
| 136 | 3-Chloro-4-fluorophenyl | —OCH₂— | —CH₃ | —OCH₃ | H | 1715, 1497, 1435, 1259, 1201, 1050, 763 |
| 137 | 4-tert.-Butylphenyl | —OCH₂— | —CH₃ | —OCH₃ | H | 1716, 1511, 1434, 1249, 1177, 1037, 828, 757 |
| 138 | 4,5-Dichlorophenyl | —OCH₂— | —CH₃ | —OCH₃ | H | 1715, 1591, 1474, 1261, 1224, 1123 |
| 139 | 2,5-Dimethylphenyl | —OCH₂— | —CH₃ | —OCH₃ | H | 1716, 1665, 1509, 1281, 1248, 1120 |
| 140 | 2-Methyl-4-(2-methoxyiminoethyl)-phenyl | —OCH₂— | —CH₂CH₃ | —OCH₃ | H | 1717, 1505, 1243, 1051 |
| 141 | 2-Methyl-4-(2-methoxyiminoethyl)-phenyl | —OCH₂— | —CH₃ | —OH | H | 1688, 1505, 1277, 1245, 1181, 1051 |
| 142 | 2-Methylphenyl | —OCH₂— | —CH₂CH₃ | —OCH₃ | H | 1717, 1494, 1460, 1241, 1192, 1122, 751 |
| 143 | 1-Phenylpyrazol-4-yl | —OCH₂— | —CH₃ | —OCH₃ | H | 1714, 1597, 1580, 1503, 1399, 1356, 1260, 1034, 944, 756 |
| 144 | 1-(4-Methylphenyl)-pyrazol-4-yl | —OCH₂— | —CH₃ | —OCH₃ | H | 1714, 1518, 1435, 1401, 1356, 1258, 1167, 1035, 945, 761 |
| 145 | 1-(4-Fluorophenyl)-pyrazol-4-yl | —OCH₂— | —CH₃ | —OCH₃ | H | 1713, 1597, 1582, 1514, 1402, 1357, 1256, 1228, 1035, 944, 837 |
| 146 | 5,7-Dimethyl-1,2-benzisoxazol-3-on-2-yl | —CH₂— | —CH₃ | —OCH₃ | H | 1772, 1715, 1465, 1435, 1349, 1263, 1251, 1202, 1058, 1037 |
| 147 | 5,7-Diethyl-1,2-benzisoxazol-3-on-2-yl | —CH₂— | —CH₃ | —OCH₃ | H | 1715, 1690, 1494, 1452, 1434, 1251, 1204, 1037, 769 |
| 148 | 5,7-Diethyl-1,2-benzisoxazol-3-yl- | —OCH₂— | —CH₃ | —OCH₃ | H | 1717, 1539, 1499, 1459, 1437, 1363, 1254, 1212, 1037 |
| 149 | 5-Fluoro-1,2-benzisoxazol-3-yl | —OCH₂— | —CH₃ | —OCH₃ | H | 96–97 |
| 150 | 5-Chloro-1,2-benzisoxazol-3-yl | —OCH₂— | —CH₃ | —OCH₃ | H | 1716, 1535, 1474, 1438, 1354, 1311, 1258, 1211, 1037, 928 |
| 151 | 5-Phenyl-1,3,4-oxa-diazol-2-on-3-yl | —CH₂— | —CH₃ | —OCH₃ | H | 102–103 |
| 152 | 5-(4-Methylphenyl)-1,3,4-oxadiazol-2-on-3-yl | —CH₂— | —CH₃ | —OCH₃ | H | 102–103 |
| 153 | 5-(4-Chlorophenyl)-1,3,4-oxadiazol-2-on-3-yl | —CH₂— | —CH₃ | —OCH₃ | H | 1786, 1715, 1491, 1408, 1252, 1205, 1091, 1036, 1009, 744 |
| 154 | 5-Phenyl-1,3,4-oxadiazol-2-yl | —SCH₂— | —CH₃ | —OCH₃ | H | 87–88 |
| 155 | 5-(4-Methylphenyl)-1,3,4-oxadiazol-2-yl | —SCH₂— | —CH₃ | —OCH₃ | H | 103–104 |
| 156 | 5-(4-Chlorophenyl)-1,3,4-oxadiazol-2-yl | —SCH₂— | —CH₃ | —OCH₃ | H | 110–111 |
| 157 | 4-Phenylthiazol-2-yl | —OCH₂— | —CH₃ | —OCH₃ | H | 1715, 1530, 1523, 1444, 1434, 1256, 1230, 1196, 758, 718 |
| 158 | 4-(4-Chlorophenyl)-thiazol-2-yl | —OCH₂— | —CH₃ | —OCH₃ | H | 1714, 1528, 1476, 1255, 1229, 1196, 1090, 1037, 758 |
| 159 | 4-Phenylthiazol-2-yl | —SCH₂— | —CH₃ | —OCH₃ | H | 1714, 1477, 1443, 1433, 1252, 1204, 1031, 767, 750, 726 |
| 160 | 4-(4-Fluorophenyl)-thiazol-2-yl | —SCH₂— | —CH₃ | —OCH₃ | H | 1714, 1483, 1434, 1266, 1253, 1204, 1156, 1031, 840 |
| 161 | 4-(4-Chlorophenyl)-thiazol-2-yl | —SCH₂— | —CH₃ | —OCH₃ | H | 1713, 1473, 1433, 1401, 1264, 1252, 1204, 1090, 1033, 1013 |

TABLE-continued

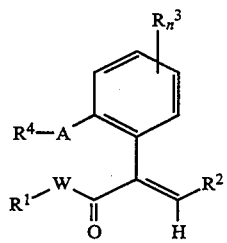

| Comp. No. | R⁴ | A | R² | W-R¹ | $R_n^3$ | Phys. data [IR (cm⁻¹); NMR (ppm); mp (°C.)] |
|---|---|---|---|---|---|---|
| 162 | 5-Methyl-2-phenyl-thiazol-4-yl | —OCH₂— | —CH₃ | —OCH₃ | H | 1716, 1553, 1499, 1434, 1338, 1251, 1140, 1037, 761, 684 |
| 163 | 5-Methyl-2-(4-chlorophenyl)-thiazol-4-yl | —OCH₂— | —CH₃ | —OCH₃ | H | 1716, 1551, 1498, 1433, 1339, 1252, 1142, 1091, 1037, 761 |
| 164 | 3-(4-Chlorophenyl)-isoxazol-5-yl | —OCH₂— | —CH₃ | —OCH₃ | H | 112–113 |
| 165 | 3-(4-Chlorophenyl)-isoxazol-5-on-2-yl | —CH₂— | —CH₃ | —OCH₃ | H | 1744, 1713, 1607, 1487, 1435, 1256, 1204, 1092, 1069, 1036 |
| 166 | 6-Chlorobenzoxazol-2-on-3-yl | —CH₂— | —CH₃ | —OCH₃ | H | 104–105 |
| 167 | 5-(4-Trifluoromethylphenyl)-1,3,4-oxadiazol-2-on-3-yl | —CH₂— | —CH₃ | —OCH₃ | H | 98–99 |
| 168 | 1-(4-Cyanophenyl)pyrazol-4-yl | —OCH₂— | —CH₃ | —OCH₃ | H | 134–136 |
| 169 | 2-n-Propyl-6-(4-chlorophenyl)-pyrimidin-4-yl | —OCH₂— | —CH₃ | —OCH₃ | H | 1717, 1583, 1547, 1492, 1431, 1344, 1253, 1210, 1092, 832 |
| 170 | 2-n-Propyl-6-phenyl-pyrimidin-4-yl | —OCH₂— | —CH₃ | —OCH₃ | H | 1717, 1581, 1550, 1497, 1451, 1345, 1253, 1211, 1037, 766 |
| 171 | 5-(4-Trifluoromethylphenyl)-1,3,4-oxadiazol-2-yl | —SCH₂— | —CH₃ | —OCH₃ | H | 81–82 |
| 172 | 6-Trifluoromethyl-2-(4-chlorophenyl)-pyrimidin-4-yl | —OCH₂— | —CH₃ | —OCH₃ | H | 97–98 |
| 173 | 4-(4-Fluorophenyl)-thiazol-2-yl | —OCH₂— | —CH₃ | —OCH₃ | H | 1714, 1535, 1523, 1489, 1315, 1255, 1230, 1195, 1156, 840 |
| 174 | 4-(2,4-Dichlorophenyl)-thiazol-2-yl | —SCH₂— | —CH₃ | —OCH₃ | H | 1715, 1464, 1433, 1252, 1204, 1104, 1035, 783, 766 |

USE EXAMPLES

Fungicidal action

Use example 1

Action on Peronospora in grapes

Leaves of potted vines of the Müller-Thurgau variety were sprayed with aqueous suspensions containing (dry basis) 80% of the active ingredients listed in the tables under nos. 11, 13, 14, 17, 30, 31, 32, 57, 64, 67, 111, 112, 115, 120, 121, 122, 123, 124, 125, 126, 127, 129, 130, 131, 132, 139, 140, 144, 145, 157, 158 and 160, and 20% of emulsifier. To assess the duration of action, the plants were set up, after the sprayed-on layer had dried, for 8 days in the greenhouse. Then the leaves were infected with a zoospore suspension of Plasmopara viticola. The plants were first placed for 48 hours in a water vapor-saturated chamber at 24° C. and then in a greenhouse for 5 days at from 20° to 30° C. To accelerate and intensify the sporangiophore discharge, the plants were then again placed in the moist chamber for 16 hours. The extent of fungus attack was then assessed on the undersides of the leaves.

Compared with a control experiment (untreated, 70% fungus attack), the plants treated with aqueous spray liquors containing 250 ppm of the active ingredients only exhibited 0 to 15% fungus attack.

Insecticidal action

The insecticidal action of the compounds of the formula I' is demonstrated in the following experiments:
The compounds were formulated
a) as a 0.1% acetonic solution or
b) as a 10% emulsion concentrate obtained by emulsifying the compound in a mixture containing 70wt % of cyclohexanol, 20wt % of Nekanil ® LN (↑ Lutensol AP6, a spreader-sticker with an emulsifying and dispersing action based on ethoxylated alkylphenols) and 10wt % of Emulphor ® EL (an emulsifier based on ethoxylated fatty alcohols).

The concentrations given in the examples were obtained by diluting the formulated compounds with acetone in the case of a) and with water in the case of b).

Upon conclusion of the experiments, the lowest concentration was determined at which the compounds, compared with the untreated control, caused 80–100% inhibition or mortality (action threshold or minimum concentration).

We claim:

1. An α-Phenylacrylic acid compound of the formula

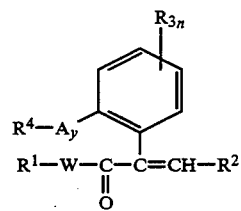

I where the variables have the following meanings:
n is 1;
y is 1;
R¹ is methyl;
R² is methyl, ethyl or methoxymethyl;
R³ is hydrogen, $R^4$ is 2,5-dimethylphenyl, 2,5-dichlorophenyl, 2-methyl-5-chlorophenyl, 2,4-dimethylphenyl, 2-chloro-5-methylphenyl, 2,3,5-trimethylphenyl or 2-methyl-5-isopropylphenyl W is oxygen;

A is —OCH$_2$—.

2. An agent for combating injurious fungi, containing a fungicidally effective amount of a compound of the formula I as set forth in claim 1 and inert additives.

3. An agent for combating pests, containing inert additives and a pesticidally effective amount of a compound of the formula I as set forth in claim 1.

* * * * *